(12) United States Patent
Malik et al.

(10) Patent No.: US 9,274,036 B2
(45) Date of Patent: Mar. 1, 2016

(54) METHOD AND APPARATUS FOR CHARACTERIZING COMPOSITE MATERIALS USING AN ARTIFICIAL NEURAL NETWORK

(71) Applicant: King Fahd University of Petroleum and Minerals, Dhahran (SA)

(72) Inventors: Muhammad Haris Malik, Dhahran (SA); Abdul Fazal Muhammad Arif, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 213 days.

(21) Appl. No.: 14/106,074

(22) Filed: Dec. 13, 2013

(65) Prior Publication Data

US 2015/0170022 A1   Jun. 18, 2015

(51) Int. Cl.
*G01N 3/30*   (2006.01)
*G06N 3/08*   (2006.01)
*G06F 17/50*  (2006.01)

(52) U.S. Cl.
CPC .............. *G01N 3/30* (2013.01); *G06F 17/5018* (2013.01); *G06N 3/084* (2013.01); *G01N 2203/0212* (2013.01); *G06F 2217/44* (2013.01)

(58) Field of Classification Search
None
See application file for complete search history.

(56) References Cited

U.S. PATENT DOCUMENTS 5,830,548 A    11/1998  Andersen et al.
2010/0049479 A1  2/2010  Coles et al.

FOREIGN PATENT DOCUMENTS

EP   1 782 297 B1   5/2013
JP   4547941        7/2010

OTHER PUBLICATIONS

Z. Zhang, K. Friedrich Artificial neural networks applied to polymer composites: a review. Compos Sci Technol, 63 (2003), pp. 2029-2044.*
Dua, Rohit, et al. "Detection and classification of impact-induced damage in composite plates using neural networks." Neural Networks, 2001. Proceedings. IJCNN'01. International Joint Conference on. vol. 1. IEEE, 2001.*
Hany El Kadi, Modeling the mechanical behavior of fiber-reinforced polymeric composite materials using artificial neural networks—A review, Composite Structures, vol. 73, Issue 1, May 2006, pp. 1-23.*
Jiang, Zhenyu, et al. "Neural network based prediction on mechanical and wear properties of short fibers reinforced polyamide composites." Materials & Design 29.3 (2008): 628-637.*

* cited by examiner

*Primary Examiner* — Stanley K Hill
*Assistant Examiner* — David H Kim
(74) *Attorney, Agent, or Firm* — Oblon, McClelland, Maier & Neustadt, L.L.P.

(57) ABSTRACT

This invention relates to a method and apparatus for characterizing composite materials, and in particular, to utilizing an artificial neural network for predicting an impact resistance of a composite material. A method for predicting an impact resistance of a composite material in accordance with the present invention includes the steps of designing an artificial neural network including a plurality of neurons, training the artificial neural network to predict the impact resistance by adjusting an output of the plurality of neurons according to sample data and known results of the sample data, inputting data of the composite material into the artificial neural network, and utilizing the artificial neural network to predict the impact resistance of the composite material.

20 Claims, 53 Drawing Sheets

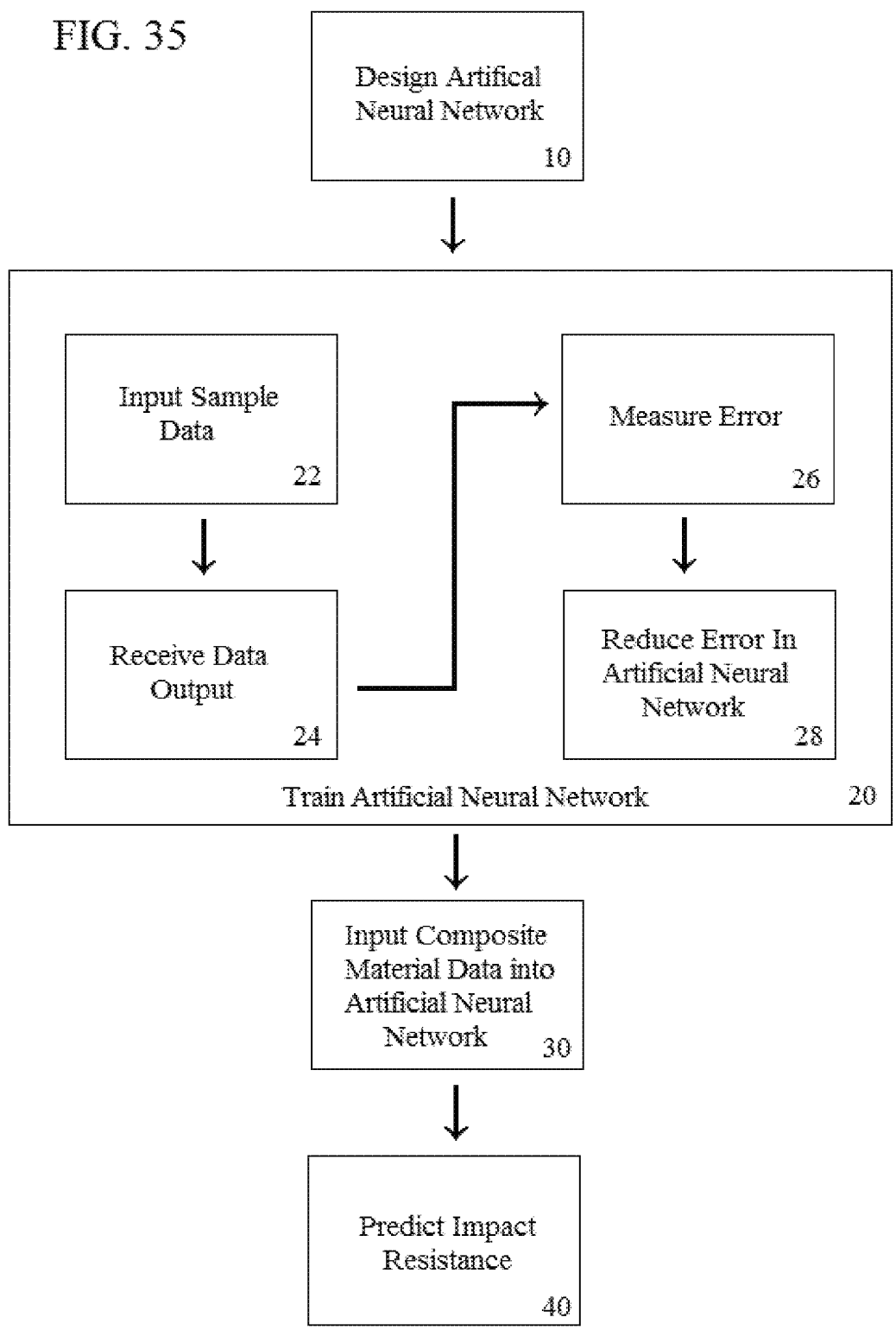

METHOD AND APPARATUS FOR CHARACTERIZING COMPOSITE MATERIALS USING AN ARTIFICIAL NEURAL NETWORK

BACKGROUND OF THE INVENTION

1. Field of the Invention

This invention relates to a method and apparatus for characterizing composite materials, and in particular, to utilizing an artificial neural network for predicting an impact resistance of a composite material.

2. Description of the Related Art

The "background" description provided herein is for the purpose of generally presenting the context of the disclosure. Work of the presently named inventor, to the extent it is described in this background section, as well as aspects of the description which may not otherwise qualify as prior art at the time of filing, are neither expressly or impliedly admitted as prior art against the present invention.

Composite materials have been in human use in different forms for thousands of years, examples of earlier use of composite materials may be seen in the mud and straw bricks.

Composite materials for construction, engineering and other similar applications are formed by combination of two or more materials in order to enjoy the benefits of the properties of the constituents. A property of composite materials is that the materials are still distinguishable and don't blend completely unlike alloys, hence, normally exhibit an interface between one another. The constituent materials retain their physical and chemical properties, only to combine to give properties that are not offered by the individual constituents.

The majority of composite materials use two constituents: a binder or matrix and reinforcement. The reinforcement is stronger and stiffer, forming a sort of backbone, while the matrix keeps the reinforcement in a set place. The binder also protects the reinforcement, which may be brittle or breakable.

As illustrated in FIG. 1, composites may be categorized in three main divisions according to the geometry of the reinforcements: (1) Particle-reinforced, (2) Fiber-reinforced, and (3) Structural Composites.

According to the type of the matrix, there are: (1) Polymer Matrix Composites, (2) Metal Matrix Composites, and (3) Ceramic Matrix Composites.

Technologically, important composites may be those in which the dispersed phase is in the form of a fiber. Design goals of fiber-reinforced composites often include high strength and/or stiffness on a weight basis. In fiber-reinforced composites, fibers are the phase that provides the strength and the ability to carry load while the matrix increases the ductility and also acts as binding agent for the fibers and also acts as load transfer medium.

Common fiber reinforcing agents include, Aluminum, Aluminum oxide, Aluminum silica, Asbestos, Beryllium, Beryllium carbide, Beryllium oxide, Carbon (Graphite), Glass (E-glass, S-glass, D-glass), Molybdenum, Polyamide (Aromatic polyamide, Aramid), e.g., Kevlar 29 and Kevlar 49, Polyester, Quartz (Fused silica), Steel, Tantalum, Titanium, Tungsten, Tungsten monocarbide.

Common resin materials include Epoxy, Phenolic, Polyester, Polyurethene, and Vinyl Ester.

Composite pipes are gradually replacing the conventional pipes in the industrial applications. Composite pipes show good resistance to corrosion compared to metallic pipes in applications where pipes are carrying fluids like water or highly corrosive sulphuric acid is present in it. This property makes them ideal for usage in pipe industry [37].

Composite pipes may be described in two categories depending upon the type of resin material: (1) Reinforced thermosetting resin pipes (RTRP), and (2) Reinforced thermoplastic pipes (RTP).

Due to their superior mechanical and thermal properties over conventional materials, fiber reinforced composite materials are preferred in the petroleum industry. As an example of the advantage gained by replacing conventional material pipelines with composite materials is that a 6-inch diameter pipe weighs 4 pound per foot, whereas copper nickel pipe with the same diameter weighs 24 pound per foot [51].

Another major area of significant interest where composite pipes may be of use is the water related applications. Lack of fresh water reservoirs put forward the need of desalination applications. The desalination application requires piping systems that are corrosion resistant [61]. Water losses due to degradation of traditional pipe systems present a significant financial and maintenance problem. Composite based piping systems provide good protection against the corrosion. Fiberglass pipe systems have become the material of choice in the desalination and water distribution industry.

There are several major advantages composite pipes offer over conventional material pipes, such as corrosion resistance. Fiberglass pipes are resistant to corrosion for a long period of time and resists corrosion to a variety of media including seawater, hot brine, acids and other chemicals [61]. Also, the composite materials have a high strength to weight ratio compared to metals and the transportation and installation of the composite materials is easier. Large lengths of composite pipes may be easily manufactured and may be assembled with relative ease on sites.

Since, composite materials are corrosion resistant; the cost of maintenance is considerably lower. Also, the fatigue resistant capability of composite pipes is better than the metallic pipes. Also, low internal friction, fire resistance, torsional stiffness and good impact resistance combined with the flexibility in design as per strength and other requirements make them ideal replacement for the current conventional materials [61].

Mechanical damages to pipes occur frequently. These damages may cause leakage of oil and gas from pipes resulting from structural failure and may lead to reduced operating pressure or stopped production, human and environmental hazards and the heavy economic losses [7].

There are, however, some issues related to the use of composite piping systems primarily the lack of test data to support the materials' long term durability. The failure caused by the mechanical damages is one of the important aspects that need to be addressed. The structural failure of these pipelines may be due to a number of effects as burst, impact, puncture, overload, buckling, fatigue and fracture.

One of the major causes of damages in pipes are considered as "External Damage" caused by foreign objects and third party damage such as caused by a farmer ploughing a drainage ditch, or a supply boat dragging its anchor around an offshore platform [24]. These structural components are often very susceptible to foreign object impact during service. These damages may be vulnerable and may go unseen especially in case of low velocity impacts since these are not visually observable. A small dent caused by such impacts may lead to significant underlying damages for example, delamination, matrix cracking, fiber breakage and fiber/matrix interfacial debonding induced within the laminate [27].

Outside forces are one of the major causes of pipeline failures. Historically, the pipelines used were made from steels. Steel is a ductile material and the specifications used in the industry are already set for its use. The ASME codes B3

1.4 for oil applications and B31.8 for gas applications provide measures for the different kind of damages and repairs [12]. These materials are tested for their ductile behavior. Impact tests are considered good method to measure toughness of pipelines.

During the product lifecycle it is always expected that damages may occur due to impact by foreign objects. Mechanical damage may occur during handling, installation and service to the composite pipes. To ensure the reliability, good impact properties against low and intermediate velocity impacts are needed. Due to the laminate structure of composite materials their behavior to impacts is different to the metallic structures. The modes of damage in composite structures due to impact may be categorized as matrix cracking, fiber breakage and/or delamination [14].

Impact generally causes low to medium energies which cause a global structural response, and often results in internal cracking and delamination, while at higher energy levels may cause penetration and excessive local shear damage [1].

The impact damage may be caused by a number of factors, some of which are for example:

Dropped tool
Damage due to mishandling
In-service impacts
Hail and debris

The composite materials are prone to low energy impacts that may be observed with the effect of delamination in the plies and may be indirectly responsible for the failure. Delamination result in lowering of the elastic moduli, strength, durability and damage tolerance [14]. Low velocity impacts may also cause matrix cracking which sometimes may not be on the surface of impact but on the internal or bottom surface, this is due to the fact that the laminate is flexible. Matrix cracking is in the perpendicular direction to the plane of the laminate and is a tensile crack. In thicker laminates, matrix cracking is near the top surface and characterized as the shear crack.

The damage in composite materials due to impact force is a complex mechanism and still there are no analytical methods that may be generally accepted to define the phenomenon.

In addition to these, the micro failure modes commonly observed in composite laminates are fiber breakage, fiber micro buckling and matrix crushing, transverse matrix cracking, transverse matrix crushing, debonding at the fiber-matrix interface and delamination [14].

SUMMARY OF THE INVENTION

The foregoing paragraphs have been provided by way of general introduction, and are not intended to limit the scope of the following claims. The described implementations, together with further advantages, will be best understood by reference to the following detailed description taken in conjunction with the accompanying drawings.

Disclosure of the inventor, Muhammad Haris Malik, "*Optimization of Impact Resistance of composite Plates and Pipes*," Thesis, King Fahd University of Petroleum & Minerals, Dhahran, Saudi Arabia, December, 2012, is hereby incorporated in its entirety. Additionally, all references addressed in this disclosure are hereby incorporated in their entireties.

By studying in detail the available literature, a number of motivations have been found to continue the work in the field of optimization of the impact resistance of composite laminated plates and pipes. It is apparent that a lot of effort by various researchers around the globe has been put into the study of the behavior and dynamic response of composite materials under low velocity impact loading. Most of the work has been focused on the damage characterization and the initiation and propagation of damage under certain conditions. These studies have provided a great insight into the behavior and response of composite laminates plates and shells when impacted by foreign objects having low-velocity impacts. While there have been a lot of parametric studies considering the effects of various factors involving both the composite structure and the impactor, there is no logical conclusion to the effects which enhances the impact resistance of such structures. It is known from these studies that the impact response of composite plates depend upon the size, shape, mass and velocity of the impactor, also the impact response is the characteristic of the material and geometric properties of the composite plate or shell itself. This is apparent that the properties and circumstances involving the impactor are not in the control of the designers; rather the composite plates or shells may be manipulated such that the impact performance of these structures may be enhanced.

The studies provide a general understanding of different effects material, geometric and boundary conditions of the composite structure have on the impact resistance. This provides the opportunity to further take these studies and develop such characteristics of materials and other factors related directly to the composite structure so that the impact performance may be increased.

An exemplary implementation of the present invention may include a method for predicting an impact resistance of a composite material. Such a method may comprise designing an artificial neural network including a plurality of neurons, training, performed by a processor, the artificial neural network to predict the impact resistance by adjusting an output of the plurality of neurons according to sample data and known results of the sample data, inputting data of the composite material into the artificial neural network, and utilizing the artificial neural network to predict the impact resistance of the composite material.

In such a method, the artificial neural network may include an input layer of neurons that receives data that is input into the artificial neural network, and an output layer of neurons that outputs the prediction of the impact resistance of the composite material. The artificial neural network may further include a hidden layer comprising a plurality of neurons, the hidden layer may receive data output from the input layer, and the hidden layer may output processed data to the output layer.

Training the artificial neural network may include inputting the sample data to the input layer, measuring an error between the known results of the sample data and the prediction output from the output layer, and reducing the error by managing the hidden layer such that data output from neurons in the input layer may be selected for input to individual neurons in the hidden layer, and applying a variable weighting factor to each neuron of the plurality of neurons in the artificial network to adjust an output of each neuron.

In such a method, training the artificial neural network may include inputting the sample data to the artificial neural network, measuring an error between the known results of the sample data and the prediction output from the artificial neural network, and reducing the error by applying a variable weighting factor to each neuron of the plurality of neurons in the artificial neural network to adjust an output of each neuron. The error may be a mean-squared error.

In such a method, the input data of the composite material may include any of the following: a stacking sequence of layers in the composite material; a layer thickness; a number of layers in the composite material; an orientation angle of the layers in the composite material; and a material composition of the layers in the composite material.

In such a method, the artificial neural network may be a feed forward network.

In another exemplary implementation of the present invention, a device may be utilized to predict an impact resistance of a composite material. Such a device may comprise a processor configured to design an artificial neural network including a plurality of neurons, train the artificial neural network to predict the impact resistance by adjusting an output the plurality of neurons according to sample data and known results of the sample data, input data of the composite material into the artificial neural network, and utilize the artificial neural network to predict the impact resistance of the composite material.

In such a device, the artificial neural network may include an input layer of neurons that receives data that is input into the artificial neural network, and an output layer of neurons that outputs result data from the artificial neural network.

In such a device, training the artificial neural network may include inputting the sample data to the artificial neural network, measuring an error between the known results of the sample data and the prediction output from the artificial neural network, and reducing the error by applying a variable weighting factor to each neuron of the plurality of neurons in the artificial neural network to adjust an output of each neuron.

Such a device may be a component in a system for predicting an impact resistance of a composite material that is in accordance with an exemplary implementation of the present invention.

In another exemplary implementation of the present invention, a non-transitory computer readable medium may store computer readable instructions that, when executed by a computer, may cause the computer to perform a method that includes designing an artificial neural network including a plurality of neurons, training the artificial neural network to predict the impact resistance by adjusting an output of the plurality of neurons according to sample data and known results of the sample data, inputting data of the composite material into the artificial neural network, and utilizing the artificial neural network to predict the impact resistance of the composite material.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 35 illustrates a flowchart of a method in accordance with an exemplary implementation of present invention.

DETAILED DESCRIPTION OF THE DRAWINGS

Figure 1:
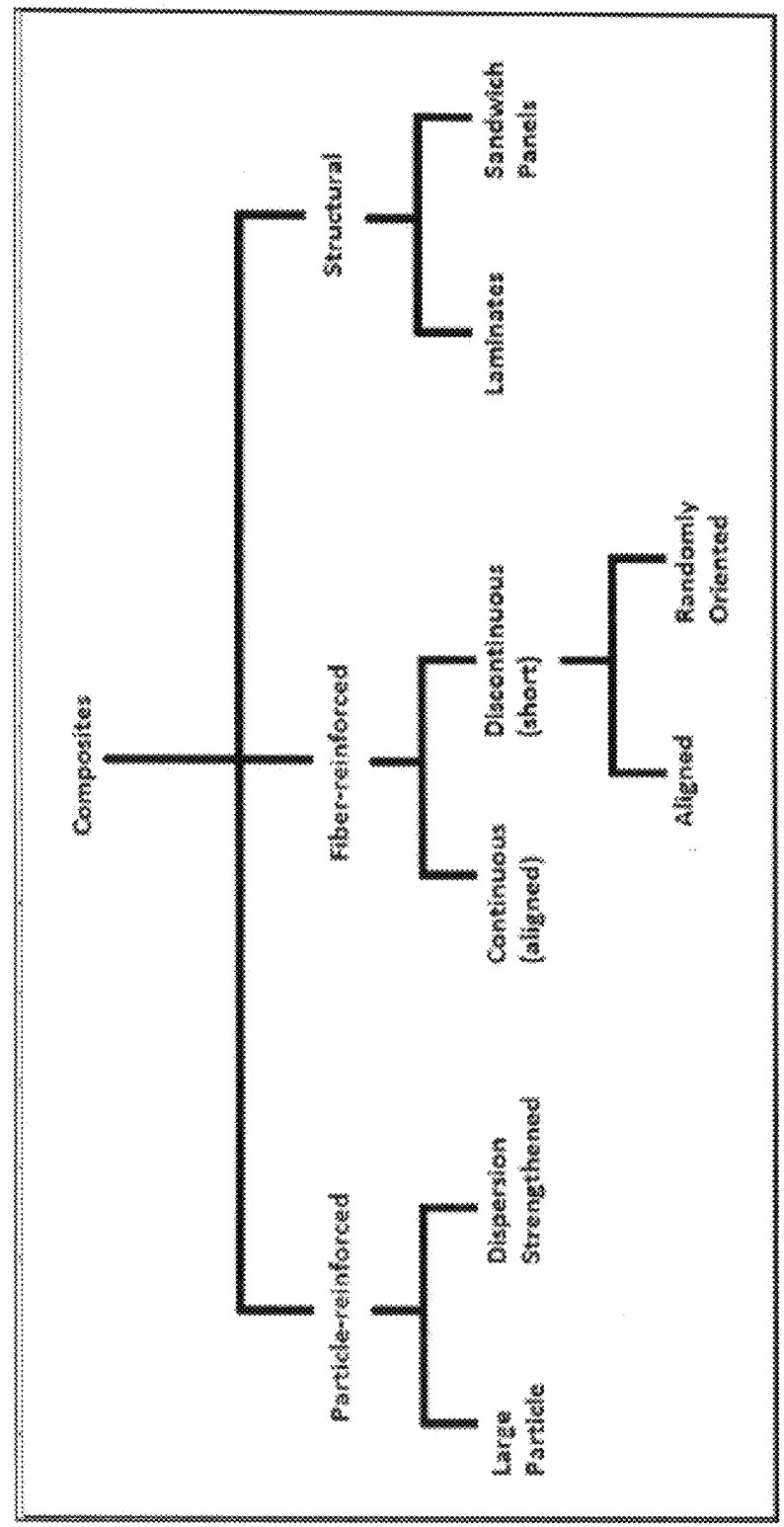
FIG. 1 illustrates a chart that categorizes composites according to geometry of the reinforcements.

Referring now to the drawings, wherein like reference numerals designate identical or corresponding parts throughout the several views.

Figure 2:
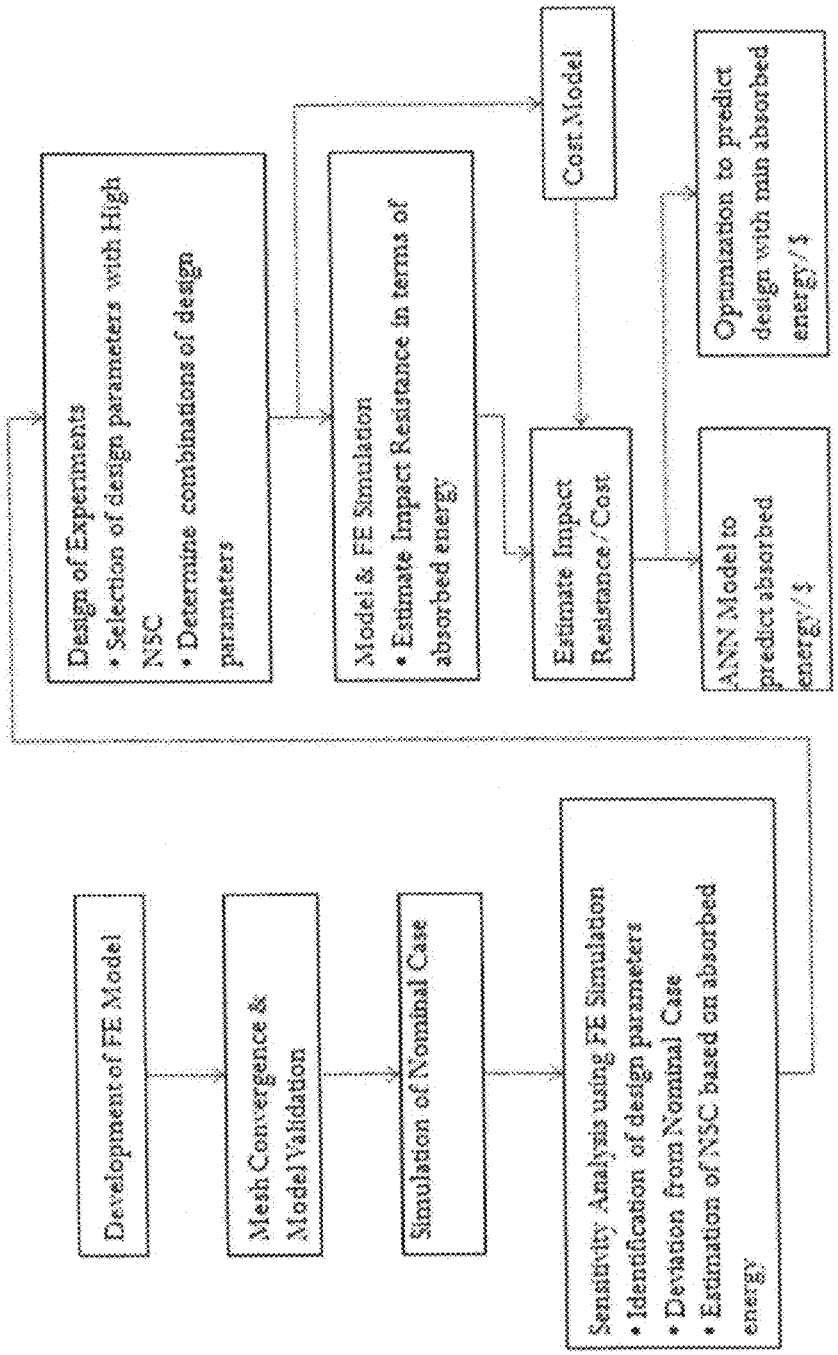
FIG. 2 illustrates a flowchart of a methodology for optimizing composite plates and pipes.

FIG. 2 illustrates a flowchart of a methodology for optimizing composite plates and pipes. In particular, the optimization of the composite plates and pipes is divided into two phases, in the initial phase a model is developed for the composite laminated plates and the study is based upon models and results from available literatures.

Experimental Studies on Plates and Laminates

There have been a number of studies on the effect of different parameters on the impact characteristics of composite plates and pipes. These studies include experimental [2,5,13, 25,58,63,66,69] numerical [6,40,41,66], and analytical [26] which discuss the impact behavior of different composite laminates and discuss the effects of various parameter changes and a number of studies which studied numerically [32,34,35,56,72,73] and a few experimental studies [43,72] have also been performed on laminated composite shells. There are a number of studies which have developed analytical or numerical techniques to study the impact response of composite plates and shells under low energy impact damage.

Yang & Cantwell [71] conducted a number of low velocity impact tests on (0°,90°) glass fiber reinforced epoxy resin to study the effects of varying key parameters on the damage initiation threshold. The results show that the impact resistance is proportional to the thickness of the composite panel. Also, the tests show that the impact resistance was not affected by the plate's geometry. A further study by Yang et al was done to study the effect of impactor shape. The focus of their study was the effect of key parameters, such as target size, projectile diameter and test temperature on damage initiation. The tests were carried out on samples of unidirectional E-glass fiber reinforced FM94 epoxy resin. The majority of tests were conducted on laminates of 1.8 mm thickness while few tests were carried out on laminates of thickness ranging from 0.8 mm to 3.6 mm. Tests were also undertaken to study the effect of temperature on the damage initiation. Tests were carried out at temperatures of 45, 60, 75 and 90° C. In these tests, the damage initiation threshold was established by increasing the impact energy until delamination just became apparent in the test samples. The samples were not subjected to multiple impact tests considering that would result in fatigue and a lower value of damage threshold. The tests conducted by Yang and Cantwell, suggested that the damage initiation force is proportional to the target thickness. The tests demonstrated dependency in the order of t3/2, where 't' is the thickness of the composite plate. This result was verified with the studies conducted earlier. They also carried out experimental studies on whether the geometry of the test specimen effects on the damage initiation threshold. This result was also supported by earlier studies that the damage initiation threshold does not depend upon the panel size. The final parameter studied was the effect of temperature and it was expected that temperature will have an effect on the matrix fracture. Tests were conducted at a number of temperatures between 23° and 90° C. A linear relationship was observed between the thickness of the panel and the damage initiation force at a particular temperature. It was observed that the damage threshold increased with temperature for thinner laminates.

Keršys, Keršienė, & Žiliukas [5] studied the impact response of woven carbon/epoxy and E-Glass/epoxy composite systems on vehicle body structures by considering energy profile diagrams and force-displacement curves. For low velocity impact tests, drop weight tests were performed. To determine the mechanism of impact damage the experiment was performed when laminated composite materials were deformed with low impact energy. The maximum energy used in the test was equal to 120 J by means of a vertically falling impactor. The total amount of energy introduced to a composite specimen and the energy absorbed by the composite specimen through the impact event are important parameters to assess impact response of the composite structures. The experiments demonstrated the fact that was also displayed by numerical studies was that the reduction in the stiffness of the composite plate. To estimate the energy absorbed during the impact a contact force F(t) was measured during the impact. This force depends upon the impactor mass 'm' and the velocity 'v'. Given an initial velocity 'v0', that is a function of acceleration due to gravity and downfall height 'H'.

$$v_0 = \sqrt{2gH}$$

Impactor speed and displacement 's' as the function of time are given by integrating the impact force:

$$v(t) = v_0 - \left(\frac{1}{m}\right)\int_0^\tau F(t)\,dt$$

$$s(t) = \int_0^\tau \left(v_0 - \left(\frac{1}{m}\right)\int_0^\tau F(t)\,dt\right).$$

The kinetic energy of the impactor and the absorbed energy $$E_{imp} = \frac{1}{2}mv^2$$

$$E_{ab}(t) = \frac{1}{2}mv_0^2 - \frac{1}{2}m\left(v_0 - \left(\frac{1}{m}\right)\int_0^\tau F(t)\,dt\right)^2.$$

It was observed that the stiffness of E-Glass/Epoxy composites during impact decreased with the increasing displacement due to great specimen deflection related with non-linear membrane effect. Force-time relationships were almost symmetrical. But the area under the force-displacement curve showed the great part of impact energy absorbed with the laminar composite at low velocity impact energies. The results show that at low impact energies of 6 J, the force value of 3.08 kN was maximum which gradually decreases to zero. But when the impact energy is greater, the maximum force value is reached when the damage under the impactor occurs after the greater total displacement.

Rilo & Ferreira [58] conducted their study on the experimental investigation of low velocity impacts on glass-epoxy laminated composite plates. The characterization of the damage was done in relation to the type of test, stacking sequence, dimensions and the maximum force of the impact.

Numerical Studies for Impact on Composite Plates

A number of studies were also carried out using the numerical approach to investigate the impact response of composite laminates and plates.

Setoodeh et al. [62] used a three dimensional elasticity based approach coupled with the layer wise laminated plate theory by J. N. Reddy. The study considers the effects of low velocity impact of general fiber reinforced laminated composite plates. A custom finite element code was developed for the impact response based on 3-D elasticity approach. Hertzian nonlinear contact law used to model the contact forces between the impactor and the target surface. The effect of impact velocity, mass of the impactor and the material properties were studied. The method applied by Setoodeh et al adopts a combined two- and one-dimensional analysis, which reduces the number of manipulations and the complexity in the formulation of the 3-D finite element method. The procedure is not completely three-dimensional yet it is capable of describing the impact behavior economically and accurately at the same time. In the FE modeling of Setoodeh et al, 9 noded quadratic surface elements with 3 noded quadratic elements in the thickness direction were used.

Farooq & Gregory [18] developed a finite element computational model to study the impact behavior and the failure of CFRP panels that are impacted with low velocity dropweight. The impactor used for the study is a flat-nosed tip object. Farooq et al used the commercially available software ABAQUS to study the critical damage regions under and near the impact zone. In-plane stresses were calculated from the model and the transverse shear stress were calculated using Trapezium rule from the standard equilibrium equations. The method used in this study is different from the Setoodeh et al as it is a 2-D model to predict the 3-D transverse shear stress. The calculated and the predicted stresses were used with failure theories to predict possible failure modes.

Farooq & Gregory [17] in the paper titled "Finite Element Simulation of Low Velocity Impact Damage Morphology in Quasi Isotropic Composite Panels Under Variable Shape Impactors" studied the barely visible impact damage (BVID), its initiation, growth and tolerance in fiber based composites under the low velocity impact. The impact damage reduces the stiffness of the composite panel and this concept was used in the model. Quasi isotropic specimens were selected to model the damage in the fiber directions. Three different specimens and three different types of impactor nose shapes were used. It is predicted that under the same loading conditions different nozzle tips produce different damages. The energy absorbed during the impact is dissipated in the form of matrix damage, fiber fracture and delamination, this result in significantly reduced stiffness. Low velocity impacts mean longer contact time between impactor and target surface which causes global deformation which may cause internal damage that may be difficult to detect. Farooq et al have studied the effect of such damages on the stiffness and the operational life of composite panels after low velocity impacts.

Tiberkak et al. [65] has investigated the response of Fiber reinforced composite under the low velocity impact loads. Mindlin's plate theory is implemented in the FE model which uses a 9-noded Lagrangian element. The study suggests that the increase in 90 degree plies increase the contact force implying a reduction in the rigidity of the laminate. Initially, threshold velocities were evaluated for matrix crack initiation. Afterwards, using appropriate failure criteria will be used to predict matrix cracking at higher velocities. The results in this study suggest that the damage occurs in the upper 90 degree plies with the dominance of transverse shear stress. The study is based upon the impact of a spherical object with low velocity upon a composite laminated plate containing a number of transversely thin layers and the contact force is applied at the center of the plate. The Mindlin plate theory takes into account the effect of transverse shear deformation and is applied in this study. The impact between the impactor and the composite plate is considered frictionless, the damping in the plate is neglected and the impactor is considered as a rigid body with isotropic properties. This study also applies the Hertzian law to calculate the contact force between the impactor and the composite plates. The study performs a parametric analysis by varying boundary conditions, stacking sequence, size of the composite plate and velocity of the impactor.

Tiberkak et al. observed no significant variations in the results with the change in boundary conditions. The effect of change of the stacking sequence shows that the contact force increases with the increase in the thickness of the 90 degree plies that mean the rigidity of the laminates is reduced. The contact forces increase with an increase in the percentage of fibers in the 90 degrees direction.

Heimbs et al. [22] conducted their analysis of impact on a composite plate with compressive preloads. Since, in real life systems the composite plates may be subjected to different stress states when it is being impacted and hence its behavior may be different from the unloaded or without stress behavior. The main issues covered by Heimbs et al are the modeling of composite laminate, its delamination and the implementation of preload. Impact loads are considered as a transient load and hence FE codes are based on explicit time integration, using small time step intervals. But the preloading is a static load making the use of implicit calculations more appropriate. That's why Heimbs et al have used specific numerical techniques for the solution of a combination of preloading and impact loadings. The results of the study were supported by a number of tests conducted on the drop weight test method. The tests were conducted for both preloaded and unloaded composite laminates. The tests conducted on compressive preloaded specimens indicated that preloading results in increased deflection of the CFRP plates and hence more material damage. This is due to the fact that more energy is absorbed and less is rebounded as elastic spring back effect which is the case with unloaded CFRP plates. The FE model was developed in LS-DYNA and it was developed with the modeling of the composite material including the intra laminar failure and delamination failure, the modeling of the preload and the impactor. The composite laminate was modeled as 24 plies of unidirectional laminas as 2-D shell elements. A number of failure criteria were defined based on the loading and the material damage such as tensile failure in matrix direction, tensile failure in fiber direction, compressive failure in matrix direction and compressive failure in the fiber direction. Failure is considered as soon as one of these criteria was met. In addition to these, strain based failure was also defined.

Interlaminar failure is another major phenomenon in the low velocity impacts of composite laminates, delamination absorbs energy upon impact and as a result the stiffness of the laminate is reduced. In LS-DYNA, there are two methods to include delamination as described by [22]. One of the methods is to use the cohesive brick elements between separate layers of shell elements with material law that may describe the damage process of the laminate connection.

The literature survey showed that so far the majority of the work in the impact analysis of composite materials has been focused on the study of composite laminates and very few studies have considered composite shells such as pipes. There is a lot of potential in the research related to the impact response of composite pipes and need to develop solutions for the improvement of impact characteristics of composite pipes subjected to low velocity impacts.

Naik and Meduri [53] studied the effect of laminate configuration on the impact behavior of composite laminates. Studies were carried out on different mixed composites, cross-ply laminates, woven-fabric composites and 3-D composites. The studies concentrated the effect of different laminate configurations on the impact response. The impactor mass, velocity and the incident impact energy were kept constant keeping in view of the typical tool drop scenario. From the study it is observed that the mixture of Unidirectional and woven fabrics demonstrates more resistance to impact damage.

Studies on Composite Shells

A limited number of studies have also been done on the impact behavior of composite shells.

Ibekwe et al. [27] discussed the effect of a thin metallic shell bonded to the outer surface of a laminated composite shell as a bumper layer. The experimental study revealed that the inclusion of a thin aluminum sheet increased the initiation energy that is the metallic sheet was able to absorb some of the impact energy. The maximum impact load and the deflection at maximum load were increased and the impact duration reduced. The higher impact loads did not cause considerable damage in the specimens with bonded aluminum sheet and only a slight reduction in the bending strength of the specimen was observed compared to the specimen without the aluminum sheet. The study by Ibekwe et al. showed that the damage was primarily in the bumper layer i.e. the aluminum sheet and it has served its purpose of absorbing the impact energy.

Yokoyama, Donadon, & de Almeida [72] presented an energy based failure model to study the impact resistance of the composite shell laminates. The damage model is formulated using a combination of stress based, continuum damage mechanics and fracture mechanics approaches within a unified procedure by using a smeared cracking formulation. The damage model was implemented in ABAQUS as a user defined material for shell elements and the damage model was validated with experimental results from previously available studies. In total five failure criterions were used in the study namely, tensile and compression fiber failure, tensile and compression matrix cracking and in-plane shear failure modes defined as:

Tensile fiber failure $\quad \dfrac{\sigma_{11}}{X_t} \geq 1$

Compression fiber failure $\quad \dfrac{|\sigma_{11}|}{X_c} \geq 1$

Tensile matrix cracking $\quad \dfrac{\sigma_{22}}{Y_t} \geq 1$

Compression matrix cracking $\quad \dfrac{|\sigma_{22}|}{Y_c} \geq 1$

In-plane shear failure $\quad \dfrac{|\tau_{12}|}{S_{12}} \geq 1$

Based on these failure criterions, damage evolution laws were developed for fiber breakage and matrix cracking. They studied the effects of three parameters namely the presence of pressure loading, the laminate thickness and curvature. The main contribution of the paper is the development of damage models and the verification. The numerical results indicated that thickness, curvature and pressure significantly affect the damage extent on pressurized composite laminates under impact loading. This becomes more visible for plates, which shows a greater susceptibility to the pressure effects. The damage extent under impact loading decreases when combined with internal pressure effects. The results indicated that larger the plate curvature higher is the amount of dissipated energy during the impact loading. Moreover, the amount of dissipated energy decreases as the plate thickness increases.

Her et al. [23] studied the effects of low velocity impacts on shell structures using ANSYS/LS-DYNA as well as the effect on the composite laminates. The effects of parameters like shell curvature, type of support boundary conditions and impactor velocity were analyzed. The results show that the structures which have smaller curvature and clamped boundary condition result in a larger contact force and less deflection. In the study by Her et al., the focus was on the evaluation of transient response of the impact on composite laminates, cylindrical and spherical shells.

Krishnamurthy et al. [36] discussed the impact response and the damage of laminated composite shells by a metallic impactor using Finite Element Method. The important parameters that formed the basis of study were impactor mass and velocity, shell curvature and stacking sequence. Also, studied was the effect of presence of initial stress.

The paper by Pinnoji and Mahajan [56] presents a numerical study on the impact resistance of composite shells laminates using energy based failure model. The damage model formulation is based on a methodology that combines stress based, continuum damage mechanics (CDM) and fracture mechanics approaches. The damage model has been implemented as a user defined material model in ABAQUS FE code within shell elements. [56]

Krishnamurthy et al. [34] studied the impact response using the classical Fourier series and the FEM. Impact response determined by the finite element method also includes a prediction of the impact-induced damage deploying the semi-empirical damage prediction model of Choi-Chang. A parametric study was carried out by the finite element method to determine the effect of varying the controlling parameters such as impactor mass, its approach velocity, curvature of the shell, on both the impact response and on the impact-induced damage. A reduction of the stiffnesses of the failed laminas on the impact response concurrently as the solution proceeded has also been incorporated.

The study by Zhao et al. focuses on the impact-induced damage initiation and propagation for laminated composite shells under low velocity impacts. The damage analysis is performed by using Tsai-Wu quadratic failure criterion, Tsai's damage modes and additional delamination formula at all Gaussian points. The damage modes considered are matrix cracking, fiber breakage and delamination. The progressive failure is expressed by reducing stiffness of the material at all failed Gaussian points. The analyses of the flat and curved laminates are compared for discussing their different damage mechanism. In addition, the influence of the stacking sequence, the thickness and the radius of curvature on damage behavior of composite shells is studied [73].

Sensitivity Analysis

Sensitivity analysis is a tool employed in engineering problems to identify the influence of input parameters on the state variables such as displacements, stresses, strains and temperature etc. The result of sensitivity analysis is the identification of a limited set of state or input variables that have greater influence on the output of the system. The main aim of the sensitivity analysis is the calculation of the sensitivity coefficients [54] which is obtained by the variation of input variables one at a time or in groups and study the variation in the output variable [57].

The sensitivity coefficient is computed by partially differentiating the state function; defining the output; with respect to the input parameters. These derivatives may be computed numerically using the basic equations defining the system output or may be calculated analytically if a closed form solution exists. This sensitivity coefficient may be calculated using analytical functions, also some combined numerical and analytical methods for calculation are available in the literature [19]. The computation of sensitivity coefficients is suggested to be normalized so that a direct comparison of all the input variables may be deduced. The actual benefit of normalized sensitivity coefficient (NSC) is that it provides an information about the order of magnitude of variation in the output variable with the change of one order of magnitude in the input variables [47].

The methodology of using sensitivity analysis is a common practice in for almost all types of numerical techniques [31]; Boundary Element Method (BEM) [33], Finite Difference Method (FDM) [33], Finite Element Method (FEM) [9] as well as hybrid and meshless strategies [15,41]. This technique provides a very helpful tool in narrowing down the complex variables involved in the design of composite structures.

Finite Element Methods are one of the best developed numerical tools for the structural analysis and the use of sensitivity analysis along with FEM has been quite common. In a study from 1993, Noor and Shah [54] used the technique to estimate the sensitivity coefficients of unidirectional fiber-reinforced composites for the effective thermal and thermoelastic properties.

The sensitivity analysis approach is successfully used in a wide range of applications. Bilal et al. [57] used the approach to identify important model parameters in their study of evaporative coolers and condensers. They use the normalized sensitivity coefficients to study the effects of input variables that have the most influence on the response variables of the condensers and cooler systems. The method used to calculate the normalized sensitivity coefficient in this study is based upon the formulation presented by Bilal et al. in their paper, which will be discussed in detail later on.

Artificial Neural Networks

Artificial Neural Networks (ANN) models are a very powerful method since they may be applied to any generic problem with few inputs and may be trained to learn from them with the expected outputs. These networks mimic the behavior of the neurons inside a human brain and it is argued that even at 0.1% of its performance, it is still an extraordinary processing system [29]. ANN models proved to be excellent tool in the approximation and interpolation in a variety of applications [10,11,21,28,39,42,44-46,55,67,70]. ANN has been used in function fitting and prediction of various mechanical properties and damage mechanisms in composite materials. ANN models are very efficient for modeling and predicting the non-linear behavior of different systems.

El Kadi [29] has presented a comprehensive review of the neural networks and the different approaches within them. ANNs are generally composed of a number of neurons spread over few layers that are interconnected. These models are trained against some target data and response set and the model are trained such that it is able to predict the output to a certain range of the training set. The progress is measured against either the mean-square error (MSE), root-mean-square error (RMSE), or normal-mean-square error (NMSE) between the observed output and the target output. The applications of ANN are in the manufacturing process optimization as well as in the monitoring and modeling the manufacturing and the mechanical behavior of fiber-reinforced composites. El Kadi has presented a brief review of all the applications of ANN in the field of fiber reinforced polymeric composites.

Bezerra et al. [11] used ANN to predict the shear stress-strain behavior of carbon/epoxy and glass/epoxy fabric composites. The authors used the multi-layered neural network model and demonstrated that about 80% of standard error of prediction was ≥0.9. In their study, they considered the stress as a function of the orientation angle by layers, specimen of fiber and the shear strain, while certain other factors like porosity, number of layers, matrix type and volumetric fraction of fibers were not studied.

Vassilopoulos et al. [67] used ANN to model the fatigue life of multidirectional GFRP composite laminates. The benefit that ANN provided the authors was the approach saved around 50% experimental effort for the whole analysis as compared to conventional methods and that too without the loss of considerable accuracy. It is mentioned that the artificial neural networks are effective tools to model fatigue life of composite materials and also to build the constant life diagrams. The authors have used the error back propagation (EBP) algorithm for the training of the neural network. The neural network used was a multilayer feed forward network having four inputs namely θ (off axis angle), R (stress ratio), $\sigma_{max}$ (maximum stress), and $\sigma_a$ (stress amplitude).

Jiang et al [28] applied the ANN model to predict the mechanical and wear properties of the short fiber reinforced polyamide composites. The polyamide composites were reinforced by short carbon and glass fibers and then optimization of the neural networks was performed. The neural network was used to predict the mechanical and wear properties as a function of the content of fibers and testing conditions. In this study, the authors have also used the back propagation neural network algorithm.

Design of Experiments

Design of experiments, or experimental design, is the design of all information-gathering exercises where variation is present, whether under the full control of the experimenter or not. The purpose of it is to study the effect of some processes or intervention on some objects. Design of experiment is a discipline which has broad applications across all the natural and social sciences. A methodology for designing experiments was proposed by Ronald A. Fisher, in his innovative book The Design of Experiments (1935).

Design of experiments is a very efficient statistical technique which may be employed in various experimental investigations [3]. The design of experiments provides the capability to understand the design effects of various factors and their statistical significance as well [50]. The design of experiments is useful at the stage of data collection as it provides a systematic and rigorous approach which generates valid, defensible and supportable data sets.

Design Optimization and Algorithms

Optimization is an integral part of design and is very beneficial for the commercial production of structures. The ability design engineers possess using composite materials is the custom made properties tailored exactly according to the needs of the structures. But, the composite materials involve more design variables compared to conventional materials which make it difficult to optimize the design and achieve maximum performance. This difficulty induces the need to use optimization techniques in the design process of composite materials.

Almeida et al. [4] used genetic algorithms for the design optimization of the composite laminated structures. The authors have discussed the adaptation of the terminologies and developing codes to use them with GA. The technique is used to study multi-objective optimization of plates under transverse or in-plane loads. The objectives of the study were the weight and the cost or the deflection and weight.

Lee et al [38] have used evolutionary algorithms for the multilayered composite structure design optimization. The objective of their study was the optimization of the stacking sequence of the composite plates. The authors have shown that the optimal solutions have lower weight, higher stiffness and affordable costs compared to other cases. They also discussed the benefits of parallel optimization systems.

Swaroop et al [68] used the optimization techniques to optimize the ply angles and the internal geometry of the helicopter rotor blades made using composite materials. The authors studied the multi objective optimization of several conflicting objectives which included the stiffness parameters, blade mass and the distance between mass center and the aerodynamic center of the blades. They discussed the transformation of multi-objective optimization to a single optimization problem and then applying a Particle Swarm Optimization technique to find the optimal solution.

Suresh et al. [64] also used the Particle Swarm Optimization for multi objective optimization of the design of box beam made of composite materials. The optimal solution was used to design a helicopter rotor blade. The ply angles and the cross-sectional area are considered the design parameters needed to optimize.

Numerical Model

Initially, a numerical model of a flat plate was developed in ABAQUS Explicit environment and used to verify against the available results from the literature. The inventor chose the model from the study of Yokoyama et al [72], the study by Yokoyama et al. was based upon experimental and numerical results. The experimental results were based upon the thesis of Biase EHC., and the same model was developed in the ABAQUS to verify the model.

The numerical model was based on the same assumptions and material models as the one for the composite flat plates. The results were validated for the filament wound composite pipes against the experimental results available in the thesis by Mohammed Khaliq Naik [52]. The study by Naik was experimental and performed in the Advanced Material Science Lab at King Fahd University of Petroleum and Minerals, and hence will be better correlated.

In the following sections, the basic parameters and characteristics of the numerical model for both the flat plates and pipes will be discussed simultaneously.

Idealizations and Assumptions

The plate and the pipe are assumed to be a 2-D shell with the layers defined in the composite section, while the impactor was considered as a 3-D rigid element with a reference point (pilot node) defined at the tip of the impactor. The initial velocity was given to the reference point of the impactor just before the impact as it is assumed to be under a free fall motion from a certain height achieving the velocity due to gravitational acceleration.

The contact is assumed to be frictionless without loss of much accuracy. It is assumed that the kinetic energy of the impactor just before the event of impact begins will be transferred to the specimen as the impact energy and this will be transferred to the subject in the form of internal energy, the amount of increase in the internal energy should be equal to the amount of decrease in the kinetic energy of the impactor as it bounces back. The amount of damage caused to the specimen as a result of impact will be evident from the amount of energy absorbed by the plate or the pipe. This energy absorbed will describe the damage to the composite specimen.

Geometric Model

In this research work, the impact performances of both composite plates and pipes have been studied. The composite plate model is modeled as the study of Yokoyama et al. [72], while the composite pipes were modeled as the experimental setup of Naik [52].

Geometric Model for Composite Flat Plate

The geometric dimensions of the composite plate and the impactor and also the stacking sequence of the plate are defined as:

TABLE 1

Geometric Dimensions of the composite plate and impactor for model validation.

| Composite Plate | | Impactor | |
|---|---|---|---|
| Length | 102 mm | Diameter | 12.7 mm |
| Width | 152 mm | Mass | 1.5 kg |
| Thickness | 4.2 mm | Velocity | 6.0608 m/s |

For the case of model validation, the laminate is consisted of 20 layers of equal thickness of 0.21 mm having the stacking sequence of $[(\pm 45)/(0,90)/(\pm 45)/(0,90)/(\pm 45)]_{2s}$. Initially, a full model was developed for the model validation purposes, which was then reduced to quarter symmetry to save the computational efforts. The results were not much affected with the quarter symmetry.

Figure 3A:
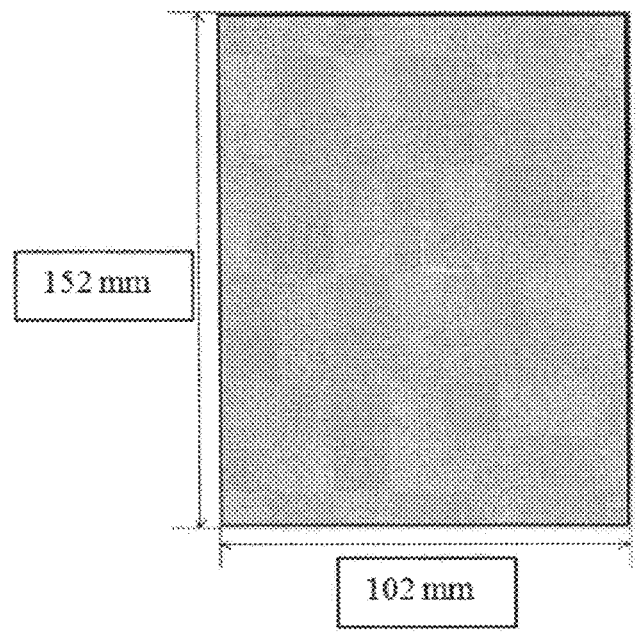
FIG. 3A illustrates a schematic drawing showing the geometric dimensions of the composite plate.
Figure 3B:
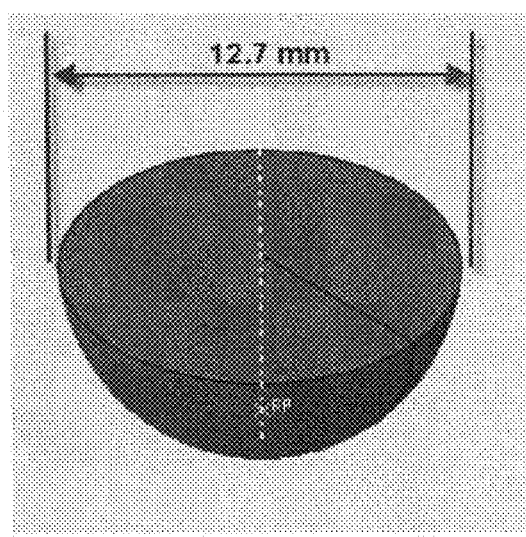
FIG. 3B illustrates a schematic drawing of a nose tip of an impactor.

FIG. 3A illustrates a schematic drawing showing the geometric dimensions of the composite plate. FIG. 3B illustrates a schematic drawing of a nose tip of an impactor. As illustrated in FIG. 3B, only the nose tip of the impactor is modeled due to the reason that the impactor is assumed to be a rigid material and the study was not interested in the stress distribution in the impactor. Therefore, it is appropriate to model only the nose tip of the impactor which comes into contact with the specimen and avoid the added complexity of the whole impactor geometry. The nose of the impactor has the dimensions as prescribed in the ASTM D2444 standards.

Figure 4:
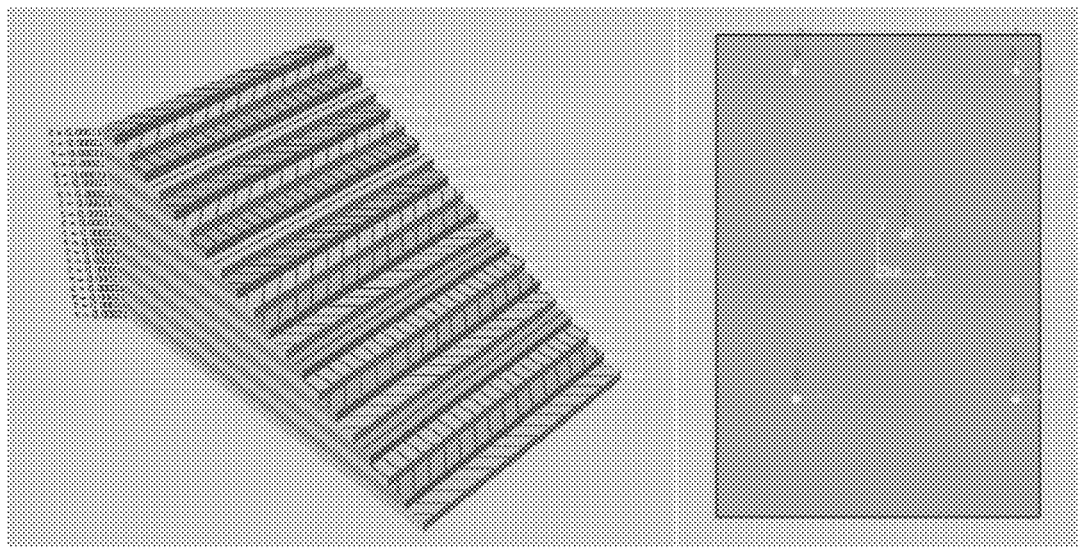
FIG. 4 illustrates a layup plot and material orientation of the composite plate.

FIG. 4 illustrates a layup plot and material orientation of the composite plate. The layers are defined as symmetric about the middle plane, and hence only the half number of layers are defined and using the option in ABAQUS of symmetric plies. The layers are defined such that the primary direction of fibers is coincident with the global x-axis, these layers and the orientation may be visualized as represented in FIG. 4.

Geometric Model for Composite Pipes

The dimensions of the composite pipes were selected so that it may be validated with the experimental results from the thesis of Mohammed Khaliq Naik [52]. These experiments and the thesis study were carried out in the King Fahd University of Petroleum and Minerals and hence have a better correlation with the future experimental works if performed. Also, the dimensions are dictated by the ASTM Standards ASTM D2444.

According to the ASTM D2444 standards, the pipe length should be at least equal to the nominal outside diameter but not less than 6 in. (152 mm) [48]. Since, the diameter of the pipe in this case is 150 mm; the length of the pipe is taken as twice the diameter as suggested.

Figure 5A:
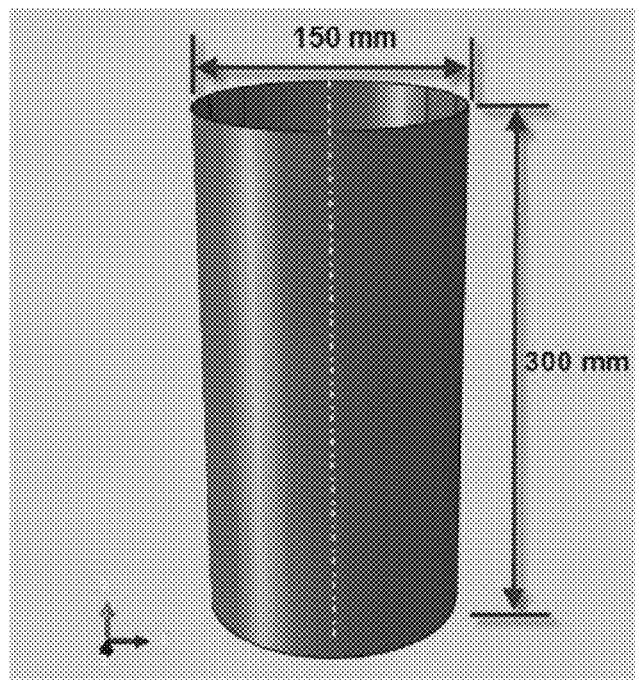
FIG. 5A illustrates a schematic drawing showing the geometric dimensions of a composite pipe.
Figure 5B:
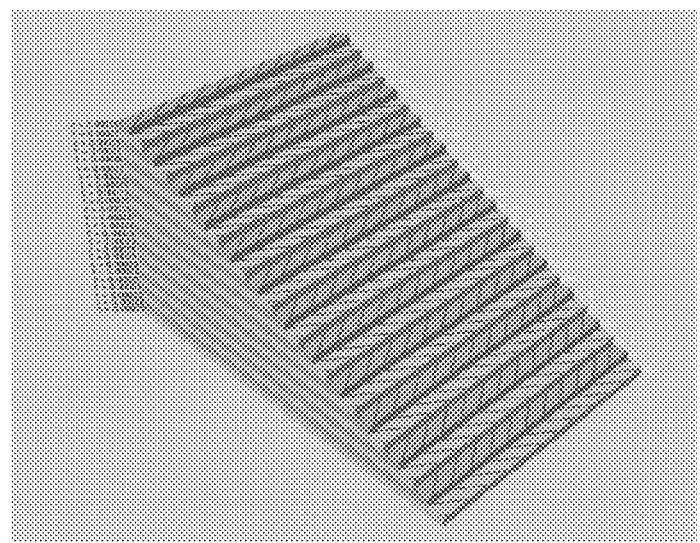
FIG. 5B illustrates a layup plot and material orientation of a composite pipe.

FIG. 5A illustrates a schematic drawing showing the geometric dimensions of a composite pipe. FIG. 5B illustrates a layup plot and material orientation of a composite pipe.

TABLE 2

Geometric Dimensions of the Composite Pipe and the Impactor for the Model Validation.

| Composite Pipe | | Impactor | |
|---|---|---|---|
| Length | 300 mm | Diameter | 12.7 mm |
| Internal Diameter | 150 mm | Mass | 10 kg |
| Thickness | 6 mm | Velocity | 2.8284 m/s |

The specimen is considered to be manufactured using filament winding technology, which generally winds fiber around a sand mandrel at a specific angle. Since, the process of winding goes from end to end on the mandrel, the winding angle varies from +θ to −θ. This kind of layers are defined in ABAQUS using the composite section without the usage of symmetric layers option as there is no mid-plane about which the layers are symmetric.

For the case of model validation, the winding angle is kept at 55° as reported in the work of Naik. The winding angle of 55° is a preferred choice of winding angle among the industry as it is known to have good performance against both the axial loading and internal pressure [8]. The number of layers is assumed to be 24 with each layer having thickness of 0.25 mm, as this is the popular layer thickness from available literature and the supplier's information in the market.

Material Modeling

Composite materials as explained in the introduction are anisotropic material having different material properties in different directions. For a layered composite, it is considered to be orthotropic with material properties in the fiber direction higher than the material properties in the two transverse directions. Most commonly, the material properties in the two transverse directions are considered to be equal, this kind of material is considered to be transversely isotropic material. The material used in the study is either carbon fiber impregnated with epoxy resin or glass fiber. Generally, flat plates are constructed using woven fabrics and the pipes are manufactured using the filament winding technology. The material properties and behavior is therefore, different as the woven fabric is usually available in the form of cross-ply woven form which makes it different from the layers from filament winding which is essentially a unidirectional construction.

Hooke's law for transversely isotropic materials defines five independent elastic constants, which are the Young's modulus and Poisson's ratio in the y-z symmetry plane, Young's modulus and Poisson's ratio in the perpendicular direction and the shear modulus in the perpendicular direction. The compliance matrix is given as the Eq. (3.1):

$$\begin{bmatrix} \varepsilon_{xx} \\ \varepsilon_{yy} \\ \varepsilon_{zz} \\ \varepsilon_{yz} \\ \varepsilon_{zx} \\ \varepsilon_{xy} \end{bmatrix} = \begin{bmatrix} \frac{1}{E_x} & -\frac{v_{yx}}{E_y} & -\frac{v_{yx}}{E_y} & 0 & 0 & 0 \\ -\frac{v_{yx}}{E_x} & \frac{1}{E_y} & -\frac{v_{zy}}{E_y} & 0 & 0 & 0 \\ -\frac{v_{xy}}{E_x} & -\frac{v_{yz}}{E_y} & \frac{1}{E_y} & 0 & 0 & 0 \\ 0 & 0 & 0 & \frac{1}{2G_{yz}} & 0 & 0 \\ 0 & 0 & 0 & 0 & \frac{1}{2G_{xy}} & 0 \\ 0 & 0 & 0 & 0 & 0 & \frac{1}{2G_{xy}} \end{bmatrix} \begin{bmatrix} \sigma_{xx} \\ \sigma_{yy} \\ \sigma_{zz} \\ \sigma_{yz} \\ \sigma_{zx} \\ \sigma_{xy} \end{bmatrix} \quad (3.1)$$

An y-z plane was considered the plane of symmetry, Ey=Ez, vxy=vxz, and vyx=vzx. The symmetry of the stress and strain tensors dictates that:

$$\frac{v_{xy}}{E_x} = \frac{v_{yx}}{E_y}, v_{yz} = v_{zy} \quad (3.2)$$

However, both woven fabric and uni-directional laminates are considered transversely isotropic, a special subcategory of orthotropic materials and following are the damage initiation models and the damage evolution models for these materials.

Damage Initiation Modeling

Since the impact of the striker will cause damage, a damage model is needed in order to describe when this damage begins and also once the damage initiates how it will progress. In this study, the damage initiation model as proposed by Hashin (1980) was used. The model as proposed by Hashin considers damage initiation in four different modes, namely, Tensile Matrix Mode:

$$\frac{1}{Y_t^2}(\sigma_{22}+\sigma_{33})^2 + \frac{1}{S_{23}^2}(\sigma_{23}^2 - \sigma_{22}\sigma_{33}) + \frac{1}{S_{12}^2}(\sigma_{12}^2 + \sigma_{31}^2) \leq 1 \quad (3.3)$$

Compressive Matrix Mode:

$$\frac{1}{Y_c}\left[\left(\frac{Y_c}{2S_{23}}\right)^2 - 1\right](\sigma_{22}+\sigma_{33}) + \frac{1}{4S_{23}^2}(\sigma_{22}+\sigma_{33})^2 + \\ \frac{1}{S_{23}^2}(\sigma_{23}^2 - \sigma_{22}\sigma_{33}) + \frac{1}{S_{12}^2}(\sigma_{12}^2 + \sigma_{31}^2) \leq 1 \quad (3.4)$$

Tensile Fiber Mode:

$$\left(\frac{\sigma_{11}}{X_t}\right)^2 + \frac{1}{S_{12}^2}(\sigma_{12}^2 + \sigma_{31}^2) \leq 1 \quad (3.5)$$

Compressive Fiber Mode:

$$\left(\frac{\sigma_{11}}{X_t}\right)^2 \leq 1 \quad (3.6)$$

Where Yt, Yc, Xt, Xc represents the longitudinal tensile and compressive and transverse tensile and compressive strengths respectively while $S_{12}$ and $S_{23}$ represents the longitudinal and transverse shear strength.

Damage Evolution Model

Damage initiation is the event at which the initial damage is caused in the laminate but once it is initiated this damage will progressively spread with further impact force. This is known as the damage evolution and this will cause the strength of the composite laminate to deteriorate and hence the resulting product will be weaker compared to earlier before impact.

A simple energy based linear softening model is used as the damage evolution model. Energy damage evolution defines damage in terms of the energy required for failure (fracture energy) after the initiation of damage. Linear softening specifies a linear softening stress-strain response for linear elastic materials or a linear evolution of the damage variable with deformation for elastic-plastic materials.

For the damage initiation in plane stress fiber reinforced composites, the damage evolution law is available in ABAQUS; it assumes that before damage initiation the material was linearly elastic, with the stiffness matrix of a plane stress orthotropic material. After, the response of the material is computed from:

$$\sigma = C_d \epsilon \quad (3.7)$$

Where ϵ is the strain and Cd is the damaged elasticity matrix, given as:

$$C_d = \frac{1}{D} \begin{bmatrix} (1-d_f)E_1 & (1-d_f)(1-d_m)v_{21}E_1 & 0 \\ (1-d_f)(1-d_m)v_{21}E_1 & (1-d_m)E_2 & 0 \\ 0 & 0 & (1-d_s)GD \end{bmatrix} \quad (3.8)$$

Where $D=1-(1-d_f)(1-d_m)v_{12}v_{21}$, $d_f$ gives the current state of fiber damage, gives the current state of matrix damage and $d_s$ gives the current state of shear damage. The damage variables $d_f$, $d_m$ and $d_s$, are derived from damage variables $d^t_f$, $d^c_f$, $d^t_m$, and $d^c_m$ corresponding to the four failure modes described for Hashin model.

$$d_f = \begin{cases} d^t_f & \text{if } \sigma_{11} \geq 0, \\ d^c_f & \text{if } \sigma_{11} < 0, \end{cases} \quad (3.9)$$

$$d_m = \begin{cases} d^t_m & \text{if } \sigma_{22} \geq 0, \\ d^c_m & \text{if } \sigma_{22} < 0, \end{cases}$$

$$d_s = 1 - (1-d^t_f)(1-d^c_f)(1-d^t_m)(1-d^c_m)$$

Figure 6:
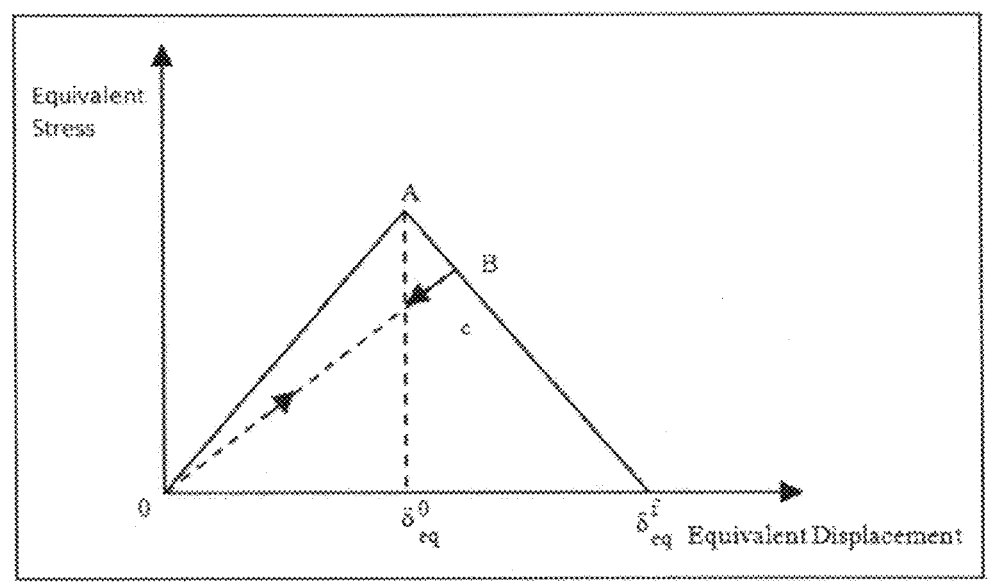
FIG. 6 illustrates a graph of linear damage evolution.

FIG. 6 illustrates a graph that charts linear damage evolution.

Where $G^t_f$, $G^c_f$, $G^t_m$, $G^c_m$ and $G_s$ are the energies dissipated during damage for fiber tension, fiber compression, matrix tension, matrix compression and in-plane shear damage modes respectively. The built-in damage evolution model in ABAQUS doesn't support the in-plane shear damage.

Material Model for Composite Plates

The composite plates are manufactured using the woven fabric of carbon fiber or glass fiber impregnated with epoxy resin. The elastic material properties for the plates are listed in Table 3 for Carbon/Epoxy system and in Table 4 for the Glass/Epoxy system.

The material properties used for the Carbon/Epoxy composite system is taken from the study of Yokoyama et al. [72] and is also used for the validation purposes. These values are quite close to the values cited in other literatures e.g. in the study by Pinnoji et al. [56], but as stated in the study by Yokoyama et al. the values are calculated experimentally. One of the points to note here is that the elastic modulus in the z-direction demonstrated by subscript 3 is missing, but this value has no consequence as the laminate material properties that affect the overall solution are the in-plane properties and the material properties that ABAQUS requires are the laminate properties which does not include $E_3$. Also, generally this modulus is considerably lower than the moduli in the other two directions for the case of woven fabric composites.

TABLE 3

Mechanical elastic properties for orthotropic layer of Carbon/Epoxy woven fabric used in composite plate modeling [72].

| $E_1$ (GPa) | $E_2$ (GPa) | $E_3$ (GPa) | $G_{12}$ (GPa) | $G_{13}$ (GPa) | $G_{23}$ (GPa) | $v_{12}$ | $v_{13}$ | $v_{23}$ |
|---|---|---|---|---|---|---|---|---|
| 60.8 | 58.25 | — | 4.55 | 4.55 | 5 | 0.07 | 0.07 | 0.4 |

The material properties for the Glass/Epoxy system are selected from the study of Menna et al. [49].

TABLE 4

Mechanical elastic properties for orthotropic layer of Glass/Epoxy woven fabric used in composite plate modeling [49].

| $E_1$ (GPa) | $E_2$ (GPa) | $E_3$ (GPa) | $G_{12}$ (GPa) | $G_{13}$ (GPa) | $G_{23}$ (GPa) | $v_{12}$ | $v_{13}$ | $v_{23}$ |
|---|---|---|---|---|---|---|---|---|
| 26 | 26 | 8 | 3.8 | 2.8 | 2.8 | 0.1 | 0.25 | 0.25 |

The damage initiation as described here is defined in terms of the stress values compared to the strength of the lamina in a particular direction under a particular loading condition. The strength values for the Carbon/Epoxy are defined a Table 5 and for the Glass/Epoxy as Table 6.

TABLE 5

Strength of composite layer in various directions for Carbon/Epoxy.

| | $X_t$ (MPa) | $X_c$ (MPa) | $Y_t$ (MPa) | $Y_c$ (MPa) | $S_{12}$ (MPa) | $S_{23}$ (MPa) |
|---|---|---|---|---|---|---|
| Ply Strengths | 621 | 760 | 594 | 707 | 125 | 125 |

TABLE 6

Strength of composite layer in various directions for Glass/Epoxy.

| | $X_t$ (MPa) | $X_c$ (MPa) | $Y_t$ (MPa) | $Y_c$ (MPa) | $S_{12}$ (MPa) | $S_{23}$ (MPa) |
|---|---|---|---|---|---|---|
| Ply Strengths | 414 | 458 | 414 | 458 | 105 | 65 |

The amount of damage due to the impact loads depend upon how the damage propagates through the sample. The damage is said to initiate when the critical strength limits were crossed and as more energy was applied by the impactor the damage progressed through the sample. The amount of energy released or the amount of energy required to propagate the damage in the composite plate depends upon the intralaminar fracture energies given in Table 7 for the Carbon/Epoxy system.

TABLE 7

Energy value for the damage evolution for Carbon/Epoxy.

| | $G^t_f$ (KJ/m$^2$) | $G^c_f$ (KJ/m$^2$) | $G^t_m$ (KJ/m$^2$) | $G^c_m$ (KJ/m$^2$) | $G_s$ (KJ/m$^2$) |
|---|---|---|---|---|---|
| Intralaminar Fracture Toughness | 160 | 25 | 10 | 2.25 | 2.25 |

The fracture toughness is not available widely and if found most of the literature studies only the critical value of the fracture toughness that is the value at which the damage or the crack initiates. For this study, stress limit as the damage initiation and the use of energy release rates for modeling the propagation of damage was selected. The value for the energy release rate in the fiber direction during tension was selected from the study of [16]. The rest of the values though have less impact on the overall performance as will be shown in the later sections. Therefore, a simple ratio was adopted for the fracture energy in the fiber direction during compression and the matrix materials and is listed in Table 8.

TABLE 8

Energy value for the damage evolution for Glass/Epoxy.

| $G_f^t$ (KJ/m$^2$) | $G_f^c$ (KJ/m$^2$) | $G_m^t$ (KJ/m$^2$) | $G_m^c$ (KJ/m$^2$) | $G_s$ (KJ/m$^2$) |
|---|---|---|---|---|
| Intralaminar Fracture Toughness 10 | 1.562 | 0.625 | 0.14 | 0.14 |

Material Model for Composite Pipes

The composite pipes are manufactured using the filament winding technology. This process of manufacturing pipes means that the layers are considered unidirectional lamina and hence the material properties and the plane of symmetry are different than the woven fabric. The elastic material properties for the Carbon/Epoxy composite pipes are selected from the study of Yokoyama et al. [72] are listed in Table 9.

TABLE 9

Mechanical elastic properties for orthotropic layer of Carbon/Epoxy unidirectional lamina used in composite plate modeling [72].

| $E_1$ (GPa) | $E_2$ (GPa) | $E_3$ (GPa) | $G_{12}$ (GPa) | $G_{13}$ (GPa) | $G_{23}$ (GPa) | $v_{12}$ | $v_{13}$ | $v_{23}$ |
|---|---|---|---|---|---|---|---|---|
| 100 | 8.11 | 8.11 | 4.65 | 4.65 | 5 | 0.3 | 0.3 | 0.4 |

The elastic material properties for the Glass/Epoxy composite pipes are used from the study of Li et al. [41]. The model validation of the GFRP (Glass Fiber Reinforced Polymers) pipes was carried out with the experimental study of Naik [52], but the thesis was mainly experimental and all the material properties were not provided. Therefore, the material properties were calibrated and validated and it was found that the material properties given in the study of Li et al. [41] closely matched the results. These material properties are tabulated in Table 10.

TABLE 10

Mechanical elastic properties for orthotropic layer of Glass/Epoxy unidirectional lamina used in composite plate modeling [41].

| $E_1$ (GPa) | $E_2$ (GPa) | $E_3$ (GPa) | $G_{12}$ (GPa) | $G_{13}$ (GPa) | $G_{23}$ (GPa) | $v_{12}$ | $v_{13}$ | $v_{23}$ |
|---|---|---|---|---|---|---|---|---|
| 30.5 | 6.9 | 6.9 | 4.65 | 4.65 | 1.6 | 0.344 | 0.344 | 0.4 |

The strength properties of the Carbon/Epoxy lamina are given in Table 11 and the strength properties of the Glass/Epoxy lamina are given in Table 12.

TABLE 11

Strength of composite layer in various directions for Carbon/Epoxy.

| $X_t$ (MPa) | $X_c$ (MPa) | $Y_t$ (MPa) | $Y_c$ (MPa) | $S_{12}$ (MPa) | $S_{23}$ (MPa) |
|---|---|---|---|---|---|
| Ply Strengths 2000 | 1000 | 100 | 160 | 140 | 140 |

TABLE 12

Strength of composite layer in various directions for Glass/Epoxy.

| $X_t$ (MPa) | $X_c$ (MPa) | $Y_t$ (MPa) | $Y_c$ (MPa) | $S_{12}$ (MPa) | $S_{23}$ (MPa) |
|---|---|---|---|---|---|
| Ply Strengths 700 | 300 | 100 | 237 | 64 | 64 |

As it is described earlier, the damage propagation is modeled using the energy release rates. These values for the CFRP are listed in the study of Yokoyama et al. [72] and are listed in the Table 13. The intralaminar fracture toughness for the GFRP pipes are used from the study of Gershom and Marom [20].

TABLE 13

Energy value for the damage evolution for Carbon/Epoxy.

| $G_f^t$ (KJ/m$^2$) | $G_f^c$ (KJ/m$^2$) | $G_m^t$ (KJ/m$^2$) | $G_m^c$ (KJ/m$^2$) | $G_s$ (KJ/m$^2$) |
|---|---|---|---|---|
| Intralaminar Fracture Toughness 100 | 25 | 2 | 2 | 2 |

TABLE 14

Energy value for the damage evolution for Glass/Epoxy.

| $G_f^t$ (KJ/m$^2$) | $G_f^c$ (KJ/m$^2$) | $G_m^t$ (KJ/m$^2$) | $G_m^c$ (KJ/m$^2$) | $G_s$ (KJ/m$^2$) |
|---|---|---|---|---|
| Intralaminar Fracture Toughness 52.5 | 20 | 2 | 2 | 2 |

Loads and Boundary Conditions

This study is based on the damage caused due to the low-velocity impact loads. These loads are applied to the striker in the form of initial velocity, which has kinetic energy equivalent to the amount of impact energy intended to hit the specimen with. During experimentation, the impact energy is controlled by the height from which the striker is dropped. The striker achieves the desired impact energy by virtue of the potential energy transferred to the kinetic energy in the free fall.

Where, 'm' is the mass of the impactor, 'h' the drop height of the impactor and 'v' is the velocity of the impactor just before it hits the test specimen.

In ABAQUS, a reference point on the striker geometry is modeled and is given the mass and the velocity with which to impact the test specimen.

$$P.E. = mgh \qquad (3.10)$$

$$K.E. = \frac{1}{2}mv^2$$

Case for Flat Plates

The impact load of 27.55 J was applied in the initial step of the explicit dynamic analysis. This energy is provided to the striker of mass 1.5 kg with an initial velocity of 6.0608 m/s.

Figure 7A:
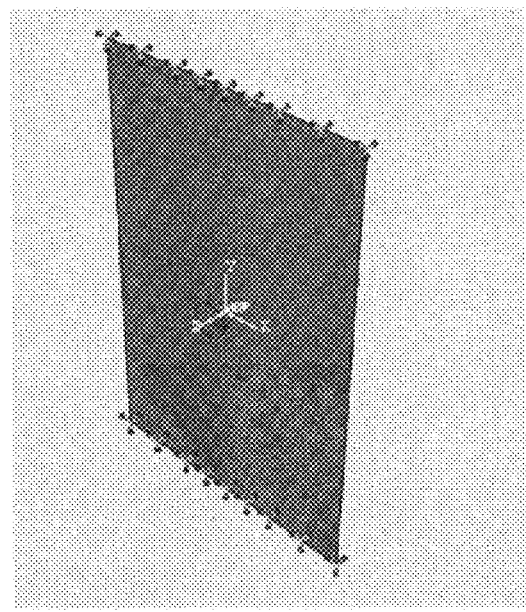
FIG. 7A illustrates boundary conditions on a full plate model.

FIG. 7A illustrates boundary conditions on a full plate model. The boundary conditions are such that the shorter edges of the plate were fully constrained while the longer edges were set to be free. The impact energy and the mass of the impactor and the boundary conditions are set according to the model from the study of Yokoyama et al. [72].

Figure 7B:
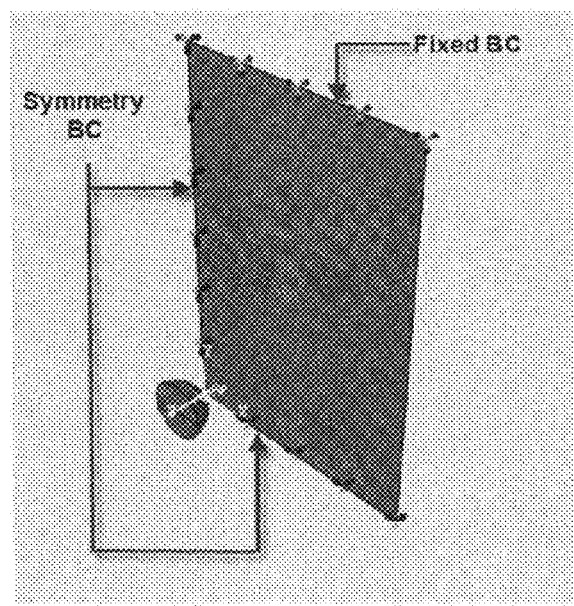
FIG. 7B illustrates boundary conditions on the quarter plate model.

The quarter plate symmetry model was developed to reduce the size of the problem, the loads were also reduced by ¼ which is achieved by dividing the mass of the impactor by 4 such that the mass will be 0.375 kg. To apply the symmetric boundary conditions, the two edges were constrained to move in the direction of the axis of symmetry, as illustrated in the FIG. 7B.

Case for Composite Pipes

The boundary conditions for the impact analysis of composite pipes are dictated by the standards provided in the ASTM D2444. It is mentioned in the standards that the pipe is supported with the help of a V-block. The design of V-block should be such that it should be equal to the length of the pipe and has a 90° included angle. The support in the numerical model is provided at approximately the patches of the pipe where the V-block is supposed to be in contact with the pipe. The results in the model validation proved that this simplification in the model was accurate.

Figure 7C:
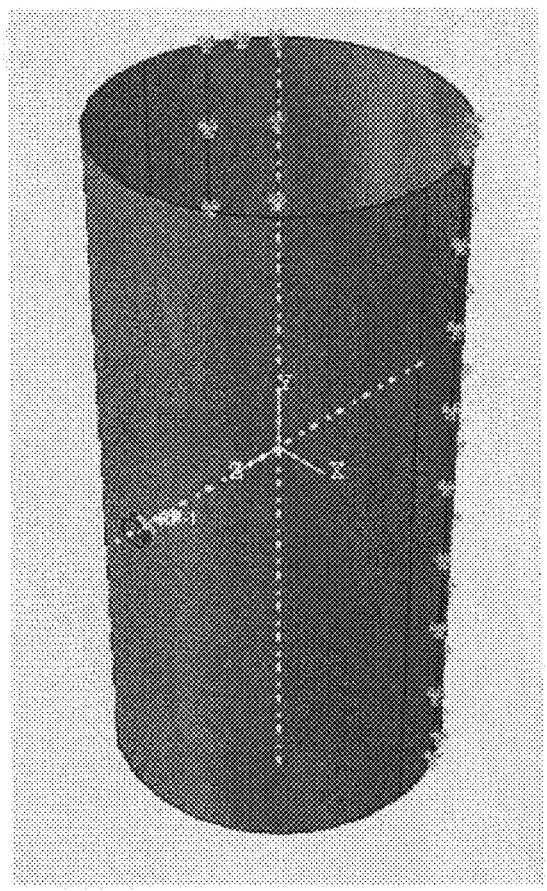
FIG. 7C illustrates boundary conditions on the composite pipe model.

FIG. 7C illustrates boundary conditions on the composite pipe model. The impact loads for the composite pipe are applied in the same way as for the plates' impact analysis. The initial velocity is provided to the striker which equates to 40 J of impact energy. The mass of the striker is selected as 10 kg and the velocity to achieve the impact energy of 40 J is 2.82843 m/s.

Element Type and Mesh

The composite plate and the pipe were modeled as the shell element, while the impactor was modeled as a rigid element. The element type S4R was used to mesh the composite plate and the pipes. The area near the impact point was more refinely meshed rather than the whole model. It is obvious that the areas away from the impact point had less influence on the numerical result. Hence, it was necessary to keep the mesh as coarse as possible in those regions so as to keep the number of nodes and elements to be solved to a minimum. This approach results in a high quality result with a much lesser amount of computational time spent.

Figure 8A:
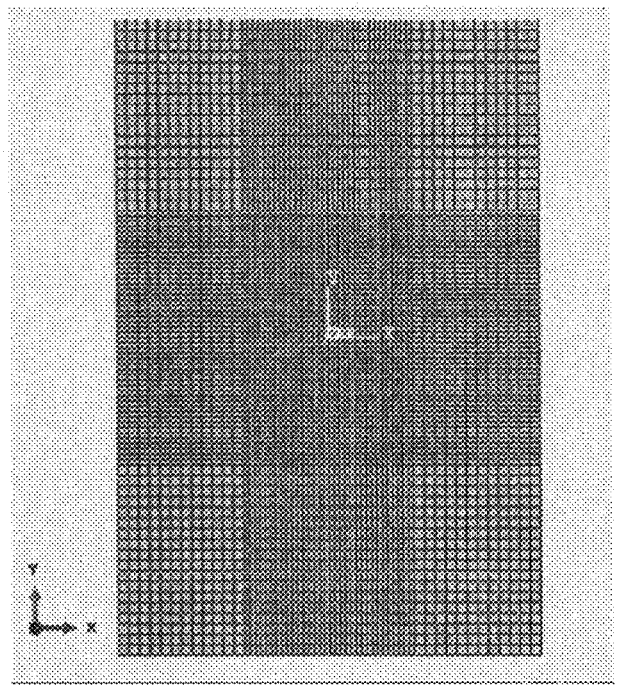
FIG. 8A illustrates a mesh configuration for the full composite plate model.
Figure 8B:
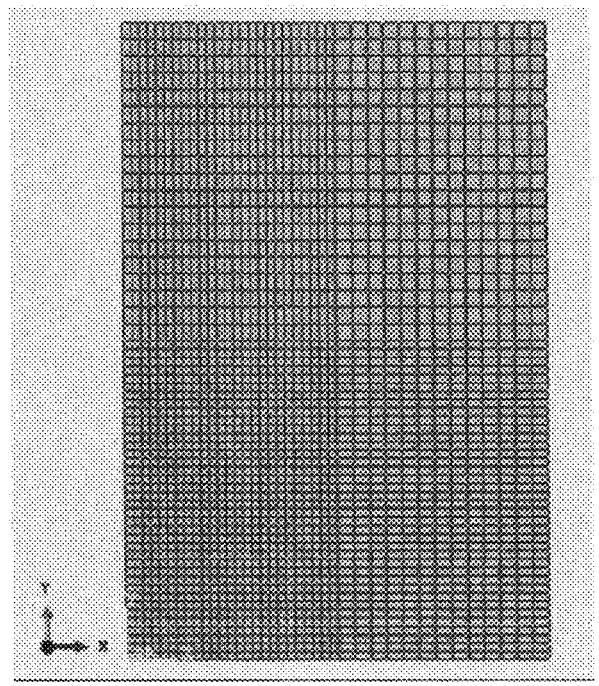
FIG. 8B illustrates a mesh configuration for the quarter plate model.
Figure 8C:
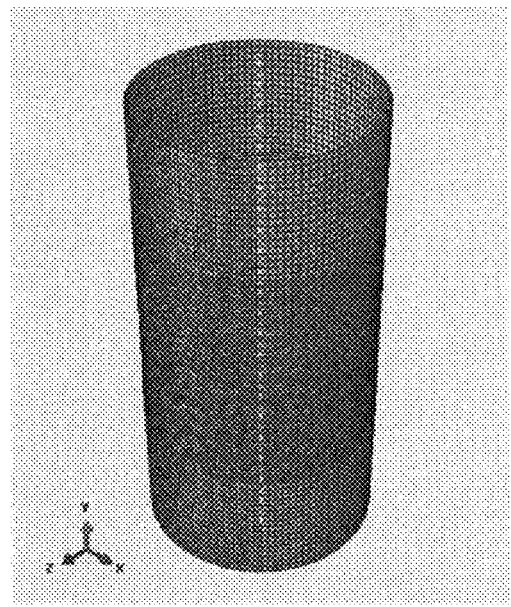
FIG. 8C illustrates a mesh configuration for the composite pipe model.

FIG. 8A illustrates a mesh configuration for the full composite plate model. FIG. 8B illustrates a mesh configuration for the quarter plate model. FIG. 8C illustrates a mesh configuration for the composite pipe model.

The mesh for the striker is not required as it is a rigid element and the study was not interested in the deformation and stress in the striker. A brief introduction about the element type used for the composite plate is discussed further.

Element Type—S4R

The thickness of the plate in this study is comparatively small than the length and the width of the plate. For such structures, shell elements are used. ABAQUS offers two types of shell elements, namely, conventional shell elements and the continuum shell elements.

S4R is a 4-node, quadrilateral, stress/displacement shell element with reduced integration and a large-strain formulation. This element is from the family of conventional shell elements and allows transverse shear deformation and uses thick shell theory as the shell thickness increases and become discrete Kirchhoff thin shell elements as the thickness decreases; the transverse shear deformation becomes very small as the shell thickness decreases.

This element type accounts for finite membrane strains and arbitrarily large rotations; therefore, they are suitable for large-strain analysis as in the case of impact analysis. Therefore, because finite strains and transverse shear deformation are expected, S4R element has been chosen for the simulation.

Model Validation and Sensitivity Analysis

Model validation is an important step of every numerical analysis. If the numerical model is able to predict the results from the similar model from other studies either numerical or experimental, it gives the confidence to use the model for the further analysis with the surety of results.

Model Validation of Composite Flat Plate

The model validation for the composite plates is carried out with the study by Yokoyama et al. [72]. The model geometry is described in Table 1, which is the same as the model used in the study of Yokoyama. In that study, Yokoyama et al. proposed a new damage initiation and evolution model to better predict the impact damage and the energy absorbed during the impact event. For this study, the study started with the built-in model for the damage initiation and the damage evolution as described earlier. It was found out that the results in this study are more closely matched from the results of the proposed model by Yokoyama et al. and also with the experimental results presented in their study.

Mesh Convergence

Mesh convergence is required to eliminate the numerical errors induced due to finite element method which approximates the whole domain in a finite number of smaller elements. The results for the mesh convergence are presented in the Table 15. The mesh was generated at two refinement levels, with a refined central region where the impactor strikes the composite plate. The composite plate is meshed using the mapped meshing technique. Initially a constant element edge length of 3 mm was used throughout the plate which resulted in the generation of 2400 elements with 2501 nodes, referred to as the refinement level 1 in the Table 15. The element edge length or edge seeds as better known in the ABAQUS environment were reduced to 2.5 mm for the refinement level 2.

At this point, the further reduction of element sizes would have resulted in a large number of elements costing computational time, a central region near the impact point was then refined further without reducing the edge lengths of the outer edges. In the first run, the central region edge length of elements was 1.25 mm and 2.5 mm for outer edges. The mesh at level 3 gave almost the double number of elements as previous level with only about 3% improvement in the dissipated energy and less than 1% of the maximum displacement. However, a further refinement was tried to make sure the convergence. Here to keep the mapped meshing, the outer element edges were reduced to seed size of 2 mm and central region to 1 mm.

TABLE 15

Mesh Convergence based on Maximum Displacement and Dissipated Energy.

| Refinement Level | Elements | Nodes | Dissipated Energy (J) | Maximum Displacement (mm) | % age Difference in Dissipated Energy | % age Difference in Displacement |
|---|---|---|---|---|---|---|
| 1 | 1700 | 1785 | 6.167 | 6.2060 | — | — |
| 2 | 2400 | 2501 | 5.0089 | 6.104 | 18.7 | 1.64 |
| 3 | 4704 | 4845 | 4.8674 | 6.062 | 2.82 | 0.688 |
| 4 | 7420 | 7597 | 4.7867 | 6.082 | 1.66 | 0.33 |

Figure 9:
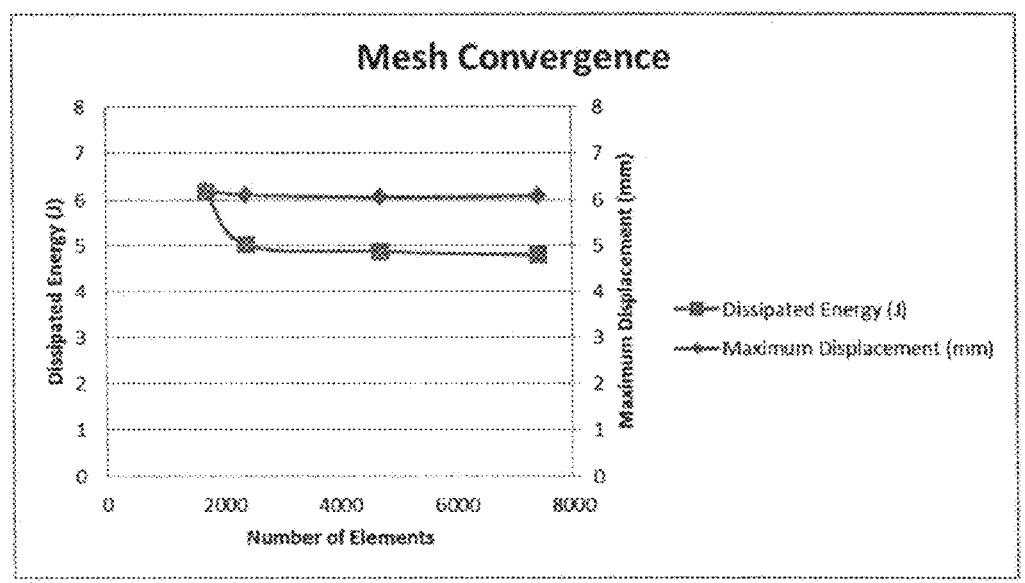
FIG. 9 illustrates mesh convergence for dissipated energy with respect to maximum displacement.

From the mesh convergence Table 15 and the related graph in FIG. 9, it is evident that the further refinement of mesh is not required and the mesh at the refinement level 3 is sufficient. However, the refinement level 4 was preferred once the model was reduced to ¼ of the original size using the quarter symmetry model.

Validated Results

The results reported in the study by Yokoyama et al. are used to validate the model. This study reveals a much closer result to the experimental values than the result from the proposed model. [72]

In Table 16 below, the results are shown for the experimental and numerical results from the previous studies for both the Hashin model and the model proposed by Yokoyama et al. and compared with the results from ABAQUS using the built-in Hashin model.

TABLE 16

Results from Yokoyama et al. and the comparison with the results.

| | Experimental (Biase) | Numerical (Yokoyama) | Numerical (Hashin Model) | Our Result | Error (% age) |
|---|---|---|---|---|---|
| Maximum Displacement (m) | 0.006018 | 0.00611 | 0.00592 | 0.006062 | 0.7% |
| Time of Impact Event (sec) | 0.0036 | 0.00354 | 0.00328 | 0.00338 | 3.05% |

Figure 10A:
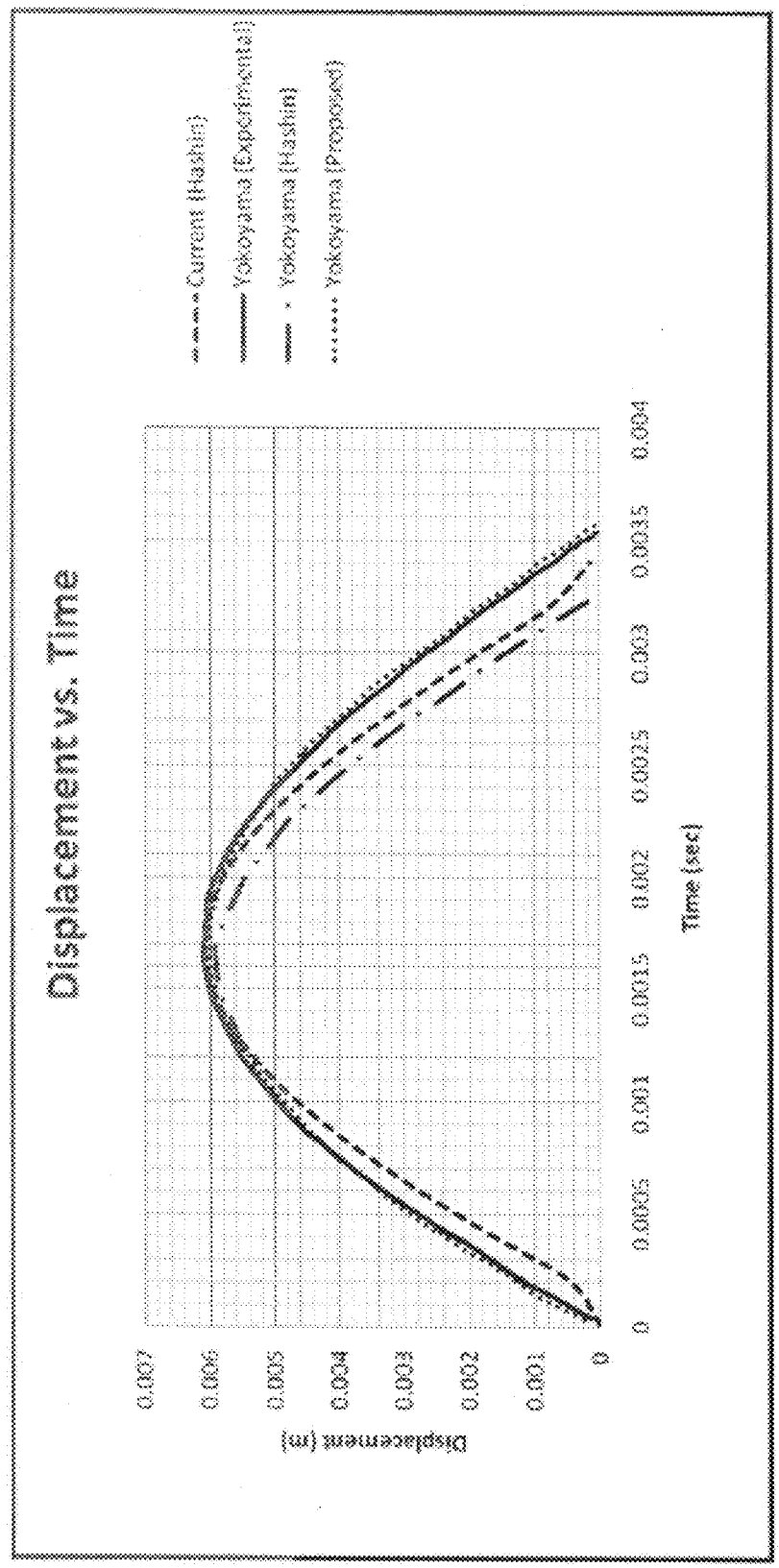
FIG. 10A illustrates maximum displacement for the composite plate with respect to time.
Figure 10B:
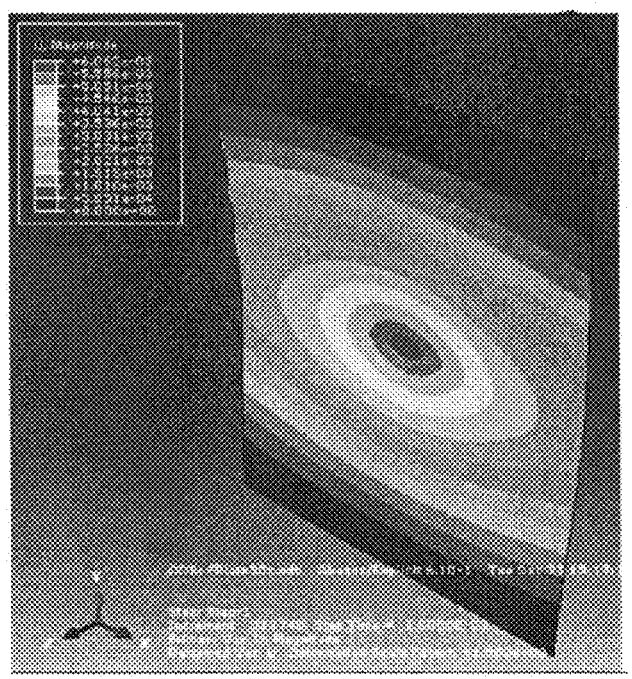
FIG. 10B illustrates a displacement contour at the instant of 1.6 msec at a kinetic energy level of zero.
Figure 11A:
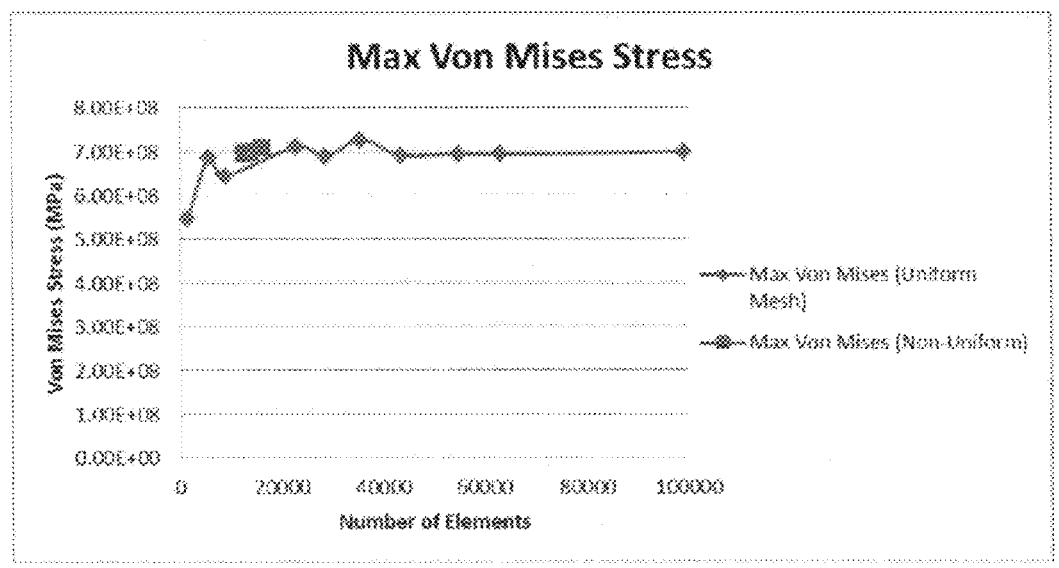
FIG. 11A illustrates mesh convergence with respect to maximum Von-Mises stress.
Figure 11B:
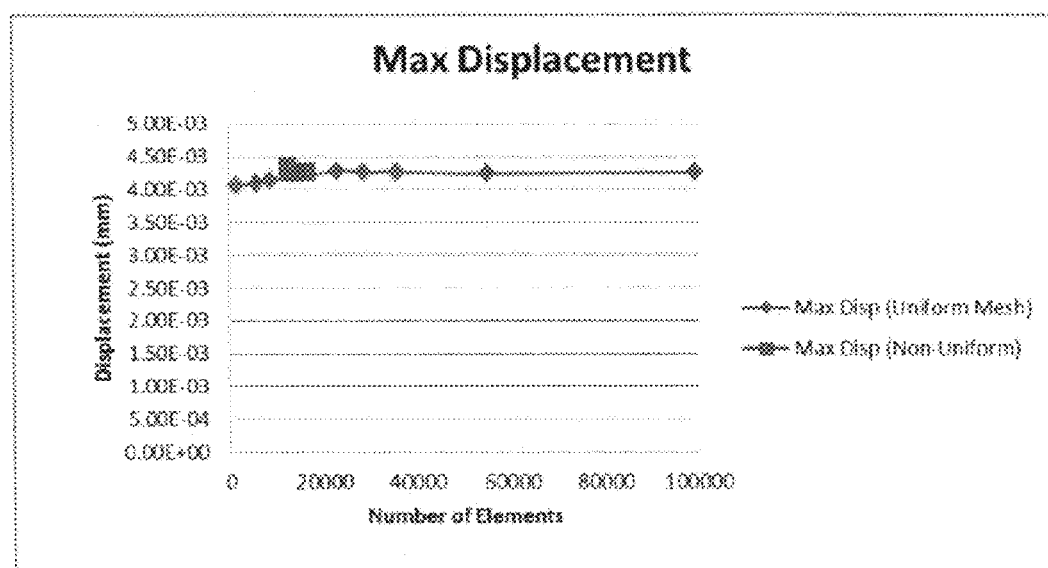
FIG. 11B illustrates mesh convergence with respect to maximum displacement.
Figure 11C:
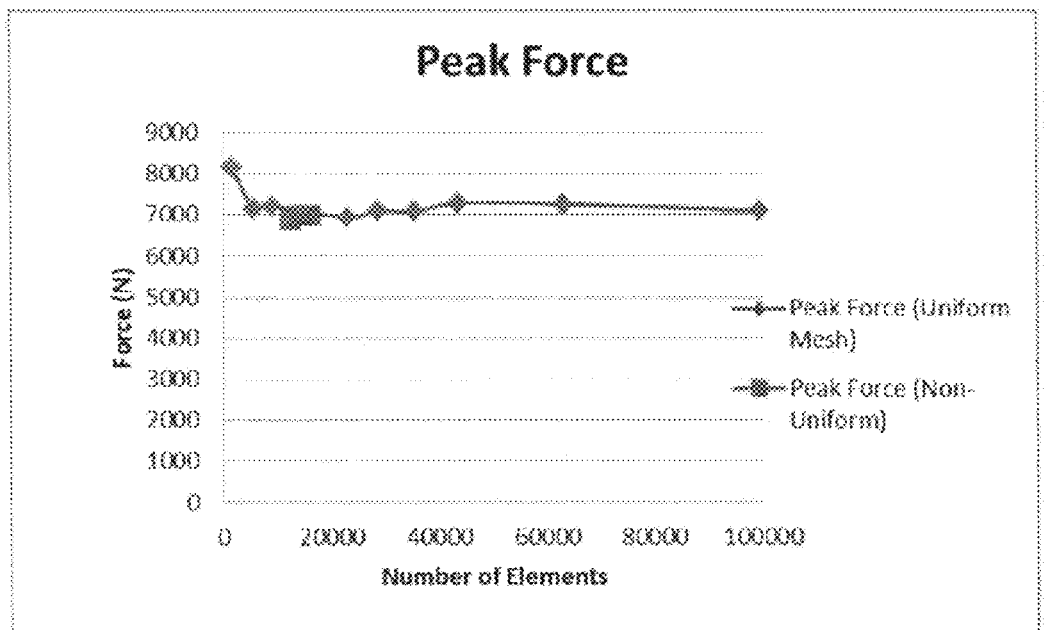
FIG. 11C illustrates mesh convergence with respect to maximum peak force.
Figure 11D:
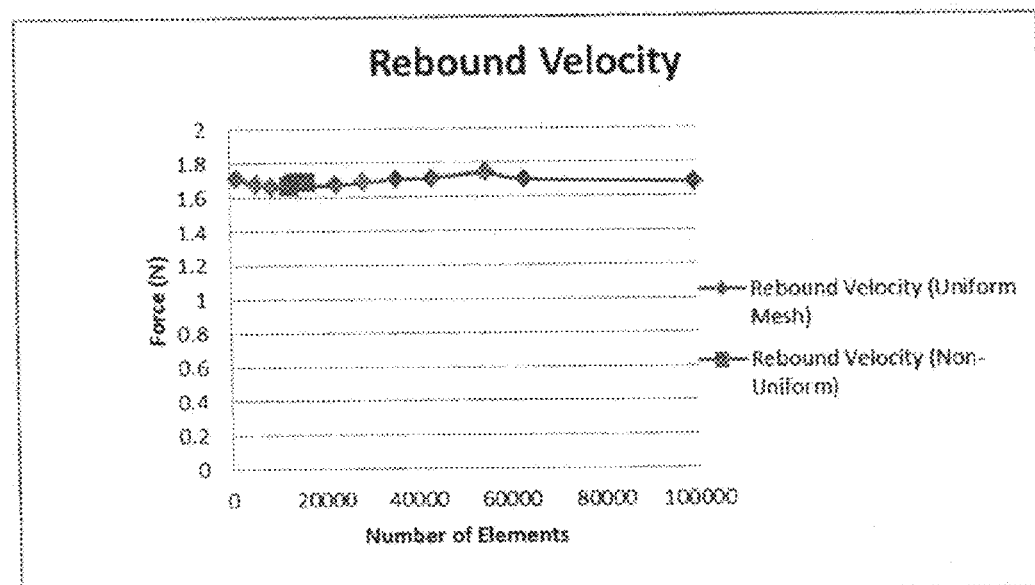
FIG. 11D illustrates mesh convergence with respect to rebound velocity of the impactor.

FIG. 10A illustrates maximum displacement for the composite plate with respect to time. FIG. 10B illustrates a displacement contour at the instant of 1.6 msec at a kinetic energy level of zero.

The results show that the maximum displacement occurs around 1.6 msec, after that the impactor bounced back with reduced velocity. This reduced velocity resulted in the loss of kinetic energy which was absorbed as internal energy in the composite plate. The kinetic energy of the impactor as it bounces back reduces to just around 22.7 J which is equal to the amount of energy absorbed in damaging the plate.

There was very little difference in the values of the full plate and the quarter plate model as it is listed in Table 17.

TABLE 17

Comparison of results between full and quarter model.

| | Full Model | Quarter Model | % age Difference |
|---|---|---|---|
| Number of Elements | 7420 | 2166 | 71% |
| Number of Nodes | 7597 | 2262 | 70% |
| Dissipated Energy (J) | 4.7867 | 4.743 3 | 0.91% |
| Maximum Displacement (mm) | 6.082 | 6.068 | 0.23% |
| Time of Impact Event (msec) | 3.38 | 3.32 | 1.78% |

Model Validation of Composite Pipe

The model validation of the composite pipe case was done using the experimental study conducted by Naik for his thesis work at Mechanical Engineering Department, King Fahd University of Petroleum and Minerals [52]. The geometry of the pipe and the impactor are already defined in Chapter 3 Table 2. The material elastic properties, the strength values and the fracture energies are listed in Tables 10, 12 and 14 respectively for the glass/epoxy system used in the study by Naik. The boundary conditions are considered as defined by the ASTM standards D2444.

In the study by Naik, they conducted the experiments at different energy levels for different pipe materials. This study selected the glass/epoxy composite pipes under the impact load of 20 J for the case of model validation. The geometric conditions and the loads are selected to be similar to the experimental setup. The experimental study by Naik presented the results in terms of peak force and therefore, this study based its validation parameter to be the peak force rather than the maximum displacement as was the case with flat plate's model validation.

Mesh Convergence

Mesh convergence is an important aspect of finite element analysis. It is necessary to refine the mesh to such a size that generates minimum amount of elements with a reasonable level of accuracy of results. For the composite pipes, the mesh convergence was carried out in two steps; initially a uniform mapped meshing was used throughout the pipe. This kind of meshing results in a very large number of elements costing a lot of computing time. To save the computing effort, a similar kind of approach was adopted as with the composite plates, that is, a finer mesh in the central region where the impactor strikes the pipe and a more coarse mesh outside. Initially, mesh convergence was carried out for a reduced number of layers in order to save computational time required to solve large number of integration points due to more layers. During the mesh convergence, the total numbers of layers were considered to be 8 with the winding angle of ±55°, each layer of 0.75 mm thickness.

For the uniform meshing, meshing was started with an element edge length of 10 mm and reducing it at each level where an element edge length was reduced to just 2.2 mm. At this mesh refinement, as may be observed from the graphs illustrated in FIGS. 11A-11D most of the values have reached the constant value and further mesh refinement was not necessary. From the Table 18, it may be noticed that at the seed level of 1.8 mm, there is a sudden jump in the maximum displacement but further mesh refinement resulted in the displacement value to go the earlier level of around 4.27 mm. Similarly, peak force also had one or two mesh levels where it increased suddenly but overall it is constant around 7000 N.

TABLE 18

Mesh Convergence with Uniform Mesh Technique.

| Seed | Elements | Nodes | Max Von Mises (MPa) | Max Disp (mm) | Peak Force (N) | Rebound Velocity (m/s) |
|---|---|---|---|---|---|---|
| 0.01 | 1536 | 1584 | 548 | 4.06 | 8163 | 1.70581 |
| 0.005 | 5700 | 5795 | 687 | 4.10 | 7157 | 1.67173 |
| 0.004 | 8816 | 8932 | 645 | 4.14 | 7229 | 1.65949 |
| 0.0025 | 23040 | 23232 | 710 | 4.28 | 6950 | 1.6705 |
| 0.0022 | 28832 | 29040 | 690 | 4.26 | 7100 | 1.68511 |
| 0.002 | 35636 | 35872 | 727 | 4.27 | 7090 | 1.70144 |
| 0.0018 | 43680 | 43940 | 692 | 5.92 | 7292 | 1.70984 |
| 0.0016 | 54896 | 55188 | 694 | 4.24 | 7523 | 1.73724 |
| 0.0015 | 63200 | 63516 | 693 | 5.97 | 7269 | 1.69964 |
| 0.0012 | 99396 | 99792 | 700 | 4.26 | 7106 | 1.67946 |
| 0.001 | 140400 | 140868 | 695 | 4.18 | 7631 | 1.73527 |

As it is evident, from the Table 18 and the graphs showing mesh convergence that the refinement level with seed size of 2.2 mm having mesh of about 30000 elements is appropriate for further studies. But, as shown in the graphs and Table 19, using the two level mesh refinements is beneficial as it reduces the element numbers by almost half and without losing major accuracy. As a result, the further study was carried out with the outer seed size of 4.4 mm and a 2.2 mm element edge length for the central near the impact zone.

TABLE 19

Mesh Convergence with Non-Uniform Mesh Technique.

| Seed | Elements | Nodes | Max Von Mises (MPa) | Max Disp (mm) | Peak Force (N) | Rebound Velocity (m/s) |
|---|---|---|---|---|---|---|
| 0.005-0.0025 | 12520 | 12640 | 696 | 4.34 | 6916 | 1.66958 |
| 0.0044-0.0022 | 13872 | 14008 | 698 | 4.26 | 7019 | 1.6841 |
| 0.004-0.002 | 16272 | 16416 | 709 | 4.27 | 6994 | 1.68893 |

Validated Results

The composite pipe model was validated with the experimental results from the thesis of Naik [52]. The validation was carried out against the impact load of 20 J with a striker of 10 kg weight. The numerical model requires the material properties for the validation which were not provided in the thesis. These values were then obtained from the available literature for similar kind of composite materials provided in the study of Li et al. [40]. In the model validation phase, the geometric dimensions were kept the same as reported in the work of Naik, but due to the fact that it doesn't provide the material properties as well as the exact number of layers and the thickness of each layer. An assumption was made considering the number of layers and thickness based on the literature available on the subject. It was assumed that the layers were 0.25 mm thick and the total numbers of layer were 24. The results are reported in Table 20.

TABLE 20

Model Validation results for the Glass/Epoxy Composite Pipe at 20 J.

| | Peak Force (N) | Deformation at Peak Force (mm) | Time of Impact Event (msec) |
|---|---|---|---|
| Naik Thesis | 6640 | 3.59 (12 J Impact) | 7.4 |
| Current Work | 6970 | 3.95 (20 J Impact) | 7.76 |
| % age Difference | 4.9% | — | 4.86% |

The results in Table 20 show that there is only about 5% difference between the results from Naik and the current numerical work, which is a sufficient level considering the above justified assumptions. In the table, the deformation at the peak force is mentioned for 12 J as there was no value for deformation at the 20 J impact tests in the thesis by Naik.

Figure 12:
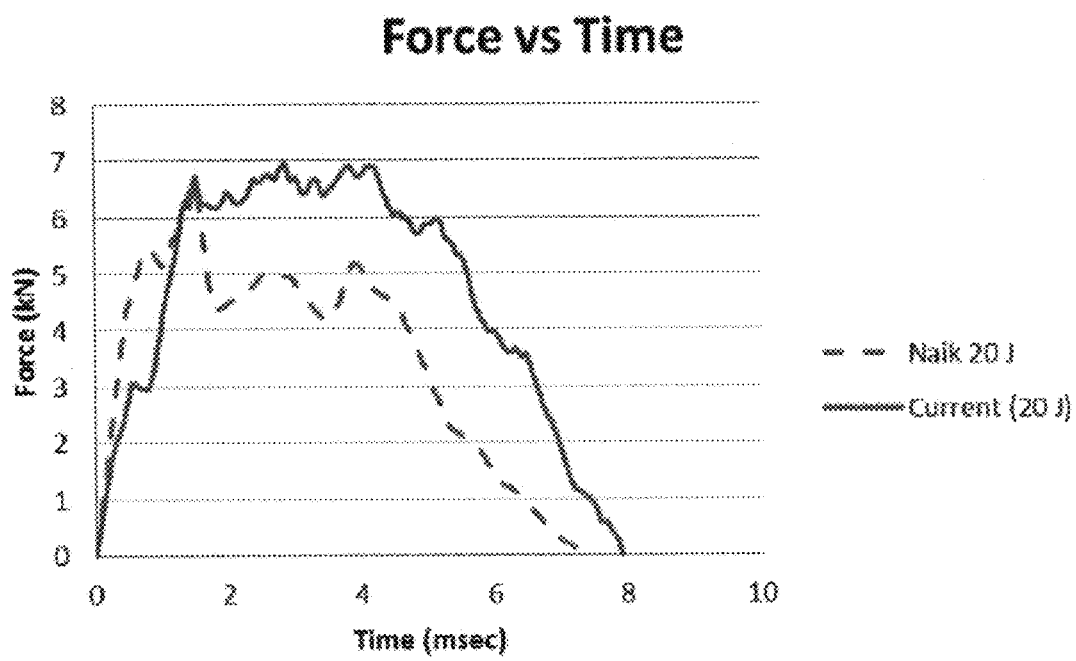
FIG. 12 illustrates a comparison force vs. time plot.

In the graph illustrated in FIG. 12, the comparison between the force vs. time plot is presented. One aspect that may be noticed that in the graph displaying the Naik's result, it shows that after the first peak force the force value remains less than the force values from the current work. This may be explained on the basis that the sudden drops occurs when the force is such that it initiates the damage and hence in the further contact the specimen is unable to offer more resistance. On the contrary, the peak force in the current research work reaches at the same point of time but it didn't dip down below enough to meet the experimental results. This may be due to the fact that the material used for experimental study has a lower tensile strength in the fiber direction compared to the material properties used in the numerical research. Nevertheless, the results as shown are close enough and the model may be safely validated.

Sensitivity Analysis

This study employs a sensitivity analysis approach to identify the parameters and quantitatively describe their degree of influence on the impact resistance of the fiber reinforced polymer composite plates. The results were then used to optimize the factors in order to achieve the best impact resistance for a certain case of composite laminate under certain conditions of impact load and boundary conditions. The studies prior to the current work have studied almost all the parameters in detail such as the thickness of the ply, stacking sequence and effect of materials etc. as discussed in the literature review, but the current focus is to know how big the effect of one parameter is with respect to others. This is needed in order to use the results in optimization studies where keeping the costs minimum is one criterion. It is well established that increasing thickness and using stronger fiber material increases the impact performance but to optimize with cost in mind, it is important to know how to maximize the performance without increasing the material costs. Hence, the needs to understand which parameter in addition to thickness have greater effects. Also, once known which material properties have greater influence, it would be beneficial to search from the available materials with the least cost and best properties.

Sensitivity Analysis Formulation

In general, the sensitivity analysis is performed by varying one input variable at a time and observing its effect on the overall output. Let's denote the independent variables or the input variables with Xi and the vector X denotes the set of these variables.

$$X = \overline{X} \pm U_x \tag{4.1}$$

Where $\overline{X}$ denotes the nominal value of the independent variable and the $U_x$ is the small change about the nominal value. The range of $\pm U_x$ is defined such that the value of X may occur within this range with a certainty of about 95%. Since the output parameter Y depends upon the input variables X, an uncertainty in X may be related to the output variable as:

$$U_Y = \frac{dY}{dX} U_X \tag{4.2}$$

Since, the input variable X is a vector of many different variables, the output variable Y must be a function of all the input variables such that;

$$Y = Y(X_1, X_2, \ldots, X_N) \tag{4.3}$$

The uncertainty in Y may be expressed in terms of the root sum square of all the individual uncertainties due to the input variables, that is;

$$U_Y = \left[ \sum_{i=1}^{N} \left( \frac{\partial Y}{\partial X_i} U_{X_i} \right)^2 \right]^{\frac{1}{2}} \tag{4.4}$$

To normalize the sensitivity coefficients, one divides with the nominal value of the output $$\left( \frac{U_Y}{\overline{Y}} \right) = \left\{ \sum_{i=1}^{N} \left[ \left( \frac{\partial Y}{\overline{Y}} \frac{\overline{X}_i}{\partial X_i} \right) \left( \frac{U_{X_i}}{\overline{X}_i} \right) \right]^2 \right\}^{\frac{1}{2}} \tag{4.5}$$

The normalized sensitivity coefficient NSC is the term in the first bracket on the right side of the equation, which is $$NSC_{X_i} = \left(\frac{\partial Y}{Y} \frac{\overline{X_i}}{\partial X_i}\right)^2 \quad (4.6)$$

Figure 13A:
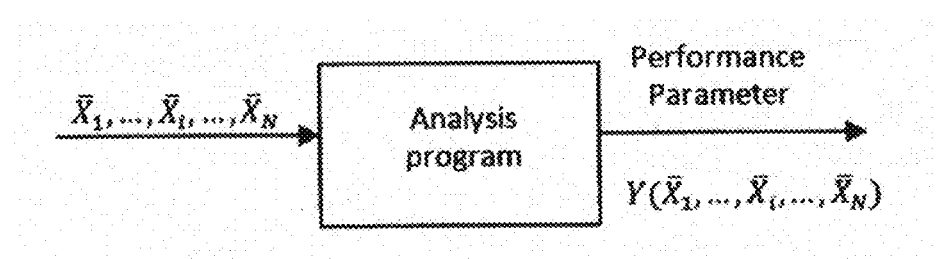
FIG. 13A illustrates a block diagram of a nominal system.
Figure 13B:
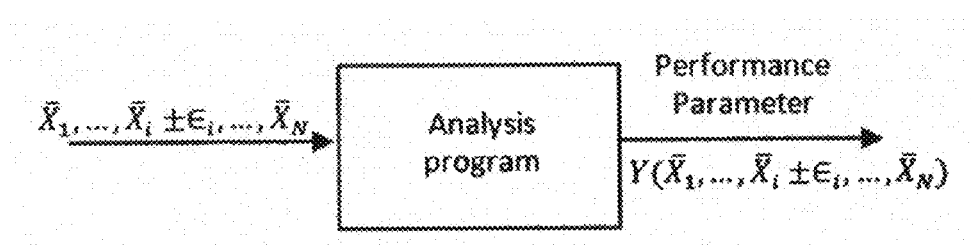
FIG. 13B illustrates a block diagram of a perturbed system.

This normalized sensitivity coefficient gives an opportunity to compare all the input variables and their effects with respect to one normalized value of the nominal output variable. FIG. 13A represents the nominal system whose values and results are selected as reference and FIG. 13B graphically represents the variation in one parameter and its effect on the output parameter.

For the sensitivity analysis of the structural problem, the general output responses are the displacements, stresses, strains or velocities [30]. The output variable in the case of impact problem is taken as amount of energy absorbed during the impact event. This is considered as during the impact event, the incident kinetic energy of the impactor is transferred to the specimen. This energy is absorbed in the form of internal energy of the specimen, which results in some of it used in the elastic deformation, some proportion of it used for plastic deformation of the fiber and epoxy while some of energy is dissipated in the damage mechanics as described by the Hashin Model. The energy used for the plastic deformation and damage is termed as the absorbed impact energy as it cannot be recovered while the energy stored in the elastic deformation is returned to the impactor.

The sensitivity coefficients are computed numerically using the finite element method, the sensitivity analysis takes the amount of absorbed energy as the output variable;

$$\{F\}[K]\{d\}+[M]\{\ddot{d}\} \quad (4.7)$$

The stiffness matrix is defined as:

$$[K]=\iiint [B]^T[D][B]dV \quad (4.8)$$

Where [D] is the material properties matrix and the matrix [B] is the geometric properties matrix of the sample.

For a case of composite plate, the stiffness matrix may be given as;

$$[K]=tA[B]^T[D][B] \quad (4.9)$$

And the Mass matrix [M] is given by:

$$[M] = \int_V [N]^T[\rho][N]dV \quad (4.10)$$

Where, the nodal mass matrix [ρ] includes the rotary inertia terms.

For a unidirectional lamina, the material properties matrix is given by:

$$[D] = \begin{bmatrix} \frac{E_1}{1-v_{12}v_{21}} & \frac{v_{12}E_2}{1-v_{12}v_{21}} & 0 \\ \frac{v_{21}E_1}{1-v_{12}v_{21}} & \frac{E_2}{1-v_{12}v_{21}} & 0 \\ 0 & 0 & G_{12} \end{bmatrix} \quad (4.11)$$

Input Variables for Sensitivity Coefficient Calculations

From the literature review, it was noted that the state variables upon which the response of the composite plate depends upon may be a number of different parameters which included, the shell thickness, number of layers and the material of the composite plate.

The studies show that the thickness of the plate, number of layers, thickness of each individual layer, stacking sequence and type of material are some of the factors influencing the impact properties. Also, some studies have been conducted with varying the impact energy by varying impactor mass or velocity. Some other variables were studied in other researches, but the parameters that considered to effect the sensitivity coefficient are the material and geometric properties as explained above because the output parameter "absorbed energy" is related to the material and geometric properties of the plate and is not directly related although effected by the constraint conditions and the impactor properties and energy.

The material properties are studied in detail individually in order to understand the material properties which have the most profound effect on the impact behavior of the composite plate. All the material properties like elastic moduli in the fiber and transverse direction, shear modulus and strength under various conditions etc. are analyzed using sensitivity analysis. The variables that are studied by this approach are listed in Table 21.

TABLE 21

List of Variables for Sensitivity Analysis

| No. | Variable | Description |
| --- | --- | --- |
| 1 | Tp | Thickness of layer/ply |
| 2 | Tl | Thickness of laminate |
| 3 | N | Number of layers |
| 4 | St | Stacking Sequence |
| 5 | $E_{11}$ | Elastic Modulus in Longitudinal Direction |
| 6 | $E_{22}, E_{33}$ | Elastic Modulus in Transverse Direction |
| 7 | $v_{12}, v_{13}$ | Poisson's Ratio in plane containing fiber |
| 8 | $v_{23}$ | Poisson's Ratio in transverse plane |
| 9 | $G_{12}, G_{13}$ | Shear Modulus in plane containing fiber |
| 10 | $G_{23}$ | Shear Modulus in transverse plane |
| 11 | $X_t$ | Tensile strength in longitudinal direction |
| 12 | $X_c$ | Compressive strength in longitudinal direction |
| 13 | $Y_t$ | Tensile strength in transverse direction |
| 14 | $Y_c$ | Compressive strength in transverse direction |
| 15 | $S_{12}$ | In-Plane Shear Strength |
| 16 | $G_f^t$ | Fracture Toughness in longitudinal tensile direction |
| 17 | $G_f^c$ | Fracture Toughness in longitudinal compressive direction |
| 18 | $G_m^t$ | Fracture Toughness in transverse tensile fracture mode |
| 19 | $G_m^c$ | Fracture Toughness in transverse compressive fracture mode |

From variable 5 to variable 18, all are related to the selection of material and the sensitivity analysis is performed on these variables to get an informative guess for future material selection.

Validated Flat Plate Model as Nominal Case

The method developed in the sensitivity analysis is considering a case to be nominal and then varying the input variables from this nominal case by ±5%. The nominal case selected for this analysis was the same as the one used for model validation and compared with the results of Yokoyama et al [72]. The advantage of applying sensitivity analysis using a validated model is because of the possibility to isolate single answers to single perturbation of a process parameter [47].

The results and the input parameters used in the model validation were selected as the nominal and the nominal values for the variables are listed in the Table 22.

TABLE 22

Nominal Values for the input variables.

| No. | Variable | Nominal Values |
|---|---|---|
| 1 | Tp | 0.21 mm |
| 2 | Tl | 4.2 mm |
| 3 | N | 20 |
| 4 | St | [45/−45/0/90/45/−45/0/90/45/−45]$_s$ |
| 5 | $E_{11}$ | 60.8 GPa |
| 6 | $E_{22} = E_{33}$ | 58.25 GPa |
| 7 | $v_{12} = v_{13}$ | 0.07 |
| 8 | $v_{23}$ | 0.4 |
| 9 | $G_{12} = G_{13}$ | 4.55 GPa |
| 10 | $G_{23}$ | 5 GPa |
| 11 | $X_t$ | 621 MPa |
| 12 | $X_c$ | 760 MPa |
| 13 | $Y_t$ | 594 MPa |
| 14 | $Y_c$ | 707 MPa |
| 15 | $S_{12}$ | 125 MPa |
| 16 | $G_f^t$ | 160 KJ/m$^2$ |
| 17 | $G_f^c$ | 25 KJ/m$^2$ |
| 18 | $G_m^t$ | 10 KJ/m$^2$ |
| 19 | $G_m^c$ | 2.25 KJ/m$^2$ |

The output variable for sensitivity analysis is chosen to be the dissipated impact energy or the energy absorbed during the impact event. The absorbed energy gives an account of the damage done to the composite plate in the event of impact. The less this energy the better the design, considering this it is best suited for the study as improvement in the impact performance of the composite plate is sought. The impact energy absorbed for the nominal case is 4.74 J.

Equivalent Elastic Modulus

The input variables like thickness of plate or the thickness of a single layer may be easily varied by 5% as defined in the approach. But, the variables like the stacking sequence or the number of layers which are not defined by a scalar cannot be varied in the same sense as other variables. For the stated reason, there was a need to develop an understanding to vary these parameters in order to better estimate their effects.

The material properties given in the Table 1 for the nominal case are for a unidirectional lamina i.e. a single ply of composite materials with all the fibers aligned in one direction. With more than one layers stacked at different orientations, they have an overall effect on the physical properties of the whole composite plate.

The stacking sequence for the nominal case corresponds to the concept of "Quasi-Isotropic" laminate, which is the case when the equivalent modulus of elasticity of the whole plate is same in the plane containing fibers, the other case happens to be when the modulus of elasticity in the plane containing fibers is not equal.

The laminate stiffness matrix is given by, $$[K] = \begin{bmatrix} A & B \\ B & D \end{bmatrix} \quad (4.12)$$

Where each A, B and D is sub-matrices defined as the Extensional Stiffness, Coupling Stiffness and the Bending Stiffness matrices. [60]

The terms of these matrices are given by $$A = \sum_{k=1}^{N} \overline{D}(z_{k+1} - z_k) \quad (4.13)$$

$$B = \frac{1}{2}\sum_{k=1}^{N} \overline{D}(z_{k+1}^2 - z_k^2) \quad (4.14)$$

And $$\begin{Bmatrix} N_x \\ N_y \\ N_{xy} \end{Bmatrix} = \begin{bmatrix} A_{11} & A_{12} & A_{16} \\ & A_{22} & A_{26} \\ sym & & A_{66} \end{bmatrix} \begin{Bmatrix} \varepsilon_x^0 \\ \varepsilon_y^0 \\ \gamma_{xy}^0 \end{Bmatrix} + \begin{bmatrix} B_{11} & B_{12} & B_{16} \\ & B_{22} & B_{26} \\ sym & & B_{66} \end{bmatrix} \begin{Bmatrix} \kappa_x \\ \kappa_y \\ 2\kappa_{xy} \end{Bmatrix} \quad (4.16)$$

Hence, $$D = \frac{1}{3}\sum_{k=1}^{N} \overline{D}(z_{k+1}^3 - z_k^3) \quad (4.15)$$

For the case of Quasi-Isotropic laminates, the terms $A_{11}$ and $A_{22}$ must be equal. The nominal case selected had the quasi isotropic behavior. In order to study the effect of stacking sequence, it was assumed that the variation in the overall elastic modulus should be studied. Hence, the overall elastic modulus was considered to be varied to study the effect of stacking sequence. For the positive variation, a stacking sequence was designed such that the elastic modulus of the laminate increases by about 5%.

The nominal stacking sequence as listed in table 1 is [45/−45/0/90/45/−45/0/90/45/−45], had the modulus of elasticity in the longitudinal direction is equal to be 38.7 GPa, the stacking sequence corresponding to 5% increase in the longitudinal elastic modulus which is 40.635 GPa is [30/−60/0/90/30/−60/0/90/30/−60]$_s$. Similarly, for the variation of −5% in the longitudinal elastic modulus which is about 36.765 GPa, the stacking sequence is [60/0/45/−45/60/0/451−45/60/0]$_s$. These layer configurations give the required equivalent longitudinal elastic modulus which is very close to the 5% variation.

Also, the number of layers was also selected as an input parameter, which means the variation would cause the number of layers in the laminate to increase and decrease by 1 layer; this would result in the change of elastic modulus of the laminate. But, it is varied in such a way that the quasi-isotropic behavior of the laminate didn't change.

The change in the parameters for the sake of sensitivity analysis is tabulated in Table 23 and the results of all the variables and their sensitivity coefficient are discussed in the next section.

TABLE 23

Variation in the nominal values of the input parameters.

| No. | Factor | Units | Nominal Value | 5% Change | X + ΔX | X − ΔX |
|---|---|---|---|---|---|---|
| X1 | Tp | mm | 0.21 | 0.0105 | 0.2205 | 0.1995 |
| X2 | N | Unitless | 20 | 1 | 21 | 19 |

TABLE 23-continued

Variation in the nominal values of the input parameters.

| No. | Factor | Units | Nominal Value | 5% Change | X + ΔX | X − ΔX |
|---|---|---|---|---|---|---|
| X3 | St | GPa | [45/−45/0/90/<br>45/−45/0/90/<br>45/−45]s ≈ 38.7 | 1.935 | [30, −60, 0, 90,<br>30, −60, 0, 90,<br>30, −60]s ≈ 40.7 | [60, 0, 45, −45,<br>60, 0, 45, −45,<br>60, 0]s ≈ 36.8 |
| X4 | $E_{11}$ | GPa | 60.8 | 3.04 | 63.84 | 57.76 |
| X5 | $E_{22} = E_{33}$ | GPa | 58.25 | 2.913 | 61.1625 | 55.3375 |
| X6 | $v_{12} = v_{13}$ | | 0.07 | 0.0035 | 0.0735 | 0.0665 |
| X7 | $v_{23}$ | | 0.4 | 0.02 | 0.42 | 0.38 |
| X8 | $G_{12} = G_{13}$ | GPa | 4.55 | $227.5 \times 10^{-3}$ | 4.7775 | 4.3225 |
| X9 | $G_{23}$ | GPa | 5 | $250 \times 10^{-3}$ | 5.25 | 4.75 |
| X10 | $X_t$ | MPa | 621 | 31.05 | 652.05 | 58.995 |
| X11 | $X_c$ | MPa | 760 | 38 | 798 | 722 |
| X12 | $Y_t$ | MPa | 594 | 29.7 | 623.7 | 564.3 |
| X13 | $Y_c$ | MPa | 707 | 35.35 | 742.35 | 671.65 |
| X14 | $S_{12}$ | MPa | 125 | 6.25 | 131.25 | 118.75 |
| X15 | $G_f^t$ | KJ/m² | 160 | 8 | 168 | 152 |
| X16 | $G_f^c$ | KJ/m² | 25 | 1.25 | 26.25 | 23.75 |
| X17 | $G_m^t$ | KJ/m² | 10 | $500 \times 10^{-3}$ | 10.5 | 9.5 |
| X18 | $G_m^c$ | KJ/m² | 2.25 | $112.5 \times 10^{-3}$ | 2.3625 | 2.1375 |

The point to note here is that the values represented in Table 23, does not represent the realistic values of any material in terms of the elastic moduli and the strength values. Rather these values has been adjusted according to the criteria of sensitivity analysis which states one variable is changed at a time by a some percentage and others keep constant and the same process is repeated for all the variables.

Results and Discussions

As per the procedure described above a total of 36 simulations were performed using the commercial FEA software ABAQUS to determine the amount of impact energy lost in damage during the impact process for each of the above defined cases. The results for few of the parameter variations were as expected while there were some results that helped understand the role of certain variables play in the impact behavior of the composite laminate.

The results for all the different cases were compiled and sorted in the order of the calculated normalized sensitivity coefficients (NSCs). The order of the list provides with the information that which variable has how much effect. The larger the NSC value, the more that variable influences the output variable which in this case is the amount of the absorbed energy. The results are tabulated as shown in the table in the descending order of NSC.

As mentioned earlier, the amount of energy absorbed in the nominal case was 4.74 J. It is observed that based on the amount of energy absorbed in each variation of variables, the NSC has different orders of magnitude.

TABLE 24 provides a sorted list of parameters in descending order with respect to the NSC.

| No. | Symbol | Energy absorbed in X + ΔX (J) | Energy absorbed in X − ΔX (J) | NSC |
|---|---|---|---|---|
| X1 | Tp | 4.59 | 5.16 | 1.4096 |
| X3 | St | 5.59 | 5.34 | 0.2899 |
| X10 | $X_t$ | 4.66 | 4.87 | 0.2001 |
| X2 | N | 4.77 | 4.88 | 0.0609 |
| X15 | $G_f^t$ | 4.70 | 4.81 | 0.0479 |
| X5 | $E_{22} = E_{33}$ | 4.80 | 4.70 | 0.0440 |
| X4 | $E_{11}$ | 4.77 | 4.72 | 0.0117 |
| X6 | $v_{12} = v_{13}$ | 4.78 | 4.75 | 0.0056 |
| X16 | $G_f^c$ | 4.74 | 4.77 | 0.0042 |
| X8 | $G_{12} = G_{13}$ | 4.74 | 4.76 | 0.0024 |
| X11 | $X_c$ | 4.77 | 4.75 | 0.0015 |
| X17 | $G_m^t$ | 4.76 | 4.74 | 0.0014 |
| X13 | $Y_c$ | 4.77 | 4.75 | $8.22 \times 10^{-4}$ |
| X14 | $S_{12}$ | 4.74 | 4.75 | $3.89 \times 10^{-4}$ |
| X12 | $Y_t$ | 4.75 | 4.76 | $3.35 \times 10^{-4}$ |
| X18 | $G_m^c$ | 4.76 | 4.76 | $1.69 \times 10^{-4}$ |
| X7 | $v_{23}$ | 4.76 | 4.76 | $1.28 \times 10^{-4}$ |
| X9 | $G_{23}$ | 4.74 | 4.73 | $6.4 \times 10^{-6}$ |

Figure 14A:
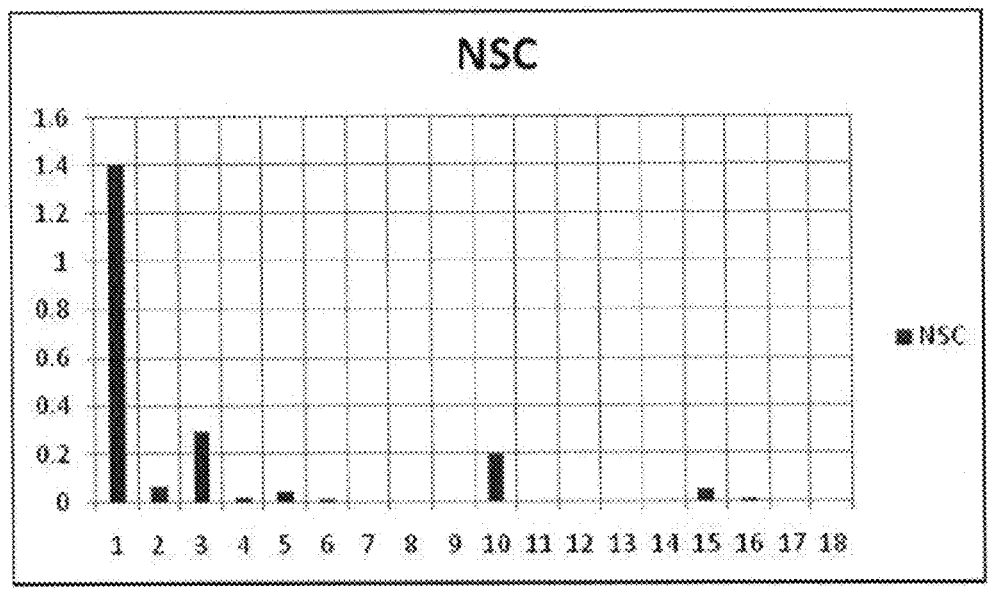
FIG. 14A illustrates a graph of normalized sensitivity coefficients for variables demonstrating a relative effect of each absorbed impact energy.
Figure 14B:
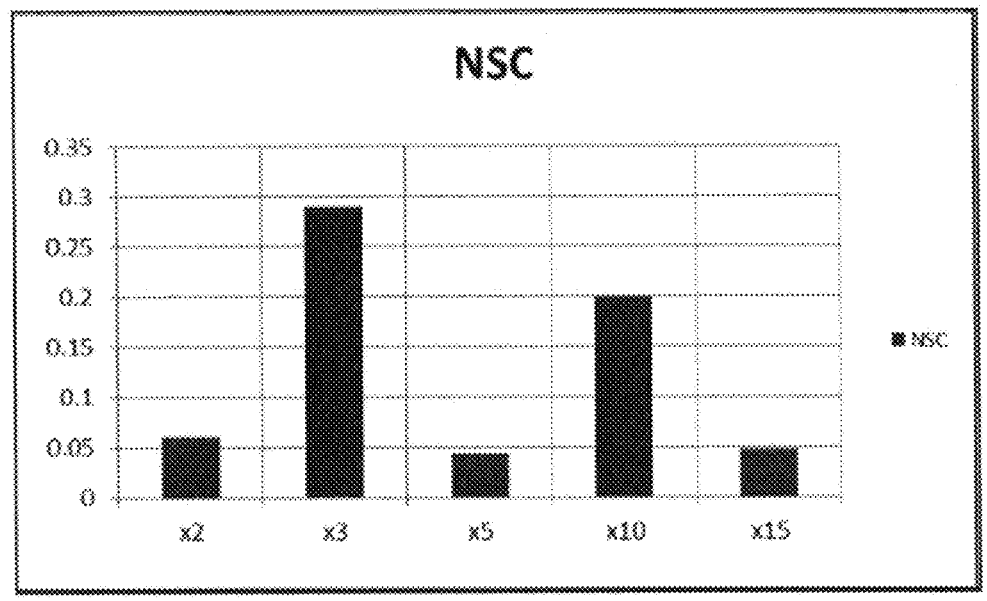
FIG. 14B illustrates a graph of normalized sensitivity coefficients for variables having a greater influence on the amount of absorbed energy except thickness.
Figure 15A:
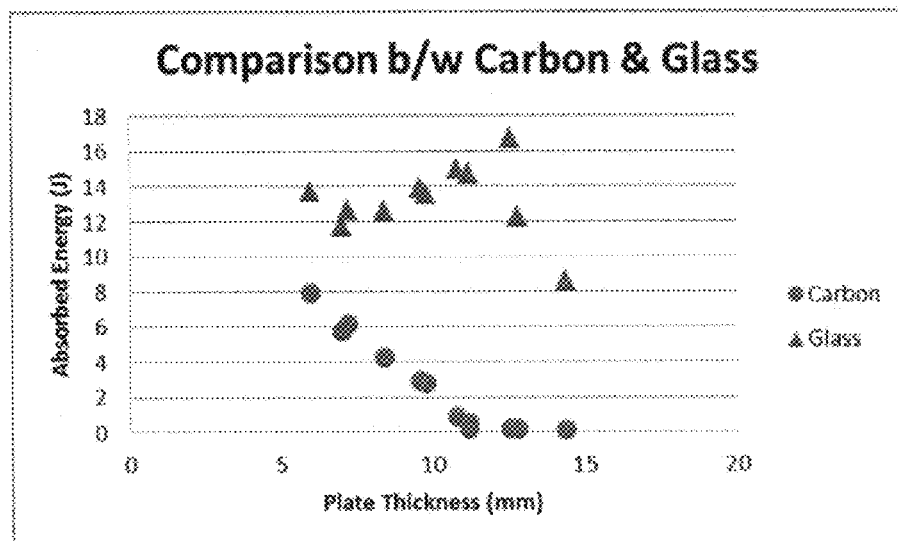
FIG. 15A illustrates a comparison of carbon and glass composite plates at varying thicknesses with stacking sequence 1.
Figure 15B:
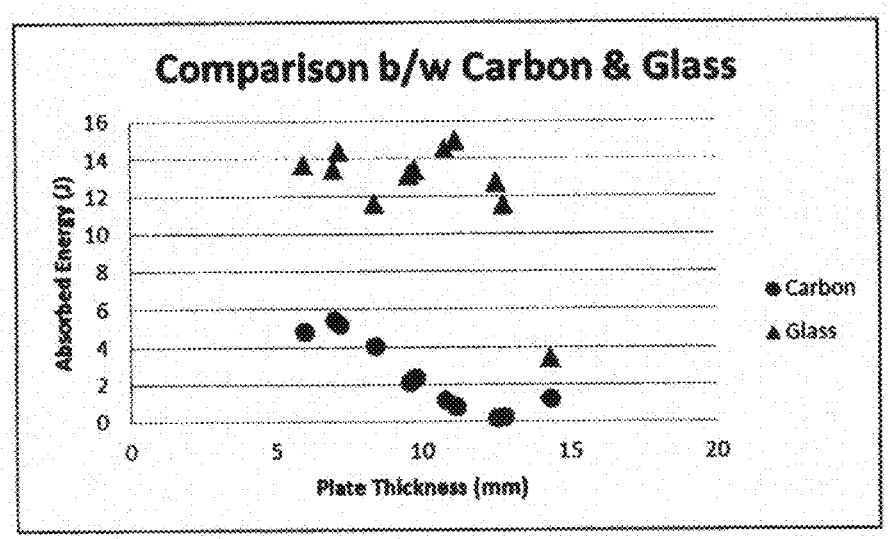
FIG. 15B illustrates a comparison of carbon and glass composite plates at varying thicknesses with stacking sequence 2.
Figure 15C:
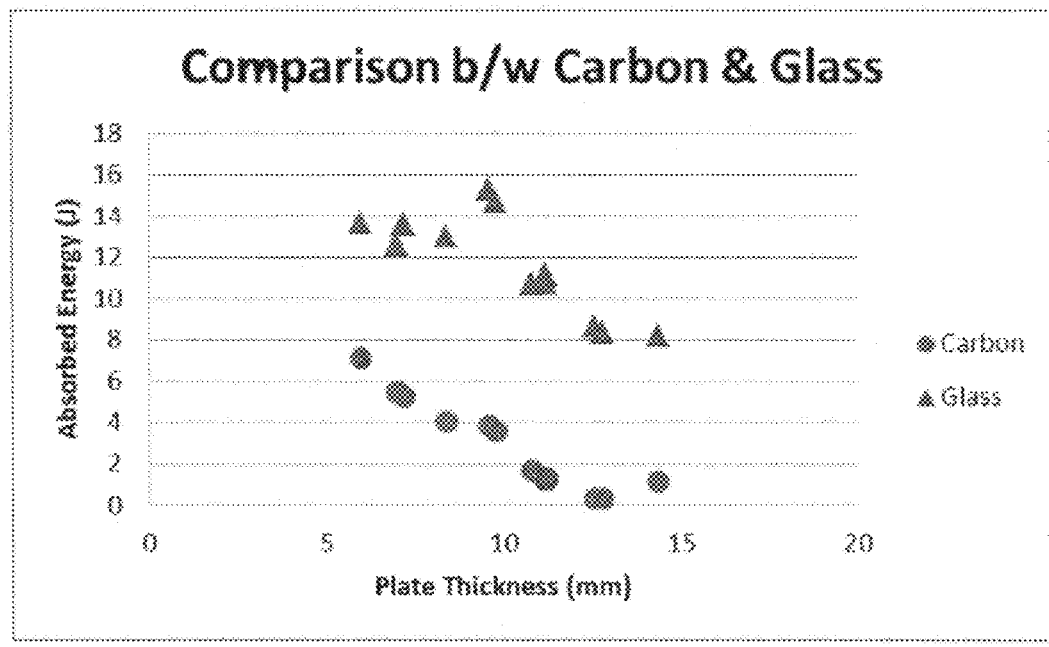
FIG. 15C illustrates a comparison of carbon and glass composite plates at varying thicknesses with stacking sequence 3.
Figure 15D:
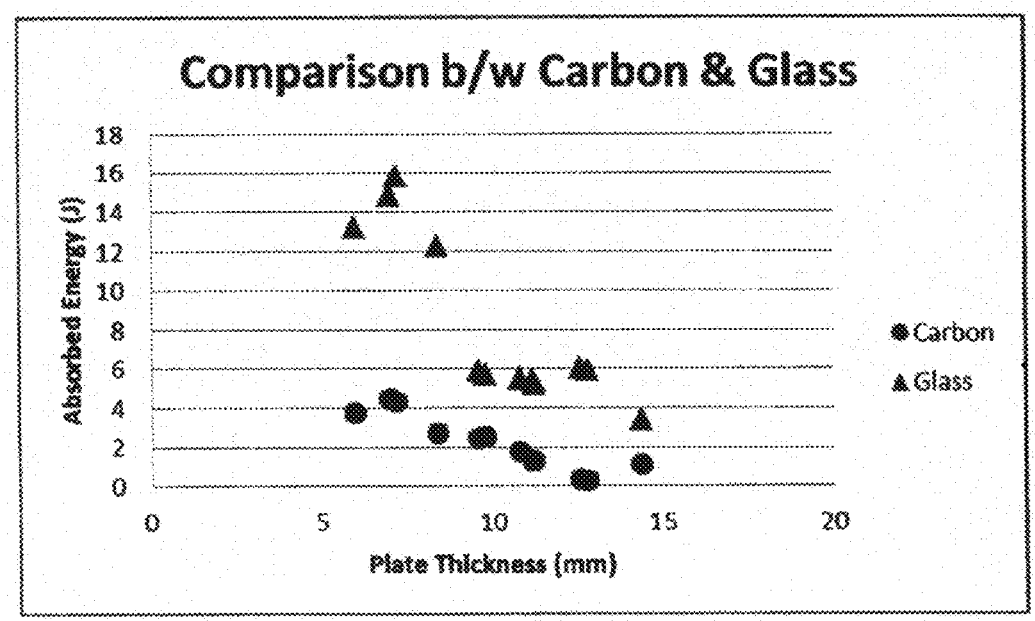
FIG. 15D illustrates a comparison of carbon and glass composite plates at varying thicknesses with stacking sequence 4.
Figure 16A:
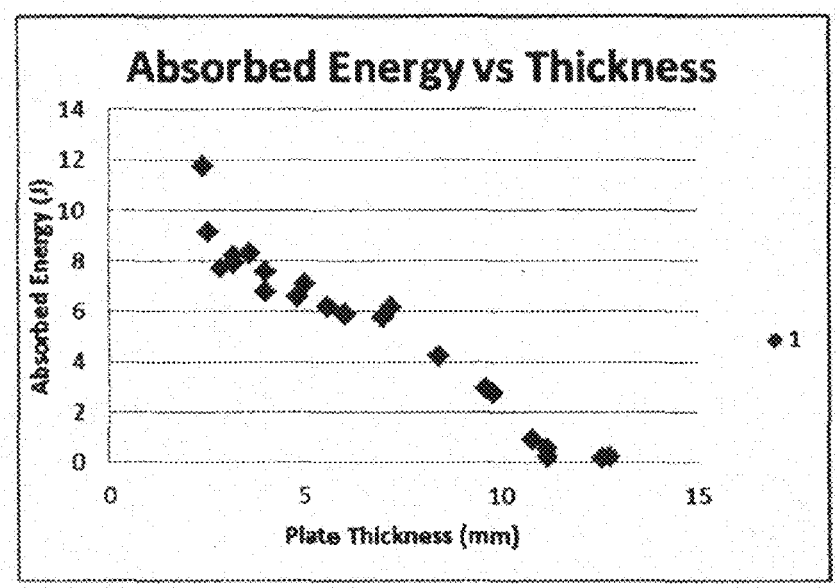
FIG. 16A illustrates scatter data for layer configuration 1 for carbon/epoxy plates.
Figure 16B:
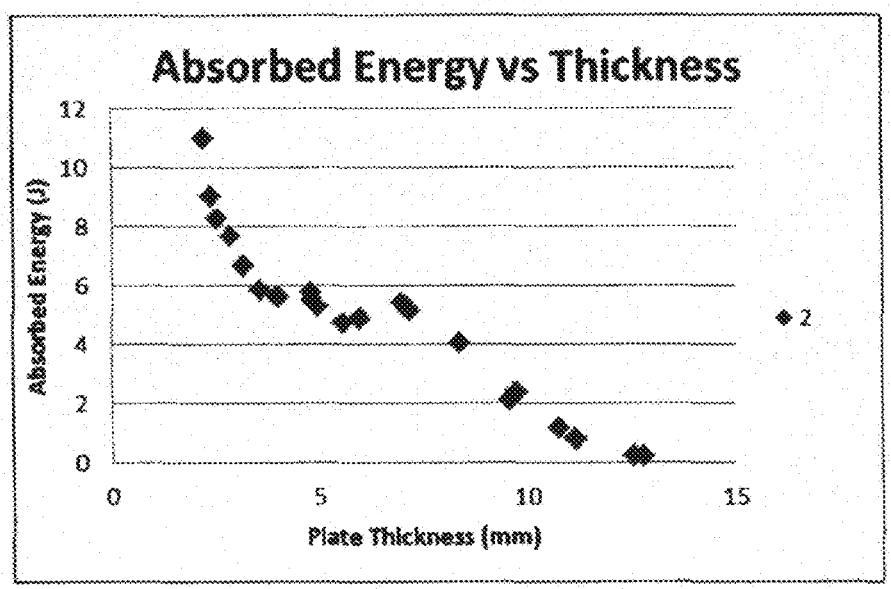
FIG. 16B illustrates scatter data for layer configuration 2 for carbon/epoxy plates.
Figure 16C:
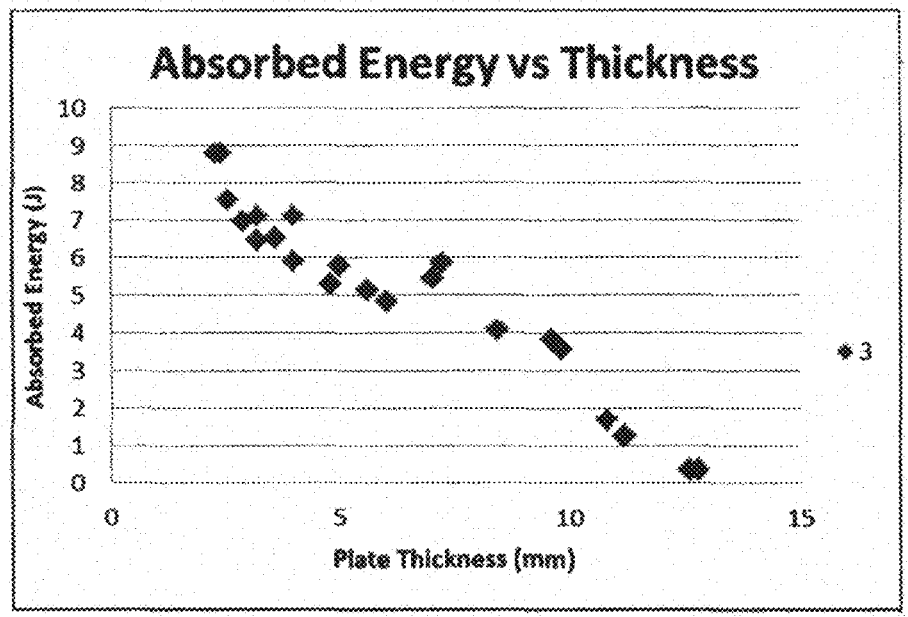
FIG. 16C illustrates scatter data for layer configuration 3 for carbon/epoxy plates.
Figure 16D:
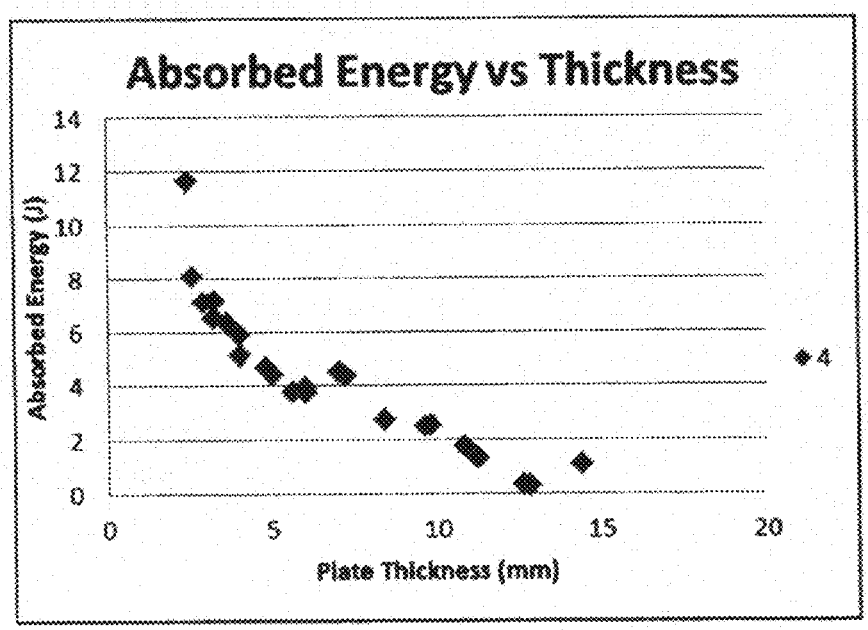
FIG. 16D illustrates scatter data for layer configuration 4 for carbon/epoxy plates.

The results of the calculated NSC are graphically represented in the FIGS. 14A and 14B. In particular, FIG. 14A illustrates a graph of normalized sensitivity coefficients for variables demonstrating a relative effect of each absorbed impact energy. FIG. 14B illustrates a graph of normalized sensitivity coefficients for variables having a greater influence on the amount of absorbed energy except thickness. The results listed in Table 24 indicate that there is a large dependence of the impact performance of composite plates on some parameters such as the thickness of the layer, number of layers, stacking sequence and the material properties like the tensile strength and the fracture toughness in the fiber direction. The other material properties studied showed dependence of the impact performance does not vary that much with the variation of standard 5% from the nominal values.

According the values listed in Table 24, the parameters considered to have significant effect are:
1) Thickness of each layer/ply
2) Stacking Sequence
3) Tensile strength in the fiber direction
4) Number of layers
5) Fracture toughness in the fiber direction during tensile loading The parameters 3 and 5 are related to the material properties and are hence dependent upon the material selection. These parameters will help in selection of material for the fiber and matrix material.

The effect of thickness of individual layers show that the increase in thickness results in the decrease in absorbed energy and of all the parameters considered the effect of thickness is most profound on the impact performance of the composite plate. This result is intuitive and in accordance with the available studies in the different literature. The effect of increasing thickness of individual layers has been studied extensively and is the most effective parameter to increase the impact resistance of composite plates. This result is backed by the available results from the studies of Zhao et al. [73]. Zhao et al. demonstrated that with the increasing thickness the damage is considerably reduced while the stacking sequence was kept constant. As discussed in the literature, the effect of thickness is most prominent among all the variables considered, is also supported by the fact that the value of NSC for the case of thickness variation is the highest which characterizes a strong dependence on the thickness of the layer.

The first parameter to study was the thickness of the individual layer, the effect of the variation reveals that the impact performance improves as the thickness is increased, i.e., the amount of energy absorbed/dissipated decreases as the thickness is increased and vice versa.

The second most important parameter is found to be the stacking sequence, one important aspect to understand is that the stacking sequence effect is not linear considering that in this study the stacking sequence is studied in terms of the equivalent elastic modulus of the whole laminate. The nominal case that was selected to be the quasi isotropic behavior has the best performance in terms of minimum impact energy absorption.

The results show that the minimum amount of energy absorbed is for the case where the laminate configuration is such that the laminate behaves as quasi-isotropic material. This result agrees with the result from the study of Aktas et al. [2]. The value of the NSC calculated for the variation in the stacking sequence suggests that the impact resistance of composite laminated plates is highly dependent upon the stacking sequence. The dependence is not linear and as the stacking sequence converges to a quasi-isotropic behavior the amount of impact energy absorbed is significantly reduced.

The other important factors were the tensile strength and the fracture toughness in the fiber direction, increasing these parameters result in lower impact energy absorption while lowering these values has inverse effect. The tensile strength of the fiber is the third most significant variable as observed by the NSC and is quite close to the NSC of stacking sequence. This has a significant effect on the understanding in the design process of structures with composite materials that are susceptible to the impact loading due to low velocity impacts. It is suggested that the material should be chosen as such which offers greater tensile strength as compared to the other material properties.

The tensile strength of the fiber has a significant effect on the absorbed impact energy as described by the damage initiation equations by Hashin (1980) given by equation (3.5), during the impact loading the plate is stretched and due to plate in tension as evident in FIG. 10A, the tensile strength of fiber plays an important role in the impact behavior of the composite plates. As evident by equation (3.5), the higher the strength value, the more stress it may bear before breakage hence less absorbed energy and better impact resistance.

Similarly, the effect of fracture toughness may be observed from the damage evolution laws described by Hashin. As shown in FIG. 6, the amount of dissipated energy is the area under the curve for the equivalent stress-displacement curve, the higher the fracture toughness the more stress composite plate may withstand before the damage.

Finally, the last factor considered was the number of layers; it similarly has not a linear relation like the stacking sequence. Increasing and decreasing by 5% the number of layers while keeping the total laminate thickness constant result in increased impact energy absorption. Hence, it may be deduced that there must be an optimal number of layers for a fixed thickness which will give the better impact performance. This observation may be related to the fact that from various studies it is observed that increasing layers with 90° orientation results in the increase in contact force as described by Tiberkak et al. [65]. Thus, there must be an optimum condition for which the amount of absorbed energy and the resulting damage will be minimum.

The other material properties that have slight influence on the impact resistance are the fracture toughness of the material in the tensile loading in the longitudinal direction and the transverse elastic modulus. Both these variables have the NSC values in the same order as the NSC for the number of layers but slightly less. Besides, both these variables having similar NSC values, their behavior is completely different. The increase in the fracture toughness $G_f^t$ results in better impact performance while the increase in transverse elastic modulus results in the increase in impact energy absorption hence it is desirable to have transverse elastic modulus low.

The rest of the material properties like the longitudinal elastic modulus, the shear modulus and the strength of the lamina in the transverse direction have very small effect on the overall impact performance of the composite plate. This may be observed by the fact that the value of NSC is of one or more order less than the NSC of stacking sequence and number of layers etc.

This section presented the model validation and the sensitivity analysis approach to ascertain the effects of various geometrical and material properties of composite materials on the impact performance of the composite laminated plates. Initial numerical model was selected from the literature and the results verified against the available numerical and experimental results. The results show quite a good agreement with the experimental results. The model was then selected as the nominal case for further evaluation of NSC using the commercial finite element solver ABAQUS explicit.

The results presented in the current study gives an insight about the effects of the considered parameters on the impact performance in terms of a normalized coefficient. The advantage of such a coefficient is that an equal amount of variation in any of the parameters will be highlighted in varying effect on the output; hence, it may be classified according to the order. ABAQUS explicit solver was used to perform the finite element simulations to find the effect of variations in all the input variables one at a time on the absorbed impact energy. The amount of energy absorbed varies significantly for the variations in the thickness of a single layer, number of layers, stacking sequence and the material properties that have significant effect were the tensile strength of the layer in the fiber direction, fracture toughness of the laminate in the tensile loading in the longitudinal direction and to some extent the elastic modulus of the transverse direction has effect on the absorbed impact energy. The only peculiar behavior is of the stacking sequence, as the stacking sequence is changed the overall elastic modulus of the laminate varies and as the behavior of the laminate moves away from that of the quasi-isotropic the amount of energy absorbed increased resulting in a poor performance compared to the nominal case.

The results from this study will help the authors in the future work in designing composite laminated plates having better impact resistance. The results will allow a more methodical approach in selecting the parameters to vary in order to achieve better impact performance of composite laminates against the low velocity impact loadings. Thus, the results from this section for the improvement of impact performance of composite plates may be summarized as follows:

The layer thickness has the most prominent effect with the more the thickness, the better the impact resistance.

Stacking sequence should be such that the overall behavior of the laminate should be close to quasi-isotropic.

The most important material property for selection of material is the tensile strength of the fiber in the longitudinal direction.

The number of layers has an effect on the impact resistance and should be selected carefully as to not just increase the layers which result in more contact force and hence greater damage.

Parametric Study of Design Variables

The main idea of this current study was to investigate the relation of the amount of damage occurring during an impact load with the number of factors such as the thickness of the layers, number of layers, orientation angles, material types and inclusion of other materials. These factors were identified using the sensitivity analysis approach discussed in the previous chapter. This way a more knowledgeable design criterion may be developed which will be optimal in terms of performance and the cost of the material. For a comprehensive study of effects of these factors, a design of experiments approach was adopted where all the possible combinations may be tried.

In this section, design of experiments approach is presented along with the discussion of the effects of these factors on the impact performance of both the composite plates and the pipes.

Design of Experiments

Design of experiments is a very useful tool to investigate the causes and effects of various factors spread over a domain. The use of design of experiments along with the finite element analysis gives an analyst a powerful tool to understand deeply the variations of the outcomes of a process and the factors causing these variations. In addition to the effects on the design or process, design of experiments gives statistical significance to understand them. The combination of finite element analysis with the design of experiments provides the opportunity for the current work to study the complete domain of the identified variables from sensitivity analysis and their relationship with the impact performance. It is evident from the literature review that so far the experimental studies conducted in the low-velocity impacts on the composite materials have not been comprehensive. This is due to the obvious reasons that the production of such large number of samples is costly and the experiments for impact loads may be classified as destructive analysis. Therefore, most of the studies conducted experimentally considered few variations in the factors like thickness or the stacking sequence.

The use of finite element analysis is therefore beneficial and advantageous to combine with the large number of experiments designed using DOE.

Numerical Experiments for Flat Plate

Previously discussed, the sensitivity analysis characterized four variables namely the thickness of the single layer, number of layers, stacking sequence and the material type to be of most significance considering the impact behavior. Therefore, here these four factors are considered in the DOE study and the different levels studied are listed in the Tables 25 and 26. Here, the materials considered are only carbon/epoxy and the glass/epoxy and the tables are listed separately for both these materials. This is due to the fact that the carbon being the stronger material has different thickness ranges in which it varies from completely damaged, i.e., penetration of the striker to the complete survival, i.e., the striker bounces back with the same speed. The stacking sequence is kept the same for both of these materials as the effect of stacking sequence in both the materials had to be compared.

An initial DOE was fashioned with three discrete levels of thickness and four discrete levels for the number of layers. These were from levels '5' to '7' for the thickness and levels from '1' to '4' for the number of layers. This combination of factors results in total 96 experiments for both types of the materials. But after the initial simulations it occurred that there are two shortcomings in this design. One, in this range the variation was not from complete damage to complete survival; it only showed the intermediate behavior. Two, the number of experiments were not sufficient enough for a good training of neural networks. Therefore, additional levels were added for both carbon and glass fiber plates to observe the complete spectrum. The results were calculated in terms of the absorbed energy with the impact energy fixed at 27.55 J. The impactor dimensions, weight and velocity are being kept constant in all the cases. The boundary conditions are also kept the same throughout all the experiments. The simulations were performed in ABAQUS Explicit environment.

TABLE 25

DOE Table for Carbon/Epoxy Composite Plates.

| Thickness (mm) | Number of Layers | Stacking Sequence |
|---|---|---|
| 0.12 | 16 | [0/30/60/90] |
| 0.14 | 20 | [45/−45/0/90] |
| 0.16 | 24 | [45/30/−30/−45] |
| 0.18 | 28 | [60/45/−45/−60] |
| 0.2 | 32 | |
| 0.25 | 36 | |
| 0.3 | | |
| 0.35 | | |
| 0.4 | | |

In total, 108 experiments were performed using the carbon/epoxy as the material for the plate. The results are quite large and are listed in the Appendix A.

TABLE 26

DOE Table for Glass/Epoxy Composite Plates.

| Thickness (mm) | Number of Layers | Stacking Sequence |
|---|---|---|
| 0.25 | 24 | [0/30/60/90] |
| 0.3 | 28 | [45/−45/0/90] |
| 0.35 | 32 | [45/30/−30/−45] |
| 0.4 | 36 | [60/45/−45/−60] |
| 0.45 | | |
| 0.5 | | |
| 0.6 | | |

Similar to the experiments conducted numerically for the carbon/epoxy plates, 108 experiments were performed for the glass/epoxy plates as well. The combinations were not all similar but the initial 48 experiments were kept. All the results are listed in the Appendix A from Table A. 1 to Table A. 8.

Effects of Fiber Material

In this study, only two materials have been selected for the comparison. The material properties are listed in the Tables 3, 5 and 7 for the carbon/epoxy composite plate and for the glass/epoxy in the Tables 4, 6 and 8. The simulations were designed such that a direct comparison may be obtained between the absorbed energy by the two materials. The elastic moduli of the carbon fiber system are greater than the glass fiber system. Also, the difference in the strength levels is also considerably high in favor of carbon based composites as well as the intralaminar fracture toughness values. The damage mechanism mentioned in the equations (3.3) to (3.6) is based upon the strength levels of the composite. Once, the damage is initiated the cracks propagate through the material which is modeled using the linear energy based damage evolution model. According to the material properties, the carbon/epoxy system should be better than the glass/epoxy system in terms of impact performance as both the strength and the fracture energies for carbon/epoxy is higher.

The results from the simulation were intuitive as the carbon/epoxy composite plate has better impact resistance compared to glass/epoxy composite plate at the same conditions of thickness, stacking sequence and boundary conditions.

FIGS. 15A-15D illustrate that the composite plates of CFRP are better against impact loads compared with the GFRP. This has already been explained above is due to the higher strength and the fracture energies of the carbon/epoxy. The results listed in the tables in Appendix A for the composite plates demonstrates that the composite plates fail completely at the thickness level of less than 6 mm for GFRP while that of CFRP may withstand the same impact load at around 2 mm.

Effects of Thickness of Plate

The sensitivity analysis showed that the biggest single factor in the impact performance of composite structures is the overall thickness of the plate or the pipe. In this section, the effect of thickness of both CFRP and GFRP plates are discussed.

From the results of sensitivity analysis, it is observed that the increasing thickness reduces the amount of absorbed energy.

A) Carbon/Epoxy Plates

This trend may be observed in the graphs for the various thicknesses for carbon/epoxy plates shown in the FIGS. 16A-16D.

The results from the ABAQUS analysis follow the intuition that with the increasing thickness the amount of absorbed energy will decrease i.e. an improvement in the impact performance of the composite plate. The results as plotted against the overall thickness of the plate show that they follow a certain trend and as a basic trial, a simple fourth order polynomial was fitted over the scattered data. The curve approximates quite accurately except for a few results which were away from the trend line.

Figure 17:
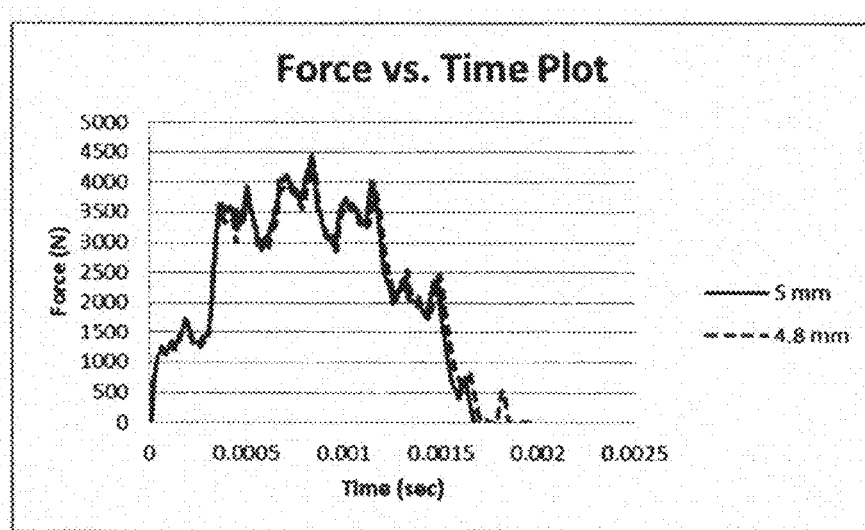
FIG. 17 illustrates a force vs. time plot of CFRP plates of two different thicknesses using the [0/30/60/90] laminate configuration.
Figure 18A:
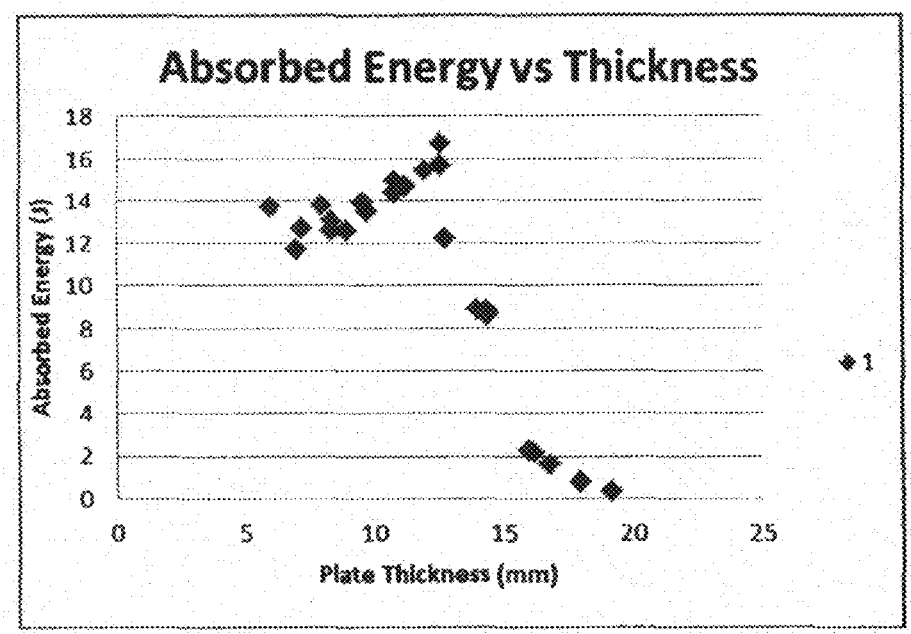
FIG. 18A illustrates scatter data for layer configuration 1 for glass/epoxy plates.
Figure 18B:
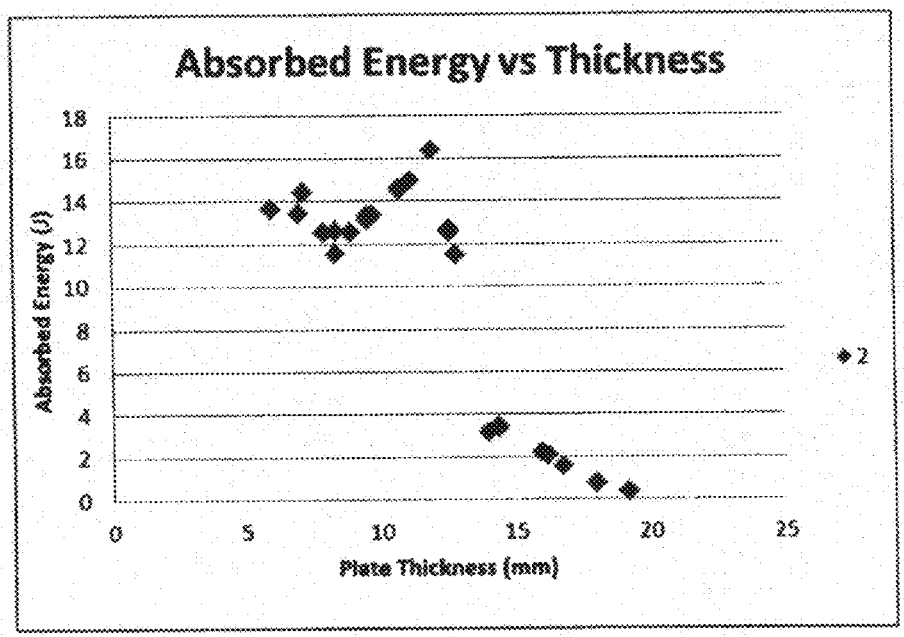
FIG. 18B illustrates scatter data for layer configuration 2 for glass/epoxy plates.
Figure 18C:
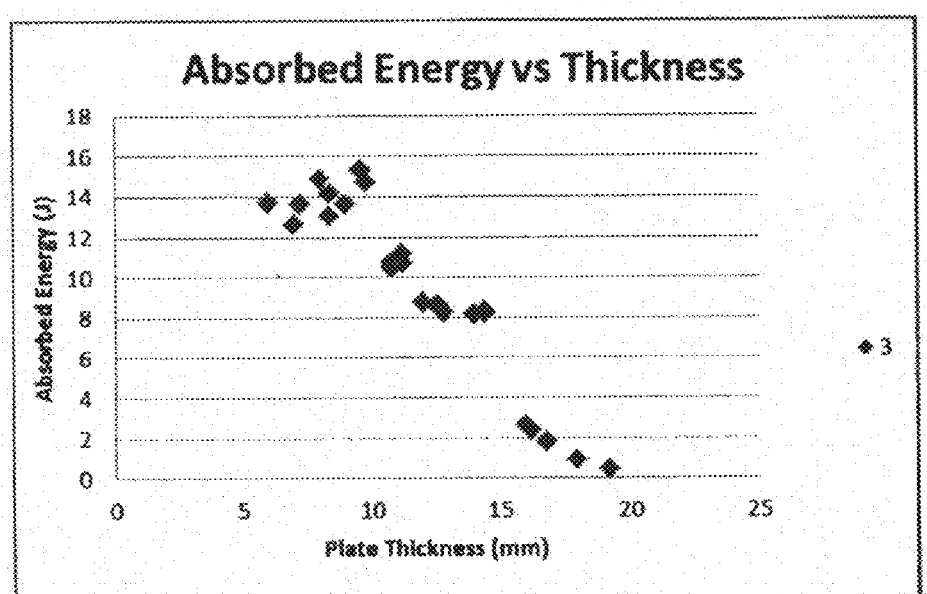
FIG. 18C illustrates scatter data for layer configuration 3 for glass/epoxy plates.
Figure 18D:
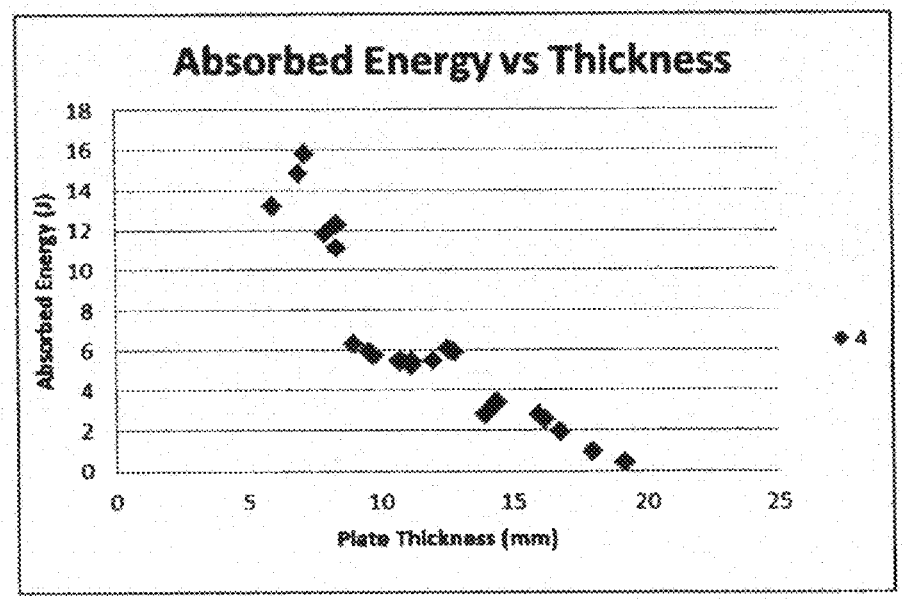
FIG. 18D illustrates scatter data for layer configuration 4 for glass/epoxy plates.

FIG. 17 illustrates a force vs. time plot of CFRP plates of two different thicknesses using the [0/30/60/90] laminate configuration.

B) Glass/Epoxy Plates

It was expected that the composite plates with glass fiber as the reinforcement material will behave in a similar fashion as the carbon fiber based plates did. However, it was found that the behavior of the glass/epoxy plates was a little peculiar as initially with the increase in thickness the absorbed energy reduced, therefore, improving the performance of the composite plates against the low velocity impact loads. However, a further increase in the overall thickness of the plate either by means of increase in layer thickness or by increasing the number of layers resulted in the decrease in performance. This behavior is strange and as compared with carbon/epoxy system was not observed in those cases. This behavior is clearly seen for all the different cases of stacking sequence. But, there is a thickness value beyond which the impact resistance starts to increase again and eventually the plate although at very large thickness performed without significant damage. These results are presented in the graphical form in the FIGS. 18A-18D.

Physically, this phenomenon may be explained such that when the thickness of the composite plate is small, the plate behaves much more like a membrane and during impact the plate stretches until all the kinetic energy is transferred to the plate and then it pushes back the impactor giving away some of the energy back to the impactor and the rest is dissipated in the form of damage within the plate. The more the thickness of the plate is increased, the stiffer it gets and the ability to bend under impact loads is reduced which increases the bending stress and hence the plate suffers more damage. At very high thickness, the plate becomes very strong and stiff which results in very low amounts of energy absorbed.

This large increase in the absorbed energy at the intermediate thickness range may be explained by the concept that the flat plates with small thickness acts like a membrane and in such thin plates the compression failure in the plane of the plate or through the thickness cannot be observed. In such cases, the maximum deformation is higher than the plate thickness [26]. This may be observed in this case as well, for example, if one considers the cases number 1 and 2 from the Table A. 5, the plate with thickness 6 mm absorbs less energy than the plate with 7.2 mm. The maximum deformation in the case 1 here was found to be 8.7 mm which is more than the plate thickness while the maximum deformation is about 6.5 mm in the case of plate with 7.2 thickness. Another interesting point observed was the calculation of the A, B and D matrices defined in the equations (4.12) to (4.16). It was observed that irrespective of the stacking sequence, the increase in absorbed energy was coincident with the same values of the sum of the members of the extensional stiffness matrix A. It is to be noted that the extensional stiffness matrix provides the relationship between the strains and the forces for the laminate. This value was quantified to be in the range of 330 to 450 GPa-m.

The same effect may be observed in the carbon/epoxy plates but because the fracture energies are high for carbon, the increase in absorbed energy with the increase in thickness is not high. Although, in some cases in FIGS. 16A-16D, where the amount of energy to increase slightly or at least didn't decrease by the same percentage as was expected.

Figure 19A:
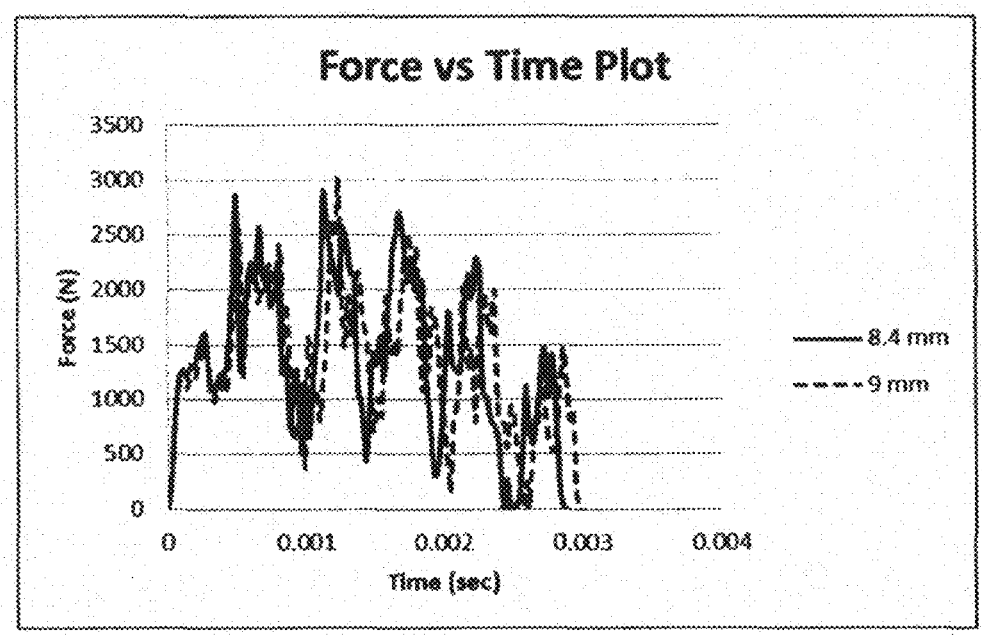
FIG. 19A illustrates a force vs. time plot of GFRP plates of two different thicknesses using [45/−45/0/90] laminate configuration.

FIG. 19A illustrates a force vs. time plot of GFRP plates of two different thicknesses using [45/−45/0/90] laminate configuration.

Figure 19B:
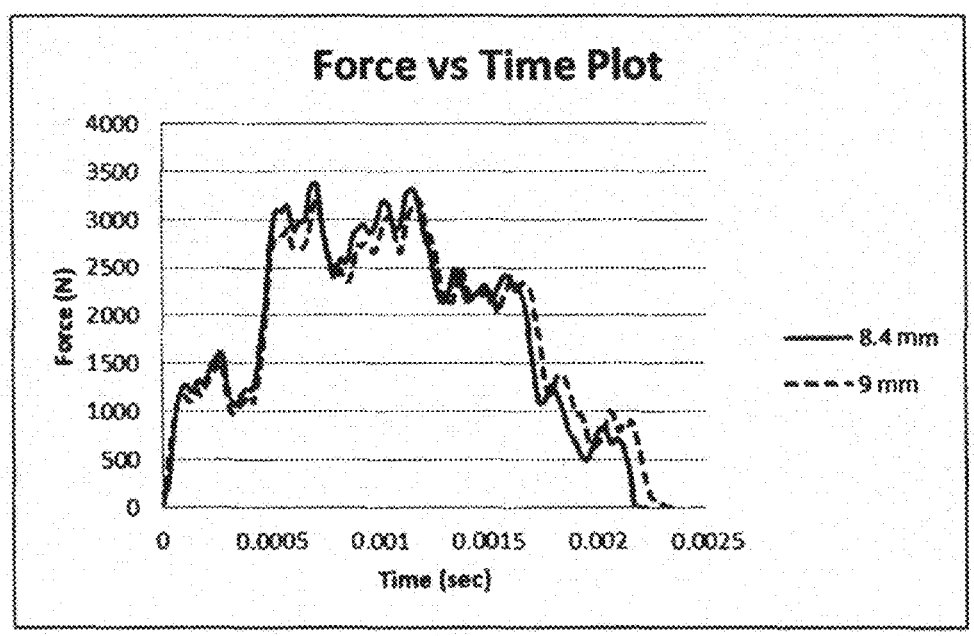
FIG. 19B illustrates a force vs. time plot of GFRP plates of two different thicknesses using [45/−45/0/90] laminate configuration with fracture energy of 40 kj/m$^2$.

A comparison of force history graphs for two carbon/epoxy laminates and two glass/epoxy laminates show that in the glass/epoxy plates the sharp falls in the force. A sudden fall in the force represents the onset of damage until the impact load is supported by the layers so far remain undamaged. In carbon/epoxy plates, the fall in force is not that high before it starts to increase which shows that after the initiation of damage it doesn't propagate so quickly. This is due to the high fracture energies of the carbon fiber. Whereas the glass/epoxy plates show a much steeper fall in the force values. This represents that the damage once initiated may propagate quite easily, that is due to the low fracture energies of the glass fiber. A comparison of the fracture energies shows that glass has $\frac{1}{16}^{th}$ of the fracture energies of the carbon. To better understand this cause, a similar glass/epoxy plate as shown in FIG. 19B was simulated with 4 times the initial fracture energy only in the tensile fiber direction. The phenomenon that impact performance deteriorates in these samples with the larger thickness was still observed but this time the difference in the amount of absorbed energies is quite low and also the force history graphs are close to the one of carbon/epoxy.

Effects of Stacking Sequence

The stacking sequence of composite laminas is the arrangement of the individual layers in specific orientation.

The ability of arranging layers according to the design gives the special advantage to composite materials over the conventional isotropic materials in better load handling capabilities. In this study, four different stacking sequences were studied. These stacking sequences are arrangement of 4 layers mentioned in Tables 25 and 26 in various directions which were then repeated to achieve the desired thickness and number of layers.

Figure 20A:
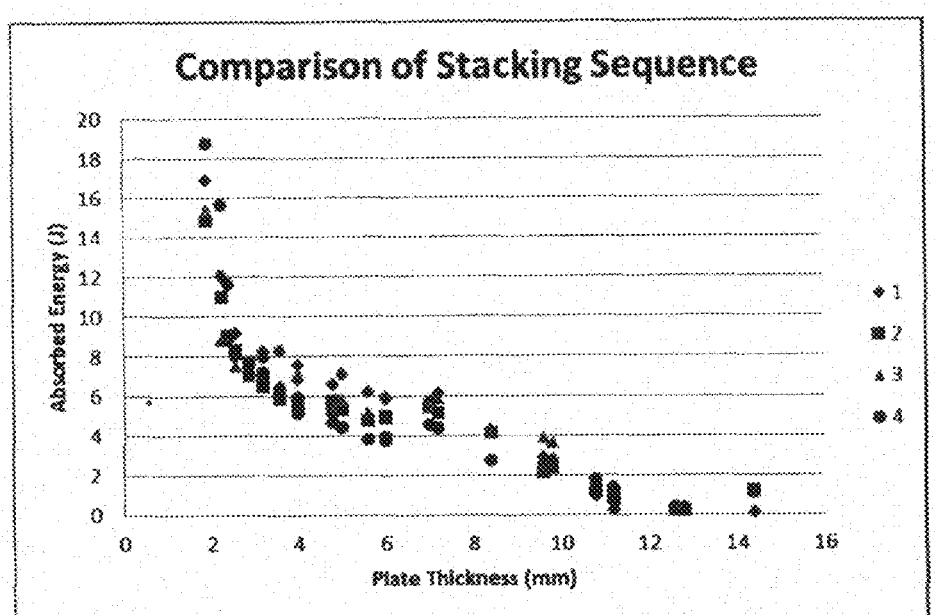
FIG. 20A illustrates absorbed energy vs. thickness for stacking sequences 1-4 for carbon/epoxy systems.
Figure 20B:
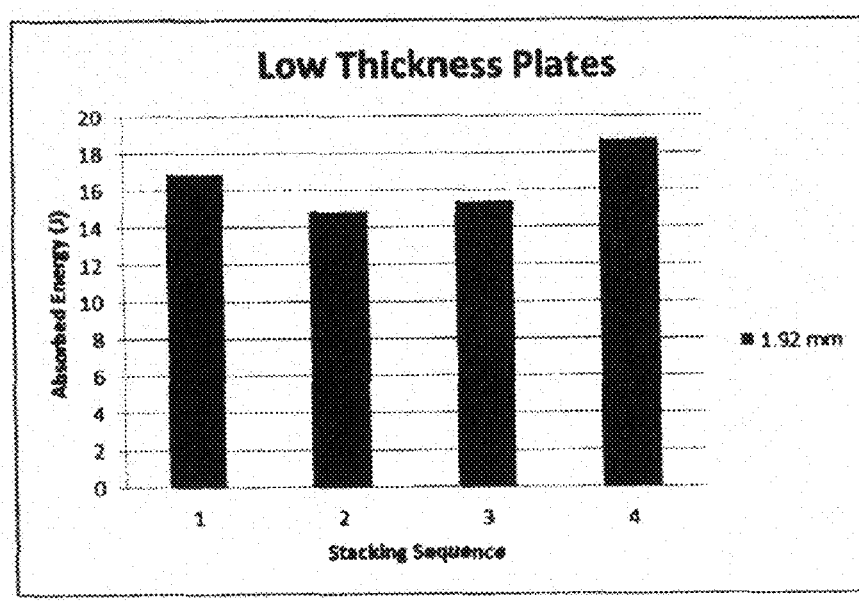
FIG. 20B illustrates a comparison of absorbed energy for stacking sequences for thin CFRP plates.

FIGS. 20A and 20B illustrate absorbed energy vs. thickness for stacking sequences 1-4 for carbon/epoxy systems. In particular, FIG. 20A plots the amount of absorbed energy for all the stacking sequences studied for this work. FIG. 20B illustrates a comparison of absorbed energy for stacking sequences for thin CFRP plates.

From these plots, it is observed that for the thinnest plates, the worst stacking sequence was 4 while the best was stacking sequence 1. This is in-line with the current research where the quasi-isotropic behavior of laminate configuration of stacking sequence 1 is suggested to be the best against the low-velocity impacts. This suggestion is correct considering the stacking sequence 1 laminate configuration distributes fibers equally in both the principal directions which are the main load bearing component in the composite materials and have equal stiffnesses in the x and y directions. The other two stacking sequences lie in between the stacking sequences of 2 and 4.

Figure 20C:
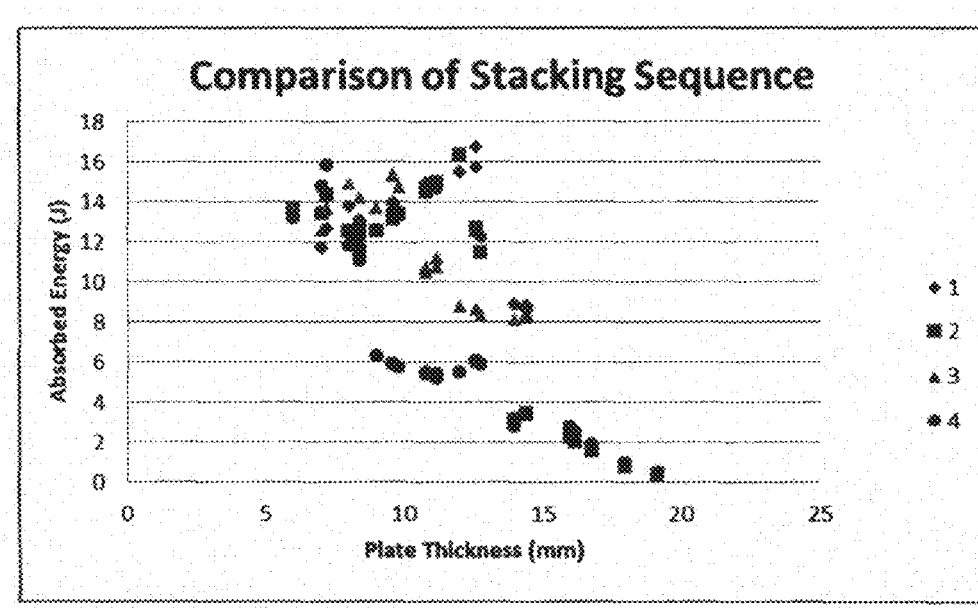
FIG. 20C illustrates absorbed energy vs. thickness for stacking sequences 1-4 for carbon/epoxy systems.
Figure 20D:
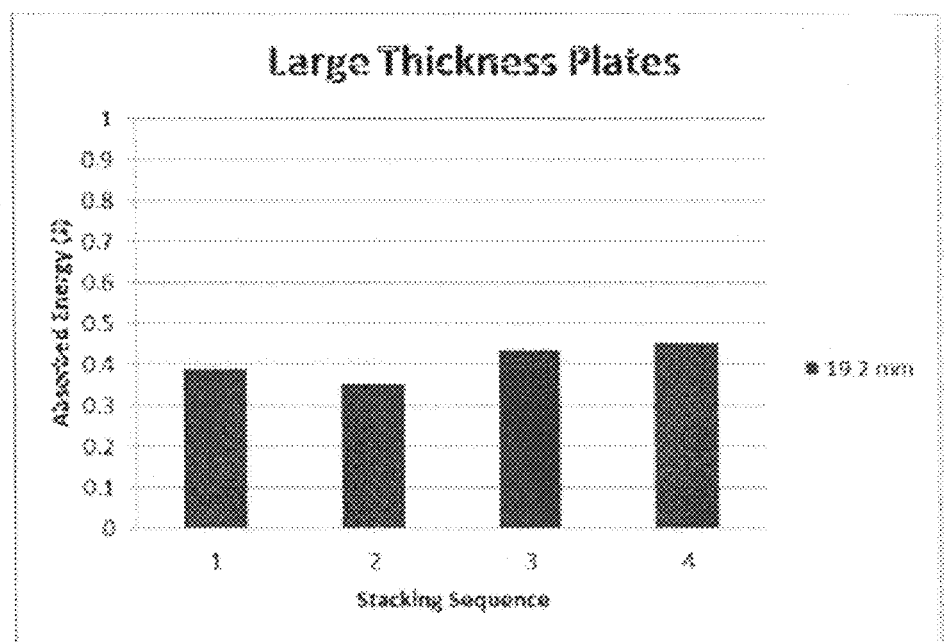
FIG. 20D illustrates a comparison of absorbed energy for stacking sequences for thick GFRP plates.

Further increasing the thickness provides more insight into the effects of stacking sequence. Here, it may be observed that in the intermediate thickness range for the carbon/epoxy plates, the best laminate configuration or the stacking sequence is the sequence number 4. However, at larger thicknesses, there is not much of a difference. FIG. 20C shows the similar behavior for the glass/epoxy plates FIG. 20D illustrates a comparison of absorbed energy for stacking sequences for thick CFRP plates.

Even for the glass/epoxy plates the stacking sequence 4 is better in terms of the absorbed energy for the moderately thick plates. This is due to the fact that the most important factor in the damage limitation is having a high tensile strength in the fiber directions. Therefore, to avoid damage due to the impact loads, the fibers should be aligned in the direction where the maximum stress is observed. If you recall the boundary conditions that were applied for the numerical model as shown in FIG. 7A, it was on the two shorter edges of the plate which makes the plate constrained in the global y-axis direction. The reason that the stacking sequence 4 has better performance is down to this reason, since it has more fibers aligned towards the y-axis and it may withstand more loads in this direction. A simple calculation of the transformation of the strengths in the x and y-axis direction show that the stacking sequence 4 has the highest strength in the y-direction followed by sequence 2. Therefore, this stacking sequence offers better performance especially in the intermediate thickness plates where the others were facing more damage.

Alternative explanations for this kind of behavior may be find in the study by Zhao et al. [73], where they observed that the maximum damage size and the maximum deflection of the composite plate decreases with the increase in the bending stiffness of transverse direction. The bending stiffness may be calculated using the equations provided earlier for the A, B and D matrices, where D matrix represents the bending stiffness matrix. Zhao et al. reported that the best stacking sequence would be the one in which the longitudinal and transverse stiffness are equal. This is true in the case where one has similar boundary conditions on all the edges. If, one has boundary conditions different on different directions, then one may optimize the stacking sequence as is in this case the sequence 4 provides the best solution according to the given boundary conditions.

Effects of Layer Thickness and Number of Layers

Sensitivity analysis results suggested that the number of layers have some effect on the impact performance of the composite plates. From the sensitivity analysis, it was observed that if the overall thickness of the plate is remained constant but the numbers of layers vary, then the amount of energy absorbed will be varied. The results as listed in the Table A. 1 to Table A. 8 suggest that this is indeed the case. But, the variation is not always as initially observed from the sensitivity analysis. The variation in the amount of absorbed energy depends upon the orientation of individual layers that are added to or removed from the stacking in compensation to keep the thickness constant.

If one considers the two cases from the carbon/epoxy plates with the same thickness but different number of layers, one observes some interesting results. It may be observed that the in case where one has 20 layers, there are four additional layers of 0° and 30° two each. As discussed earlier during the effects of stacking sequence, these four additional layers are just keeping the overall thickness constant but in fact are reducing the number of fibers from the layers of 60° and 90°. As you by now know that these layers when transformed along the principal directions share larger share of the strength in the y-axis where it was deduced that the majority of the stress would be produced. Hence, the observation in this case is that the additions of these 0° and 30° layers are doing more harm than good. As may be seen in from the amount of energy absorbed increased in the case of 20 layers compared to the case of 16 layers.

Figure 21A:
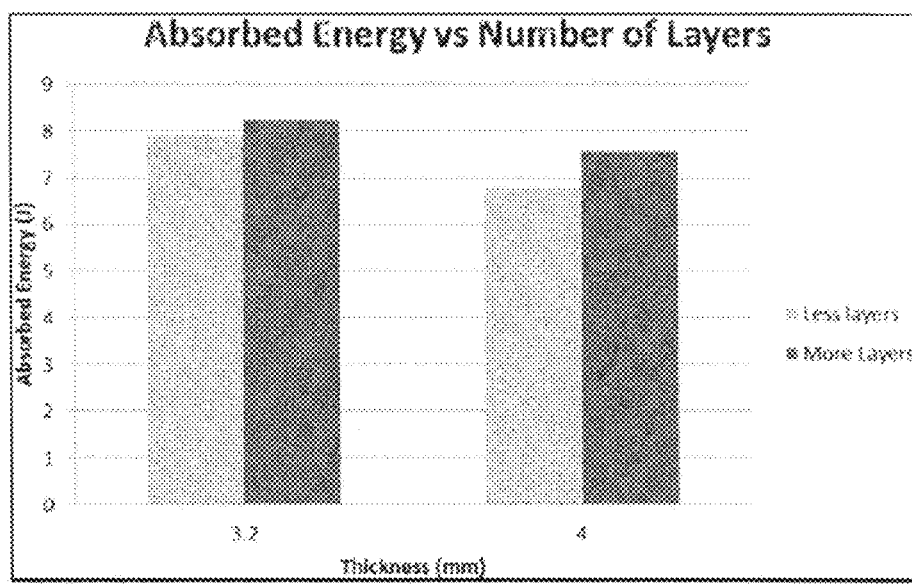
FIG. 21A illustrates a comparison of an amount of absorbed energy for CFRP plates with 16 layers and CFRP plates with 20 layers.

FIG. 21A illustrates a chart that compares an amount of absorbed energy for CFRP plates with 16 layers and CFRP plates with 20 layers.

TABLE 27

Orientation of individual layers for two cases of carbon/epoxy plate

| Thickness of layer (mm) | Number of Layers | Total Thickness (mm) | Absorbed Energy (J) |
|---|---|---|---|
| 0.16 | 20 | 3.2 | 8.227648 |
| 0.2 | 16 | 3.2 | 7.894729 |
| 0.25 | 16 | 4 | 6.78549 |
| 0.2 | 20 | 4 | 7.570117 |

Figure 21B:
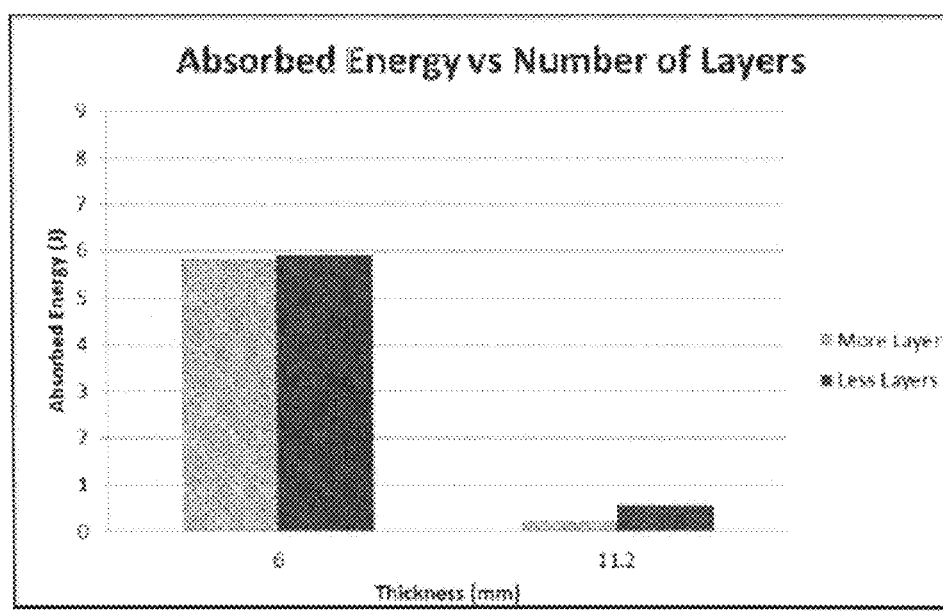
FIG. 21B illustrates a comparison of an amount of absorbed energy based on a number of layers for GFRP plates with a fixed thickness.

By virtue of the above explanation, it might be argued that if one increases the number of layers keeping the thickness constant in such a way that some of the fibers from the 0° and 30° layers are removed and added to 60° and 90° orientated layers, then one might observe improvement in the impact performance. By comparing the results from Table 28 and FIG. 21B, it is observed that is indeed the case.

TABLE 28

Orientation of individual layers for two cases of carbon/epoxy plate.

| Thickness of layer (mm) | Number of Layers | Total Thickness (mm) | Absorbed Energy (J) |
|---|---|---|---|
| 0.3 | 20 | 6 | 5.915478 |
| 0.25 | 24 | 6 | 5.849285 |
| 0.35 | 32 | 11.2 | 0.2031 |
| 0.4 | 28 | 11.2 | 0.56125 |

Figure 21C:
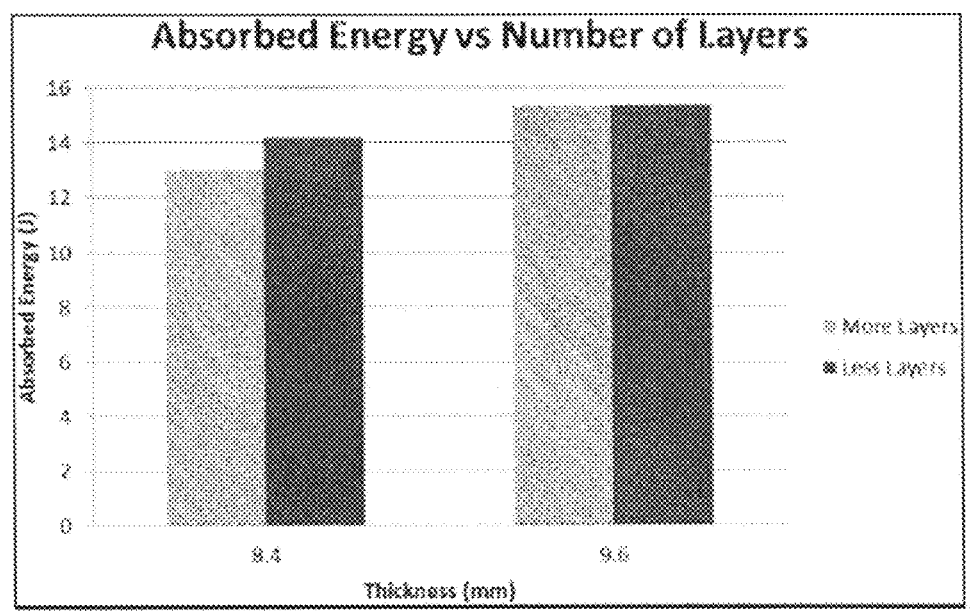
FIG. 21C illustrates a comparison of GFRP plates with an increase in performance and an increase in layers.
Figure 21D:
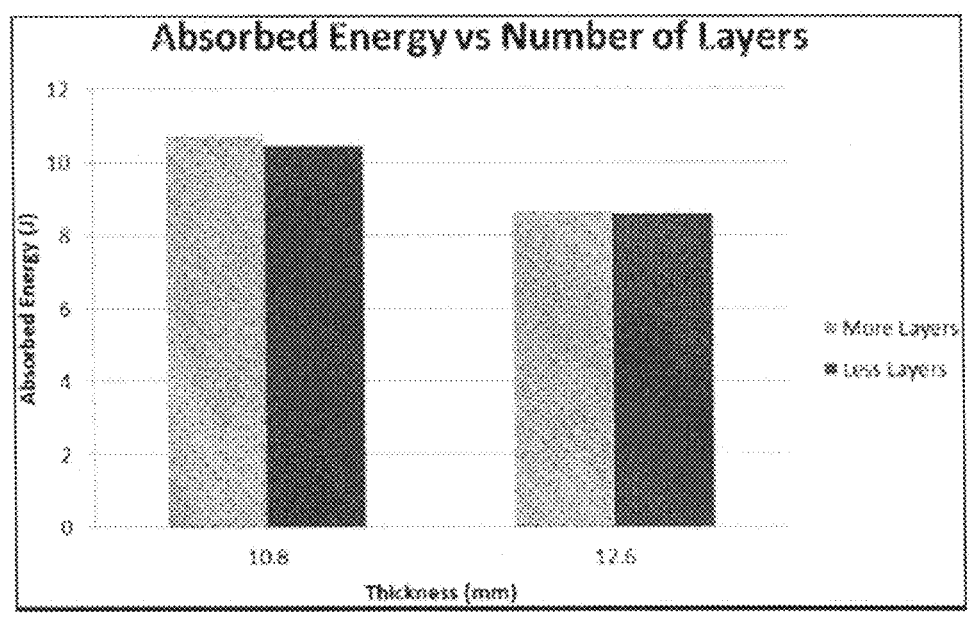
FIG. 21D illustrates a comparison of GFRP plates with a decrease in performance and an increase in layers.
Figure 22A:
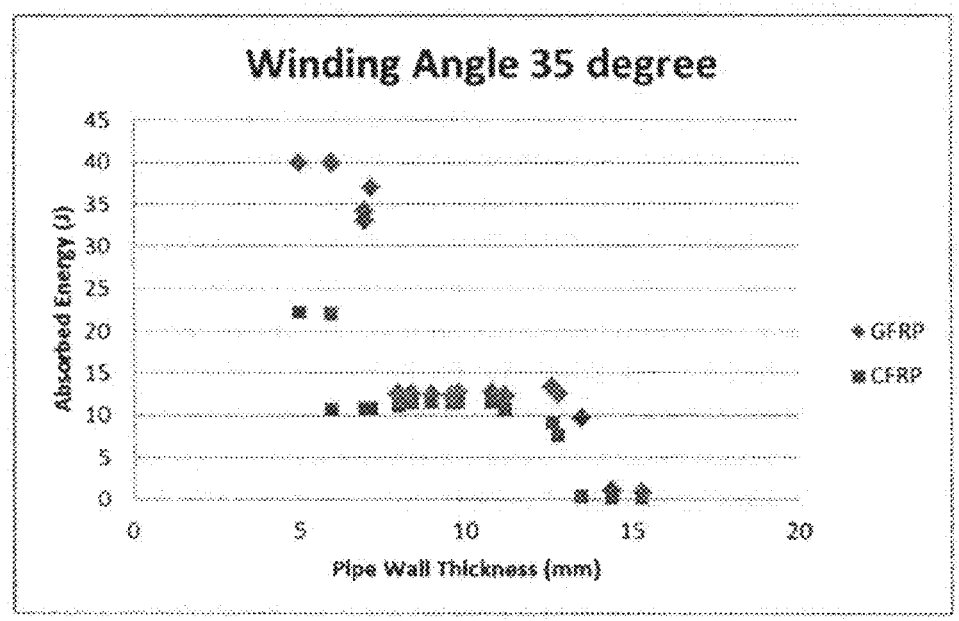
FIG. 22A illustrates absorbed energies for CFRP and GFRP pipes with an 35° winding angle.
Figure 22B:
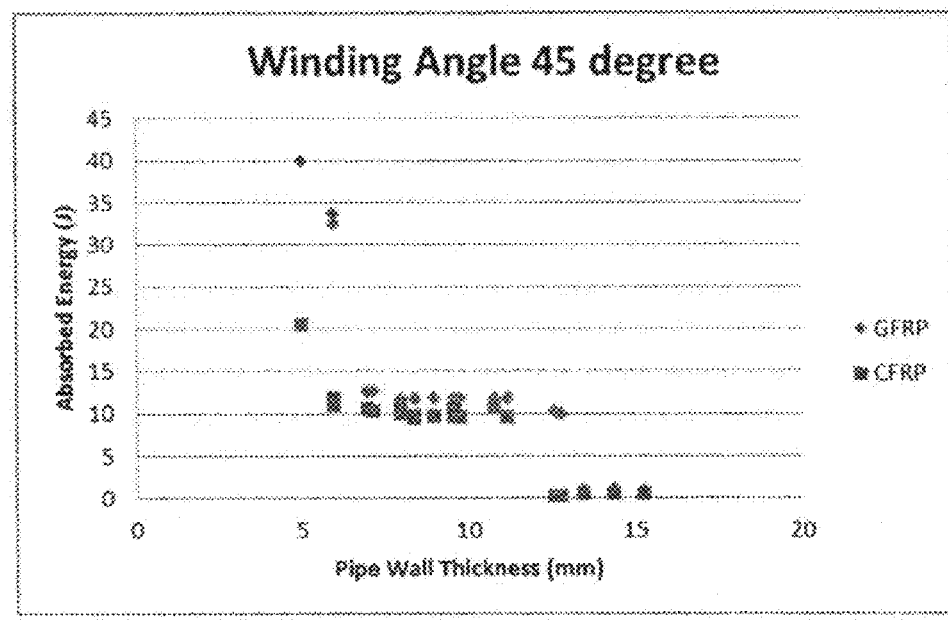
FIG. 22B illustrates absorbed energies for CFRP and GFRP pipes with an 45° winding angle.
Figure 22C:
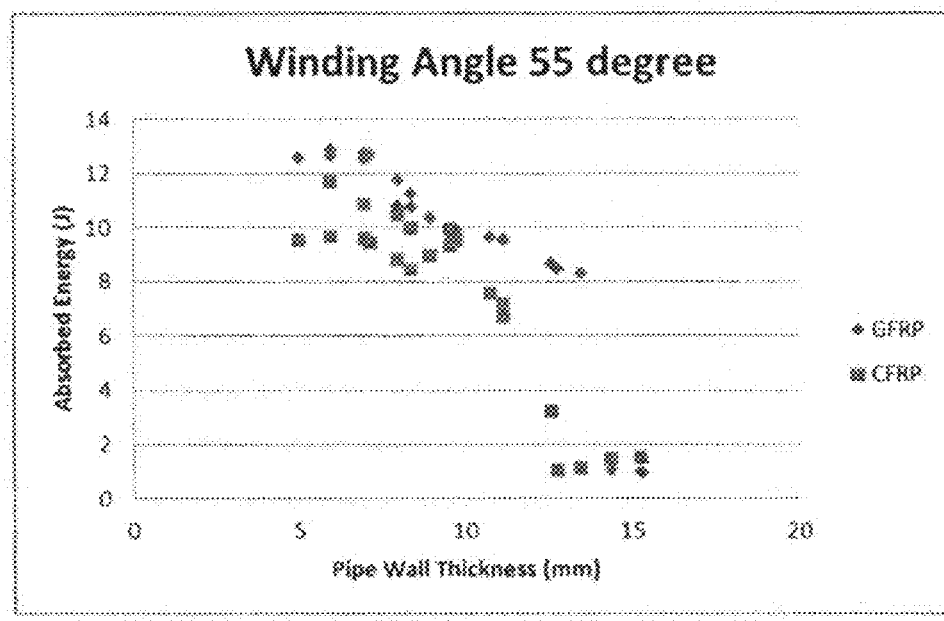
FIG. 22C illustrates absorbed energies for CFRP and GFRP pipes with an 55° winding angle.
Figure 22D:
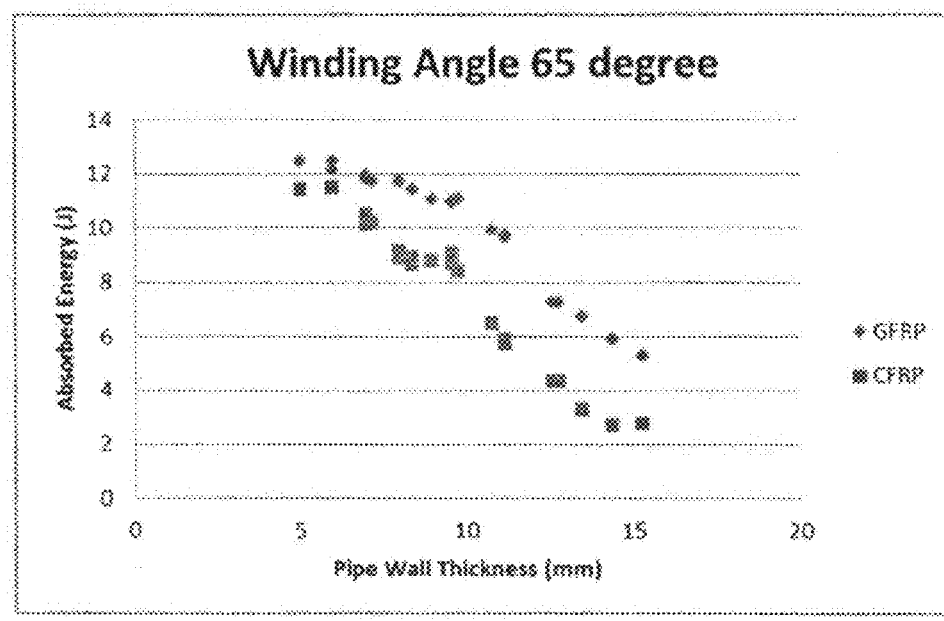
FIG. 22D illustrates absorbed energies for CFRP and GFRP pipes with an 65° winding angle.
Figure 22E:
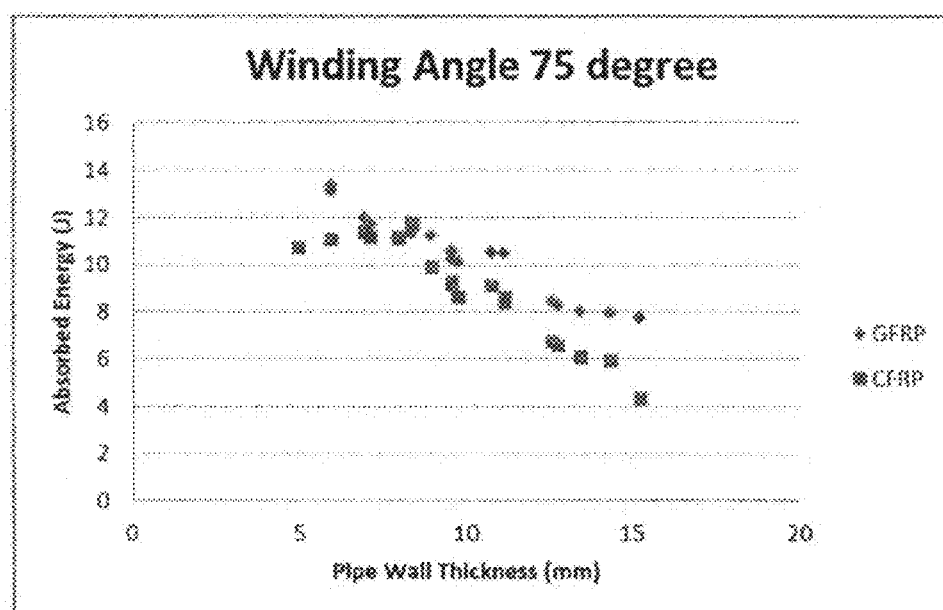
FIG. 22E illustrates absorbed energies for CFRP and GFRP pipes with an 75° winding angle.
Figure 23A:
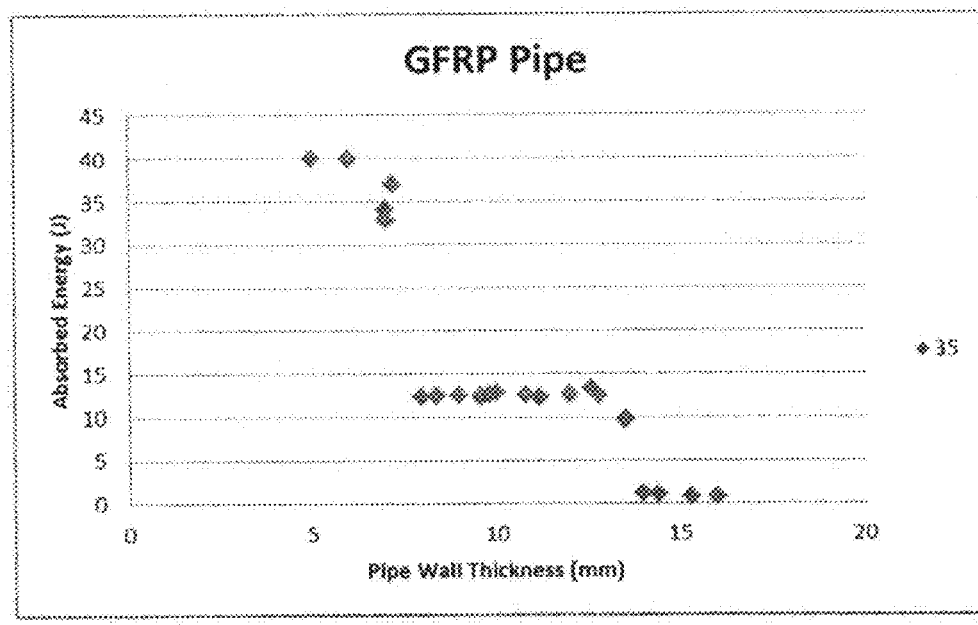
FIG. 23A illustrates absorbed energy vs. thickness of a plate for 35° winding angle GFRP pipes.
Figure 23B:
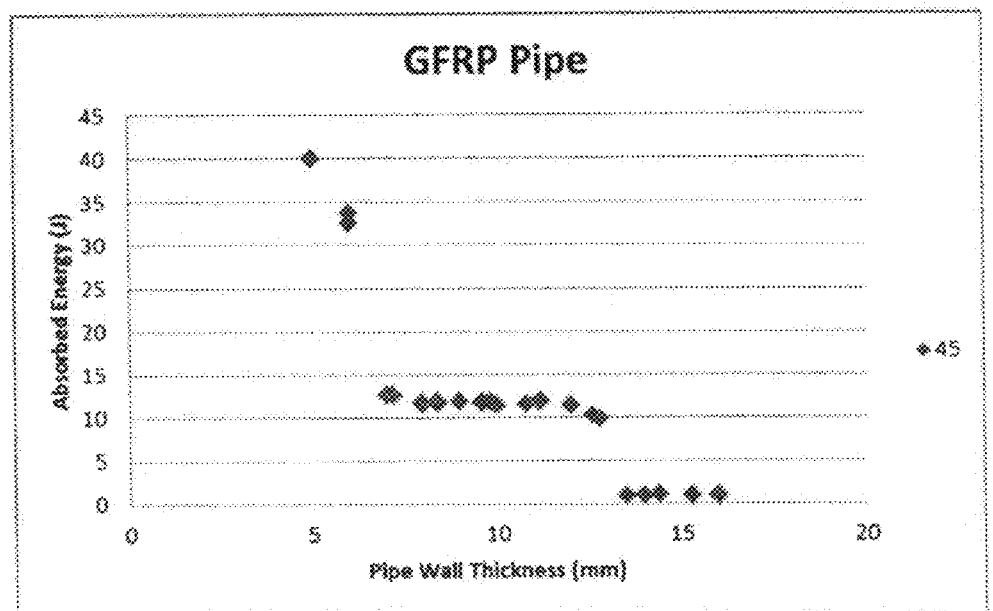
FIG. 23B illustrates absorbed energy vs. thickness of a plate for 45° winding angle GFRP pipes.
Figure 23C:
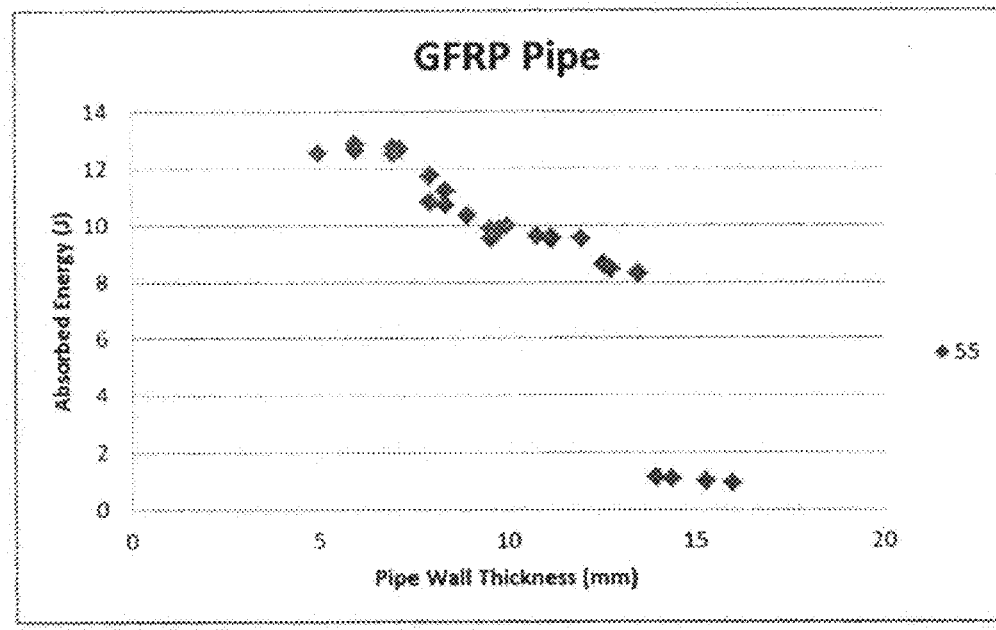
FIG. 23C illustrates absorbed energy vs. thickness of a plate for 55° winding angle GFRP pipes.
Figure 23D:
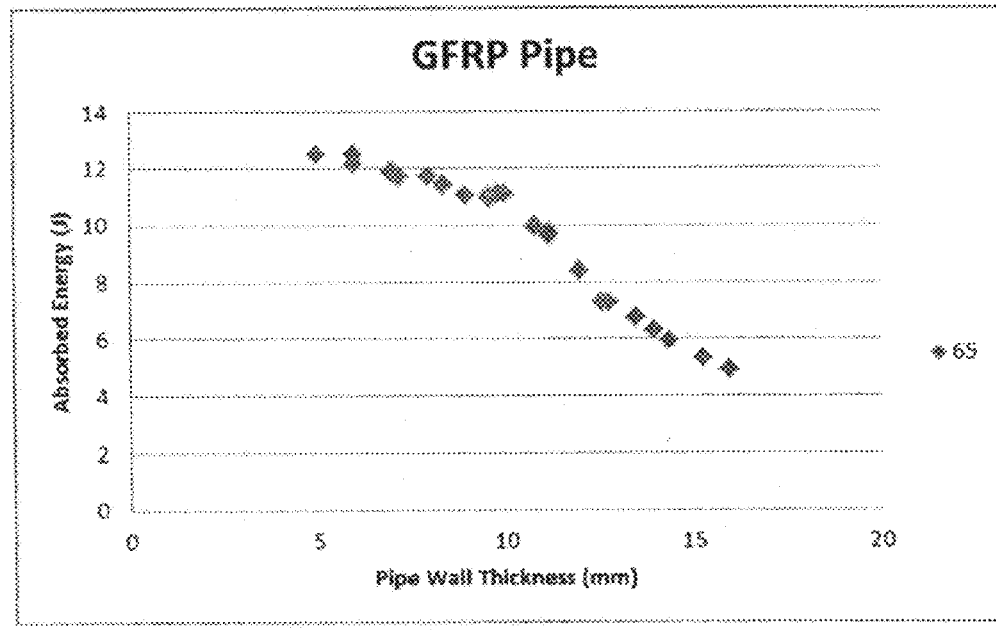
FIG. 23D illustrates absorbed energy vs. thickness of a plate for 65° winding angle GFRP pipes.
Figure 23E:
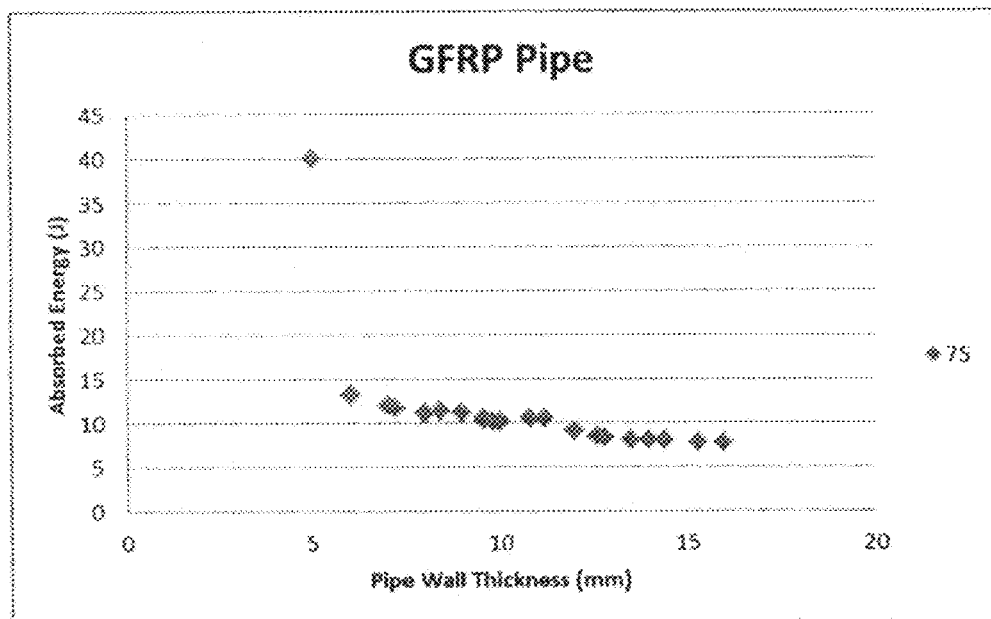
FIG. 23E illustrates absorbed energy vs. thickness of a plate for 75° winding angle GFRP pipes.
Figure 23F:
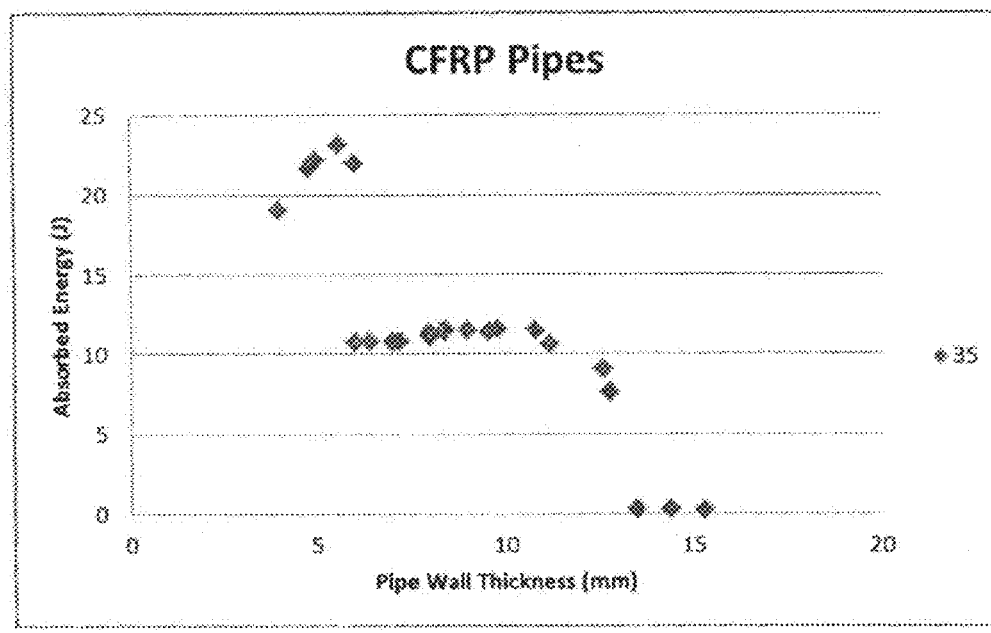
FIG. 23F illustrates absorbed energy vs. thickness of a plate for 35° winding angle CFRP pipes.
Figure 23G:
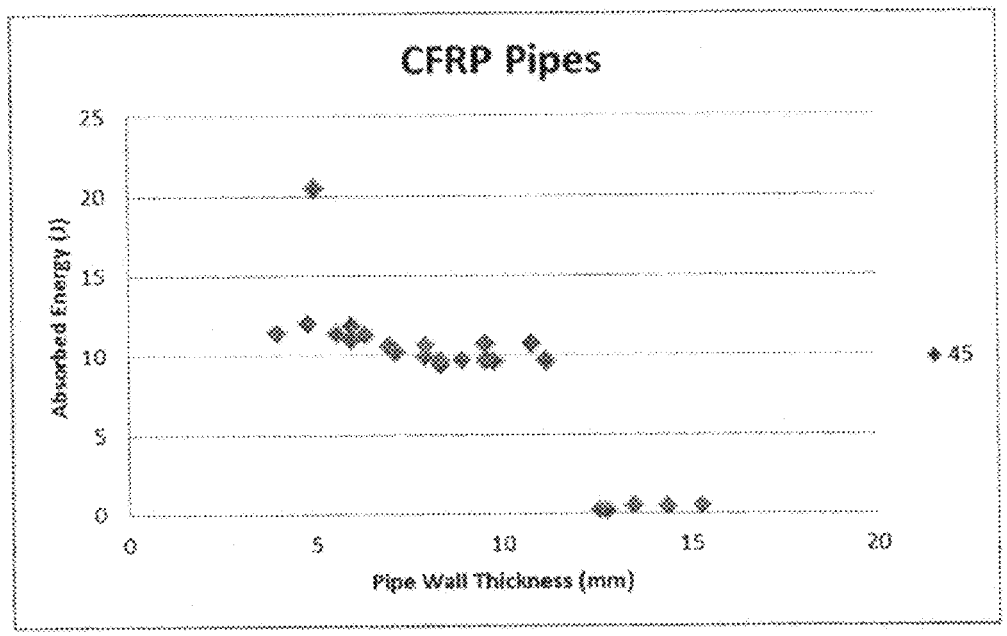
FIG. 23G illustrates absorbed energy vs. thickness of a plate for 45° winding angle CFRP pipes.
Figure 23H:
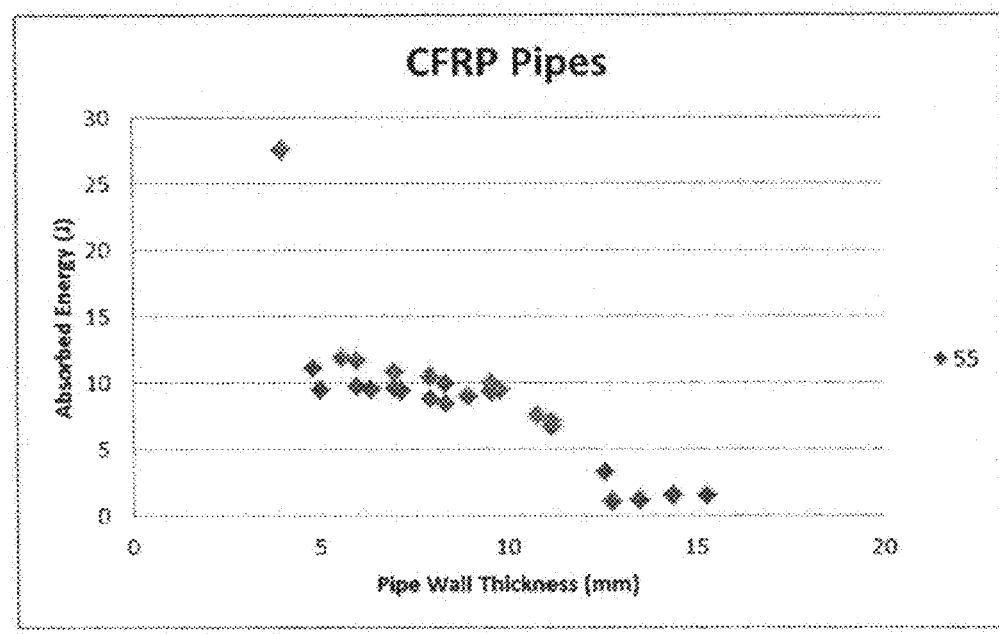
FIG. 23H illustrates absorbed energy vs. thickness of a plate for 55° winding angle CFRP pipes.
Figure 23I:
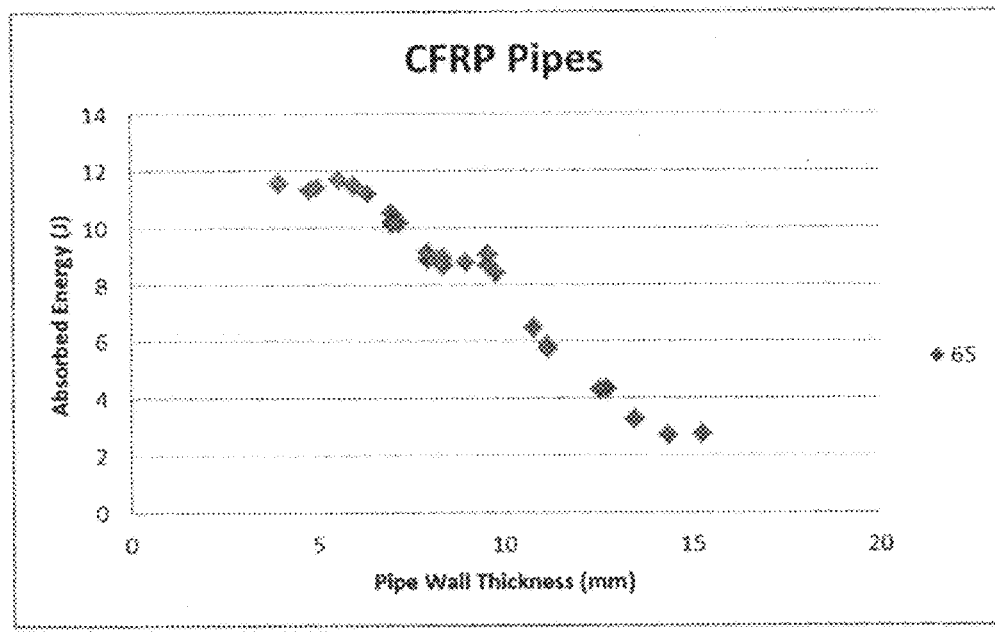
FIG. 23I illustrates absorbed energy vs. thickness of a plate for 65° winding angle CFRP pipes.
Figure 23J:
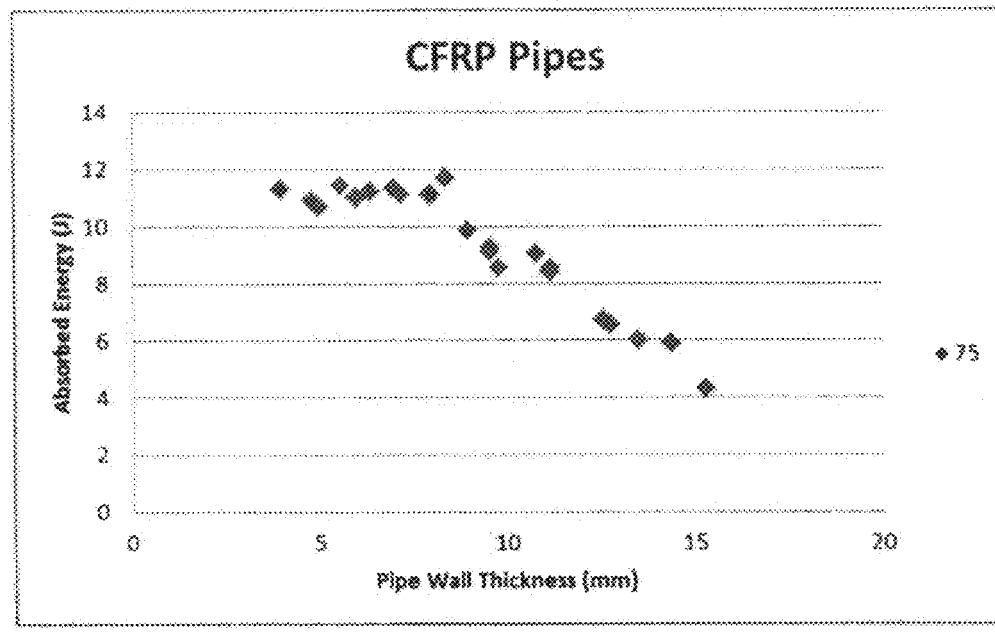
FIG. 23J illustrates absorbed energy vs. thickness of a plate for 75° winding angle CFRP pipes.

The same behavior may be observed for the glass/epoxy plates as demonstrated from the results in Table 29 and FIG. 21C for the situation where the addition of layers results in the improvement of impact performance. This is due to the same reason as explained above that this is due to the addition of layers which may bear more load in the direction of the stress and hence improve the overall impact performance. While Table 30 and FIG. 21D represents the case where the addition of layers decrease performance.

TABLE 29

Orientation angles of GFRP plates where increasing layers increase performance.

| Thickness of layer (mm) | Number of Layers | Total Thickness (mm) | Absorbed Energy (J) |
|---|---|---|---|
| 0.35 | 24 | 8.4 | 14.20262381 |
| 0.3 | 28 | 8.4 | 13.02287113 |
| 0.3 | 32 | 9.6 | 15.32878983 |
| 0.4 | 24 | 9.6 | 15.3788138 |

TABLE 30

Orientation angles of GFRP plates where increasing layers decrease performance.

| Thickness of layer (mm) | Number of Layers | Total Thickness (mm) | Absorbed Energy (J) |
|---|---|---|---|
| 0.3 | 36 | 10.8 | 10.72389162 |
| 0.45 | 24 | 10.8 | 10.4629225 |
| 0.35 | 36 | 12.6 | 8.650227096 |
| 0.45 | 28 | 12.6 | 8.588431527 |

Numerical Experiments for Composite Pipes

Following on from the study of effects of the parameters on the impact performance of the composite plates, the study is carried out for the composite pipes as well. The factors that have influence on the impact performance are the same as found from the sensitivity analysis study and one also studied their effects for the composite plates as well. The difference between plates and the pipes is in the type of lamina and the lamina's orientation angle. Since, it is known that the composite pipes are manufactured using the filament winding technique, the type of lamina considered in this study is the unidirectional lamina. The material properties for carbon/epoxy and glass/epoxy are listed in the Tables 9, 11 and 13 and Tables 10, 12 and 14 respectively. Also, the pipes manufactured using filament winding technology have only two orientations, i.e., ±0, therefore here it was studied different winding angles rather than a combination of layer orientations as studied for the composite flat plates.

The design of experiments is again applied to gather the results for the composite pipes where the complete damage to the complete survival configurations is selected. The layer thickness is selected based on the commercial availability of carbon and glass fibers. The winding angle was selected from 35° to 75° with an interval of 10°. This is selected on the basis of the study of Rosenow [59] in which he studied the effect of variation of winding angles on the filament wound glass fiber reinforced polyester. The author studied winding angles from 15° to 85°. In his study, the author suggested that the winding angle of 55° was optimal for the hoop to axial stress ratio of 2, while for only pressure loadings without axial stress the optimal winding angle was 75°.

Initially, experiments were designed with 4 distinct layer thicknesses, 5 sets of number of layers and 5 different winding angles. This design gave a total of 100 simulations to be carried out. Later on, two additional layer thicknesses and a further set of simulations were run with total number of layers up to 40 for the glass fibers and 16 layers for the carbon fibers. These simulations were added for the reason to have all the variation from maximum damage to minimum damage. Also, after the initial simulations it was noted that more simulations should be tried around the mean angle of 55° and therefore 4 new winding angles were added. Table 31 and 32 give the values for all the selected factors for glass/epoxy and carbon/epoxy pipes respectively.

TABLE 31

DOE table for the GFRP pipes.

| Thickness | Number of Layers | Winding Angles |
|---|---|---|
| 0.25 | 20 | 35 |
| 0.3 | 24 | 45 |
| 0.35 | 28 | 50 |
| 0.375 | 32 | 52.5 |
| 0.4 | 36 | 55 |
| 0.425 | 40 | 57.5 |
|  |  | 60 |
|  |  | 65 |
|  |  | 75 |

TABLE 32

DOE table for the CFRP pipes.

| Thickness | Number of Layers | Winding Angles |
|---|---|---|
| 0.25 | 16 | 35 |
| 0.3 | 20 | 45 |
| 0.35 | 24 | 50 |
| 0.375 | 28 | 52.5 |
| 0.4 | 32 | 55 |
| 0.425 | 36 | 57.5 |
|  |  | 60 |
|  |  | 65 |
|  |  | 75 |

The load and the boundary conditions are applied as described in the numerical model earlier. The impact energy of 40 J was applied using an initial velocity given to the striker. In total, 162 different combinations were simulated for each glass and carbon fiber based composite pipes. The results are tabulated in the appendix A from Table A. 15 to Table A. 30. In total, 162 simulations were performed for each carbon and glass based composite pipes.

Effects of Fiber Material

Two types of materials carbon and glass are used as fiber reinforcement for the composite pipes. It is clear from the material properties Tables 9 to 14 presented earlier that the carbon fiber is much stronger than the glass fiber and also the fracture energies are higher for the carbon. For this reason, it may be argued that the CFRP pipes will perform better under impact loads than GFRP and indeed this is the case if one looks at the results presented in the Table A. 15 to Table A. 30. For the same geometric conditions, the amount of absorbed energy in the CFRP pipes is lower than that of GFRP pipes.

From the scatter plots of the two types of material presented in FIGS. 22A-22E, the observation that the carbon/epoxy pipes will perform better than the glass/epoxy pipes is correct. From these plots, it may also be observed that the difference in the amount of damage, which is the absorbed energy, is very high in thin walled pipes. But, in the moderately thick walled pipes, although the carbon pipes perform better but the difference is reduced. But, in very thick pipes, again the difference becomes quite significant.

Effects of Thickness

The increase in the overall wall thickness of pipe is assumed to be significant by virtue of the results previously observed in the sensitivity analysis approach and also the results from the analysis of flat plates demonstrated the same phenomenon. FIGS. 23A-23J illustrate the variation in the amount of absorbed energies for both the GFRP and CFRP pipes vs. thickness. It may be observed from these plots that there is a range of thickness values for all the winding angles and for both material types, during which the increasing thickness doesn't improve the impact performance. The same phenomenon was observed by Zhao et al. [73] in their study, they noticed that the damage threshold velocity was not affected by the increase in the thickness of the plates. They further reported that although the damage is almost unaffected but the damaged area reduced with the increase in the thickness of the plates. The same results may be deduced for this range of thickness values where there is no improvement in the impact resistance of the pipes. But, one does observe that after crossing this thickness range a sudden drop in the amount of absorbed energy which is not reported in the study of Zhao et al. as they studied only three cases for the thickness variations.

In all of these cases where the increase in thickness doesn't improve the impact resistance, it was observed that the vibration in the pipe increased. This as explained earlier for the case of flat plates, where it was observed an increase in the amount of absorbed energy is due to the fact that the overall stiffness of the structure increases with increase in the thickness but not sufficient enough. Hence, one observes vibrations which is the cause of more absorbed energy as explained by Krishnamurthy et al. [36] in their research that the energy absorbed upon impact is the sum of the strain energy and the kinetic energy of each of the modes of vibration.

Effects of Winding Angle

Figure 24A:
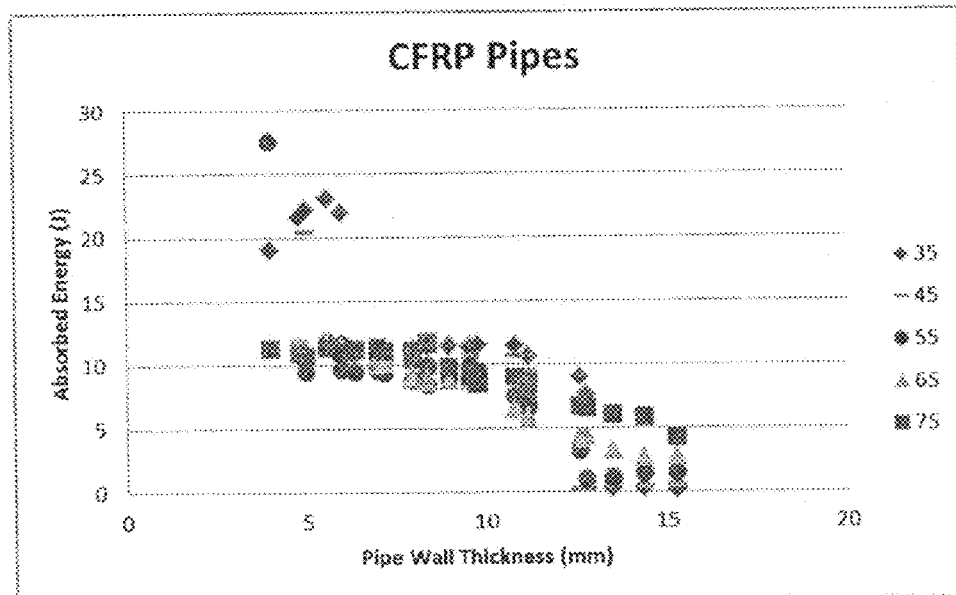
FIG. 24A illustrates absorbed energy for CFRP pipes with winding angles of 35°-75°.
Figure 24B:
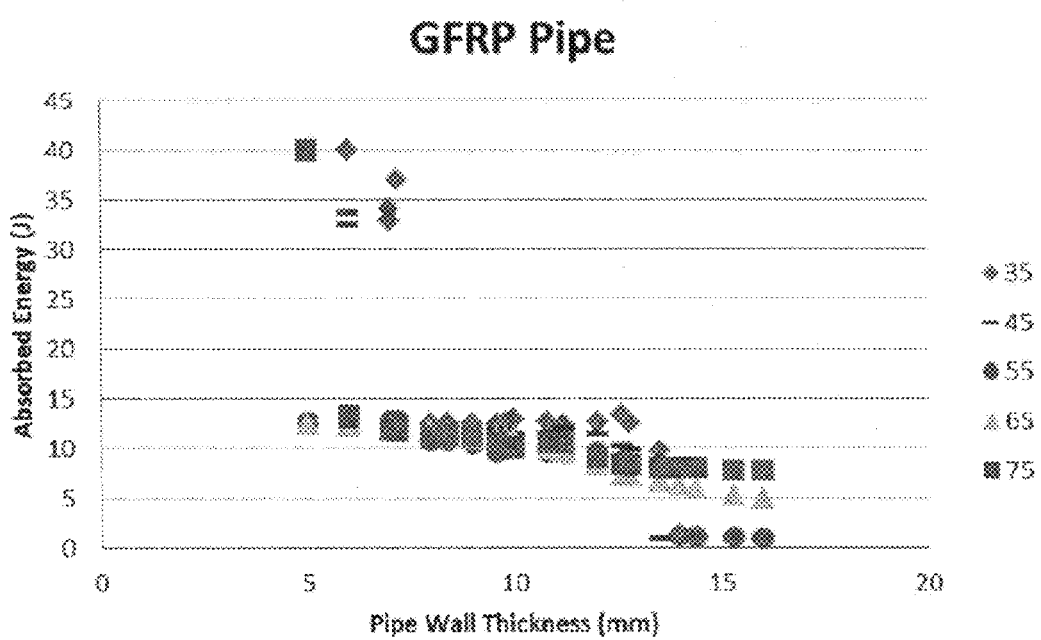
FIG. 24B illustrates absorbed energy for GFRP pipes with winding angles of 35°-75°.

The choice of the variation of the winding angle depended upon the study by Rosenow [59]. Based on the conclusions provided by Rosenow, 5 different winding angles from 35° to 75° with an interval of 10° were selected. The results show that the pipes with winding angles of 35° and 75° are particularly worse than the rest in handling the impact loads. The results are represented in the FIGS. 24A and 24B it is observed that in most of the cases the pipes with winding angle of 55° have the least absorbed energy and better impact resistance.

From the above graphs, it is clear that for most of the pipe thickness irrespective of the fiber material, the orientation of 55° performs better. In some cases, 45° and 65° winding angles were slightly better. In order to further examine, a further cases were simulated with angles ranging from 50°, 52.5°, 57.5° and 60°.

Close observation of these figures and the relevant tables in the appendix show that for glass fiber pipes, there is not much of a difference in terms of absorbed energy for smaller thickness pipes. However, when the thickness is increased the 55° winding angle pipes were better in performance compared to the rest. The observation is reversed for the carbon based pipes where at smaller thickness 55° were slightly better and increasing thickness results in slightly worse performance but the difference is not that much.

Figure 25A:
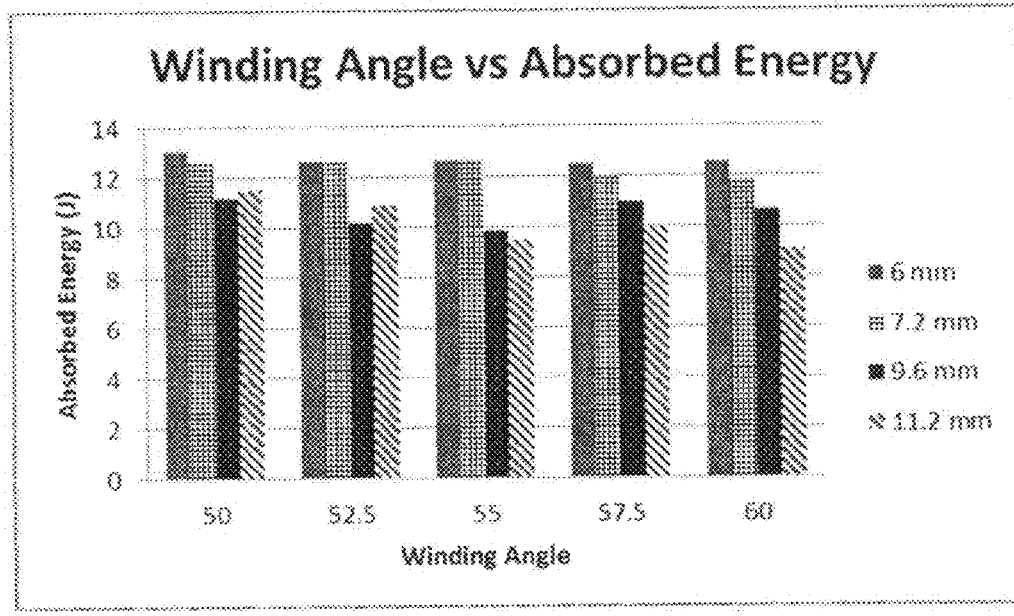
FIG. 25A illustrates variations in absorbed energy with respect to winding angle for CFRP pipes.
Figure 25B:
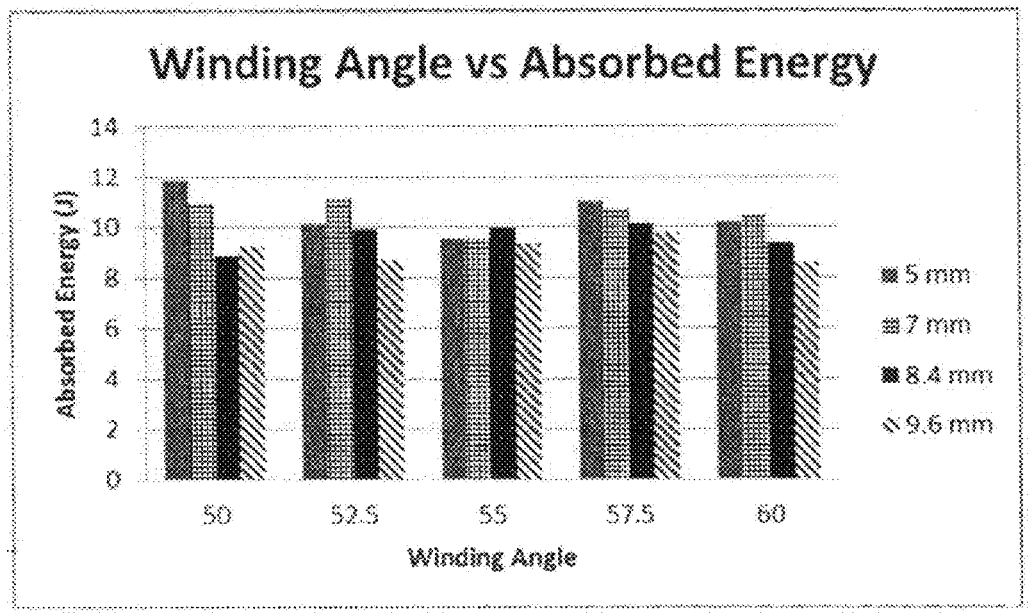
FIG. 25B illustrates variations in absorbed energy with respect to winding angle for GFRP pipes.
Figure 26A:
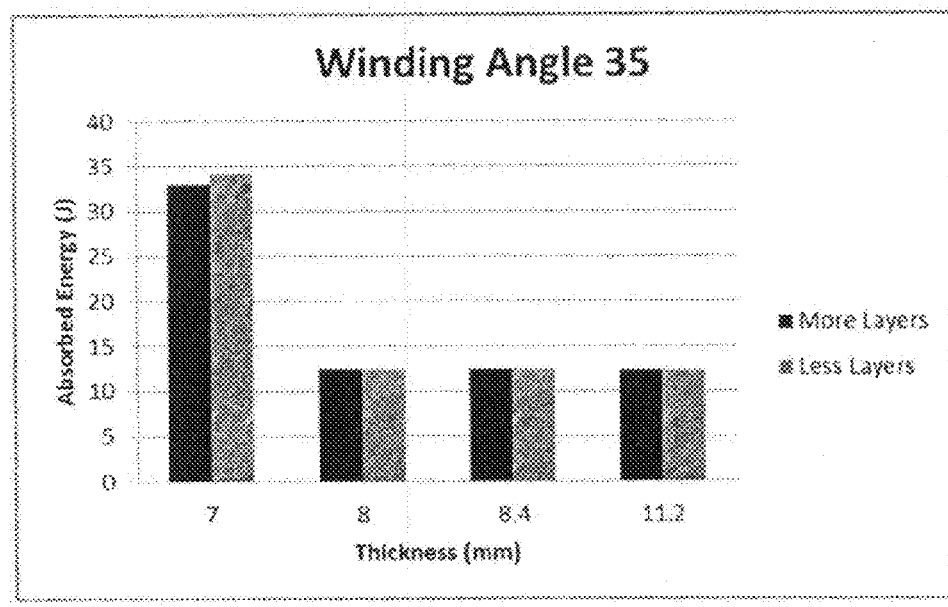
FIG. 26A illustrates absorbed energy in equal thickness plates with a varying number of layers for 35° winding angle GFRP pipes.
Figure 26B:
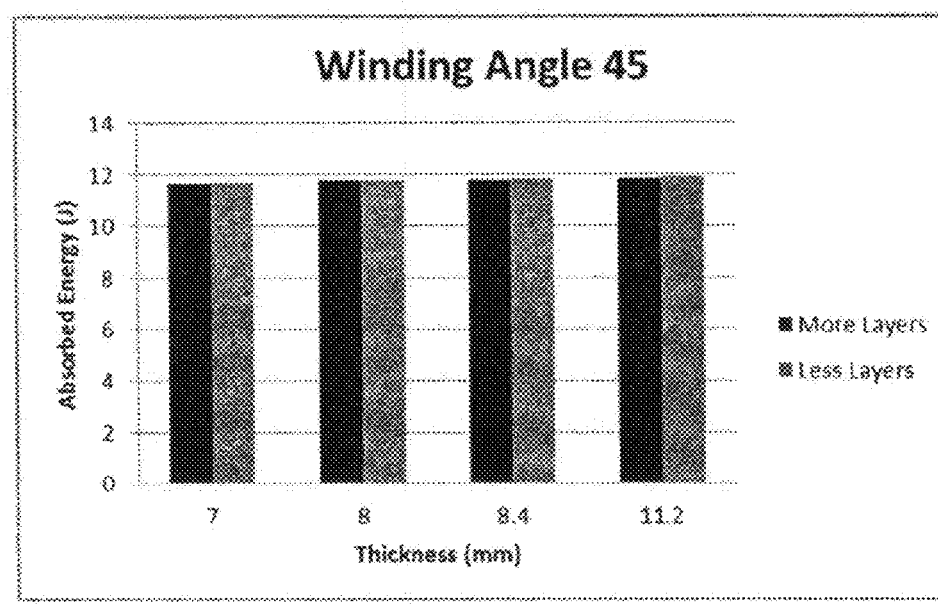
FIG. 26B illustrates absorbed energy in equal thickness plates with a varying number of layers for 45° winding angle GFRP pipes.
Figure 26C:
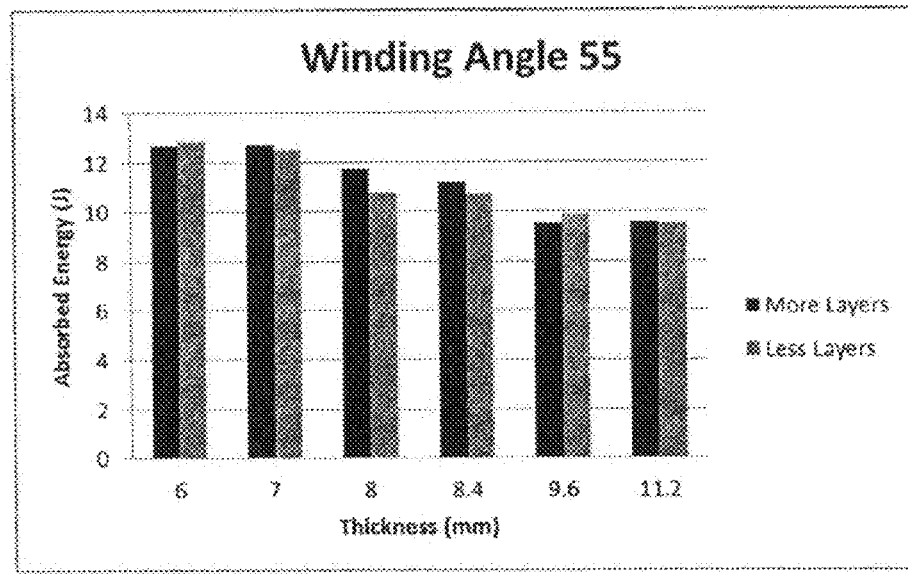
FIG. 26C illustrates absorbed energy in equal thickness plates with a varying number of layers for 55° winding angle GFRP pipes.
Figure 26D:
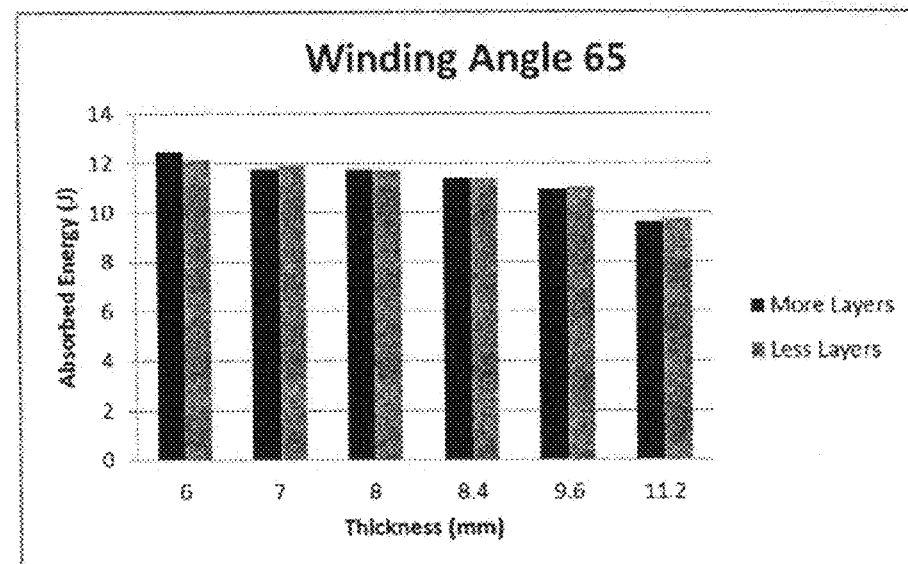
FIG. 26D illustrates absorbed energy in equal thickness plates with a varying number of layers for 65° winding angle GFRP pipes.
Figure 26E:
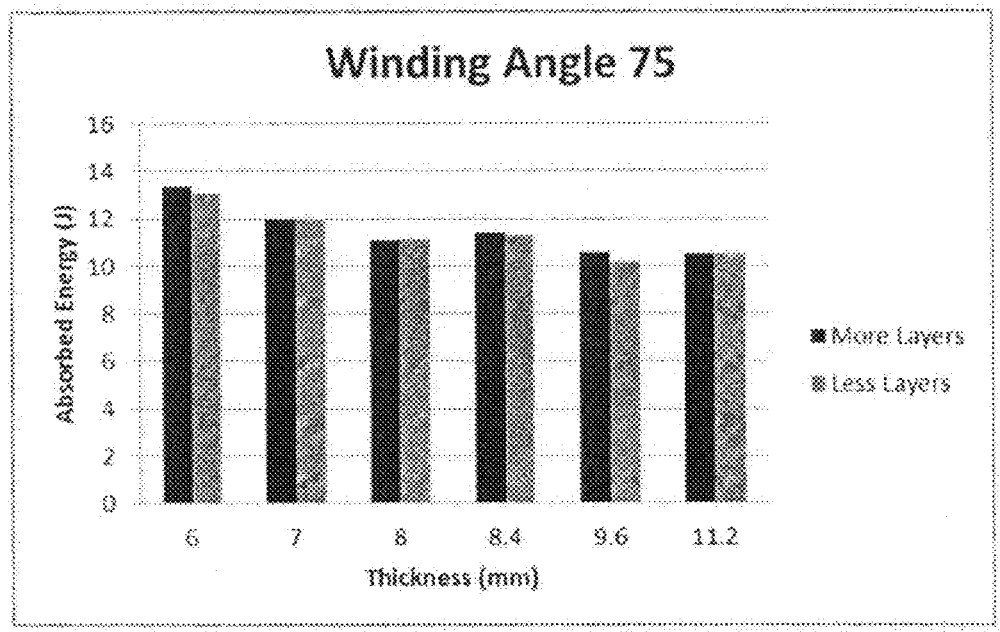
FIG. 26E illustrates absorbed energy in equal thickness plates with a varying number of layers for 75° winding angle GFRP pipes.
Figure 26F:
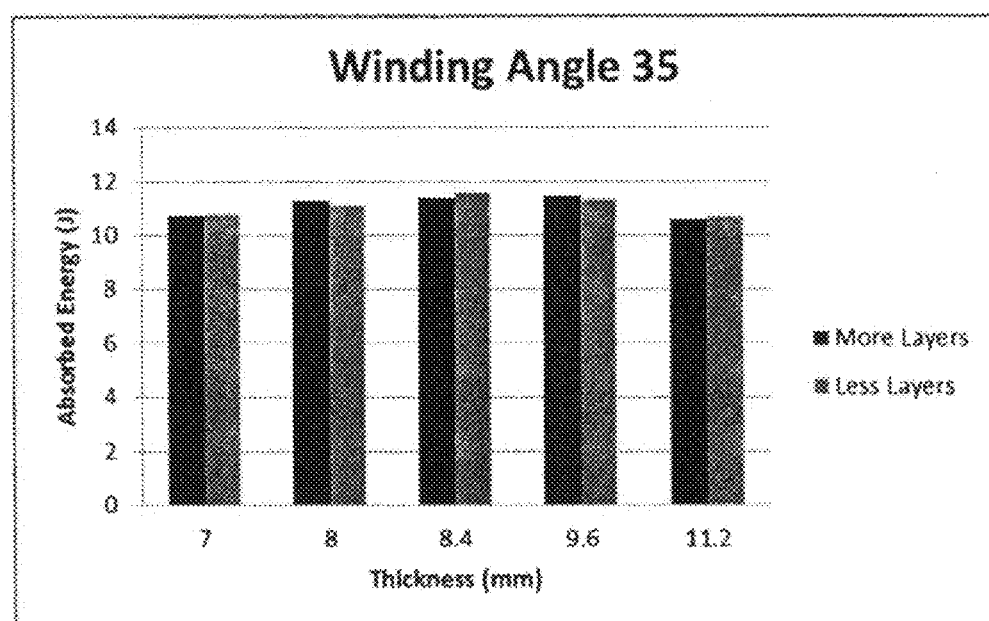
FIG. 26F illustrates absorbed energy in equal thickness plates with a varying number of layers for 35° winding angle CFRP pipes.
Figure 26G:
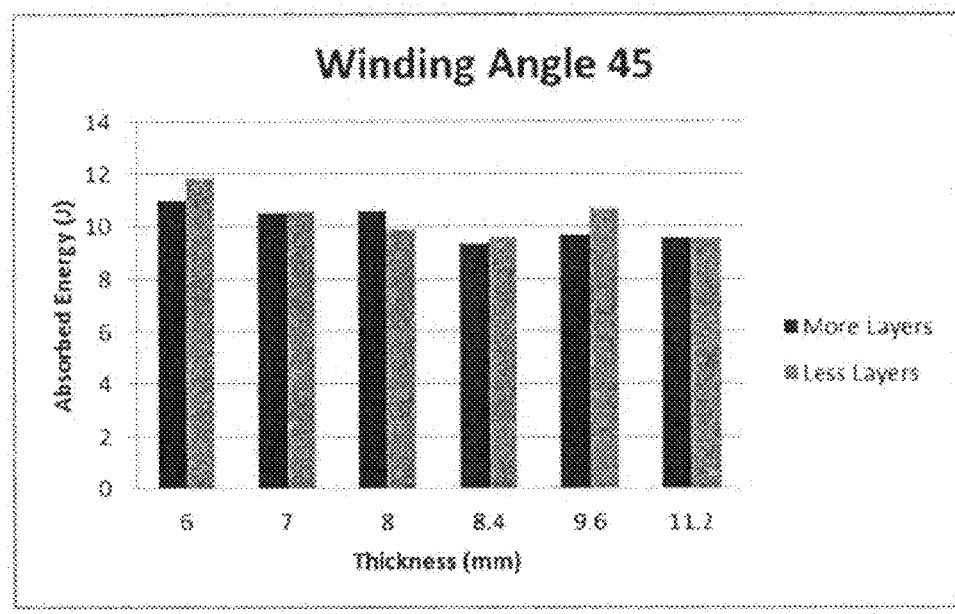
FIG. 26G illustrates absorbed energy in equal thickness plates with a varying number of layers for 45° winding angle CFRP pipes.
Figure 26H:
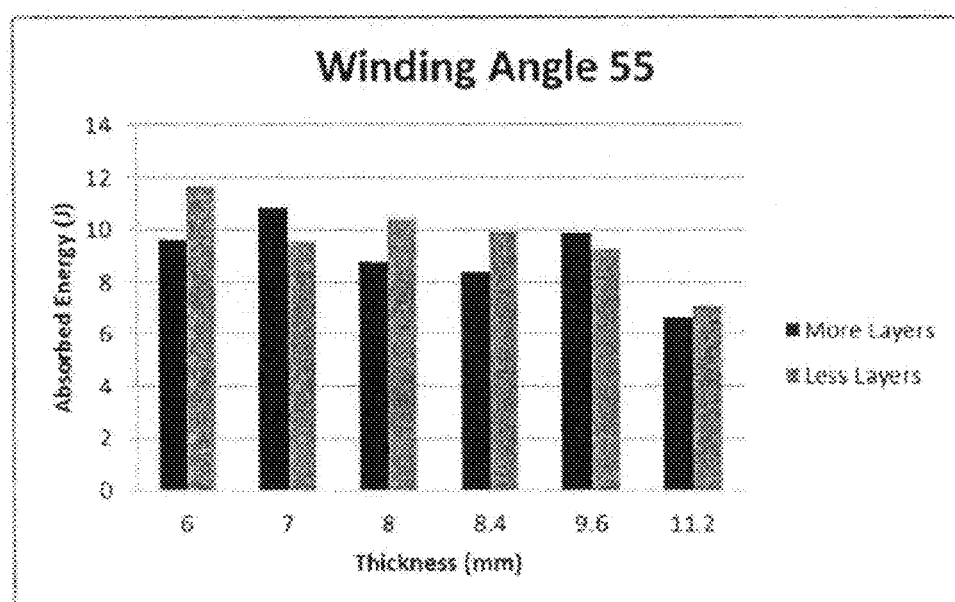
FIG. 26H illustrates absorbed energy in equal thickness plates with a varying number of layers for 55° winding angle CFRP pipes.
Figure 26I:
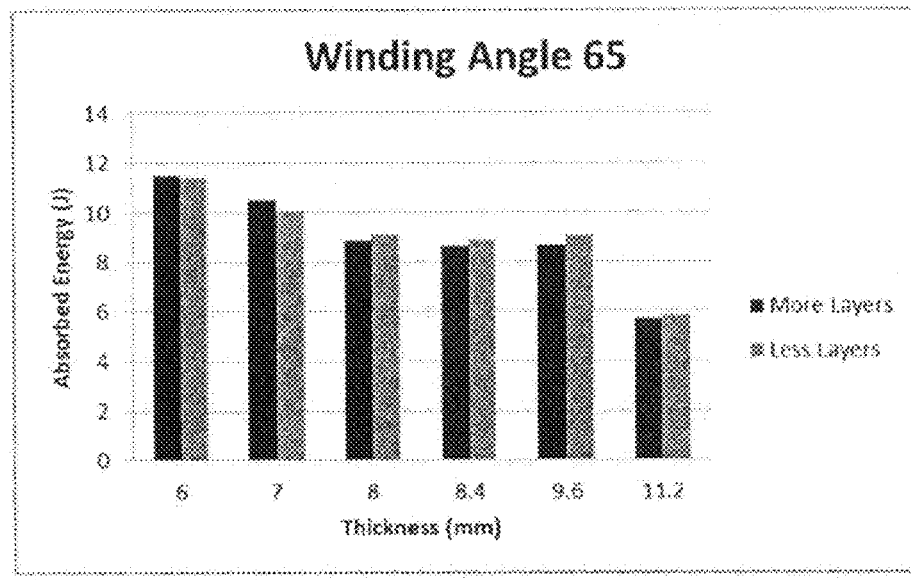
FIG. 26I illustrates absorbed energy in equal thickness plates with a varying number of layers for 65° winding angle CFRP pipes.
Figure 26J:
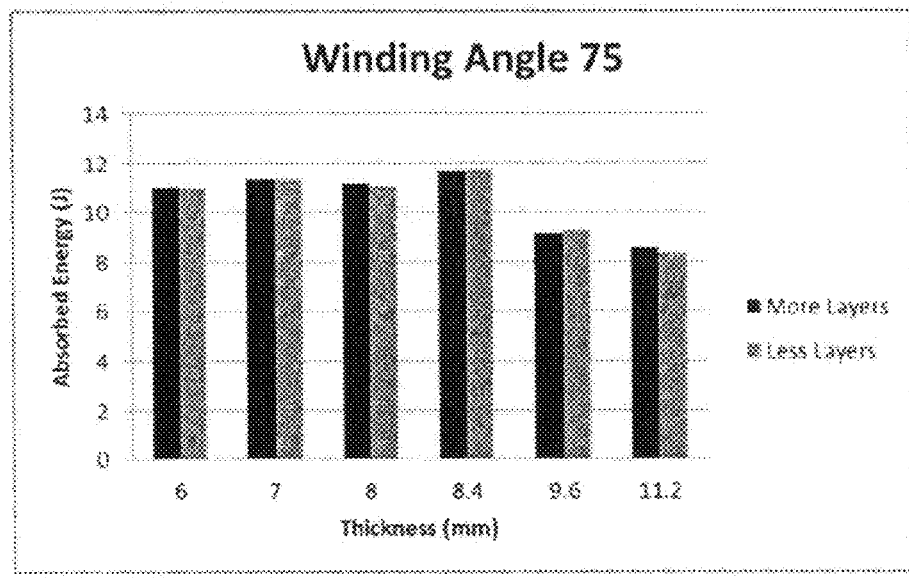
FIG. 26J illustrates absorbed energy in equal thickness plates with a varying number of layers for 75° winding angle CFRP pipes.

FIGS. 25A and 25 B illustrate variations in absorbed energy with respect to winding angle for CFRP pipes and GFRP pipes, respectively.

The reason for the better performance of 55° winding angle pipes is that the impact force tries to bend the pipe near the impact point, hence winding angles of 55° which is reported to perform better when loaded with both hoop stress and axial stress performs better in the case of impact loads as well. The slight difference may be attributed to other reasons such as the number of layers, thickness of the wall or the boundary conditions.

The fiber orientation in the 55° winding angles is better in terms of performance because it may carry both axial and hoop stresses effectively as stated earlier and during impact, the bending due to the loads creates stress in both the longitudinal and circumferential directions. Hence, 55° winding angle is preferred. If one bases further analysis on this assumption, it may be inferred that the winding angles of 35° or even less are since more aligned with the longitudinal axis of the pipe may withstand more longitudinal or axial stresses but will be weaker in the circumferential direction. On the other hand 75° winding angles are more close to the hoop winding which is known to handle internal pressure and hoop stresses will perform better in the loadings that put the pipe under circumferential stresses but will fail in the axial loadings.

Effects of Layer Thickness and Number of Layers

It is reported in the work of Zhao et al. [73] that the stacking sequence has some major influence on the impact performance of the curved shells. It is reported in their work that the damage is reduced with the increase in the interface number in the laminated shells. The interface number may be understood as the number of time the fiber orientations are changed within a laminate. For example, in a laminate where [45/−45/0/90] is the stacking of layers, there are 4 interface changes while in a laminate where [$45_2$/$-45_2$/$0_2$/$90_2$] is the stacking of layers the interface number is still 4 in spite of the fact that the number of layers are twice that of the earlier sample.

The above result suggests that in the pipes where the individual layers have less thickness and to achieve the overall thickness of the pipe numbers of layers are increased will be better than the other way round. The simulations performed however, suggested that the increase in number of layers keeping the overall thickness constant has little effect on the amount of absorbed energy or in some cases it has adverse effect. This may be observed in the graphs of FIGS. 26A-26J. Here, the results are not always in the favor of more layers. This may be due to a fact that the results described in the study of Zhao et al. [73] is for curved shell and the current study is for pipes, therefore, the geometry and the boundary changes may affect the influence of number of layers differently than for flat plates or curved plates.

Inclusion of Embedding

From the study so far, it is understood that the tensile strength of the fiber and the fracture energies of the fiber materials are one of the important contributors. In order to improve the performance of the composite plates and pipes, it is therefore advisable to use materials such as carbon or graphite which have higher tensile strengths and fracture energies. But, the cost factor is also important since the idea is to design such that the performance is optimal with respect to the minimum costs.

To achieve better impact resistance at a lower cost is the main aim. Because the glass/epoxy systems are less expensive compared to carbon/epoxy. This section discusses the kinds of materials included and their placement in the glass/epoxy plates and pipes to enhance the overall impact performance of the structures.

Embedding Type

For the composite flat plates, the main fiber material is chosen to be glass with addition of carbon fibers. Since, the flat plates are manufactured using the woven fabric only the carbon/epoxy woven fabric was used along with the glass/epoxy fabric. From the material properties Tables 1-14, it is known that the carbon/epoxy laminas are much stronger than the glass/epoxy. Also, from the simulations run for both type of materials and the results listed in the tables in the Appendix A confirmed that the carbon/epoxy plates perform much better than the glass/epoxy. Therefore, some layers from the composite plate were replaced by carbon fibers. The studies prior to this one already concluded that for the case considered in this thesis for composite plates, the best stacking sequence will be number 4, i.e., [60/45/−45/−60], which were used in order to study the effects of inclusion of other fiber materials. The other conditions of the load and the boundary conditions and the impactor remain the same as in the study for the composite plates.

Similarly, for pipes the results already studied were utilized to enhance the impact resistance of the composite pipes made using glass fiber filament winding by the addition of other materials in the winding process. Usually, the pipes are manufactured using continuous filament winding of one type of fiber material impregnated with the epoxy resin but it is not impossible to break the fibers after completion of layers and then include other fibers with the same epoxy resin to improve the performance. In fact, it is a common practice in the aerospace industry to manufacture composite rocket motor casings with different winding angles and different kinds of fibers to achieve the desired design criteria which is mostly dependent upon multi-loads situation to be encountered during service. For the composite pipes, it was observed that the pipes with carbon fiber offer quite an advantage over the pipes with glass fiber. But for both the types of material the best winding angle was the same as 55°. Also, inclusion of a layer of woven fabric may be studied as it may be beneficial considering the woven fabric has better strength characteristic in both the directions compared to the unidirectional lamina. Therefore, for this study inclusion of unidirectional carbon/epoxy and woven carbon/epoxy layers in the glass/epoxy composite pipes have been studied. For the study, the loads and the boundary conditions are kept the same as in the previous studies discussed above.

Effects of Placement of Embedding

The inclusion of other materials alone cannot guarantee an increase in the performance of the structure, the placement of the embedding is also necessary. Since, the material to be included is based on the superior strength and better performance, it should be placed where the damage initiates. To understand the relation between the placement of the inclusions and the impact performance, different placements were tried for the carbon layers in the composite plate that mainly consisted of glass fibers. Following different combinations were tried with the position of woven carbon lamina as:

Top and Bottom layers
Middle 2 layers
Top 2 layers
Bottom 2 layers
Single top and bottom layers and 2 middle layers
Single Top and Middle layers In addition to different positions, different thickness of the carbon layers and glass layers were considered. As described earlier, the stacking sequence considered is number 4 i.e., [60/45/−45/−60].

Figure 27A:
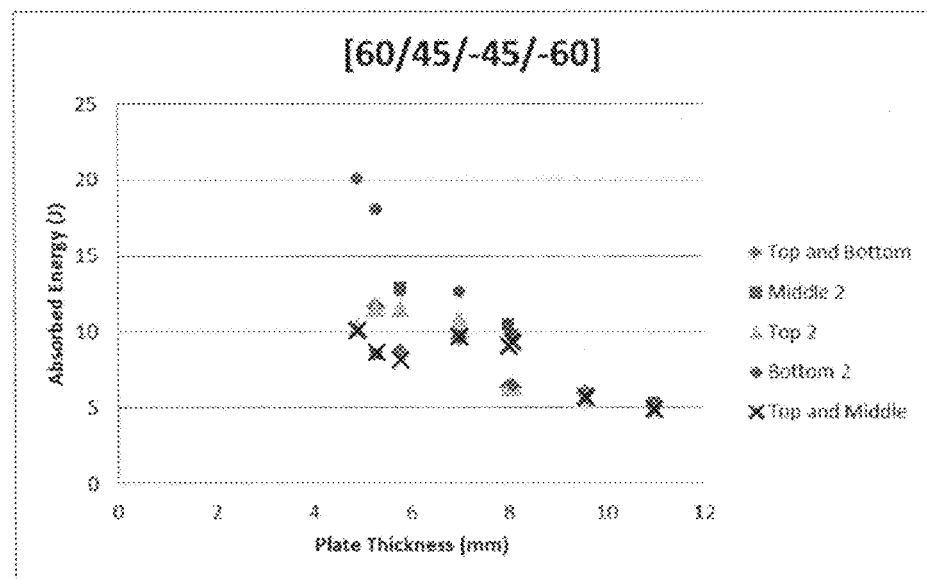
FIG. 27A illustrates absorbed energy vs. plate thickness for combinations of varying composite layers and woven carbon lamina.
Figure 27B:
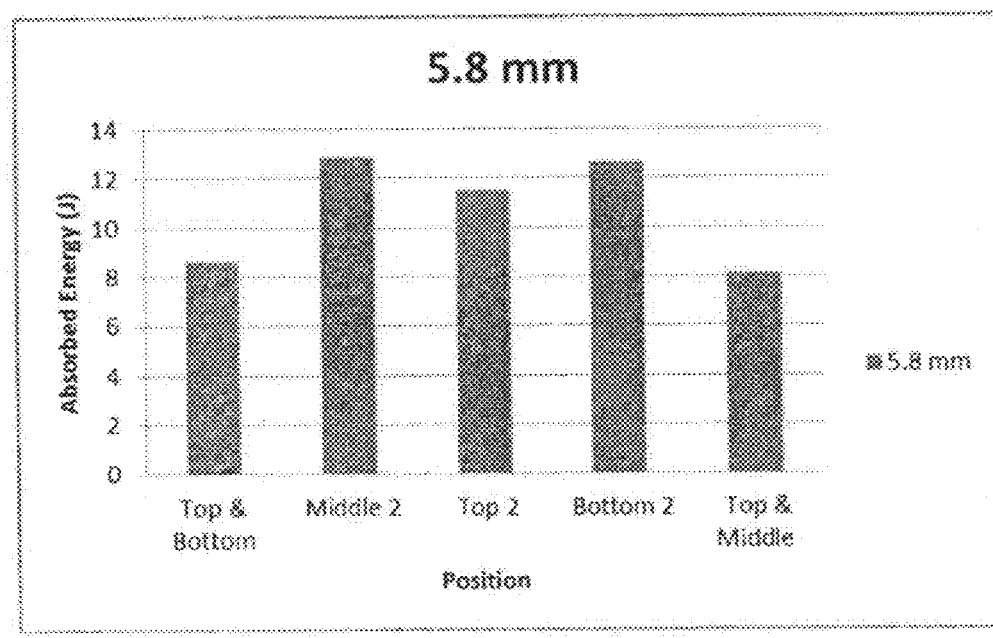
FIG. 27B illustrates absorbed energy vs. the position of the carbon layer for a 5.8 mm plate.
Figure 27C:
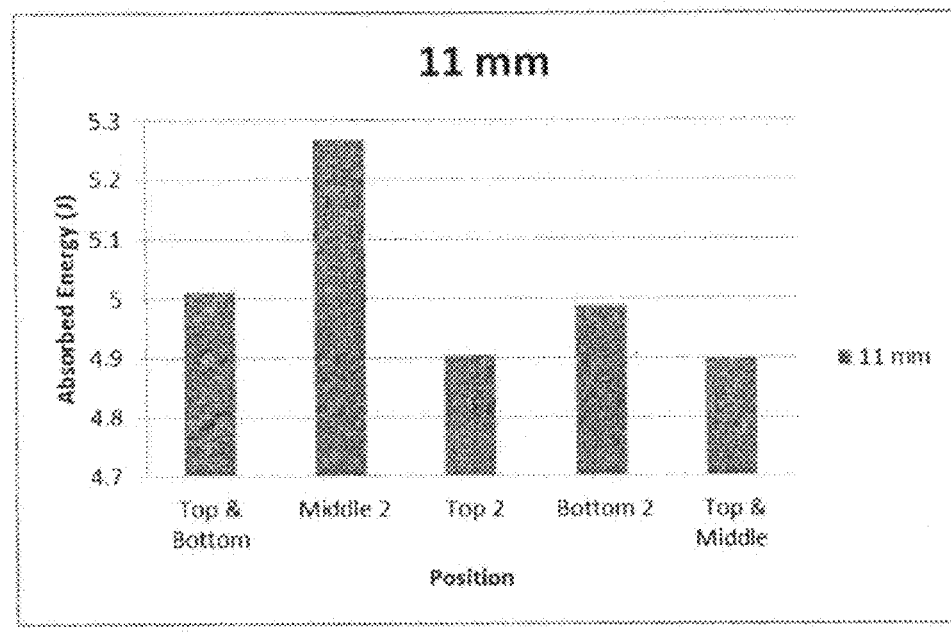
FIG. 27C illustrates absorbed energy vs. the position of the carbon layer for a 11 mm plate.

The results for these simulations are tabulated in the Appendix A. Table A. 9 to Table A. 14 and the graphical representation is provided in the FIGS. 27A-27C. From the results, it is evident that the greatest effect of the inclusion and placement of the carbon layers is when the overall plate thickness is small. Once, the plate thickness is increased, most of the load bearing capacity is taken by the glass fiber layers and hence effectiveness is not measured. In the low thickness plates, the placement of the carbon fiber layers is thus important and it is observed that the most efficient placement when one carbon layer is placed at the top and one in the middle. The top 2 layers of carbon perform slightly worse but this may be attributed to the fact that the first layer is 60° while the second one was only 45° compared to the case where one top and one middle layers are replaced both of them being the 60° layers. Another important result to be noticed that the increase in the absorbed energy observed for the glass/epoxy systems FIG. 18D with the increase in thickness was negated quite a bit by the introduction of carbon/epoxy layers especially when these layers are replaced at the top only, top and middle and cases with top and bottom. Therefore, it may be deduced that the carbon layers introduction at the top and middle gives the better impact performance at a slightly higher cost.

Similar procedure was adopted to study the effect of carbon/epoxy layers, both woven and unidirectional layers, on the impact performance of the composite pipes. From the results presented earlier, it is inferred that the damage initiates at the top layer that is the closest layer to the impact point. Therefore, different layer combinations with woven fabric and unidirectional fibers were tried and the results are presented in the Appendix A. Table A. 31 to Table A. 34. The winding angle was kept at 55° as it was found out to be the optimal angle of winding against the impact loads.

Figure 28A:
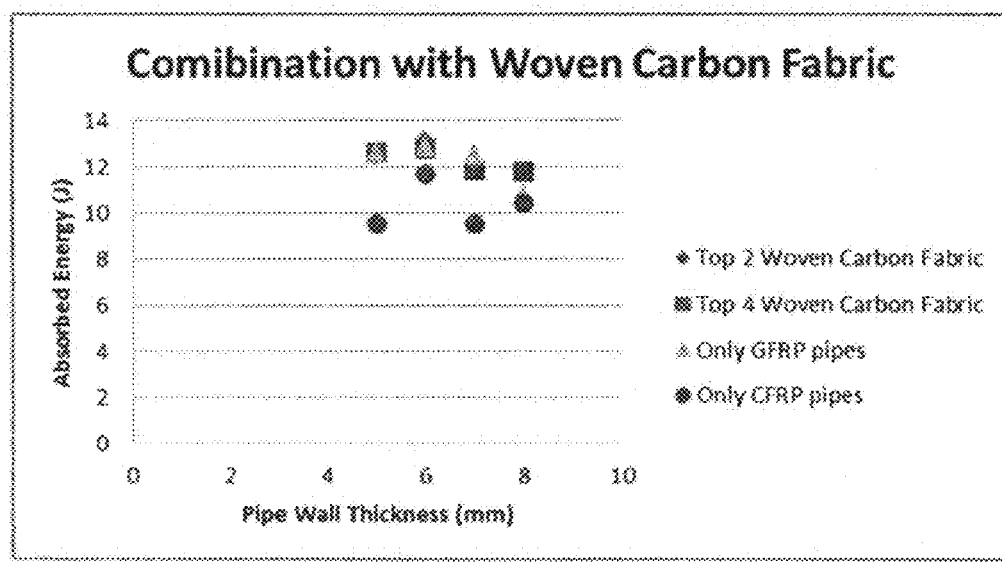
FIG. 28A illustrates absorbed energy vs. pipe wall thickness of GFRP and CFRP pipes with different combinations of woven carbon fabric layers.
Figure 28B:
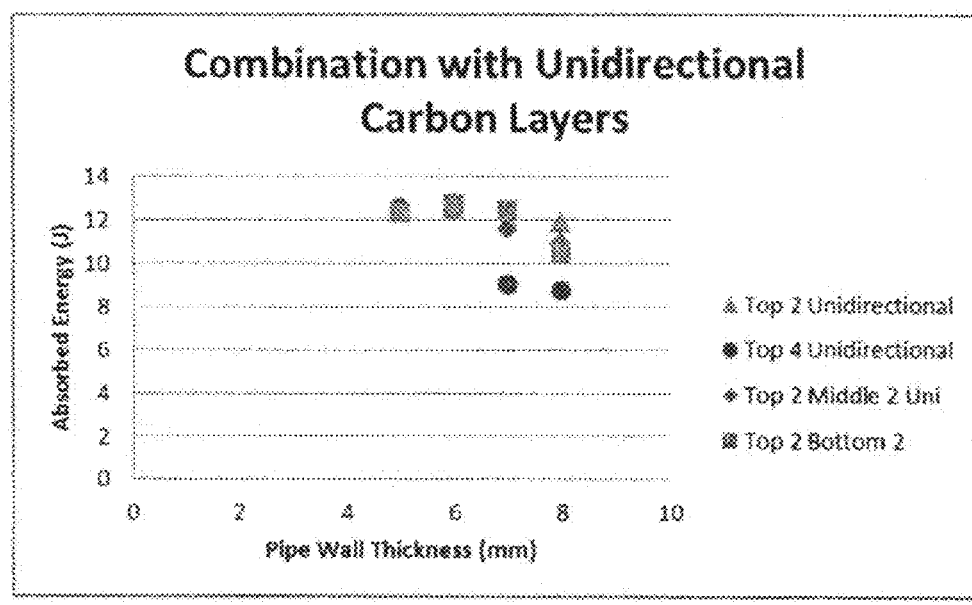
FIG. 28B illustrates absorbed energy vs. pipe wall thickness of hybrid CFRP and GFRP pipes with different layer orientations.

The results suggest that the inclusion of top layers as the woven carbon fabric doesn't improve the impact performance. This is due to the reason that the most important strength factor in withstanding impact loads is the tensile strength and in this case the tensile strength of unidirectional glass fiber is slightly more than the woven carbon fabric. The inclusion of woven carbon fabric is thus not recommended as it will increase the costs without increasing the impact performance. On the other hand, the inclusion of unidirectional carbon layers suggests that there is an advantage especially when top 4 layers were replaced. In the case of top 4 layers of carbon fibers, the impact performance is in fact better than the pure carbon based pipes. This is therefore highly recommended configuration considering less expensive with better resistance against impact loads. The results are graphically represented in FIGS. 28A and 28B.

This section includes the results and discussion for the simulations carried out in order to study the effects of various parameters upon the impact performance of the composite structures. These parameters were identified by the sensitivity analysis but their exact nature and the explanation of their behavior cannot be provided by the sensitivity analysis. The approach considered in this chapter was to design a set of experiments to be performed numerically. Simulations were performed using ABAQUS explicit for both flat plates and pipes. The design variables and their effects have been studied in detail. Few of these parameters have already been studied in the available literature and the results from the current work is studied and compared with the already available literature. The parameters studied in this chapter were selected after the sensitivity analysis and were selected such that they are directly related to the designing of the composite plates and pipes. Factors such as the impactor mass, geometry and the boundary conditions were kept constant as most of the times in real life applications these factors will be outside the control of the designer. The simulations were performed in two phases initially a complete DOE table was constructed but later on more variations of the factors were added to complete the analysis in a way that the complete range of variables is selected from being safe to complete penetration of the impactor. The main conclusions drawn from this chapter are summarized as follows:

The most profound effect of all the variables was that of the thickness of the plates and the pipes. The crucial observation in the analysis of this factor is that the dependence of impact performance on the thickness of the structure is not directly proportional. In fact, it was found that there was a range of thickness where actually the performance is worse than before. This observation is explained by the ability of the thin structures to withstand bending without undergoing vibrations. The increase in thickness increases the structural rigidity which in turn effects adversely due to the unnecessary induced vibrations upon impact.

The stacking sequence of the composite plates has a significant role in the impact performance. Although not directly studied, this is due to the boundary conditions effect. It is suggested that during the design phase knowledge of the kind of boundary conditions is better. Hence, it is recommended that the more fiber should be aligned in the direction where the boundary conditions are such that they restraint the bending of the plate.

The conclusion from the chapter 4 that the numbers of layers have an effect but they have to be chosen carefully is further explained based on the orientation of the added layers. It is important to have as more as possible fibers in the direction of the maximum stress during the impact to delay the damage initiation process.

The material properties which have a significant effect on the impact resistance of any composite structures are the tensile strength of the fiber and the energy release rates during damage propagation. Care must be taken in the selection of material and designing of the composite structures as to maximum utilize the tensile strength of the fibers.

The improvement in the impact resistance of the composite plates without increasing costs by much may be achieved through the introduction of carbon/epoxy layers in place of glass/epoxy layers. These layers of carbon/epoxy should be introduced in places where the damage initiates. Also, the layers to be replaced should be selected carefully keeping in mind that those layers should be replaced that increases the bending stiffness of the plate.

The best stacking sequence or the orientation angles of the layers is the one that aligns more fibers in the direction of maximum stress caused due to the presence of boundary condition effects.

The inclusion of woven fabric in the filament wound composite pipes may be beneficial if the woven fabric selected has a higher tensile strength than the unidirectional glass or carbon fibers.

Optimization of Design Parameters

The optimization of the impact resistance of the composite plates and pipes against low velocity impact loads is important in terms of a number of advantages. Optimized solutions are lighter in terms of weight hence saving materials and resulting in low cost efficient products. Generally, optimization is performed on a selected function commonly termed as the cost function which is the function of several variables. The cost function, if properly defined, may be used with a variety of techniques of optimization. The basic optimization idea is to minimize or maximize this cost function by choosing the input variables in such manner that it forms the best possible solution among a set of possible solutions. The history of optimization dates back to the first known optimization technique of Steepest Descent pioneered by Gauss. With the advent of last century the available techniques are more refined and now find themselves being employed in a multitude of scientific and technological fields. Mathematically, the problem is represented as:

$$\text{Optimize } y = f(x_1, x_2, \ldots, x_n) \tag{6.1}$$

$$\text{Subject to } g_j(x_1, x_2, \ldots, x_n) \begin{Bmatrix} \leq \\ = \\ \geq \end{Bmatrix} b_j \tag{6.2}$$

$$j = 1, 2, \ldots, m$$

Optimization Problem

The cost function represented in Eq. (6.1) by 'y' is the amount of absorbed energy and the cost of the plate or the pipe. The dependent variables $X_1$, $X_2$ etc. are the layer thickness, orientation angles or stacking sequence, number of layers and the material type. There are two objectives to minimize simultaneously which makes the problem as multi-objective optimization, but the objectives here are not contradictory, therefore, may be combined in one single function.

There are a number of optimization techniques available as described in the literature review section. Any optimization technique is based upon the cost function, which in this case is not defined analytically. To get the cost function, models like linear regression model or other similar techniques are used. Because the data is not well structured and has a lot of variations from point to point, regression models were unable to predict the empirical mathematical equation. To obtain a function that may predict the amount of absorbed energy which will then be used as the cost function, artificial neural networks were utilized. The ANN model available with the commercially available software MATLAB®, the ANN model may be used for function fitting of highly non-linear data. This technique was then used and optimized to get the best possible model that may predict the amount of absorbed energy.

Artificial Neural Networks

Artificial Neural Network (ANN) or sometimes called Neural Network is an interconnected group of artificial neurons that uses a mathematical model or computational model for information processing based on a connectionist approach to computation. It is an adaptive system whose structure is modifiable based on the external or internal information that flows through the network. The name is given because of its ability to learn like human brain by examples. This technique is useful in pattern recognition, model fitting or data classification. Once trained, ANN may be used to predict the outcome of new independent data different from the training set. The ability of ANN model to learn by example highly non-linear and noisy data is useful in this approach where statistical data is dealt with. This feature is very useful in this problem where a mathematical relationship of the factors considered by sensitivity analysis with the absorbed impact energy is not available but with the help of FEA simulations a lot of training data is available to us.

A neural network is a set of connected neurons, these neurons receive impulses from either input cells or other neurons and apply a function and transmit the output to other neurons or the final output cells. The neural networks may be multi-layered in which case one layer receives information from the preceding layer of neurons and passes the output to the subsequent layers.

A neuron is a real function of the input vector ($y_1, y_2, \ldots, y_k$). The output is a function described as:

$$f(x_j) = f\left(\alpha_j + \sum_{i=1}^{k} w_{ij} y_j\right) \quad (6.3)$$

Figure 29:
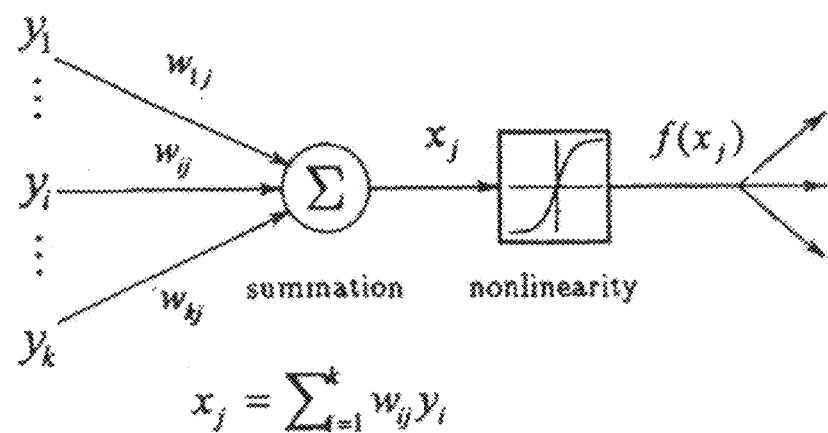
FIG. 29 illustrates a graphical representation of a single neuron in an artificial neural network.

Where, $f$ is a typically a function as sigmoid (log or tan h) function. A graphical representation of neuron is illustrated in FIG. 29.

Feed Forward Networks

Figure 30:
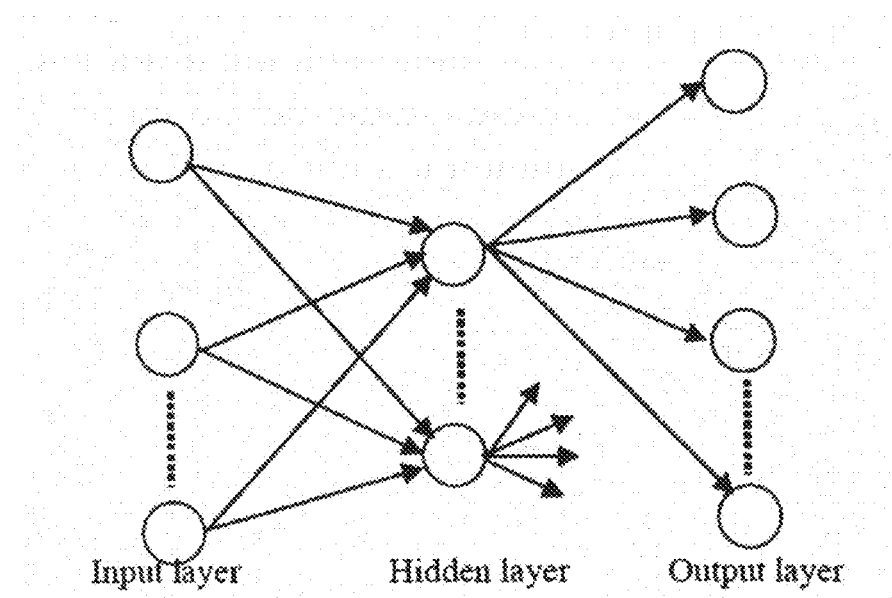
FIG. 30 illustrates a multi-layered feed forward artificial neural network.

A feed forward network works in the forward direction i.e. the flow of information is in only one direction along the connections from the input layer through the hidden layers of neurons to the final output layer. There is no feedback loop in these networks and hence the output does not affect the performance of the previous layers or the same layer. FIG. 30 illustrates a multi-layered feed forward artificial neural network.

ANN Model for Flat Plates

Two separate ANN models were generated for the carbon/epoxy and the glass/epoxy plates. In total there were 108 different simulation data for each type of material.

Data set available for training ANN in this study is 108 samples, few iterations of ANN models were tried coupled with a differential evolution algorithm for the optimization of the ANN model in terms of the number of neurons and the hidden layers. The data set was randomly distributed in three sets, for the training, testing and validation of the model. The training was carried out by randomly selecting 94 data points and the rest were divided equally for the testing and validation.

The optimization algorithm of differential evolution was used to find the best ANN model, an objective function was defined which computes the maximum error from one ANN model at a time which was based on the number of neurons. This optimization of the ANN model was necessary to find the best possible configuration of ANN models which depend upon the number of hidden layers and neurons. The ANN model configuration thus obtained was then train to predict the amount of absorbed energy for the composite plates. Two separate models were used to predict the behavior of composite plates based on carbon or glass fibers.

The carbon/epoxy composite plates' impact behavior was well defined compared to the glass/epoxy composite plates. It is noted that the more the data follows a pattern, the better the correlation will be, as the ANN model described earlier uses the target response to calculate the weights of each neurons. The model for carbon/epoxy plates needed only 21 neurons and a single hidden layer containing all the neurons. The model is generally supposed to predict the behavior accurately when the absolute error between the predicted and the targeted values is at least 2 orders less in magnitude.

The ANN model for carbon/epoxy system has a root mean square error of just 0.08 J with the maximum error of 0.6242 J.

TABLE 33

Testing ANN for 21 neurons for CFRP plates.

| Input1 (thickness mm) | Input2 (Number of Layers) | Input3 (Stacking Sequence) | Actual response (Abaqus) J | Simulated Response (ANN) J | Difference |
|---|---|---|---|---|---|
| 0.3 | 20 | 1 | 5.9155 | 6.105 | −0.1895 |
| 0.25 | 16 | 1 | 6.7855 | 6.8955 | −0.11 |
| 0.25 | 20 | 3 | 5.7807 | 5.6217 | 0.159 |
| 0.35 | 28 | 1 | 2.7507 | 2.5044 | 0.2463 |
| 0.16 | 16 | 3 | 7.5475 | 7.3142 | 0.2333 |

TABLE 33-continued

Testing ANN for 21 neurons for CFRP plates.

| Input1 (thickness mm) | Input2 (Number of Layers) | Input3 (Stacking Sequence) | Actual response (Abaqus) J | Simulated Response (ANN) J | Difference |
|---|---|---|---|---|---|
| 0.3 | 16 | 1 | 6.5986 | 6.4669 | 0.1317 |
| 0.25 | 20 | 1 | 7.074 | 7.0582 | 0.0158 |
| 0.18 | 16 | 1 | 7.7121 | 8.0439 | −0.3318 |
| 0.25 | 28 | 1 | 5.7693 | 5.7452 | 0.0241 |
| 0.18 | 16 | 4 | 7.1083 | 7.08 | 0.0283 |
| 0.4 | 28 | 3 | 1.2529 | 1.3213 | −0.0684 |
| 0.4 | 32 | 1 | 0.2346 | 0.0313 | 0.2033 |
| 0.2 | 24 | 4 | 4.631 | 4.7639 | −0.1329 |
| 0.25 | 20 | 2 | 5.3035 | 5.3961 | −0.0926 |

Figure 31A:
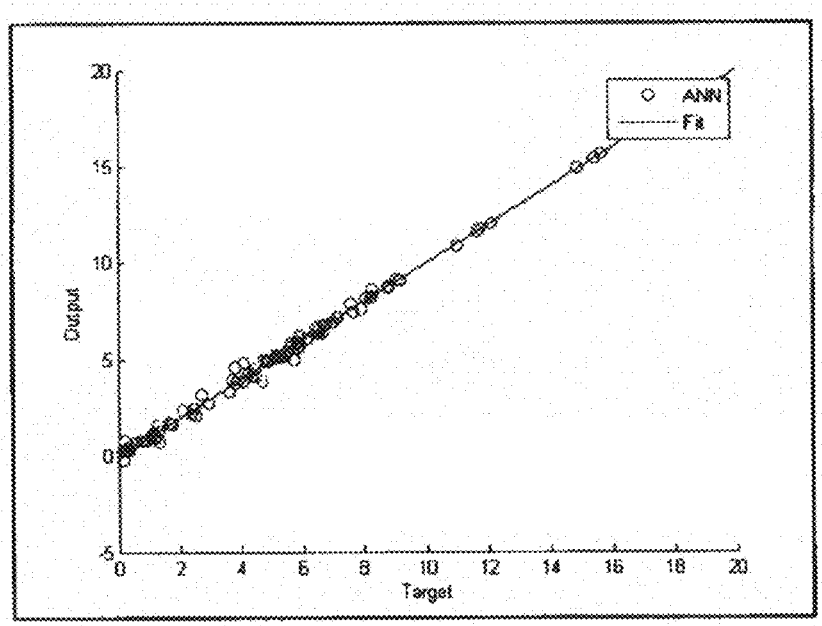
FIG. 31A illustrates a correlation between a predicted response and a target response for CFRP plates.
Figure 31B:
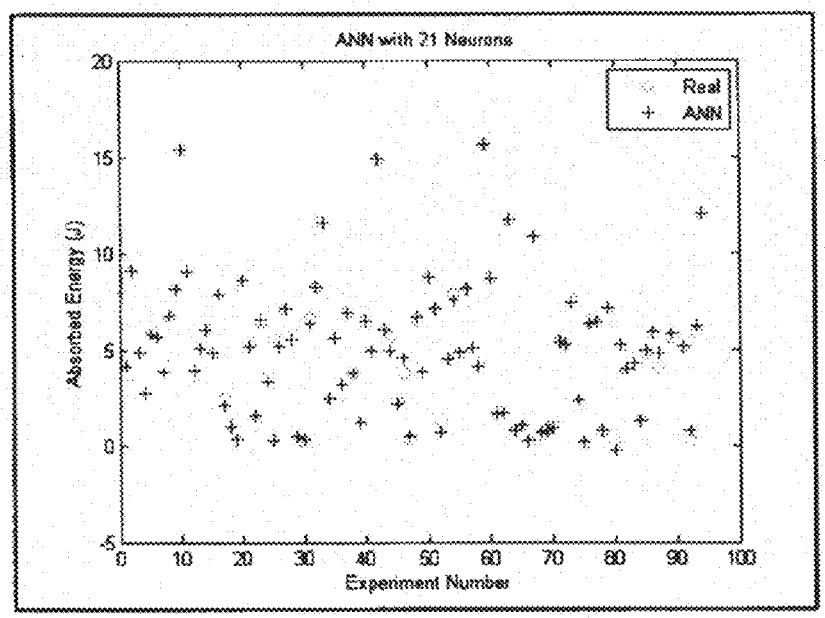
FIG. 31B illustrates scatter data of an actual response and vs. a predicted response for CFRP plates.

A separate verification was carried out with simulations from ABAQUS and the ANN model for the cases presented in Table 34. The verification gives the further confidence in the ANN model and its use in generating the population for the optimization process. FIG. 31A shows the correlation between the target and the predicted response while FIG. 31B represents the difference between the actual and the predicted response.

TABLE 34

Independent test cases to verify ANN model.

| Input1 (thickness mm) | Input2 (No. of Layers) | Input3 (Stacking Sequence) | Actual response (Abaqus) J | Simulated Response (ANN) J | Difference |
|---|---|---|---|---|---|
| 0.24 | 24 | 1 | 5.9006 | 5.9836 | −0.083 |
| 0.16 | 30 | 4 | 4.6322 | 5.0069 | −0.3747 |
| 0.22 | 26 | 2 | 4.6903 | 4.9347 | −0.2444 |
| 0.14 | 18 | 3 | 7.7589 | 8.5684 | −0.8095 |
| 0.36 | 32 | 2 | 0.5093 | 0.6132 | −0.1039 |

A similar ANN model was trained to predict the glass/epoxy composite plates. The ANN model for glass fiber plates uses 24 neurons in a single layer and is able to predict the amount of absorbed energy with maximum error of 1.1047 J and root mean square error of 0.33 J.

TABLE 35

Testing ANN for 24 neurons for GFRP plates.

| Input1 (thickness mm) | Input2 (Number of Layers) | Input3 (Stacking Sequence) | Actual response (Abaqus) J | Simulated Response (ANN) J | Difference |
|---|---|---|---|---|---|
| 0.6 | 28 | 1 | 1.6022 | 1.653 1 | −0.0509 |
| 0.25 | 32 | 3 | 14.8979 | 14.9839 | −0.086 |
| 0.4 | 28 | 3 | 11.1732 | 11.0837 | 0.0895 |
| 0.25 | 32 | 1 | 13.8011 | 12.9575 | 0.8436 |
| 0.45 | 36 | 4 | 2.5115 | 2.4935 | 0.018 |
| 0.35 | 36 | 3 | 8.6502 | 8.2851 | 0.3651 |
| 0.4 | 36 | 1 | 8.5923 | 8.8273 | −0.235 |
| 0.4 | 28 | 2 | 14.9456 | 14.0875 | 0.8581 |
| 0.35 | 32 | 4 | 5.187 | 5.7195 | −0.5325 |
| 0.45 | 32 | 3 | 8.2871 | 8.5516 | −0.2645 |
| 0.5 | 36 | 2 | 0.7561 | 0.7411 | 0.015 |
| 0.3 | 24 | 1 | 12.686 | 12.8399 | −0.1539 |
| 0.25 | 36 | 4 | 6.3016 | 5.7934 | 0.5082 |
| 0.35 | 24 | 4 | 11.046 | 11.6601 | −0.6141 |

Figure 32A:
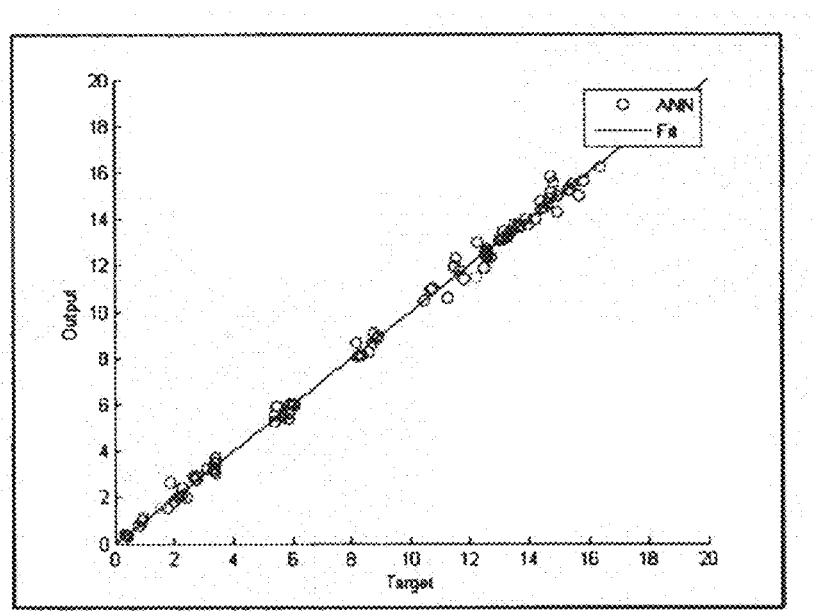
FIG. 32A illustrates a correlation between a predicted response and a target response for GFRP plates.
Figure 32B:
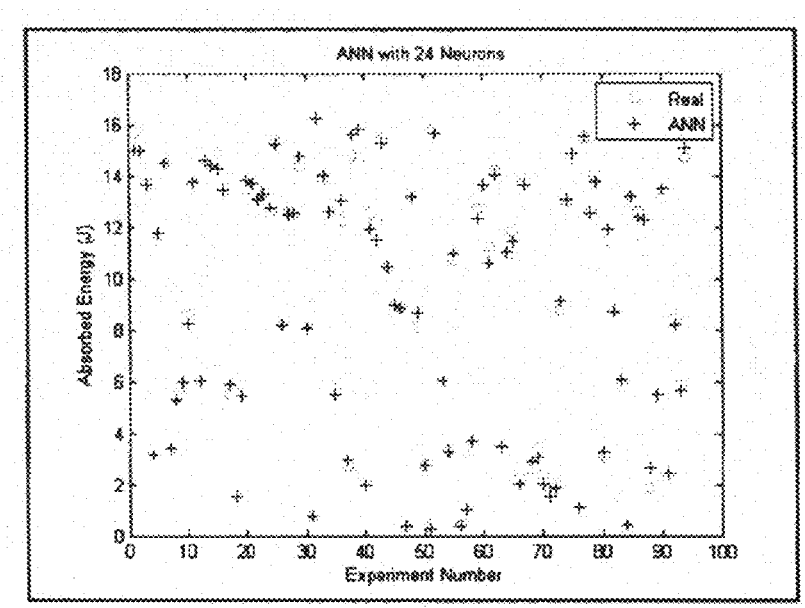
FIG. 32B illustrates scatter data of an actual response and vs. a predicted response for GFRP plates.

FIG. 32A illustrates a correlation between a predicted response and a target response for GFRP plates. FIG. 32B illustrates scatter data of an actual response and vs. a predicted response for GFRP plates.

TABLE 36

Independent test cases to verify ANN model for GFRP plates.

| Input1 (thickness mm) | Input2 (No. of Layers) | Input3 (Stacking Sequence) | Actual response (Abaqus) J | Simulated Response (ANN) J | Difference |
| --- | --- | --- | --- | --- | --- |
| 0.26 | 24 | 2 | 13.37359 | 15.5417 | 2.1681 |
| 0.42 | 30 | 4 | 6.14928 | 6.2809 | 0.1316 |
| 0.35 | 26 | 1 | 12.69973 | 13.153 | 0.4532 |
| 0.54 | 34 | 2 | 0.602984 | 0.6865 | 0.0835 |
| 0.36 | 36 | 3 | 8.449098 | 8.3282 | −0.1209 |

The number of data samples for training is the same for carbon and glass fiber plates but the error is more pronounced for the glass fiber plates due to the reason that the data for the response is not following a pattern which makes it harder to model ANN. This error may be reduced by introducing more data for training purposes.

ANN Model for Pipes

The training of ANN models for composite pipes is trickier as may be observed from the graphs presented earlier. It may be observed that in most of the cases for carbon and glass fiber pipes, there is a range where the absorbed energy value remains more or less the same and then it decreases suddenly. This sudden change is modeled using more neurons in the ANN models. In total there are 162 points for the training and validation which is almost 1.5 times that of the plates.

For the carbon fiber pipes, the ANN model is particularly worse in the correlation. Even with 100 neurons distributed a single hidden layer; the root mean square error is as high as 0.32 J and the maximum error is about 1.49 J.

TABLE 37

Testing ANN for 100 neurons for CFRP pipes.

| Input1 (thickness mm) | Input2 (Number of Layers) | Input3 (Stacking Sequence) | Actual response (Abaqus) J | Simulated Response (ANN) J | Difference |
| --- | --- | --- | --- | --- | --- |
| 0.425 | 55 | 36 | 0.3935 | 1.3454 | −0.9519 |
| 0.35 | 55 | 32 | 6.646 | 6.3746 | 0.2714 |
| 0.3 | 45 | 16 | 11.9603 | 11.9681 | −0.0078 |
| 0.4 | 55 | 28 | 7.1349 | 6.9401 | 0.1948 |
| 0.4 | 65 | 32 | 4.3499 | 4.0834 | 0.2665 |
| 0.35 | 57.5 | 20 | 10.6618 | 9.8097 | 0.8521 |
| 0.25 | 75 | 32 | 11.1477 | 11.1986 | −0.0509 |
| 0.425 | 45 | 36 | 0.5237 | 0.5876 | −0.0639 |
| 0.35 | 75 | 32 | 8.5637 | 7.654 | 0.9097 |
| 0.25 | 57.5 | 24 | 11.1164 | 9.6288 | 1.4876 |
| 0.3 | 35 | 28 | 11.3783 | 11.3015 | 0.0768 |
| 0.25 | 45 | 28 | 10.5071 | 10.5036 | 0.0035 |
| 0.25 | 52.5 | 24 | 11.3505 | 11.233 | 0.1175 |
| 0.3 | 65 | 28 | 8.6457 | 8.3328 | 0.3129 |

Figure 33A:
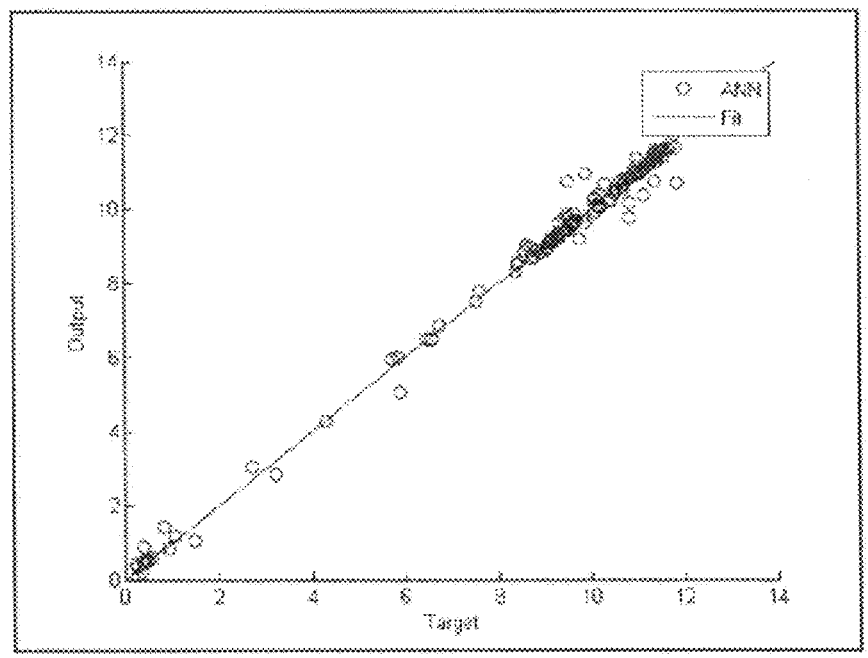
FIG. 33A illustrates a correlation between a predicted response and a target response for CFRP pipes.
Figure 33B:
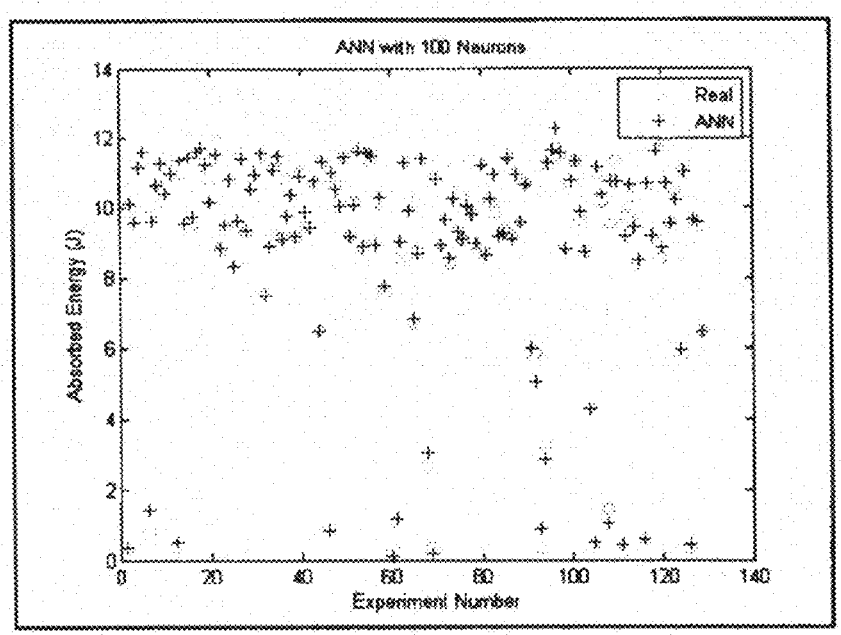
FIG. 33B illustrates scatter data of an actual response and vs. a predicted response for CFRP pipes.

FIG. 33A illustrates a correlation between a predicted response and a target response for CFRP pipes. FIG. 33B illustrates scatter data of an actual response and vs. a predicted response for CFRP pipes.

The prediction performance of ANN model for the glass fiber pipes is much better with a maximum error of 1.026 J and root mean square error of only 0.26 J. These results from ANN model are not accurate enough but the absolute error in most of the cases is small enough to consider the model for prediction. The numbers of neurons used in this model are 37 and the number of hidden layer is 1.

TABLE 38

Testing ANN for 37 neurons for GFRP pipes.

| Input1 (thickness mm) | Input2 (Number of Layers) | Input3 (Stacking Sequence) | Actual response (Abaqus) J | Simulated Response (ANN) J | Difference |
| --- | --- | --- | --- | --- | --- |
| 0.3 | 55 | 40 | 9.5385 | 9.6133 | −0.0748 |
| 0.35 | 65 | 28 | 11.1121 | 11.1812 | −0.0691 |
| 0.35 | 65 | 20 | 11.9186 | 11.8575 | 0.0611 |
| 0.25 | 65 | 36 | 11.0703 | 11.0599 | 0.0104 |
| 0.375 | 65 | 36 | 6.7361 | 6.7112 | 0.0249 |
| 0.35 | 55 | 36 | 8.6462 | 9.2142 | −0.568 |
| 0.4 | 50 | 28 | 11.5286 | 11.5219 | 0.0067 |
| 0.3 | 57.5 | 28 | 11.4357 | 11.6259 | −0.1902 |
| 0.35 | 75 | 40 | 7.9836 | 8.1484 | −0.1648 |
| 0.25 | 35 | 32 | 12.4234 | 12.1281 | 0.2953 |
| 0.25 | 57.5 | 28 | 12.0485 | 12.1576 | −0.1091 |
| 0.425 | 35 | 36 | 0.8283 | 0.6212 | 0.2071 |
| 0.35 | 75 | 32 | 10.4983 | 10.4393 | 0.059 |
| 0.25 | 65 | 28 | 11.7907 | 11.7143 | 0.0764 |

Figure 34A:
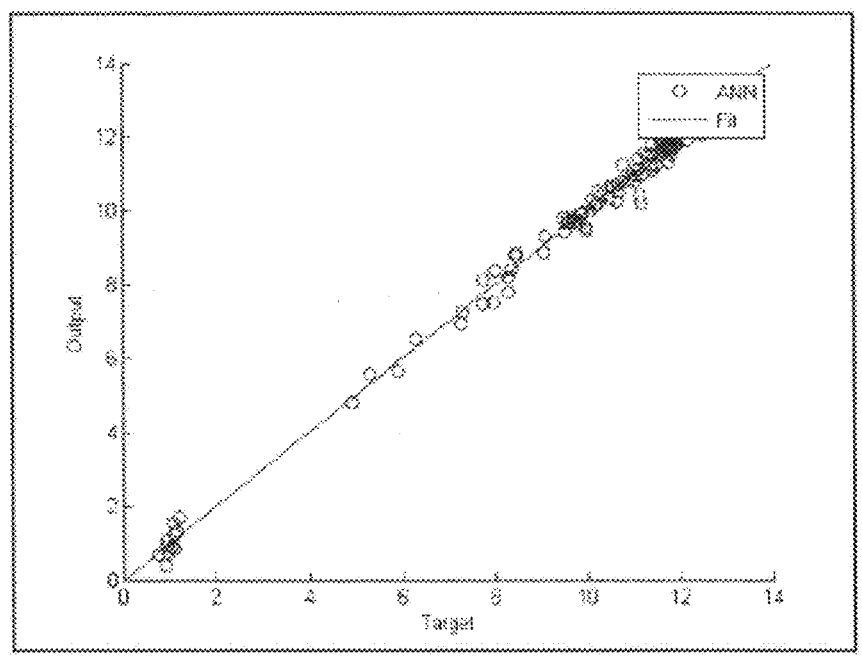
FIG. 34A illustrates a correlation between a predicted response and a target response for GFRP pipes.
Figure 34B:
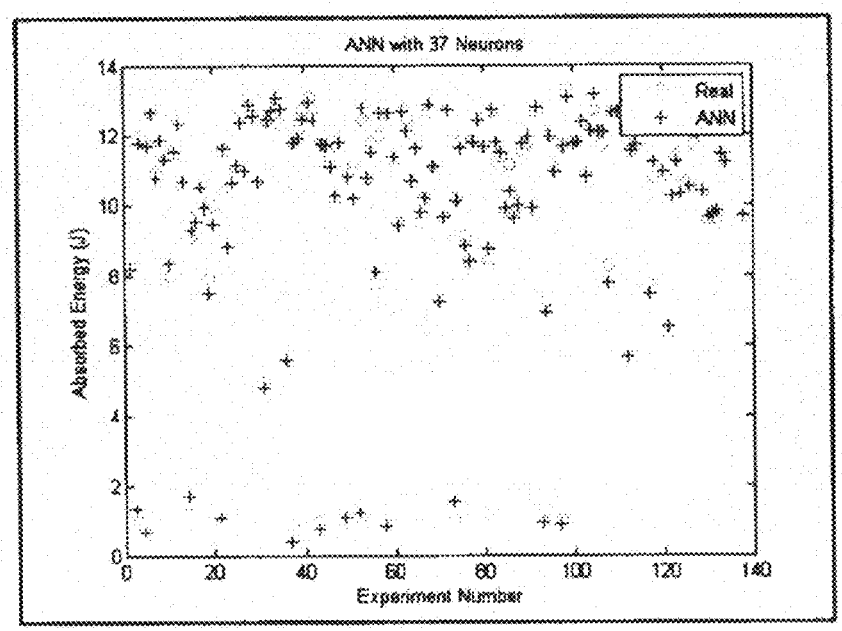
FIG. 34B illustrates scatter data of an actual response and vs. a predicted response for GFRP pipes.

FIG. 34A illustrates a correlation between a predicted response and a target response for GFRP pipes. FIG. 34B illustrates scatter data of an actual response and vs. a predicted response for GFRP pipes.

Cost Models

Composite materials and their production is an expensive process. It has always been the focus of major design and development teams to reduce the costs while simultaneously achieve maximum performance. The idea for this study is optimizing the impact performance with respect to the costs. To estimate the costs related to the composite plates and pipes, it is necessary to develop a cost model which may relate the costs of the material and the production with the samples. A simple yet realistic cost model is proposed in this section, the cost model adopted here is given by:

$$CF = X + [(C1/100) + (C2/100)] * X \qquad (6.4)$$

In this equation, CF represents the total costs, whereas X is assumed to be the material costs. In general, material costs are considered to be the maximum and the other costs like labor costs 'C1' and the other overheads 'C2' are considered to be some fraction of the material costs.

An online survey for the prices of the different types of fibers gave a basic idea of the material costs. The prices listed in the Table 39 are for a reference and may vary depending upon a number of factors ranging from the supplier to the texture of the fiber.

TABLE 39

Material costs of different types of fibers.

| Material | Type | Price |
| --- | --- | --- |
| Carbon fiber | Woven fabric | 200 USD per m$^2$ |
| Glass fiber | Woven fabric | 12 USD per m$^2$ |
| Carbon fiber | Unidirectional | 900 USD per kg |
| Glass fiber | Unidirectional | 30 USD per kg |

Based on these prices for the materials used in the manufacturing of composite plates and pipes, it is obvious that the optimization with respect to the cost is important.

Differential Evolution Algorithms

Differential evolution algorithms were developed in mid 90s as an optimization technique by Rainer Storn and Kenneth Price. It is a simple and robust population based optimization technique with few control variables and fast convergence. Being an evolutionary algorithm, the DE technique is suited for solving non-linear and non-differentiable optimization problems. DE is a kind of search technique which works on finding the candidate solution among a population. DE algorithms generate new populations from the existing one based on certain parameters like mutations and crossovers. The details about the differential evolution algorithm are not discussed here. For this problem, an initial population size of 200, with a crossover of 0.8 and a total of 100 generations is used to find the optimal solution.

Cost Optimization

The results from the all the analysis as discussed in previous chapters indicate that the improvement in impact resistance is not linearly dependent on the factors considered. Thus, it is necessary to study the cost optimization of both the composite plates and the composite pipes. A differential evolution algorithm was adopted to optimize the amount of absorbed energy by the plate or the pipe and the cost model was used to predict the cost of making that sample.

Separate optimizations for the CFRP plates and the GFRP plates was carried out and compared with the costs for both types of materials. It is assumed here that in addition to the cost and the impact performance, the weight of the structure and the thickness of the plate should also be a factor in finding the best compromise.

For GFRP plates, a series of runs of the optimization algorithm, it was found that the optimal solution is a plate having 36 number of layers using stacking sequence 4 with the thickness of each layer to be about 0.57 mm. At this configuration, the ANN model predicts the absorbed energy by the plate to be 0.004 J. The weight of the composite plate with this configuration is 0.56 kg and assuming the price listed in Table 39, the cost is estimated to be 14 USD. But it is known that the sheets of 0.57 mm may not be available commercially while 0.6 mm thick woven fabrics are available. Therefore, a design of composite plate with glass fiber to be used with 0.6 mm thick layers and 36 layers in total with the stacking sequence 4 is proposed. This configuration will weigh about 0.59 kg and cost of 14.75 USD.

Similarly, for CFRP plates, the optimal solution was found to be plate with 32 layers of stacking sequence 1 and the thickness of each layer to 0.38 mm. This configuration will weigh about 0.29 kg and the amount of absorbed energy as predicted by the ANN model is 0.102 J. The cost of this plate would be around 260 USD which is a lot as compared to just 14 USD for the glass plate although it saves almost half of the weight of the glass plate. Simulations were performed for both CFRP plates and the GFRP plates with absorbed energy of 0.21 J and 0.31 J respectively. The results show that the ANN prediction model and optimization algorithm performs well.

As concluded earlier, a best configuration would be to use the stacking sequence 4 with mainly GFRP layers and replacing top and middle layers with the CFRP layers. This configuration is believed to perform better in terms of less weight and thickness with some increase in price.

Also, the same optimization procedure is applied to the composite pipes. The results from ANN in this case have some error but the procedure in general is applicable. This ANN model may skip some of the better results but due to the error in estimation of the absorbed energy, the optimization algorithm would reject a better one in favor of a worse but reliable solution. About 10 runs of optimization algorithm were performed and the most repeated configuration was selected. It was found from the optimization routine for the carbon fiber pipes; the best solution would be to have winding angle of 42.5° with total 36 layers and having each layer of 0.425 mm thick. According to ANN model this configuration would absorb energy of about 0.2 J. The price estimate for this type of pipe is about 1370 USD while the weight is about 6.8 kg. A simulation was performed in ABAQUS for this configuration which reports absorbed energy of 0.3 J.

Optimization for the glass fiber pipes suggested that optimal solution to be pipes with winding angle of 51° with total of 40 layers and each layer of about 0.4 mm thick. According to the ANN model this configuration would absorb around 0.965 J of energy. The cost estimate for this configuration of pipe is about 250 USD. This pipe weighs around 9 kgs. Simulation of GFRP pipe with the optimized configuration using ABAQUS suggests the results are quite accurate as the predicted absorbed energy is close to the one from simulation which is 0.88 J.

A simulation in the ABAQUS environment of the proposed solution from the optimization algorithm confirmed the results for all the cases. As was the case with plates, the compromise between price and the weight may be achieved by replacing top layers of GFRP pipes with the carbon fiber layers as previously discussed.

The main conclusions from this section may be summarized as:

ANN models are very strong and useful tools for the function fitting of non-linear behavior and as observed in the case of CFRP plates are able to predict the absorbed energy with very little error.

The accuracy of the ANN models depend upon the behavior of the training data sets, if there are too much sudden variations in the training data as was observed in the results from the composite pipes then the model may be prone to errors.

A better way to model ANN with training data as in this case is to simulate and generate a very big training data. In this study, there were around 100 data each for the flat plates and about 150 for the pipes apart from the ones that were used to validate the results. As a rule of thumb, it is suggested that the data size should be in the range of 500-1000 for a very accurate model.

The results and discussions about the findings were already discussed in detail with each section. The following may be summarized as the conclusions:

The Hashin damage model used as the damage initiation model in this research is accurate enough to predict the onset of damage without loss of much accuracy.

Sensitivity analysis is a useful tool in determining the factors influencing the most on the impact performance of the FRP plates and pipes.

The amount of absorbed energy considered as an indication for the amount of damage is affected mainly by the thickness of the layers, number of layers, stacking sequence and the material properties.

Material properties like the tensile strength of the fiber and the fracture energies of the laminate during the tensile loading in the longitudinal direction are more influential than other mechanical properties of the fiber or the binder material used.

Quasi isotropic laminates show good performance in all conditions. But, the stacking sequence other than quasi isotropic laminates may have optimal performance if the boundary conditions are such that they restrict deformation in any particular direction and allow in the other directions.

Influence of boundary conditions may be controlled by aligning more layers to counter the stress produced as a result of bending.

The numbers of layers also have an effect on the impact resistance and should be selected carefully as to not just increase the layers which result in more contact force and hence greater damage.

Design of experiment is a useful method to statistically study the variation in the impact performance of the FRP plates and pipes with respect to the variables identified using sensitivity analysis.

The effect of thickness of the laminate is the most interesting one compared to the other factors. The thickness is not directly proportional to the impact performance of the plates or the pipes. Thin plates have better performance compared to plates that are thick but not rigid enough.

The amount of dissipated energy transferred to the specimen is not always in the form of damage dissipation but some of the energy is transferred to the specimen which generates unnecessary vibration. Based on the above two conclusions, the specimen thickness should be such that it is stiff and thick enough to withstand the impact loads without suffering from the vibrations.

It is important to have as more fibers as possible in the direction of the maximum stress during the impact to delay the damage initiation process.

The design of the structure and the choice of material should be such that the maximum utilization of the tensile strength of the fiber materials may be achieved.

The inclusion of woven fabric in the filament wound composite pipes may be beneficial if the woven fabric selected has a higher tensile strength than the unidirectional glass or carbon fibers.

Using the optimization algorithm, it was suggested that the optimal stacking sequence for the flat plates would be the sequence number 4 from this study.

The inclusion of carbon fibers in the flat plates and the pipes may enhance the impact resistance quite a lot with the added advantage of weight savings as well as reduced thickness at a slightly higher price.

Obviously, numerous modifications and variations of the present invention are possible in light of the above teachings. It is therefore to be understood that within the scope of the appended claims, the invention may be practiced otherwise than as specifically described herein.

A method in accordance with an exemplary implementation of present invention is illustrated in FIG. 35. As illustrated in FIG. 35, a method for predicting an impact resistance of a composite material may begin in Step 10.

In Step 10, an artificial neural network may be designed. Discussion relating to artificial neural networks has been previously presented relating to FIG. 30. In an exemplary implementation of the present invention, the artificial neural network may be designed to include a plurality of layers, each layer including a plurality of neurons. The artificial neural network may be a feed forward network. As illustrated in FIG. 30, an artificial neural network may be designed to include an input layer and an output layer. Additionally, the artificial neural network may include one or more hidden layers.

The input layer of the artificial neural network may be designed to include a plurality of neurons. Each neuron in the input layer may receive data that is input into the artificial neural network. In an exemplary implementation of the present invention, each neuron in the input layer may perform a process upon data that is input. After performance of the process, each neuron may then output data to one or more neurons in a next layer of the artificial neural network. In an exemplary implementation, each neuron of the input layer may output data to one or more neurons in the hidden layer.

In an exemplary implementation of the present invention, the artificial neural network further includes a single hidden layer, as illustrated in FIG. 30. However, other exemplary implementations of the present invention may include zero or more than one hidden layer within the artificial neural network.

The hidden layer may be designed to include a plurality of neurons. Each neuron in the hidden layer may receive data from one or more neurons in the input layer of the artificial neural network. In an exemplary implementation of the present invention, each neuron in the hidden layer may perform a process upon the input data. After performance of the process, each neuron of the hidden layer may then output data to one or more neurons in the output layer of the artificial neural network.

The output layer of the artificial neural network may be designed to include a plurality of neurons. Each neuron in the output layer of the artificial neural network may receive data from one or more neurons in a previous layer of the artificial neural network. In an exemplary implementation, each neuron in the output layer may receive data from one or more neurons in the hidden layer. In alternative implementations, each neuron in the output layer may receive data from one or more neurons in an additional layer within the artificial neural network.

The artificial neural network may be designed according to the type of data to be input into the artificial neural network. Data that may be input into the artificial neural network regarding the composite material may include, for example:

stacking sequence of layers in the composite material;
layer thickness;
number of layers in the composite material;
orientation angle of the layers in the composite material; and/or
a material composition of the layers in the composite material.

However, other data relating to the composite material may be input into the artificial neural network for computation that is required so as to predict an impact resistance of the composite material, as previously discussed. For example, the artificial neural network may receive data relating to dimensional information of each layer in the composite material, dimensional information of the composite material as a whole, and/or the shape and structure of the composite material. Alternatively, the artificial neural network may also be designed in accordance with factors such as processing power, time, the amount of data required for an accurate prediction, and/or cost.

Additionally, data may be input into the artificial neural network so as to train the artificial neural network to more accurately predict an impact resistance of the composite material. Such data input is discussed in Step 20.

In Step 20, the artificial neural network is trained to more accurately predict an impact resistance of the composite material. Step 20 may include Steps 22, 24, 26 and/or 28.

In Step 22, sample data is input into the input layer of the artificial neural network. The sample data may include input data relating to a sample composite material that has a known impact resistance. That is, the sample data may relate to a sample composite material in which the impact resistance is already known, and thus, need not be predicted. The sample data may be used so as to train or tune the artificial neural network to more accurately predict an impact resistance of the composite material.

After the sample data is fed into the artificial neural network in Step 22, the artificial neural network processes the sample data. In Step 24, a predicted impact resistance may be output from the artificial neural network relating to the sample composite material. In Step 26, an error of the predicted impact resistance may be calculated by measuring a difference between the known impact resistance of the sample composite material and the predicted impact resistance that was output from the artificial neural network. In exemplary implementations of the present invention, the error may be a mean-squared error. Alternatively, the error may be calculated by other methods.

After the error is acquired in Step 26, the artificial neural network may be trained by reducing an error in the predicted impact resistance calculated by the artificial neural network. In Step 28, the error may be reduced by adjusting inputs and outputs of neurons in the artificial neuron network. In particular, the error may be reduced by applying a variable weighting factor to each neuron in the artificial neural network to adjust an output of each neuron. In other words, an output a neuron may be increased or decreased by a factor so as to increase or decrease the impact of the neuron's output within the next layer's processing. The variable weighting factor may be any whole or fraction, positive or negative.

Additionally, the error may be reduced by managing what data is input into each neuron in the hidden layer. For example, data output from neurons in the input layer may be selected for input to a neuron in the hidden layer. In other words, for each neuron in the hidden layer, data output from neurons in the input layer may be input or may not be input. Further, data input into each neuron within the hidden layer may be individually managed such that individual neurons in the hidden layer may receive input from different input layer neurons. As a result, data that is input into each neuron of the hidden layer may be managed so as to manage a processing of each neuron in the hidden layer.

In implementations of the present invention that include more than one hidden layer, or include other additional layers, inputs of data for neurons in each additional hidden layer or other layer may be individually managed so as to manage a processing of each neuron in each layer.

Furthermore, the error may be reduced by both (1) adjusting inputs and outputs of neurons in the artificial neuron network, and (2) managing what data is input into each neuron in the hidden layer. However, in other exemplary implementations, the error may be reduced by alternatively (1) adjusting inputs and outputs of neurons in the artificial neuron network, or (2) managing what data is input into each neuron in the hidden layer.

Once the inputs and outputs of neurons in the artificial neural network have been modified, Steps 22, 24, 26 and 28 may be repeated multiple times with the same sample data and/or different sample data so as to further train the artificial neural network.

After the artificial neural network has been trained to predict an impact resistance of a composite material, the method proceeds to Step 30. In Step 30, data relating to the composite material may be input into the artificial neural network. The data may be input in a manner similar or analogous to the input of data in Step 22.

After data relating to the composite material has been input into the artificial neural network, the artificial neural network processes the input data. The method then proceeds to Step 40. In Step 40, a predicted impact resistance may be calculated and output from the artificial neural network relating to the composite material.

The method as previously described and illustrated in FIG. 35 may be further utilized with the artificial neural network to predict an optimized design of a plate or pipe comprising the composite material.

An alternative implementation of the present invention may include a computer readable medium that stores computer readable instructions that, when executed by a computer, may cause the computer to perform the method for predicting an impact resistance of a composite material, as previously described and illustrated in FIG. 35.

In another exemplary implementation of the present invention, a device comprising a processor may be configured to perform the method for predicting an impact resistance of a composite material, as described above and illustrated in FIG. 35. Such a device is illustrated in FIG. 36.

Figure 36:
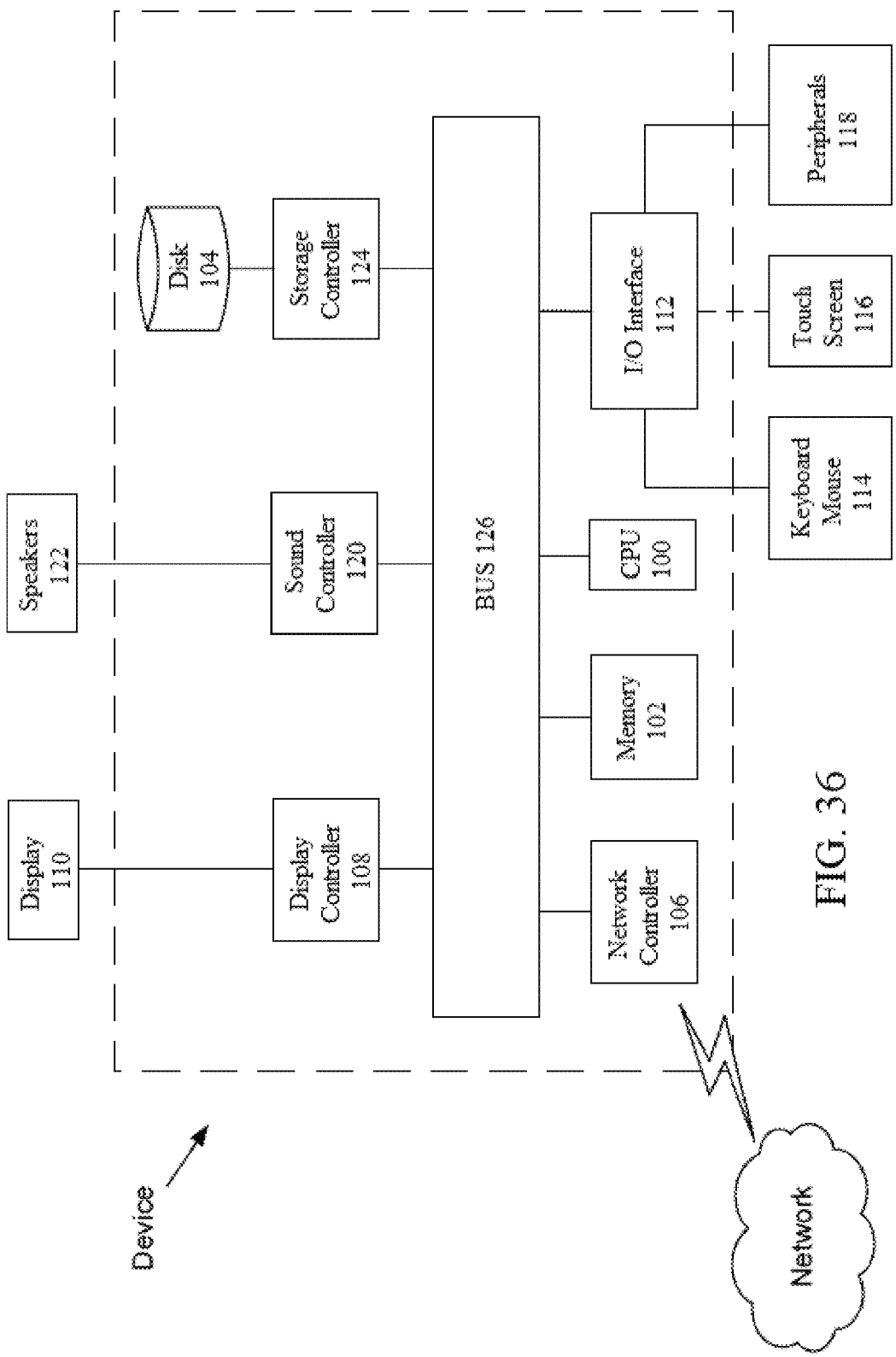
FIG. 36 illustrates an apparatus in accordance with an exemplary implementation of the present invention.

In FIG. 36, the device includes a CPU 100 which may perform the method described above and illustrated in FIG. 35. The process data and instructions may be stored in memory 102. These processes and instructions may also be stored on a storage medium disk 104 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the device communicates, such as a server or computer.

Further, the claimed advancements may be provided as a utility application, background daemon, or component of an operating system, or combination thereof, executing in conjunction with CPU 100 and an operating system such as Microsoft Windows 7, UNIX, Solaris, LINUX, Apple MAC-OS and other systems known to those skilled in the art.

CPU 100 may be a Xenon or Core processor from Intel of America or an Opteron processor from AMD of America, or may be other processor types that would be recognized by one of ordinary skill in the art. Alternatively, the CPU 100 may be implemented on an FPGA, ASIC, PLD or using discrete logic circuits, as one of ordinary skill in the art would recognize. Further, CPU 100 may be implemented as multiple processors cooperatively working in parallel to perform the instructions of the inventive processes described above.

The device in FIG. 36 also includes a network controller 106, such as an Intel Ethernet PRO network interface card from Intel Corporation of America, for interfacing with a network. As can be appreciated, the network can be a public network, such as the Internet, or a private network such as an LAN or WAN network, or any combination thereof and can also include PSTN or ISDN sub-networks. The network can also be wired, such as an Ethernet network, or can be wireless such as a cellular network including EDGE, 3G and 4G wireless cellular systems. The wireless network can also be WiFi, Bluetooth, or any other wireless form of communication that is known.

The device further includes a display controller 108, such as a NVIDIA GeForce GTX or Quadro graphics adaptor from NVIDIA Corporation of America for interfacing with display 110, such as a Hewlett Packard HPL2445w LCD monitor. A general purpose I/O interface 112 interfaces with a keyboard and/or mouse 114 as well as a touch screen panel 116 on or separate from display 110. General purpose I/O interface also connects to a variety of peripherals 118 including printers and scanners, such as an OfficeJet or DeskJet from Hewlett Packard.

The device may be utilized to output the predicted impact resistance. Once the predicted impact resistance is output from the artificial neural network, components of the device may output the prediction to a recipient. For example, display 110, touch panel 116, network controller 106 and/or speakers/microphone 122 may output the prediction to a recipient. Network controller 106 may output the prediction over the network. Further, the prediction may be stored locally within memory 102, storage medium disk 104, or recorded in another removable internal or external storage medium.

A sound controller 120 is also provided in the device, such as Sound Blaster X-Fi Titanium from Creative, to interface with speakers/microphone 122 thereby providing sounds and/or music.

The general purpose storage controller 124 connects the storage medium disk 104 with communication bus 126, which may be an ISA, EISA, VESA, PCI, or similar, for interconnecting all of the components of the device. A description of the general features and functionality of the display 110, keyboard and/or mouse 114, as well as the display controller 108, storage controller 124, network controller 106, sound controller 120, and general purpose I/O interface 112 is omitted herein for brevity as these features are known.

In various implementations of the present invention, the artificial neural network may be located over a network and accessible by the device via network controller 106. Alternatively, the artificial neural network may be accessed by the device via I/O interface 112. In other exemplary implementations of the present invention, the functionality of the artificial neural network may be executed by CPU 100.

Additionally, an exemplary implementation of the present invention may include a system for predicting an impact resistance of a composite material. In such a configuration, the system may include a device, as previously discussed and illustrated in FIG. 36, the device executing the method as previously discussed and illustrated in FIG. 35, as well as the artificial neural network.

The foregoing discussion discloses and describes merely exemplary implementations of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

APPENDICES

A.1 Results for the Composite Plates

TABLE A. 1

List of experiments numerically solved for the layer configuration 1 for Carbon/Epoxy plates

| S. No. | Layer Thickness (mm) | Number of Layers | Total Thickness of Plate (mm) | Rebound Velocity (m/s) | Absorbed Energy (J) |
|---|---|---|---|---|---|
| 1 | 0.12 | 16 | 1.92 | 3.7716 | 16.8809 |
| 2 | 0.14 | 16 | 2.24 | 4.5403 | 12.0893 |
| 3 | 0.16 | 16 | 2.56 | 4.9512 | 9.1643 |
| 4 | 0.18 | 16 | 2.88 | 5.1430 | 7.71212 |
| 5 | 0.12 | 20 | 2.4 | 4.5898 | 11.7503 |
| 6 | 0.16 | 20 | 3.2 | 5.0757 | 8.2276 |
| 7 | 0.18 | 20 | 3.6 | 5.0685 | 8.2824 |
| 8 | 0.2 | 16 | 3.2 | 5.1193 | 7.8947 |
| 9 | 0.25 | 16 | 4 | 5.2618 | 6.7855 |
| 10 | 0.3 | 16 | 4.8 | 5.2854 | 6.5986 |
| 11 | 0.2 | 20 | 4 | 5.1614 | 7.5701 |
| 12 | 0.25 | 20 | 5 | 5.2251 | 7.0740 |
| 13 | 0.3 | 20 | 6 | 5.3709 | 5.9155 |
| 14 | 0.2 | 24 | 4.8 | 5.2905 | 6.6578 |

TABLE A. 1-continued

List of experiments numerically solved for the layer configuration 1 for Carbon/Epoxy plates

| S. No. | Layer Thickness (mm) | Number of Layers | Total Thickness of Plate (mm) | Rebound Velocity (m/s) | Absorbed Energy (J) |
|---|---|---|---|---|---|
| 15 | 0.25 | 24 | 6 | 5.3791 | 5.8493 |
| 16 | 0.3 | 24 | 7.2 | 5.3403 | 6.1606 |
| 17 | 0.2 | 28 | 5.6 | 5.3385 | 6.1756 |
| 18 | 0.25 | 28 | 7 | 5.3890 | 5.7693 |
| 19 | 0.3 | 28 | 8.4 | 5.5732 | 4.2549 |
| 20 | 0.35 | 28 | 9.8 | 5.7503 | 2.7507 |
| 21 | 0.4 | 28 | 11.2 | 5.9987 | 0.56125 |
| 22 | 0.3 | 32 | 9.6 | 5.7284 | 2.9391 |
| 23 | 0.35 | 32 | 11.2 | 6.0384 | 0.2031 |
| 24 | 0.4 | 32 | 12.8 | 6.0349 | 0.2346 |
| 25 | 0.3 | 36 | 10.8 | 5.9588 | 0.9193 |
| 26 | 0.35 | 36 | 12.6 | 6.0409 | 0.18073 |
| 27 | 0.4 | 36 | 14.4 | 6.0486 | 0.11064 |

TABLE A. 2

List of experiments numerically solved for the layer configuration 2 for Carbon/Epoxy plates

| S. No. | Layer Thickness (mm) | Number of Layers | Total Thickness of Plate (mm) | Rebound Velocity (m/s) | Absorbed Energy (J) |
|---|---|---|---|---|---|
| 1 | 0.12 | 16 | 1.92 | 4.11064 | 14.8770 |
| 2 | 0.14 | 16 | 2.24 | 4.69889 | 10.9903 |
| 3 | 0.16 | 16 | 2.56 | 5.06889 | 8.2798 |
| 4 | 0.18 | 16 | 2.88 | 5.14636 | 7.6862 |
| 5 | 0.12 | 20 | 2.4 | 4.96802 | 9.0391 |
| 6 | 0.16 | 20 | 3.2 | 5.2784 | 6.6539 |
| 7 | 0.18 | 20 | 3.6 | 5.37821 | 5.8561 |
| 8 | 0.2 | 16 | 3.2 | 5.26623 | 6.7501 |
| 9 | 0.25 | 16 | 4 | 5.40544 | 5.6359 |
| 10 | 0.3 | 16 | 4.8 | 5.42364 | 5.4881 |
| 11 | 0.2 | 20 | 4 | 5.41088 | 5.5918 |
| 12 | 0.25 | 20 | 5 | 5.44628 | 5.3035 |
| 13 | 0.3 | 20 | 6 | 5.49541 | 4.9003 |
| 14 | 0.2 | 24 | 4.8 | 5.39271 | 5.7390 |
| 15 | 0.25 | 24 | 6 | 5.50199 | 4.8461 |
| 16 | 0.3 | 24 | 7.2 | 5.46472 | 5.1526 |
| 17 | 0.2 | 28 | 5.6 | 5.51426 | 4.7447 |
| 18 | 0.25 | 28 | 7 | 5.43048 | 5.4324 |
| 19 | 0.3 | 28 | 8.4 | 5.59542 | 4.0685 |
| 20 | 0.35 | 28 | 9.8 | 5.79284 | 2.3823 |
| 21 | 0.4 | 28 | 11.2 | 5.97076 | 0.8125 |
| 22 | 0.3 | 32 | 9.6 | 5.82705 | 2.0841 |
| 23 | 0.35 | 32 | 11.2 | 5.97504 | 0.7742 |
| 24 | 0.4 | 32 | 12.8 | 6.03607 | 0.2244 |
| 25 | 0.3 | 36 | 10.8 | 5.93021 | 1.1745 |
| 26 | 0.35 | 36 | 12.6 | 6.03809 | 0.2061 |
| 27 | 0.4 | 36 | 14.4 | 5.92846 | 1.1900 |

TABLE A. 3

List of experiments numerically solved for the layer configuration 3 for Carbon/Epoxy plates

| S. No. | Layer Thickness (mm) | Number of Layers | Total Thickness of Plate (mm) | Rebound Velocity (m/s) | Absorbed Energy (J) |
|---|---|---|---|---|---|
| 1 | 0.12 | 16 | 1.92 | 4.02354 | 15.4083 |
| 2 | 0.14 | 16 | 2.24 | 5.00151 | 8.7887 |
| 3 | 0.16 | 16 | 2.56 | 5.1643 | 7.5475 |
| 4 | 0.18 | 16 | 2.88 | 5.23933 | 6.9621 |
| 5 | 0.12 | 20 | 2.4 | 5.00133 | 8.7900 |
| 6 | 0.16 | 20 | 3.2 | 5.30247 | 6.4629 |
| 7 | 0.18 | 20 | 3.6 | 5.29392 | 6.5308 |
| 8 | 0.2 | 16 | 3.2 | 5.21854 | 7.1251 |

TABLE A. 3-continued

List of experiments numerically solved for the layer configuration 3 for Carbon/Epoxy plates

| S. No. | Layer Thickness (mm) | Number of Layers | Total Thickness of Plate (mm) | Rebound Velocity (m/s) | Absorbed Energy (J) |
|---|---|---|---|---|---|
| 9  | 0.25 | 16 | 4    | 5.21853 | 7.1252 |
| 10 | 0.3  | 16 | 4.8  | 5.44782 | 5.2909 |
| 11 | 0.2  | 20 | 4    | 5.37119 | 5.9127 |
| 12 | 0.25 | 20 | 5    | 5.38755 | 5.7807 |
| 13 | 0.3  | 20 | 6    | 5.50416 | 4.8282 |
| 14 | 0.2  | 24 | 4.8  | 5.44647 | 5.3020 |
| 15 | 0.25 | 24 | 6    | 5.50308 | 4.8371 |
| 16 | 0.3  | 24 | 7.2  | 5.37818 | 5.8564 |
| 17 | 0.2  | 28 | 5.6  | 5.46656 | 5.1375 |
| 18 | 0.25 | 28 | 7    | 5.42745 | 5.4571 |
| 19 | 0.3  | 28 | 8.4  | 5.59528 | 4.0696 |
| 20 | 0.35 | 28 | 9.8  | 5.64996 | 3.6085 |
| 21 | 0.4  | 28 | 11.2 | 5.92138 | 1.2529 |
| 22 | 0.3  | 32 | 9.6  | 5.62214 | 3.8437 |
| 23 | 0.35 | 32 | 11.2 | 5.91947 | 1.2699 |
| 24 | 0.4  | 32 | 12.8 | 6.02044 | 0.3657 |
| 25 | 0.3  | 36 | 10.8 | 5.87043 | 1.7035 |
| 26 | 0.35 | 36 | 12.6 | 6.02154 | 0.3560 |
| 27 | 0.4  | 36 | 14.4 | 5.93517 | 1.1303 |

TABLE A. 4

List of experiments numerically solved for the layer configuration 4 for Carbon/Epoxy plates

| S. No. | Layer Thickness (mm) | Number of Layers | Total Thickness of Plate (mm) | Rebound Velocity (m/s) | Absorbed Energy (J) |
|---|---|---|---|---|---|
| 1  | 0.12 | 16 | 1.92 | 3.42872 | 18.7329 |
| 2  | 0.14 | 16 | 2.24 | 3.98288 | 15.6525 |
| 3  | 0.16 | 16 | 2.56 | 5.09185 | 8.1048 |
| 4  | 0.18 | 16 | 2.88 | 5.22069 | 7.1083 |
| 5  | 0.12 | 20 | 2.4  | 4.60535 | 11.6431 |
| 6  | 0.16 | 20 | 3.2  | 5.21299 | 7.1686 |
| 7  | 0.18 | 20 | 3.6  | 5.31472 | 6.3653 |
| 8  | 0.2  | 16 | 3.2  | 5.2942  | 6.5286 |
| 9  | 0.25 | 16 | 4    | 5.46716 | 5.1326 |
| 10 | 0.3  | 16 | 4.8  | 5.522   | 4.6806 |
| 11 | 0.2  | 20 | 4    | 5.37021 | 5.9206 |
| 12 | 0.25 | 20 | 5    | 5.55184 | 4.4328 |
| 13 | 0.3  | 20 | 6    | 5.61302 | 3.9205 |
| 14 | 0.2  | 24 | 4.8  | 5.52799 | 4.6310 |
| 15 | 0.25 | 24 | 6    | 5.63551 | 3.7308 |
| 16 | 0.3  | 24 | 7.2  | 5.56273 | 4.3420 |
| 17 | 0.2  | 28 | 5.6  | 5.62726 | 3.8005 |
| 18 | 0.25 | 28 | 7    | 5.543   | 4.5064 |
| 19 | 0.3  | 28 | 8.4  | 5.75417 | 2.7171 |
| 20 | 0.35 | 28 | 9.8  | 5.77615 | 2.5271 |
| 21 | 0.4  | 28 | 11.2 | 5.91357 | 1.3223 |
| 22 | 0.3  | 32 | 9.6  | 5.78399 | 2.4591 |
| 23 | 0.35 | 32 | 11.2 | 5.9137  | 1.3211 |
| 24 | 0.4  | 32 | 12.8 | 6.02662 | 0.3099 |
| 25 | 0.3  | 36 | 10.8 | 5.86668 | 1.7365 |
| 26 | 0.35 | 36 | 12.6 | 6.02121 | 0.3588 |
| 27 | 0.4  | 36 | 14.4 | 5.94022 | 1.0853 |

TABLE A. 5

List of experiments numerically solved for the layer configuration 1 for Glass/Epoxy plates

| S. No. | Layer Thickness (mm) | Number of Layers | Total Thickness of Plate (mm) | Rebound Velocity (m/s) | Absorbed Energy (J) |
|---|---|---|---|---|---|
| 1  | 0.25 | 24 | 6    | 4.29654 | 13.7048 |
| 2  | 0.3  | 24 | 7.2  | 4.45182 | 12.6860 |
| 3  | 0.35 | 24 | 8.4  | 4.38999 | 13.0960 |
| 4  | 0.4  | 24 | 9.6  | 4.25182 | 13.9915 |
| 5  | 0.45 | 24 | 10.8 | 4.1855  | 14.4112 |
| 6  | 0.5  | 24 | 12   | 4.01153 | 15.4807 |
| 7  | 0.6  | 24 | 14.4 | 5.00643 | 8.7517 |
| 8  | 0.25 | 28 | 7    | 4.59771 | 11.6958 |
| 9  | 0.3  | 28 | 8.4  | 4.46418 | 12.6033 |
| 10 | 0.35 | 28 | 9.8  | 4.32582 | 13.5155 |
| 11 | 0.4  | 28 | 11.2 | 4.14263 | 14.6790 |
| 12 | 0.25 | 32 | 8    | 4.28157 | 13.8011 |
| 13 | 0.3  | 32 | 9.6  | 4.26511 | 13.9066 |
| 14 | 0.35 | 32 | 11.2 | 4.13433 | 14.7305 |
| 15 | 0.25 | 36 | 9    | 4.46612 | 12.5903 |
| 16 | 0.3  | 36 | 10.8 | 4.09504 | 14.9730 |
| 17 | 0.35 | 36 | 12.6 | 3.80239 | 16.7064 |
| 18 | 0.4  | 32 | 12.8 | 4.51516 | 12.2600 |
| 19 | 0.4  | 36 | 14.4 | 5.02762 | 8.5923 |
| 20 | 0.45 | 28 | 12.6 | 3.97484 | 15.7005 |
| 21 | 0.45 | 32 | 14.4 | 4.99326 | 8.8505 |
| 22 | 0.45 | 36 | 16.2 | 5.81877 | 2.1564 |
| 23 | 0.5  | 28 | 14   | 4.98613 | 8.9039 |
| 24 | 0.5  | 32 | 16   | 5.80594 | 2.2683 |
| 25 | 0.5  | 36 | 18   | 5.97269 | 0.7952 |
| 26 | 0.6  | 28 | 16.8 | 5.88193 | 1.6022 |
| 27 | 0.6  | 32 | 19.2 | 6.01784 | 0.3892 |

TABLE A. 6

List of experiments numerically solved for the layer configuration 2 for Glass/Epoxy plates

| S. No. | Layer Thickness (mm) | Number of Layers | Total Thickness of Plate (mm) | Rebound Velocity (m/s) | Absorbed Energy (J) |
|---|---|---|---|---|---|
| 1  | 0.25 | 24 | 6    | 4.3052  | 13.6489 |
| 2  | 0.3  | 24 | 7.2  | 4.18788 | 14.3962 |
| 3  | 0.35 | 24 | 8.4  | 4.46527 | 12.5960 |
| 4  | 0.4  | 24 | 9.6  | 4.35886 | 13.3003 |
| 5  | 0.45 | 24 | 10.8 | 4.15121 | 14.6256 |
| 6  | 0.5  | 24 | 12   | 3.86215 | 16.3628 |
| 7  | 0.6  | 24 | 14.4 | 5.67396 | 3.4046 |
| 8  | 0.25 | 28 | 7    | 4.3385  | 13.4331 |
| 9  | 0.3  | 28 | 8.4  | 4.61759 | 11.5584 |
| 10 | 0.35 | 28 | 9.8  | 4.35215 | 13.3441 |
| 11 | 0.4  | 28 | 11.2 | 4.0995  | 14.9456 |
| 12 | 0.25 | 32 | 8    | 4.47352 | 12.5407 |
| 13 | 0.3  | 32 | 9.6  | 4.38341 | 13.1393 |
| 14 | 0.35 | 32 | 11.2 | 4.10035 | 14.9403 |
| 15 | 0.25 | 36 | 9    | 4.47352 | 12.5407 |
| 16 | 0.3  | 36 | 10.8 | 4.17267 | 14.4916 |
| 17 | 0.35 | 36 | 12.6 | 4.44619 | 12.7235 |
| 18 | 0.4  | 32 | 12.8 | 4.62489 | 11.5078 |
| 19 | 0.4  | 36 | 14.4 | 5.67654 | 3.3827 |
| 20 | 0.45 | 28 | 12.6 | 4.4747  | 12.5328 |
| 21 | 0.45 | 32 | 14.4 | 5.6774  | 3.3753 |
| 22 | 0.45 | 36 | 16.2 | 5.83351 | 2.0276 |
| 23 | 0.5  | 28 | 14   | 5.70682 | 3.1242 |
| 24 | 0.5  | 32 | 16   | 5.81129 | 2.2217 |
| 25 | 0.5  | 36 | 18   | 5.97706 | 0.7561 |
| 26 | 0.6  | 28 | 16.8 | 5.88858 | 1.5435 |
| 27 | 0.6  | 32 | 19.2 | 6.02185 | 0.3530 |

TABLE A. 7

List of experiments numerically solved for the layer configuration 3 for Glass/Epoxy plates

| S. No. | Layer Thickness (mm) | Number of Layers | Total Thickness of Plate (mm) | Rebound Velocity (m/s) | Absorbed Energy (J) |
|---|---|---|---|---|---|
| 1 | 0.25 | 24 | 6 | 4.29723 | 13.7004 |
| 2 | 0.3 | 24 | 7.2 | 4.30629 | 13.6419 |
| 3 | 0.35 | 24 | 8.4 | 4.21859 | 14.2026 |
| 4 | 0.4 | 24 | 9.6 | 4.02843 | 15.3788 |
| 5 | 0.45 | 24 | 10.8 | 4.77313 | 10.4629 |
| 6 | 0.5 | 24 | 12 | 5.0023 | 8.7827 |
| 7 | 0.6 | 24 | 14.4 | 5.05658 | 8.3732 |
| 8 | 0.25 | 28 | 7 | 4.46288 | 12.6120 |
| 9 | 0.3 | 28 | 8.4 | 4.40108 | 13.0229 |
| 10 | 0.35 | 28 | 9.8 | 4.13868 | 14.7035 |
| 11 | 0.4 | 28 | 11.2 | 4.67287 | 11.1732 |
| 12 | 0.25 | 32 | 8 | 4.10725 | 14.8979 |
| 13 | 0.3 | 32 | 9.6 | 4.0367 | 15.3288 |
| 14 | 0.35 | 32 | 11.2 | 4.73406 | 10.7415 |
| 15 | 0.25 | 36 | 9 | 4.30269 | 13.6651 |
| 16 | 0.3 | 36 | 10.8 | 4.73654 | 10.7240 |
| 17 | 0.35 | 36 | 12.6 | 5.01993 | 8.6502 |
| 18 | 0.4 | 32 | 12.8 | 5.0657 | 8.3040 |
| 19 | 0.4 | 36 | 14.4 | 5.07679 | 8.2197 |
| 20 | 0.45 | 28 | 12.6 | 5.02813 | 8.5884 |
| 21 | 0.45 | 32 | 14.4 | 5.06793 | 8.2871 |
| 22 | 0.45 | 36 | 16.2 | 5.78836 | 2.4212 |
| 23 | 0.5 | 28 | 14 | 5.08497 | 8.1573 |
| 24 | 0.5 | 32 | 16 | 5.76298 | 2.6410 |
| 25 | 0.5 | 36 | 18 | 5.96128 | 0.8974 |
| 26 | 0.6 | 28 | 16.8 | 5.86131 | 1.7838 |
| 27 | 0.6 | 32 | 19.2 | 6.01275 | 0.4351 |

TABLE A. 8

List of experiments numerically solved for the layer configuration 4 for Glass/Epoxy plates

| S. No. | Layer Thickness (mm) | Number of Layers | Total Thickness of Plate (mm) | Rebound Velocity (m/s) | Absorbed Energy (J) |
|---|---|---|---|---|---|
| 1 | 0.25 | 24 | 6 | 4.37745 | 13.1785 |
| 2 | 0.3 | 24 | 7.2 | 3.95406 | 15.8241 |
| 3 | 0.35 | 24 | 8.4 | 4.69099 | 11.0460 |
| 4 | 0.4 | 24 | 9.6 | 5.37575 | 5.8760 |
| 5 | 0.45 | 24 | 10.8 | 5.43519 | 5.3940 |
| 6 | 0.5 | 24 | 12 | 5.42735 | 5.4579 |
| 7 | 0.6 | 24 | 14.4 | 5.68184 | 3.3375 |
| 8 | 0.25 | 28 | 7 | 4.1224 | 14.8044 |
| 9 | 0.3 | 28 | 8.4 | 4.51686 | 12.2485 |
| 10 | 0.35 | 28 | 9.8 | 5.39647 | 5.7086 |
| 11 | 0.4 | 28 | 11.2 | 5.433 | 5.4119 |
| 12 | 0.25 | 32 | 8 | 4.57902 | 11.8244 |
| 13 | 0.3 | 32 | 9.6 | 5.37565 | 5.8768 |
| 14 | 0.35 | 32 | 11.2 | 5.46052 | 5.1870 |
| 15 | 0.25 | 36 | 9 | 5.3227 | 6.3016 |
| 16 | 0.3 | 36 | 10.8 | 5.4226 | 5.4966 |
| 17 | 0.35 | 36 | 12.6 | 5.35458 | 6.0464 |
| 18 | 0.4 | 32 | 12.8 | 5.3718 | 5.9078 |
| 19 | 0.4 | 36 | 14.4 | 5.67569 | 3.3899 |
| 20 | 0.45 | 28 | 12.6 | 5.35868 | 6.0134 |
| 21 | 0.45 | 32 | 14.4 | 5.67957 | 3.3569 |
| 22 | 0.45 | 36 | 16.2 | 5.77795 | 2.5115 |
| 23 | 0.5 | 28 | 14 | 5.75044 | 2.7493 |
| 24 | 0.5 | 32 | 16 | 5.75055 | 2.7484 |
| 25 | 0.5 | 36 | 18 | 5.95438 | 0.9590 |
| 26 | 0.6 | 28 | 16.8 | 5.84955 | 1.8871 |
| 27 | 0.6 | 32 | 19.2 | 6.01049 | 0.4555 |

TABLE A. 9

Combinations for Top and Bottom layers of Carbon/epoxy and Results

| No. | Carbon layer thickness (mm) | Glass layer thickness (mm) | Total Plate Thickness (mm) | Number of Layers | Rebound Velocity (m/s) | Absorbed Energy (J) |
|---|---|---|---|---|---|---|
| 1 | 0.2 | 0.35 | 16 | 5.3 | 4.6045 | 11.6491 |
| 2 | 0.2 | 0.3 | 20 | 5.8 | 5.0184 | 8.6616 |
| 3 | 0.2 | 0.3 | 24 | 7 | 4.8861 | 9.6449 |
| 4 | 0.2 | 0.35 | 24 | 8.1 | 5.3202 | 6.3213 |
| 5 | 0.25 | 0.35 | 28 | 9.6 | 5.3720 | 5.9063 |
| 6 | 0.25 | 0.25 | 32 | 8 | 5.3137 | 6.3734 |
| 7 | 0.25 | 0.35 | 32 | 11 | 5.4819 | 5.0114 |
| 1 | 0.2 | 0.35 | 16 | 5.3 | 5.0352 | 8.5348 |
| 2 | 0.2 | 0.3 | 20 | 5.8 | 4.4225 | 12.8813 |
| 3 | 0.2 | 0.3 | 24 | 7 | 4.7797 | 10.4161 |
| 4 | 0.2 | 0.35 | 24 | 8.1 | 4.8720 | 9.7481 |
| 5 | 0.25 | 0.35 | 28 | 9.6 | 5.37442 | 5.8867 |
| 6 | 0.25 | 0.25 | 32 | 8 | 4.77254 | 10.4671 |
| 7 | 0.25 | 0.35 | 32 | 11 | 5.45069 | 5.2675 |

TABLE A. 11

Combinations for Top 2 layers of Carbon/epoxy and Results

| No. | Carbon layer thickness (mm) | Glass layer thickness (mm) | Total Plate Thickness (mm) | Number of Layers | Rebound Velocity (m/s) | Absorbed Energy (J) |
|---|---|---|---|---|---|---|
| 1 | 0.2 | 0.35 | 16 | 5.3 | 4.61488 | 11.5772 |
| 2 | 0.2 | 0.25 | 20 | 4.9 | 4.78974 | 10.3438 |
| 3 | 0.2 | 0.3 | 20 | 5.8 | 4.62342 | 11.5180 |
| 4 | 0.2 | 0.3 | 24 | 7 | 4.73144 | 10.7601 |
| 5 | 0.2 | 0.35 | 24 | 8.1 | 5.30862 | 6.4139 |
| 6 | 0.25 | 0.35 | 28 | 9.6 | 5.41414 | 5.5653 |
| 7 | 0.25 | 0.25 | 32 | 8 | 5.3265 | 6.2713 |
| 8 | 0.25 | 0.35 | 32 | 11 | 5.49488 | 4.9047 |

TABLE A. 12

Combinations for Bottom 2 layers of Carbon/epoxy and Results

| No. | Carbon layer thickness (mm) | Glass layer thickness (mm) | Total Plate Thickness (mm) | Number of Layers | Rebound Velocity (m/s) | Absorbed Energy (J) |
|---|---|---|---|---|---|---|
| 1 | 0.2 | 0.35 | 16 | 5.3 | 3.55864 | 18.05206 |
| 2 | 0.2 | 0.25 | 20 | 4.9 | 3.15915 | 20.06483 |
| 3 | 0.2 | 0.3 | 20 | 5.8 | 4.45159 | 12.68751 |
| 4 | 0.2 | 0.3 | 24 | 7 | 4.46224 | 12.61631 |
| 5 | 0.2 | 0.35 | 24 | 8.1 | 5.29749 | 6.50245 |
| 6 | 0.25 | 0.35 | 28 | 9.6 | 5.39965 | 5.682835 |
| 7 | 0.25 | 0.25 | 32 | 8 | 4.7856 | 10.37352 |
| 8 | 0.25 | 0.35 | 32 | 11 | 5.4845 | 4.9899 |

TABLE A. 13

Combinations for Top, Bottom and Middle 2 layers of Carbon/epoxy

| No. | Carbon layer thickness (mm) | Glass layer thickness (mm) | Total Plate Thickness (mm) | Number of Layers | Rebound Velocity (m/s) | Absorbed Energy (J) |
|---|---|---|---|---|---|---|
| 1 | 0.2 | 0.25 | 16 | 3.8 | 5.03532 | 8.5342 |
| 2 | 0.2 | 0.35 | 16 | 5 | 5.1643 | 7.5479 |
| 3 | 0.2 | 0.3 | 20 | 5.6 | 5.00095 | 8.7929 |
| 4 | 0.2 | 0.3 | 24 | 6.8 | 4.9959 | 8.8309 |
| 5 | 0.2 | 0.35 | 24 | 7.8 | 5.31015 | 6.4017 |

TABLE A. 14

Combinations for Top and Middle layers of Carbon/epoxy and Results

| No. | Carbon layer thickness (mm) | Glass layer thickness (mm) | Total Plate Thickness (mm) | Number of Layers | Rebound Velocity (m/s) | Absorbed Energy (J) |
|---|---|---|---|---|---|---|
| 1 | 0.2 | 0.35 | 16 | 5.3 | 5.02165 | 8.6373 |
| 2 | 0.2 | 0.25 | 20 | 4.9 | 4.82216 | 10.1101 |
| 3 | 0.2 | 0.3 | 20 | 5.8 | 5.08829 | 8.1320 |
| 4 | 0.2 | 0.3 | 24 | 7 | 4.87564 | 9.7211 |
| 5 | 0.2 | 0.35 | 24 | 8.1 | 4.9283 | 9.3339 |
| 6 | 0.25 | 0.35 | 28 | 9.6 | 5.39191 | 5.7455 |
| 7 | 0.25 | 0.25 | 32 | 8 | 4.96792 | 9.0398 |
| 8 | 0.25 | 0.35 | 32 | 11 | 5.4955 | 4.8993 |

A.2 Results for the Composite Pipes

TABLE A. 15

Results of numerical simulation for the Carbon/epoxy pipes having 20 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 35 | 5 | 1.88815 | 22.1744 |
| 2 | 0.3 | 35 | 6 | 2.42007 | 10.7163 |
| 3 | 0.35 | 35 | 7 | 2.41699 | 10.7908 |
| 4 | 0.4 | 35 | 8 | 2.40259 | 11.1378 |
| 5 | 0.25 | 45 | 5 | 1.97629 | 20.4714 |
| 6 | 0.3 | 45 | 6 | 2.37435 | 11.8123 |
| 7 | 0.35 | 45 | 7 | 2.42622 | 10.5673 |
| 8 | 0.4 | 45 | 8 | 2.45385 | 9.8931 |
| 9 | 0.25 | 55 | 5 | 2.46942 | 9.5098 |
| 10 | 0.3 | 55 | 6 | 2.37988 | 11.6809 |
| 11 | 0.35 | 55 | 7 | 2.46786 | 9.5483 |
| 12 | 0.4 | 55 | 8 | 2.43165 | 10.4354 |
| 13 | 0.25 | 65 | 5 | 2.39083 | 11.4197 |
| 14 | 0.3 | 65 | 6 | 2.38887 | 11.4665 |
| 15 | 0.35 | 65 | 7 | 2.4453 | 10.1025 |
| 16 | 0.4 | 65 | 8 | 2.48513 | 9.1206 |
| 17 | 0.25 | 75 | 5 | 2.422 | 10.6696 |
| 18 | 0.3 | 75 | 6 | 2.40684 | 11.0356 |
| 19 | 0.35 | 75 | 7 | 2.39423 | 11.3383 |
| 20 | 0.4 | 75 | 8 | 2.40487 | 11.0830 |

TABLE A. 16

Results of numerical simulation for the Carbon/epoxy pipes having 24 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 35 | 6 | 1.90173 | 21.9171 |
| 2 | 0.3 | 35 | 7.2 | 2.41621 | 10.8096 |
| 3 | 0.35 | 35 | 8.4 | 2.38414 | 11.5794 |
| 4 | 0.4 | 35 | 9.6 | 2.39278 | 11.3730 |
| 5 | 0.25 | 45 | 6 | 2.40896 | 10.9846 |
| 6 | 0.3 | 45 | 7.2 | 2.44188 | 10.1861 |
| 7 | 0.35 | 45 | 8.4 | 2.46463 | 9.6280 |
| 8 | 0.4 | 45 | 9.6 | 2.42102 | 10.6933 |
| 9 | 0.25 | 55 | 6 | 2.46441 | 9.6334 |
| 10 | 0.3 | 55 | 7.2 | 2.47285 | 9.4251 |
| 11 | 0.35 | 55 | 8.4 | 2.45131 | 9.9554 |
| 12 | 0.4 | 55 | 9.6 | 2.47772 | 9.3045 |
| 13 | 0.25 | 65 | 6 | 2.38813 | 11.4842 |
| 14 | 0.3 | 65 | 7.2 | 2.44234 | 10.1749 |
| 15 | 0.35 | 65 | 8.4 | 2.49357 | 8.9105 |
| 16 | 0.4 | 65 | 9.6 | 2.48778 | 9.0548 |
| 17 | 0.25 | 75 | 6 | 2.40684 | 11.0356 |
| 18 | 0.3 | 75 | 7.2 | 2.40243 | 11.1417 |
| 19 | 0.35 | 75 | 8.4 | 2.37773 | 11.7320 |
| 20 | 0.4 | 75 | 9.6 | 2.47919 | 9.2681 |

TABLE A. 17

Results of numerical simulation for the Carbon/epoxy pipes having 28 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 35 | 7 | 2.41827 | 10.7599 |
| 2 | 0.3 | 35 | 8.4 | 2.39256 | 11.3783 |
| 3 | 0.35 | 35 | 9.8 | 2.38517 | 11.5548 |
| 4 | 0.4 | 35 | 11.2 | 2.42129 | 10.6868 |
| 5 | 0.25 | 45 | 7 | 2.4287 | 10.5071 |
| 6 | 0.3 | 45 | 8.4 | 2.47588 | 9.3501 |
| 7 | 0.35 | 45 | 9.8 | 2.46703 | 9.5688 |
| 8 | 0.4 | 45 | 11.2 | 2.46637 | 9.5851 |
| 9 | 0.25 | 55 | 7 | 2.41547 | 10.8275 |
| 10 | 0.3 | 55 | 8.4 | 2.51334 | 8.4156 |
| 11 | 0.35 | 55 | 9.8 | 2.47131 | 9.4631 |
| 12 | 0.4 | 55 | 11.2 | 2.56379 | 7.1349 |
| 13 | 0.25 | 65 | 7 | 2.42896 | 10.5008 |
| 14 | 0.3 | 65 | 8.4 | 2.50417 | 8.6457 |
| 15 | 0.35 | 65 | 9.8 | 2.51416 | 8.3950 |
| 16 | 0.4 | 65 | 11.2 | 2.61311 | 5.8583 |
| 17 | 0.25 | 75 | 7 | 2.39331 | 11.3603 |
| 18 | 0.3 | 75 | 8.4 | 2.38041 | 11.6682 |
| 19 | 0.35 | 75 | 9.8 | 2.50703 | 8.5740 |
| 20 | 0.4 | 75 | 11.2 | 2.51475 | 8.3802 |

TABLE A. 18

Results of numerical simulation for the Carbon/epoxy pipes having 32 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 35 | 8 | 2.39549 | 11.3081 |
| 2 | 0.3 | 35 | 9.6 | 2.39064 | 11.4242 |
| 3 | 0.35 | 35 | 11.2 | 2.42538 | 10.5877 |
| 4 | 0.4 | 35 | 12.8 | 2.54531 | 7.6070 |
| 5 | 0.25 | 45 | 8 | 2.42531 | 10.5894 |
| 6 | 0.3 | 45 | 9.6 | 2.46261 | 9.6778 |
| 7 | 0.35 | 45 | 11.2 | 2.46798 | 9.5453 |
| 8 | 0.4 | 45 | 12.8 | 2.82109 | 0.2073 |

TABLE A. 18-continued

Results of numerical simulation for the
Carbon/epoxy pipes having 32 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 9 | 0.25 | 55 | 8 | 2.49993 | 8.7517 |
| 10 | 0.3 | 55 | 9.6 | 2.45368 | 9.8973 |
| 11 | 0.35 | 55 | 11.2 | 2.58279 | 6.6460 |
| 12 | 0.4 | 55 | 12.8 | 2.79102 | 1.0510 |
| 13 | 0.25 | 65 | 8 | 2.49593 | 8.8517 |
| 14 | 0.3 | 65 | 9.6 | 2.50256 | 8.6860 |
| 15 | 0.35 | 65 | 11.2 | 2.61836 | 5.7210 |
| 16 | 0.4 | 65 | 12.8 | 2.67021 | 4.3510 |
| 17 | 0.25 | 75 | 8 | 2.40218 | 11.1477 |
| 18 | 0.3 | 75 | 9.6 | 2.48446 | 9.1373 |
| 19 | 0.35 | 75 | 11.2 | 2.50744 | 8.5637 |
| 20 | 0.4 | 75 | 12.8 | 2.58654 | 6.5491 |

TABLE A. 19

Results of numerical simulation for the
Carbon/epoxy pipes having 36 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 35 | 9 | 2.38755 | 11.4980 |
| 2 | 0.3 | 35 | 10.8 | 2.3883 | 11.4801 |
| 3 | 0.35 | 35 | 12.6 | 2.4877 | 9.0567 |
| 4 | 0.4 | 35 | 14.4 | 2.81955 | 0.2507 |
| 5 | 0.25 | 45 | 9 | 2.46453 | 9.6305 |
| 6 | 0.3 | 45 | 10.8 | 2.42175 | 10.6756 |
| 7 | 0.35 | 45 | 12.6 | 2.82005 | 0.2366 |
| 8 | 0.4 | 45 | 14.4 | 2.81233 | 0.4540 |
| 9 | 0.25 | 55 | 9 | 2.49248 | 8.9377 |
| 10 | 0.3 | 55 | 10.8 | 2.5481 | 7.5359 |
| 11 | 0.35 | 55 | 12.6 | 2.71305 | 3.1968 |
| 12 | 0.4 | 55 | 14.4 | 2.77641 | 1.4577 |
| 13 | 0.25 | 65 | 9 | 2.49985 | 8.7537 |
| 14 | 0.3 | 65 | 10.8 | 2.58909 | 6.4831 |
| 15 | 0.35 | 65 | 12.6 | 2.67148 | 4.3160 |
| 16 | 0.4 | 65 | 14.4 | 2.73159 | 2.6921 |
| 17 | 0.25 | 75 | 9 | 2.45539 | 9.8553 |
| 18 | 0.3 | 75 | 10.8 | 2.48717 | 9.0699 |
| 19 | 0.35 | 75 | 12.6 | 2.57949 | 6.7312 |
| 20 | 0.4 | 75 | 14.4 | 2.61093 | 5.9152 |
| 21 | 0.375 | 35 | 13.5 | 2.81827 | 0.2868 |
| 22 | 0.425 | 35 | 15.3 | 2.8215 | 0.1957 |
| 23 | 0.375 | 45 | 13.5 | 2.81148 | 0.4779 |
| 24 | 0.425 | 45 | 15.3 | 2.80985 | 0.5237 |
| 25 | 0.375 | 55 | 13.5 | 2.78844 | 1.1230 |
| 26 | 0.425 | 55 | 15.3 | 2.77505 | 1.4955 |
| 27 | 0.375 | 65 | 13.5 | 2.70996 | 3.2806 |
| 28 | 0.425 | 65 | 15.3 | 2.72913 | 2.7592 |
| 29 | 0.375 | 75 | 13.5 | 2.60633 | 6.0352 |
| 30 | 0.425 | 75 | 15.3 | 2.67199 | 4.3023 |

TABLE A. 20

Results of numerical simulation for the
Carbon/epoxy pipes having 16 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 35 | 4 | 2.04884 | 19.0113 |
| 2 | 0.3 | 35 | 4.8 | 1.91739 | 21.6181 |
| 3 | 0.35 | 35 | 5.6 | 1.83941 | 23.0829 |
| 4 | 0.4 | 35 | 6.4 | 2.41512 | 10.8360 |
| 5 | 0.25 | 45 | 4 | 2.39079 | 11.4206 |
| 6 | 0.3 | 45 | 4.8 | 2.36811 | 11.9603 |
| 7 | 0.35 | 45 | 5.6 | 2.3956 | 11.3055 |
| 8 | 0.4 | 45 | 6.4 | 2.39885 | 11.2276 |
| 9 | 0.25 | 55 | 4 | 1.57573 | 27.5854 |
| 10 | 0.3 | 55 | 4.8 | 2.40525 | 11.0739 |
| 11 | 0.35 | 55 | 5.6 | 2.37488 | 11.7997 |
| 12 | 0.4 | 55 | 6.4 | 2.47032 | 9.4876 |
| 13 | 0.25 | 65 | 4 | 2.38487 | 11.5620 |
| 14 | 0.3 | 65 | 4.8 | 2.39637 | 11.2871 |
| 15 | 0.35 | 65 | 5.6 | 2.38004 | 11.6770 |
| 16 | 0.4 | 65 | 6.4 | 2.40016 | 11.1962 |
| 17 | 0.25 | 75 | 4 | 2.39583 | 11.3000 |
| 18 | 0.3 | 75 | 4.8 | 2.41153 | 10.9226 |
| 19 | 0.35 | 75 | 5.6 | 2.39003 | 11.4388 |
| 20 | 0.4 | 75 | 6.4 | 2.39868 | 11.2317 |

TABLE A. 21

Results of numerical simulation for the Carbon/epoxy pipes having
20 layers and angles between 50° and 60°

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 50 | 5 | 2.37267 | 11.8522 |
| 2 | 0.3 | 50 | 6 | 2.39215 | 11.3881 |
| 3 | 0.35 | 50 | 7 | 2.41011 | 10.9568 |
| 4 | 0.4 | 50 | 8 | 2.48405 | 9.1475 |
| 5 | 0.25 | 52.5 | 5 | 2.44559 | 10.0954 |
| 6 | 0.3 | 52.5 | 6 | 2.40921 | 10.9785 |
| 7 | 0.35 | 52.5 | 7 | 2.40164 | 11.1606 |
| 8 | 0.4 | 52.5 | 8 | 2.44105 | 10.2064 |
| 9 | 0.25 | 57.5 | 5 | 2.4085 | 10.9956 |
| 10 | 0.3 | 57.5 | 6 | 2.4444 | 10.1245 |
| 11 | 0.35 | 57.5 | 7 | 2.42232 | 10.6618 |
| 12 | 0.4 | 57.5 | 8 | 2.42097 | 10.6945 |
| 13 | 0.25 | 60 | 5 | 2.44265 | 10.1673 |
| 14 | 0.3 | 60 | 6 | 2.47024 | 9.4896 |
| 15 | 0.35 | 60 | 7 | 2.43268 | 10.4103 |
| 16 | 0.4 | 60 | 8 | 2.47767 | 9.3058 |

TABLE A. 22

Results of numerical simulation for the Carbon/epoxy pipes having
24 layers and angles between 50° and 60°

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 50 | 6 | 2.38059 | 11.6640 |
| 2 | 0.3 | 50 | 7.2 | 2.46575 | 9.6004 |
| 3 | 0.35 | 50 | 8.4 | 2.49698 | 8.8255 |
| 4 | 0.4 | 50 | 9.6 | 2.48156 | 9.2093 |
| 5 | 0.25 | 52.5 | 6 | 2.39372 | 11.3505 |
| 6 | 0.3 | 52.5 | 7.2 | 2.48235 | 9.1897 |
| 7 | 0.35 | 52.5 | 8.4 | 2.4537 | 9.8968 |
| 8 | 0.4 | 52.5 | 9.6 | 2.50164 | 8.7090 |
| 9 | 0.25 | 57.5 | 6 | 2.40348 | 11.1164 |
| 10 | 0.3 | 57.5 | 7.2 | 2.41616 | 10.8109 |
| 11 | 0.35 | 57.5 | 8.4 | 2.4444 | 10.1245 |
| 12 | 0.4 | 57.5 | 9.6 | 2.45988 | 9.7450 |
| 13 | 0.25 | 60 | 6 | 2.43162 | 10.4361 |
| 14 | 0.3 | 60 | 7.2 | 2.43659 | 10.3151 |
| 15 | 0.35 | 60 | 8.4 | 2.4763 | 9.3397 |
| 16 | 0.4 | 60 | 9.6 | 2.5066 | 8.5848 |

TABLE A. 23

Results of numerical simulation for the Glass/epoxy pipes having 20 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 35 | 5 | 0 | Penetrate |
| 2 | 0.3 | 35 | 6 | 0 | Penetrate |
| 3 | 0.35 | 35 | 7 | 1.08274 | 34.1384 |
| 4 | 0.4 | 35 | 8 | 2.3477 | 12.4415 |
| 5 | 0.25 | 45 | 5 | 0 | Penetrate |
| 6 | 0.3 | 45 | 6 | 1.22598 | 32.4849 |
| 7 | 0.35 | 45 | 7 | 2.33975 | 12.6278 |
| 8 | 0.4 | 45 | 8 | 2.37994 | 11.6794 |
| 9 | 0.25 | 55 | 5 | 2.34227 | 12.5689 |
| 10 | 0.3 | 55 | 6 | 2.32993 | 12.8571 |
| 11 | 0.35 | 55 | 7 | 2.34418 | 12.5241 |
| 12 | 0.4 | 55 | 8 | 2.41696 | 10.7915 |
| 13 | 0.25 | 65 | 5 | 2.34617 | 12.4774 |
| 14 | 0.3 | 65 | 6 | 2.35908 | 12.1737 |
| 15 | 0.35 | 65 | 7 | 2.36987 | 11.9186 |
| 16 | 0.4 | 65 | 8 | 2.37815 | 11.7220 |
| 17 | 0.25 | 75 | 5 | 0 | Penetrate |
| 18 | 0.3 | 75 | 6 | 2.31988 | 13.0908 |
| 19 | 0.35 | 75 | 7 | 2.36784 | 11.9667 |
| 20 | 0.4 | 75 | 8 | 2.40273 | 11.1344 |

TABLE A. 24

Results of numerical simulation for the Glass/epoxy pipes having 24 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 35 | 6 | 0 | Penetrate |
| 2 | 0.3 | 35 | 7.2 | 0.77370 | 37.0070 |
| 3 | 0.35 | 35 | 8.4 | 2.34652 | 12.4692 |
| 4 | 0.4 | 35 | 9.6 | 2.35183 | 12.3445 |
| 5 | 0.25 | 45 | 6 | 1.12588 | 33.6620 |
| 6 | 0.3 | 45 | 7.2 | 2.33701 | 12.6919 |
| 7 | 0.35 | 45 | 8.4 | 2.37526 | 11.7907 |
| 8 | 0.4 | 45 | 9.6 | 2.37449 | 11.8090 |
| 9 | 0.25 | 55 | 6 | 2.33816 | 12.6650 |
| 10 | 0.3 | 55 | 7.2 | 2.33665 | 12.7003 |
| 11 | 0.35 | 55 | 8.4 | 2.41873 | 10.7487 |
| 12 | 0.4 | 55 | 9.6 | 2.45415 | 9.8857 |
| 13 | 0.25 | 65 | 6 | 2.34628 | 12.4749 |
| 14 | 0.3 | 65 | 7.2 | 2.37862 | 11.7108 |
| 15 | 0.35 | 65 | 8.4 | 2.39118 | 11.4113 |
| 16 | 0.4 | 65 | 9.6 | 2.40827 | 11.0012 |
| 17 | 0.25 | 75 | 6 | 2.3087 | 13.3495 |
| 18 | 0.3 | 75 | 7.2 | 2.37866 | 11.7099 |
| 19 | 0.35 | 75 | 8.4 | 2.39493 | 11.3216 |
| 20 | 0.4 | 75 | 9.6 | 2.4412 | 10.2027 |

TABLE A. 25

Results of numerical simulation for the Glass/epoxy pipes having 28 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 35 | 7 | 1.18648 | 32.9613 |
| 2 | 0.3 | 35 | 8.4 | 2.34749 | 12.4465 |
| 3 | 0.35 | 35 | 9.8 | 2.34058 | 12.6084 |
| 4 | 0.4 | 35 | 11.2 | 2.35438 | 12.2845 |
| 5 | 0.25 | 45 | 7 | 2.33806 | 12.6674 |
| 6 | 0.3 | 45 | 8.4 | 2.37643 | 11.7629 |
| 7 | 0.35 | 45 | 9.8 | 2.37471 | 11.8038 |
| 8 | 0.4 | 45 | 11.2 | 2.36973 | 11.9219 |
| 9 | 0.25 | 55 | 7 | 2.33516 | 12.7351 |
| 10 | 0.3 | 55 | 8.4 | 2.39867 | 11.2319 |
| 11 | 0.35 | 55 | 9.8 | 2.45515 | 9.8612 |
| 12 | 0.4 | 55 | 11.2 | 2.46985 | 9.4992 |
| 13 | 0.25 | 65 | 7 | 2.37526 | 11.7907 |
| 14 | 0.3 | 65 | 8.4 | 2.392 | 11.3917 |
| 15 | 0.35 | 65 | 9.8 | 2.40366 | 11.1121 |
| 16 | 0.4 | 65 | 11.2 | 2.45935 | 9.7580 |
| 17 | 0.25 | 75 | 7 | 2.36673 | 11.9929 |
| 18 | 0.3 | 75 | 8.4 | 2.39012 | 11.4366 |
| 19 | 0.35 | 75 | 9.8 | 2.44531 | 10.1023 |
| 20 | 0.4 | 75 | 11.2 | 2.42834 | 10.5158 |

TABLE A. 26

Results of numerical simulation for the Glass/epoxy pipes having 32 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 35 | 8 | 2.34847 | 12.4234 |
| 2 | 0.3 | 35 | 9.6 | 2.35175 | 12.3464 |
| 3 | 0.35 | 35 | 11.2 | 2.35126 | 12.3579 |
| 4 | 0.4 | 35 | 12.8 | 2.34264 | 12.5602 |
| 5 | 0.25 | 45 | 8 | 2.38248 | 11.6189 |
| 6 | 0.3 | 45 | 9.6 | 2.37675 | 11.7553 |
| 7 | 0.35 | 45 | 11.2 | 2.37343 | 11.8342 |
| 8 | 0.4 | 45 | 12.8 | 2.45558 | 9.8506 |
| 9 | 0.25 | 55 | 8 | 2.37704 | 11.7484 |
| 10 | 0.3 | 55 | 9.6 | 2.4683 | 9.5375 |
| 11 | 0.35 | 55 | 11.2 | 2.46654 | 9.5809 |
| 12 | 0.4 | 55 | 12.8 | 2.51122 | 8.4689 |
| 13 | 0.25 | 65 | 8 | 2.37831 | 11.7182 |
| 14 | 0.3 | 65 | 9.6 | 2.41152 | 10.9229 |
| 15 | 0.35 | 65 | 11.2 | 2.46551 | 9.6063 |
| 16 | 0.4 | 65 | 12.8 | 2.5584 | 7.2729 |
| 17 | 0.25 | 75 | 8 | 2.40355 | 11.1147 |
| 18 | 0.3 | 75 | 9.6 | 2.4265 | 10.5605 |
| 19 | 0.35 | 75 | 11.2 | 2.42906 | 10.4983 |
| 20 | 0.4 | 75 | 12.8 | 2.51793 | 8.3001 |

TABLE A. 27

Results of numerical simulation for the Glass/epoxy pipes having 36 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 35 | 9 | 2.34385 | 12.5318 |
| 2 | 0.3 | 35 | 10.8 | 2.34026 | 12.6159 |
| 3 | 0.35 | 35 | 12.6 | 2.31136 | 13.2881 |
| 4 | 0.4 | 35 | 14.4 | 2.7913 | 1.0432 |
| 5 | 0.25 | 45 | 9 | 2.3753 | 11.7897 |
| 6 | 0.3 | 45 | 10.8 | 2.38331 | 11.5992 |
| 7 | 0.35 | 45 | 12.6 | 2.44123 | 10.2020 |
| 8 | 0.4 | 45 | 14.4 | 2.79047 | 1.0664 |
| 9 | 0.25 | 55 | 9 | 2.43497 | 10.3546 |
| 10 | 0.3 | 55 | 10.8 | 2.46449 | 9.6314 |
| 11 | 0.35 | 55 | 12.6 | 2.50415 | 8.6462 |
| 12 | 0.4 | 55 | 14.4 | 2.7895 | 1.0934 |
| 13 | 0.25 | 65 | 9 | 2.4054 | 11.0703 |
| 14 | 0.3 | 65 | 10.8 | 2.45222 | 9.9331 |
| 15 | 0.35 | 65 | 12.6 | 2.55745 | 7.2972 |
| 16 | 0.4 | 65 | 14.4 | 2.61074 | 5.9202 |
| 17 | 0.25 | 75 | 9 | 2.39953 | 11.2113 |
| 18 | 0.3 | 75 | 10.8 | 2.42708 | 10.5464 |
| 19 | 0.35 | 75 | 12.6 | 2.5115 | 8.4618 |
| 20 | 0.4 | 75 | 14.4 | 2.53095 | 7.9715 |
| 21 | 0.375 | 35 | 13.5 | 2.46227 | 9.6861 |

TABLE A. 27-continued

Results of numerical simulation for the Glass/epoxy pipes having 36 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 22 | 0.425 | 35 | 15.3 | 2.79899 | 0.8283 |
| 23 | 0.375 | 45 | 13.5 | 2.79539 | 0.9290 |
| 24 | 0.425 | 45 | 15.3 | 2.79574 | 0.9192 |
| 25 | 0.375 | 55 | 13.5 | 2.51755 | 8.3097 |
| 26 | 0.425 | 55 | 15.3 | 2.79256 | 1.0080 |
| 27 | 0.375 | 65 | 13.5 | 2.5793 | 6.7361 |
| 28 | 0.425 | 65 | 15.3 | 2.63406 | 5.3086 |
| 29 | 0.375 | 75 | 13.5 | 2.52931 | 8.0130 |
| 30 | 0.425 | 75 | 15.3 | 2.53922 | 7.7618 |

TABLE A. 28

Results of numerical simulation for the Glass/epoxy pipes having 40 layers

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 35 | 10 | 2.32956 | 12.8658 |
| 2 | 0.3 | 35 | 12 | 2.34196 | 12.5761 |
| 3 | 0.35 | 35 | 14 | 2.78597 | 1.1919 |
| 4 | 0.4 | 35 | 16 | 2.80272 | 0.7238 |
| 5 | 0.25 | 45 | 10 | 2.38761 | 11.4966 |
| 6 | 0.3 | 45 | 12 | 2.39204 | 11.3907 |
| 7 | 0.35 | 45 | 14 | 2.79567 | 0.9211 |
| 8 | 0.4 | 45 | 16 | 2.79667 | 0.8932 |
| 9 | 0.25 | 55 | 10 | 2.45024 | 9.9816 |
| 10 | 0.3 | 55 | 12 | 2.46826 | 9.5385 |
| 11 | 0.35 | 55 | 14 | 2.78827 | 1.1278 |
| 12 | 0.4 | 55 | 16 | 2.79438 | 0.9572 |
| 13 | 0.25 | 65 | 10 | 2.40469 | 11.0873 |
| 14 | 0.3 | 65 | 12 | 2.51472 | 8.3809 |
| 15 | 0.35 | 65 | 14 | 2.59576 | 6.3102 |
| 16 | 0.4 | 65 | 16 | 2.64831 | 4.9323 |
| 17 | 0.25 | 75 | 10 | 2.44626 | 10.0791 |
| 18 | 0.3 | 75 | 12 | 2.48627 | 9.0923 |
| 19 | 0.35 | 75 | 14 | 2.53047 | 7.9836 |
| 20 | 0.4 | 75 | 16 | 2.53942 | 7.7567 |

TABLE A. 29

Results of numerical simulation for the Glass/epoxy pipes having 24 layers with winding angles between 50° and 60°

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 50 | 6 | 2.31991 | 13.0901 |
| 2 | 0.3 | 50 | 7.2 | 2.33779 | 12.6737 |
| 3 | 0.35 | 50 | 8.4 | 2.3796 | 11.6875 |
| 4 | 0.4 | 50 | 9.6 | 2.40056 | 11.1866 |
| 5 | 0.25 | 52.5 | 6 | 2.33659 | 12.7017 |
| 6 | 0.3 | 52.5 | 7.2 | 2.33785 | 12.6723 |
| 7 | 0.35 | 52.5 | 8.4 | 2.34672 | 12.4645 |
| 8 | 0.4 | 52.5 | 9.6 | 2.4401 | 10.2296 |
| 9 | 0.25 | 57.5 | 6 | 2.34376 | 12.5339 |
| 10 | 0.3 | 57.5 | 7.2 | 2.36829 | 11.9560 |
| 11 | 0.35 | 57.5 | 8.4 | 2.38649 | 11.5233 |
| 12 | 0.4 | 57.5 | 9.6 | 2.40847 | 10.9964 |
| 13 | 0.25 | 60 | 6 | 2.3424 | 12.5658 |
| 14 | 0.3 | 60 | 7.2 | 2.37386 | 11.8239 |
| 15 | 0.35 | 60 | 8.4 | 2.40307 | 11.1263 |
| 16 | 0.4 | 60 | 9.6 | 2.42099 | 10.6940 |

TABLE A. 30

Results of numerical simulation for the Glass/epoxy pipes having 28 layers with winding angles between 50° and 60°

| S. No. | Layer Thickness (mm) | Winding Angle (degree) | Total Thickness of Plate (mm) | Rebound Velocity (m/s) | Absorbed Energy (J) |
|---|---|---|---|---|---|
| 1 | 0.25 | 50 | 7 | 2.34138 | 12.5897 |
| 2 | 0.3 | 50 | 8.4 | 2.37784 | 11.7294 |
| 3 | 0.35 | 50 | 9.8 | 2.40265 | 11.1364 |
| 4 | 0.4 | 50 | 11.2 | 2.38627 | 11.5286 |
| 5 | 0.25 | 52.5 | 7 | 2.33777 | 12.6742 |
| 6 | 0.3 | 52.5 | 8.4 | 2.36277 | 12.0866 |
| 7 | 0.35 | 52.5 | 9.8 | 2.42132 | 10.6860 |
| 8 | 0.4 | 52.5 | 11.2 | 2.41214 | 10.9079 |
| 9 | 0.25 | 57.5 | 7 | 2.36438 | 12.0485 |
| 10 | 0.3 | 57.5 | 8.4 | 2.39016 | 11.4357 |
| 11 | 0.35 | 57.5 | 9.8 | 2.42214 | 10.6662 |
| 12 | 0.4 | 57.5 | 11.2 | 2.44986 | 9.9909 |
| 13 | 0.25 | 60 | 7 | 2.37223 | 11.8626 |
| 14 | 0.3 | 60 | 8.4 | 2.38314 | 11.6032 |
| 15 | 0.35 | 60 | 9.8 | 2.42183 | 10.6737 |
| 16 | 0.4 | 60 | 11.2 | 2.48559 | 9.1092 |

TABLE A. 31

Combinations for Top 2 layers of Woven Carbon/epoxy and Results for 55° filament wound pipes

| No. | Carbon layer thickness (mm) | Glass layer thickness (mm) | Total Plate Thickness (mm) | Number of Layers | Rebound Velocity (m/s) | Absorbed Energy (J) |
|---|---|---|---|---|---|---|
| 1 | 0.25 | 0.25 | 20 | 5 | 2.34429 | 12.5215 |
| 2 | 0.3 | 0.3 | 20 | 6 | 2.3181 | 13.1320 |
| 3 | 0.35 | 0.35 | 20 | 7 | 2.36128 | 12.1218 |
| 4 | 0.4 | 0.4 | 20 | 8 | 2.37573 | 11.7795 |

TABLE A. 32

Combinations for Top 4 layers of Woven Carbon/epoxy and Results for 55° filament wound pipes

| No. | Carbon layer thickness (mm) | Glass layer thickness (mm) | Total Plate Thickness (mm) | Number of Layers | Rebound Velocity (m/s) | Absorbed Energy (J) |
|---|---|---|---|---|---|---|
| 1 | 0.25 | 0.25 | 20 | 5 | 2.33811 | 12.66621 |
| 2 | 0.3 | 0.3 | 20 | 6 | 2.33318 | 12.78136 |
| 3 | 0.35 | 0.35 | 20 | 7 | 2.3728 | 11.8491 |
| 4 | 0.4 | 0.4 | 20 | 8 | 2.37544 | 11.78642 |

TABLE A. 33

Combinations for Top 2 layers of Unidirectional Carbon/epoxy and Results for 55° filament wound pipes

| No. | Carbon layer thickness (mm) | Glass layer thickness (mm) | Total Plate Thickness (mm) | Number of Layers | Rebound Velocity (m/s) | Absorbed Energy (J) |
|---|---|---|---|---|---|---|
| 1 | 0.25 | 0.25 | 20 | 5 | 2.34126 | 12.59251 |
| 2 | 0.3 | 0.3 | 20 | 6 | 2.34276 | 12.55738 |
| 3 | 0.35 | 0.35 | 20 | 7 | 2.36739 | 11.97732 |
| 4 | 0.4 | 0.4 | 20 | 8 | 2.3716 | 11.87757 |

TABLE A. 34

Combinations for Top 4 layers of Unidirectional Carbon/epoxy and Results for 55° filament wound pipes

| No. | Carbon layer thickness (mm) | Glass layer thickness (mm) | Total Plate Thickness (mm) | Number of Layers | Rebound Velocity (m/s) | Absorbed Energy (J) |
|---|---|---|---|---|---|---|
| 1 | 0.25 | 0.25 | 20 | 5 | 2.34404 | 12.52738 |
| 2 | 0.3 | 0.3 | 20 | 6 | 2.33466 | 12.74681 |
| 3 | 0.35 | 0.35 | 20 | 7 | 2.48928 | 9.017425 |
| 4 | 0.4 | 0.4 | 20 | 8 | 2.50019 | 8.74525 |

NOMENCLATURE

| | | |
|---|---|---|
| E11 | Elastic Modulus in Longitudinal Direction | [N/m$^2$] |
| E22 | Elastic Modulus in Transverse Direction | [N/m$^2$] |
| E33 | Elastic Modulus in Transverse Direction | [N/m$^2$] |
| v12 | Poisson's Ratio in plane containing fiber | [Unitless] |
| v13 | Poisson's Ratio in plane containing fiber | [Unitless] |
| v23 | Poisson's Ratio in transverse plane | [Unitless] |
| G12 | Shear Modulus in plane containing fiber | [N/m$^2$] |
| G13 | Shear Modulus in plane containing fiber | [N/m$^2$] |
| G23 | Shear Modulus in transverse plane | [N/m$^2$] |
| Xt | Tensile strength in fiber direction | [N/m$^2$] |
| Xc | Compressive strength in fiber direction | [N/m$^2$] |
| Yt | Tensile strength in transverse direction | [N/m$^2$] |
| Yc | Compressive strength in transverse direction | [N/m$^2$] |
| S12 | In-Plane Shear Strength | [N/m$^2$] |
| $G_f^t$ | Fracture Toughness in longitudinal tensile direction | [J/m$^2$] |
| $G_f^c$ | Fracture Toughness in longitudinal compressive direction | [J/m$^2$] |
| $G_m^t$ | Fracture Toughness in transverse tensile fracture mode | [J/m$^2$] |
| $G_m^c$ | Fracture Toughness in transverse compressive fracture mode | [J/m$^2$] |
| Gs | In-Plane Fracture Toughness | [J/m$^2$] |
| NSC | Normalized Sensitivity Coefficient | [Unitless] |
| CFRP | Carbon Fiber Reinforced Polymer | |
| GFRP | Glass Fiber Reinforced Polymer | |

REFERENCES

[1] S. Abrate, Impact on Composite Structures, Cambridge University Press, Cambridge, UK, 1998.

[2] M. Aktas, C. Atas, B. Icten, R. Karakuzu, An experimental investigation of the impact response of composite laminates, Composite Structures. 87 (2009) 307-313.

[3] E. Al-Momani, I. Rawabdeh, An application of finite element method and design of experiments in the optimization of sheet metal blanking process, Jordan Journal of Mechanical and Industrial Engineering. 2 (2008) 53-63.

[4] F. S. Almeida, a. M. Awruch, Design optimization of composite laminated structures using genetic algorithms and finite element analysis, Composite Structures. 88 (2009) 443-454.

[5] A. Z. Arturas KERSYS, Neringa KERSIENE, Experimental Research of the Impact Response of E-Glass/Epoxy and Carbon/Epoxy Composite Systems, Materials Science. 16 (2010) 324-329.

[6] Z. Aslan, R. Karakuzu, B. Okutan, The response of laminated composite plates under low-velocity impact loading, Composite Structures. 59 (2003) 119-127.

[7] Y. Bai, Pipelines and Risers, Elsevier Ltd, Oxford, UK, 2001.

[8] H. Bakaiyan, H. Hosseini, E. Ameri, Analysis of multi-layered filament-wound composite pipes under combined.pdf, Composite Structures. 88 (2009) 532-541.

[9] K.-J. Bathe, Finite Element Procedures, Prentice Hall, New York, 1996.

[10] A. Bezazi, S. Pierce, K. Worden, E. Harkati, Fatigue life prediction of sandwich composite materials under flexural tests using a Bayesian trained artificial neural network, International Journal of Fatigue. 29 (2007) 738-747.

[11] E. M. Bezerra, a. C. Ancelotti, L. C. Pardini, J. a. F. F. Rocco, K. Iha, C. H.C. Ribeiro, Artificial neural networks applied to epoxy composites reinforced with carbon and E-glass fibers: Analysis of the shear mechanical properties, Materials Science and Engineering: A. 464 (2007) 177-185.

[12] K. Brownlee, C. Alexander, Methodology for Assessing the Effects of Plain Dents, Wrinkle Bends, and Mechanical Damage on Pipeline Integrity, in: NACE International Corrosion 2007 Conference & Expo, Nashville, Tenn., USA, 2007: pp. 1-19.

[13] W. J. Cantwell, Geometrical effects in the low velocity impact response of GFRP, Composites Science and Technology. 67 (2007) 1900-1908.

[14] A. Chib, Parametric Study of Low Velocity Impact Analysis on Composite Tubes, Wichita State University, 2006.

[15] J. Dolbow, T. Belytschko, Numerical Integration of the Galerkin Weak Form in Meshfree Methods 1 Introduction, Computational Mechanics. 23 (1999) 219-230.

[16] M. V. Donadon, B. G. Falzon, L. Iannucci, J. M. Hodgkinson, Intralaminar toughness characterisation of unbalanced hybrid plain weave laminates, Composites Part A: Applied Science and Manufacturing. 38 (2007) 1597-1611.

[17] U. Farooq, K. Gregory, Finite Element Simulation of Low Velocity Impact Damage Morphology in Quasi_ Isotropic Composite Panels Under Variable Shape Impactors, European Journal of Scientific Research. 25 (2009) 636-648.

[18] U. Farooq, K. Gregory, Explicit Dynamic Simulation of Drop-Weight Low Velocity Impact on Carbon Fibrous Composite Panels, ARPN Journal of Engineering and Applied Sciences. 5 (2010) 50-61.

[19] J. Fish, A. Ghouali, Multiscale analytical sensitivity analysis for composite materials, International Journal for Numerical Methods in Engineering. 50 (2001) 1501-1520.

[20] B. Gershon, G. Marom, Fracture toughness and mechanical properties of glass fibre-epoxy composites, Journal of Material Science. 10 (1975) 1549-1556.

[21] H. M. Gomes, A.M. Awruch, P. A. M. Lopes, Reliability based optimization of laminated composite structures using genetic algorithms and Artificial Neural Networks, Structural Safety. 33 (2011) 186-195.

[22] S. Heimbs, S. Heller, P. Middendorf, Simulation of Low Velocity Impact on Composite Plates with Compressive Preload, Material II-Composites. (2008) 11-24.

[23] S.-C. Her, Y.-C. Liang, The finite element analysis of composite laminates and shell structures subjected to low velocity impact, Composite Structures. 66 (2004) 277-285.

[24] P. Hopkins, The Structural Integrity Of Oil And Gas Transmission Pipelines, Comprehensive Structural Integrity. 1 (2002) 1-62.

[25] R. Hosseinzadeh, M. M. Shokrieh, L. Lessard, Damage behavior of fiber reinforced composite plates subjected to drop weight impacts, Composites Science and Technology. 66 (2006) 61-68.

[26] L. Iannucci, M. L. Willows, An energy based damage mechanics approach to modeling impact onto woven com-

[27] S. I. Ibekwe, G. Li, S.-S. Pang, B. H. Smith, Low Velocity Impact Response of a Laminated Composite Tube with a Metallic Bumper Layer, in: ICCE-14 FOURTEENTH ANNUAL INTERNATIONAL CONFERENCE ON COMPOSITES/NANO ENGINEERING, 2006: pp. 3-4.

[28] Z. Jiang, L. Gyurova, Z. Zhang, K. Friedrich, A. K. Schlarb, Neural network based prediction on mechanical and wear properties of short fibers reinforced polyamide composites, Materials & Design. 29 (2008) 628-637.

[29] H. El Kadi, Modeling the mechanical behavior of fiber-reinforced polymeric composite materials using artificial neural networks—A review, Composite Structures. 73 (2006) 1-23.

[30] M. Kamiński, Sensitivity analysis of homogenized characteristics for some elastic composites, Computer Methods in Applied Mechanics and Engineering. 192 (2003) 1973-2005.

[31] M. M. Kamiński, Computational mechanics of composite materials, 1st ed., Springer, Lodz, Poland, 2004.

[32] S. M. R. Khalili, M. Soroush, a. Davar, O. Rahmani, Finite element modeling of low-velocity impact on laminated composite plates and cylindrical shells, Composite Structures. 93 (2011) 1363-1375.

[33] M. Kleiber (Ed.), Handbook of Computational Solid Mechanics, 1st ed., Springer Verlag, Warsaw, Poland, 1998.

[34] K. Krishnamurthy, Impact response and damage in laminated composite cylindrical shells, Composite Structures. 59 (2003) 15-36.

[35] K. S. Krishnamurthy, P. Mahajan, R. K. Mittal, A parametric study of the impact response and damage of laminated cylindrical composite shells, Composites Science and Technology. 61 (2001) 1655-1669.

[36] K. S. Krishnamurthy, P. Mahajan, R. K. Mittal, A parametric study of the impact response and damage of laminated cylindrical composite shells, Composites Science and Technology. 61 (2001) 1655-1669.

[37] P. Laney, Use of Composite Pipe Materials in the Transportation of Natural Gas, Renewable Energy. (n.d.).

[38] D. S. Lee, C. Morillo, G. Bugeda, S. Oller, E. Onate, Multilayered composite structure design optimisation using distributed/parallel multi-objective evolutionary algorithms, Composite Structures. 94 (2012) 1087-1096.

[39] M. Lefik, D. P. Boso, B. a. Schrefler, Artificial Neural Networks in numerical modeling of composites, Computer Methods in Applied Mechanics and Engineering. 198 (2009) 1785-1804.

[40] C. Li, N. Hu, Y. Yin, H. Sekine, Low-velocity impact-induced damage of continuous fiber-reinforced composite laminates. Part I. An FEM numerical model, Composites Part A: Applied Science and Manufacturing. 33 (2002) 1055-1062.

[41] C. Li, N. Hu, J. Cheng, H. Fukunaga, H. Sekine, Low-velocity impact-induced damage of continuous fiber-reinforced composite laminates. Part II. Verification and numerical investigation, Composites Part A: Applied Science and Manufacturing. 33 (2002) 1063-1072.

[42] P. a. M. Lopes, H. M. Gomes, a. M. Awruch, Reliability analysis of laminated composite structures using finite elements and neural networks, Composite Structures. 92 (2010) 1603-1613.

[43] G.-M. Luo, Y.-J. Lee, Quasi-static simulation of constrained layered damped laminated curvature shells subjected to low-velocity impact, Composites Part B: Engineering. 42 (2011) 1233-1243.

[44] E.-S. Mahdi, H. El Kadi, Crushing behavior of laterally compressed composite elliptical tubes: Experiments and predictions using artificial neural networks, Composite Structures. 83 (2008) 399-412.

[45] H. Man, G. Prusty, Neural network modeling for damage behaviour of composites using full-field strain measurements, Composite Structures. 93 (2011) 383-391.

[46] L. Marin, D. Trias, P. Badalló, G. Rus, J. a. Mayugo, Optimization of composite stiffened panels under mechanical and hydrothermal loads using neural networks and genetic algorithms, Composite Structures. 94 (2012) 3321-3326.

[47] M. Masi, S. Fogliani, S. Carra, Sensitivity Analysis on Indium Phosphide Liquid Encapsulated Czochralski Growth, Crystal Research and Technology. 34 (1999) 1157-1167.

[48] A. S. for T. and Materials, Standard Test Method for Determination of the Impact Resistance of Thermoplastic Pipe and Fittings by Means of a Tup (Falling Weight) 1, Book of Standards. 08 (1999) 1-8.

[49] C. Menna, D. Asprone, G. Caprino, V. Lopresto, A. Prota, Numerical simulation of impact tests on GFRP composite laminates, International Journal of Impact Engineering. 38 (2011) 677-685.

[50] M. J. Moeller, R. S. Thomas, H. Maruvada, N. S. Chandra, M. Zebrowski, F. M. Company, An Assessment of an FEA Body Model for Design Capability, Sounds and Vibrations. (2004) 24-28.

[51] S. S. P. Montestruc A. N., M. A. Stubblefield, R. H. L. V. A. Cundy, Composite Piping Systems to Improve Oil and Gas Production, Corrosion. (1995) 47-53.

[52] M. K. Naik, The Effect of Environmental Conditions on the Hydrostatic Burst Pressure and Impact Performance of Glass Fiber Reinforced Thermoset Pipes, King Fahd University of Petroleum and Minerals, 2005.

[53] N. K. Naik, S. Meduri, Polymer-matrix composites subjected to low-velocity impact: effect of laminate configuration, Composites Science and Technology. 61 (2001) 1429-1436.

[54] A. K. Noor, R. S. Shah, Effective thermoelastic and thermal properties of unidirectional fiber-reinforced composites and their sensitivity coefficients, Composite Structures. 26 (1993) 7-23.

[55] M. Peer, M. Mandyarfar, T. Mohammadi, Evaluation of a mathematical model using experimental data and artificial neural network for prediction of gas separation, 17 (2008) 135-141.

[56] P. K. Pinnoji, P. Mahajan, Analysis of impact-induced damage and delamination in the composite shell of a helmet, Materials and Design. 31 (2010) 3716-3723.

[57] B. A. Qureshi, S. M. Zubair, A comprehensive design and rating study of evaporative coolers and condensers. Part II. Sensitivity analysis, International Journal of Refrigeration. 29 (2006) 659-668.

[58] N. F. Rilo, L. M. S. Ferreira, Experimental study of low-velocity impacts on glass-epoxy laminated composite plates, International Journal of Mechanics and Materials in Design. 4 (2008) 291-300.

[59] M. W. K. Rosenow, Wind Angle Effects in Glass Fibre-reinforced Polyester Filament Wound Pipes, Composites. 15 (1984) 144-152.

[60] D. Roylance, Laminated composite plates, in: Mechanics of Materials, John Wiley & Sons, Cambridge, Mass., USA, 2000: pp. 1-17.

[61] Z. Salibi, Performance of reinforced thermosetting resin pipe systems in desalination applications: a long-term solution to corrosion —The Arabian Gulf example, Desalination. 138 (2001) 379-384.

[62] A. R. Setoodeh, P. Malekzadeh, K. Nikbin, Low velocity impact analysis of laminated composite plates using a 3D elasticity based layerwise FEM, Materials & Design. 30 (2009) 3795-3801.

[63] B. Sun, D. Hu, B. Gu, Transverse impact damage and energy absorption of 3-D multi-structured knitted composite, Composites Part B: Engineering. 40 (2009) 572-583.

[64] S. Suresh, P. B. Sujit, a. K. Rao, Particle swarm optimization approach for multi-objective composite box-beam design, Composite Structures. 81 (2007) 598-605.

[65] R. Tiberkak, M. Bachene, S. Rechak, B. Necib, Damage prediction in composite plates subjected to low velocity impact, Composite Structures. 83 (2008) 73-82.

[66] V. Tita, J. de Carvalho, D. Vandepitte, Failure analysis of low velocity impact on thin composite laminates: Experimental and numerical approaches, Composite Structures. 83 (2008) 413-428.

[67] A. Vassilopoulos, E. Georgopoulos, V. Dionysopoulos, Artificial neural networks in spectrum fatigue life prediction of composite materials, International Journal of Fatigue. 29 (2007) 20-29.

[68] S. B. Visweswaraiah, H. Ghiasi, D. Pasini, L. Lessard, Multi-objective optimization of a composite rotor blade cross-section, Composite Structures. (2012).

[69] S. E. Watkins, F. Akhavan, R. Dua, K. Chandrashekhara, D. C. Wunsch, Impact-induced damage characterization of composite plates using neural networks, Smart Materials and Structures. 16 (2007) 515-524.

[70] G. Xiao, Z. Zhu, Friction materials development by using DOE/RSM and artificial neural network, Tribology International. 43 (2010) 218-227.

[71] F. J. Yang, W. J. Cantwell, Impact damage initiation in composite materials, Composites Science and Technology. 70 (2010) 336-342.

[72] N. O. Yokoyama, M. V. Donadon, S. F. M. de Almeida, A numerical study on the impact resistance of composite shells using an energy based failure model, Composite Structures. 93 (2010) 142-152.

[73] G. P. Zhao, C. D. Cho, Damage initiation and propagation in composite shells subjected to impact, Composite Structures. 78 (2007) 91-100.

What is claimed is:

1. A method for predicting an impact resistance of a composite material, the method comprising:
    designing an artificial neural network including a plurality of neurons;
    employing, by a processor, a sensitivity analysis to identify a parameter and quantitatively describe a degree of influence of the parameter on the impact resistance of the composite material;
    training, by the processor, the artificial neural network to predict the impact resistance by adjusting an output of the plurality of neurons according to the parameter and the degree of influence identified in the employed sensitivity analysis;
    inputting data of the composite material into the artificial neural network; and
    utilizing the artificial neural network to predict the impact resistance of the composite material.

2. The method according to claim 1, wherein the artificial neural network includes:
    an input layer of neurons that receives data that is input into the artificial neural network; and
    an output layer of neurons that outputs a prediction of the impact resistance of the composite material.

3. The method according to claim 1, wherein training the artificial neural network further includes:
    inputting sample data to the artificial neural network;
    measuring an error between known results of the sample data and the prediction output from the artificial neural network; and
    reducing the error by applying a variable weighting factor to each neuron of the plurality of neurons in the artificial neural network to adjust an output of each neuron.

4. The method according to claim 3, wherein the error is a mean-squared error.

5. The method according to claim 1, wherein the input data of the composite material includes:
    a stacking sequence of layers in the composite material;
    a layer thickness;
    a number of layers in the composite material;
    an orientation angle of the layers in the composite material; and
    a material composition of the layers in the composite material.

6. The method according to claim 1, wherein the artificial neural network is a feed forward network.

7. The method according to claim 2, wherein the artificial neural network further includes a hidden layer comprising a plurality of neurons,
    the hidden layer receives data output from the input layer, and
    the hidden layer outputs processed data to the output layer.

8. The method according to claim 7, wherein training the artificial neural network further includes:
    inputting sample data to the input layer;
    measuring an error between known results of the sample data and the prediction output from the output layer; and
    reducing the error by:
    managing the hidden layer such that data output from neurons in the input layer may be selected for input to individual neurons in the hidden layer, and
    applying a variable weighting factor to each neuron of the plurality of neurons in the artificial neural network to adjust an output of each neuron.

9. A device for predicting an impact resistance of a composite material, the device comprising:
    a processor configured to:
        design an artificial neural network including a plurality of neurons;
        employ a sensitivity analysis to identify a parameter and quantitatively describe a degree of influence of the parameter on the impact resistance of the composite material;
        train the artificial neural network to predict the impact resistance by adjusting an output the plurality of neurons according to the parameter and the degree of influence identified in the employed sensitivity analysis;
        input data of the composite material into the artificial neural network; and
        utilize the artificial neural network to predict the impact resistance of the composite material.

10. A system for predicting an impact resistance of a composite material, the system comprising:
    the device according to claim 9; and
    the artificial neural network.

11. The device according to claim 9, wherein the artificial neural network includes:
   an input layer of neurons that receives data that is input into the artificial neural network; and
   an output layer of neurons that outputs a prediction of the impact resistance of the composite material.

12. The device according to claim 9, wherein training the artificial neural network further includes:
   inputting sample data to the artificial neural network;
   measuring an error between known results of the sample data and the prediction output from the artificial neural network; and
   reducing the error by applying a variable weighting factor to each neuron of the plurality of neurons in the artificial neural network to adjust an output of each neuron.

13. A non-transitory computer readable medium storing computer readable instructions that when executed by a computer cause the computer to perform a method comprising:
   designing an artificial neural network including a plurality of neurons;
   employing a sensitivity analysis to identify a parameter and quantitatively describe a degree of influence of the parameter on the impact resistance of the composite material;
   training the artificial neural network to predict the impact resistance by adjusting an output of the plurality of neurons according to the parameter and the degree of influence identified in the employed sensitivity analysis;
   inputting data of the composite material into the artificial neural network; and
   utilizing the artificial neural network to predict the impact resistance of the composite material.

14. The non-transitory computer readable medium of claim 13, wherein the artificial neural network includes:
   an input layer of neurons that receives data that is input into the artificial neural network; and
   an output layer of neurons that outputs a prediction of the impact resistance of the composite material.

15. The non-transitory computer readable medium of claim 13, wherein training the artificial neural network further includes:
   inputting sample data to the artificial neural network;
   measuring an error between known results of the sample data and the prediction output from the artificial neural network; and
   reducing the error by applying a variable weighting factor to each neuron of the plurality of neurons in the artificial neural network to adjust an output of each neuron.

16. The non-transitory computer readable medium of claim 15, wherein the error is a mean-squared error.

17. The non-transitory computer readable medium of claim 13, wherein the input data of the composite material includes:
   a stacking sequence of layers in the composite material;
   a layer thickness;
   a number of layers in the composite material;
   an orientation angle of the layers in the composite material; and
   a material composition of the layers in the composite material.

18. The non-transitory computer readable medium of claim 13, wherein the artificial neural network is a feed forward network.

19. The non-transitory computer readable medium of claim 14, wherein the artificial neural network further includes a hidden layer comprising a plurality of neurons,
   the hidden layer receives data output from the input layer, and
   the hidden layer outputs processed data to the output layer.

20. The non-transitory computer readable medium of claim 19, wherein training the artificial neural network further includes:
   inputting sample data to the input layer;
   measuring an error between known results of the sample data and the prediction output from the output layer; and
   reducing the error by:
   managing the hidden layer such that data output from neurons in the input layer may be selected for input to individual neurons in the hidden layer, and
   applying a variable weighting factor to each neuron of the plurality of neurons in the artificial neural network to adjust an output of each neuron.

* * * * *